United States Patent
Teranishi et al.

(10) Patent No.: US 10,759,870 B2
(45) Date of Patent: Sep. 1, 2020

(54) MULTISPECIFIC ANTIGEN-BINDING MOLECULES HAVING BLOOD COAGULATION FACTOR VIII (FVIII) COFACTOR FUNCTION-SUBSTITUTING ACTIVITY AND PHARMACEUTICAL FORMULATIONS CONTAINING SUCH A MOLECULE AS AN ACTIVE INGREDIENT

(71) Applicant: Chugai Seiyaku Kabushiki Kaisha, Tokyo (JP)

(72) Inventors: Yuri Teranishi, Shizuoka (JP); Kazuki Kato, Shizuoka (JP); Hikaru Koga, Shizuoka (JP); Tomoyuki Igawa, Shizuoka (JP); Kazuki Yamaguchi, Shizuoka (JP); Tetsuhiro Soeda, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/099,341

(22) PCT Filed: Sep. 27, 2018

(86) PCT No.: PCT/JP2018/035832
§ 371 (c)(1),
(2) Date: Nov. 6, 2018

(87) PCT Pub. No.: WO2019/065795
PCT Pub. Date: Apr. 4, 2019

(65) Prior Publication Data
US 2020/0223940 A1    Jul. 16, 2020

(30) Foreign Application Priority Data
Sep. 29, 2017 (JP) .................... 2017-189647

(51) Int. Cl.
*A61K 39/395*    (2006.01)
*C07K 16/36*    (2006.01)

(52) U.S. Cl.
CPC .......... *C07K 16/36* (2013.01); *C07K 2317/24* (2013.01); *C07K 2317/31* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Maggio et al. | |
| 4,444,878 A | 4/1984 | Paulus | |
| 4,474,893 A | 10/1984 | Reading | |
| 5,496,549 A | 3/1996 | Yamazaki et al. | |
| 5,591,828 A | 1/1997 | Bosslet et al. | |
| 5,744,446 A | 4/1998 | Lollar et al. | |
| 6,005,091 A | 12/1999 | Blackburn et al. | |
| 6,010,902 A | 1/2000 | Ledbetter et al. | |
| 7,018,632 B2 | 3/2006 | Lindhofer et al. | |
| 7,033,590 B1 | 4/2006 | Scheiflinger et al. | |
| 7,538,196 B2 | 5/2009 | Jung | |
| 7,691,380 B2 | 4/2010 | Thorpe et al. | |
| 7,732,149 B2 | 6/2010 | Kojima et al. | |
| 8,030,461 B2 | 10/2011 | Kojima | |
| 8,062,635 B2 * | 11/2011 | Hattori ...................... | A61P 7/04 424/136.1 |
| 8,337,841 B2 | 12/2012 | Kojima et al. | |
| 9,334,331 B2 * | 5/2016 | Igawa .................... | C07K 16/36 |
| 10,450,381 B2 | 10/2019 | Igawa et al. | |
| 2002/0062010 A1 | 5/2002 | Arathoon et al. | |
| 2003/0207346 A1 | 11/2003 | Arathoon et al. | |
| 2005/0266425 A1 | 12/2005 | Zauderer et al. | |
| 2007/0041978 A1 | 2/2007 | Hattori et al. | |
| 2008/0075712 A1 | 3/2008 | Hattori et al. | |
| 2009/0324589 A1 | 12/2009 | Igawa et al. | |
| 2010/0003254 A1 * | 1/2010 | Hattori ................... | C07K 16/36 424/136.1 |
| 2012/0237517 A1 | 9/2012 | Hattori et al. | |
| 2013/0018174 A1 | 1/2013 | Igawa et al. | |
| 2013/0330345 A1 | 12/2013 | Igawa et al. | |
| 2014/0037632 A1 | 2/2014 | Igawa et al. | |
| 2014/0370018 A1 | 12/2014 | Igawa et al. | |
| 2014/0370020 A1 | 12/2014 | Kuramochi et al. | |
| 2016/0222129 A1 | 8/2016 | Igawa et al. | |
| 2017/0022293 A1 | 1/2017 | Igawa et al. | |
| 2017/0145111 A1 | 5/2017 | Hattori et al. | |
| 2017/0253663 A1 | 9/2017 | Yoneyama | |
| 2018/0002443 A1 | 1/2018 | Hattori et al. | |
| 2018/0244800 A1 | 8/2018 | Hattori et al. | |
| 2019/0112390 A1 | 4/2019 | Hattori et al. | |
| 2019/0185578 A1 | 6/2019 | Igawa et al. | |
| 2019/0315884 A1 | 10/2019 | Igawa et al. | |
| 2019/0359728 A1 | 11/2019 | Hattori et al. | |

FOREIGN PATENT DOCUMENTS

| | | |
|---|---|---|
| CA | 2019559 | 1/2002 |
| CA | 2603264 | 10/2006 |
| CA | 3031082 | 1/2018 |
| EP | 0 369 566 | 5/1990 |
| EP | 0 404 097 | 9/1996 |
| EP | 0 979 281 | 2/2000 |
| EP | 1 327 681 | 7/2003 |
| EP | 1 693 448 | 8/2006 |
| EP | 1 220 923 | 6/2007 |

(Continued)

OTHER PUBLICATIONS

"FDA Grants Roche Breakthrough Therapy Designation on Hemophilia Drug". BioPharm International. UBM. Apr. 19, 2018. from http://www.biopharninternational.com/fda-grants-roche-breakthrough-therapy-designation-hemophilia-drug.*

(Continued)

*Primary Examiner* — Michael Szperka
(74) *Attorney, Agent, or Firm* — Fish & Richardson P.C.

(57) ABSTRACT

Bispecific antibodies whose FIX activation-inhibiting activity is not elevated and whose FVIII cofactor function-substituting activity is elevated have been successfully discovered.

61 Claims, 30 Drawing Sheets
Specification includes a Sequence Listing.

(56) References Cited

FOREIGN PATENT DOCUMENTS

| | | |
|---|---|---|
| EP | 1 876 236 | 1/2008 |
| EP | 1 505 148 | 4/2009 |
| EP | 1 605 058 | 5/2009 |
| EP | 1 688 488 | 8/2011 |
| EP | 2 238 985 | 8/2012 |
| EP | 2 526 963 | 11/2012 |
| EP | 2 644 698 | 10/2013 |
| JP | H02-145187 | 6/1990 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | H06-104071 | 12/1994 |
| JP | H08-510555 | 11/1996 |
| JP | H10-165184 | 6/1998 |
| JP | H10-511085 | 10/1998 |
| JP | H11-71288 | 3/1999 |
| JP | H11-506310 | 6/1999 |
| JP | 3032287 | 4/2000 |
| JP | 2001-523971 | 11/2001 |
| JP | 2002-518041 | 6/2002 |
| JP | 2003-055398 | 2/2003 |
| JP | 2003-509049 | 3/2003 |
| JP | 2008-510466 | 4/2008 |
| JP | 2011-137000 | 7/2011 |
| JP | 2014-511836 | 5/2014 |
| JP | 2015-502409 | 1/2015 |
| JP | 2015-504434 | 2/2015 |
| JP | 2015-514684 | 5/2015 |
| JP | 2015-536349 | 12/2015 |
| JP | 2016-508117 | 3/2016 |
| JP | 2017-511139 | 4/2017 |
| KR | 2013/0102113 | 9/2013 |
| KR | 2013/0102640 | 9/2013 |
| NO | 20062087 | 7/2006 |
| RU | 2339696 | 11/2008 |
| TW | 2007/14313 | 4/2007 |
| TW | I452135 | 9/2014 |
| TW | I452136 | 9/2014 |
| WO | WO 91/08770 | 6/1991 |
| WO | WO 93/11161 | 6/1993 |
| WO | WO 94/13804 | 6/1994 |
| WO | WO 95/01571 | 1/1995 |
| WO | WO 96/01653 | 1/1996 |
| WO | WO 96/07754 | 3/1996 |
| WO | WO 96/16673 | 6/1996 |
| WO | WO 96/26964 | 9/1996 |
| WO | WO 96/27011 | 9/1996 |
| WO | WO 98/50431 | 11/1998 |
| WO | WO 99/10494 | 4/1999 |
| WO | WO 99/67359 | 12/1999 |
| WO | WO 01/19992 | 3/2001 |
| WO | WO 01/90192 | 11/2001 |
| WO | WO 02/06838 | 1/2002 |
| WO | WO 02/30463 | 4/2002 |
| WO | WO 02/33073 | 4/2002 |
| WO | WO 03/35835 | 1/2003 |
| WO | WO 03/42231 | 5/2003 |
| WO | WO 03/87163 | 10/2003 |
| WO | WO 03/91424 | 11/2003 |
| WO | WO 2004/009618 | 1/2004 |
| WO | WO 2004/060919 | 7/2004 |
| WO | WO 2004/065611 | 8/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2006/031370 | 3/2006 |
| WO | WO 2006/106905 | 10/2006 |
| WO | WO 2006/109592 | 10/2006 |
| WO | WO 2007/114319 | 10/2007 |
| WO | WO 2007/114325 | 10/2007 |
| WO | WO 2007/147901 | 12/2007 |
| WO | WO 2009/084659 | 7/2009 |
| WO | WO 2009/089004 | 7/2009 |
| WO | WO 2010/129304 | 11/2010 |
| WO | WO 2011/090088 | 2/2011 |
| WO | WO 2011/078332 | 6/2011 |
| WO | WO 2012/067176 | 5/2012 |
| WO | WO-2012067176 A1 * | 5/2012 ............. C07K 16/36 |
| WO | WO 2012/131555 | 10/2012 |
| WO | WO 2013/065708 | 5/2013 |
| WO | Wo 2013/076186 | 5/2013 |
| WO | WO 2013/096291 | 6/2013 |
| WO | WO 2013/124451 | 8/2013 |
| WO | WO 2013/131866 | 9/2013 |
| WO | WO 2014/081955 | 5/2014 |
| WO | WO 2014/082179 | 6/2014 |
| WO | WO 2015/150447 | 10/2015 |
| WO | WO 2015/181805 | 12/2015 |
| WO | WO 2015/194233 | 12/2015 |
| WO | WO 2016/001810 | 1/2016 |
| WO | WO 2016/166014 | 10/2016 |
| WO | WO 2016/171202 | 10/2016 |
| WO | WO 2017/110980 | 6/2017 |
| WO | WO 2017/188356 | 11/2017 |
| WO | WO 2017/205014 | 11/2017 |
| WO | WO 2018/016881 | 1/2018 |
| WO | WO 2018/021450 | 2/2018 |
| WO | WO 2018/181870 | 10/2018 |

OTHER PUBLICATIONS

Schmidt et al., Human Physiology, Moscow, 1996, v.2, pp. 431-436 (with what we believe to be the corresponding pages in English).
Schmidt et al., Chapter 18, Section 18.6, "Hemostasis and Coagulation," Human Physiology, Second, Completely Revised Edition, Springer-Verlag, 1989, pp. 418-423.
Schmidt et al., Human Physiology, Moscow, 1996, v.3, p. 764 (with what we believe to be the corresponding pages in English).
Schmidt et al., Chapter 29, "Enzymes of the pancreatic juice," Human Physiology, Second, Completely Revised Edition, Springer-Verlag, 1989, p. 716.
U.S. Appl. No. 16/825,513, filed Mar. 20, 2020, Hattori et al.
Kim et al., "Antibody light chain variable domains and their biophysically improved versions for human immunotherapy," mAbs, Jan.-Feb. 2014, 6(1):219-35. doi: 10.4161/mabs.26844.
U.S. Appl. No. 10/575,905, Hattori et al., filed Apr. 30, 2007 (abandoned).
U.S. Pat. No. 8,062,635, Hattori et al., issued Nov. 22, 2011.
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019.
U.S. Pat. No. 9,334,331, Igawa et al., issued May 10, 2016.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Pat. No. 10,450,381, Igawa et al., issued Oct. 22, 2019.
U.S. Appl. No. 15/288,965, Igawa et al., filed Oct. 7, 2016 (abandoned).

(56) References Cited

OTHER PUBLICATIONS

U.S. Appl. No. 16/459,791, Igawa et al., filed Jul. 2, 2019.
U.S. Appl. No. 16/093,495, Saeki et al., filed Oct. 12, 2018.
U.S. Appl. No. 16/061,429, Igawa et al., filed Jun. 12, 2018.
U.S. Appl. No. 16/318,883, Igawa et al., filed Jan. 18, 2019.
U.S. Appl. No. 16/496,089, Shima et al., filed Sep. 20, 2019.
Japan Patent Office, Notice of Reasons for Rejection in JP application No. 2018-553263, dated Dec. 5, 2018 (with English translation), 17 pages.
Japan Patent Office, Decision to Grant a Patent in JP application No. 2018-553263, dated Mar. 4, 2019 (with English translation), 8 pages.
U.S. Pat. No. 8,062,635, Hattori et al., issued Nov. 22, 2001.
U.S. Appl. No. 16/226,798, Hattori et al., filed Dec. 20, 2018.
U.S. Appl. No. 15/132,996, Igawa et al., filed Apr. 19, 2016.
U.S. Appl. No. 16/061,429, Igawa et al., filed June 12, 2016.
U.S. Appl. No. 16/318,883, filed Jan. 18, 2019, Igawa et al.
U.S. Appl. No. 16/459,791, filed Jul. 2, 2019, Igawa et al.
Cardoso et al., "Neutralizing Human Anti Crotoxin scFv Isolated from a Nonimmunized Phage Library," Scand J Immunol, Apr. 2000, 51(4):337-44.
Davie, "A Brief Historical Review of the Waterfall/Cascade of Blood Coagulation," J Biol Chem, Dec. 19, 2003, 278(51):50819-32. Epub Oct. 21, 2003.
Griffiths et al., "Human anti-self antibodies with high specificity from phage display libraries," EMBO J, Feb. 1993, 12(2):725-34.
ALPROLIX Intravenous, May 2019, 16 pages. (with English translation).
Astermark et al., "A randomized comparison of bypassing agents in hemophilia complicated by an inhibitor: the FEIBA NovoSeven Comparative (FENOC) Study," Blood, Jan. 15, 2007, 109(2):546-51. Epub Sep. 21, 2006.
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Coppola et al., "Acquired Inhibitors of Coagulation Factors: Part 1—Acquired Hemophilia A," Semin Thromb Hemost, Jul. 2012, 38(5):433-46. doi: 10.1055/s-0032-1315757. Epub Jun. 27, 2012.
Franchini et al., "Acquired haemophilia A: A 2013 update," Thromb Haemost, Dec. 2013, 110(6):1114-20. doi: 10.1160/TH13-05-0363. Epub Sep. 5, 2013.
Guidelines for the management of hemophilia, World Federation of Hemophilia, 2005, 52 pages.
Hagiwara et al., "Effect of Emicizumab in improving coagulation ability in the presence of minor amount of Factor IX," Japanese Journal of Thrombosis and Hemostasis, Apr. 1, 2017, 28(2):190 0-012 (with English translation).
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
Kruse-Jarres, "Inhibitors: our greatest challenge. Can we minimize the incidence?," Haemophilia, Jan. 2013, 19(Suppl 1):2-7. doi: 10.1111/hae. 12049.
Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.
Minami et al., "Bispecific Antibody ACE910 Improves Plasma Coagulation Function of Factor XI-Deficient Patient," Japanese Journal of Thrombosis and Hemostasis, 2015, 26(2):188 0-024 (with English translation).
Miyata, "Molecular Defects of Factor IX," Japanese Journal of Thrombosis and Hemostasis, 1991, 2(1):1-11 (with English translation).

Nishimura et al., "Factor IX Fukuoka. Substitution of ASN$^{92}$ by his in the second epidermal growth factor-like domain results in defective interaction with factors VIIIa/X," J Biol Chem, Nov. 15, 1993, 268(32):24041-6.
Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).
Shima et al, "The Forefront and Prospects of Hemophilia Treatment," J Jpn Pediatr Soc, Mar. 1, 2017, 121(3):543-552 (with English translation).
Tarantino et al., "Safety of human-plasma-derived clotting factor products and their role in haemostasis in patients with haemophilia: meeting report," Haemophilia, Sep. 2007, 13(5):663-9.
U.S. Appl. No. 10/575,905, Hattori el al., filed Apr. 30, 2007 (abandoned).
U.S. Appl. No. 13/434,643, Hattori el al., filed Mar. 29, 2012 (abandoned).
U.S. Appl. No. 15/172,727, Hattori el al., filed Jun. 3, 2016 (abandoned).
U.S. Appl. No. 15/701,630, Hattori el al., filed Sep. 12, 2017 (abandoned).
U.S. Appl. No. 16/226,798, Hattori el al., filed Dec. 20, 2018 (abandoned).
U.S. Appl. No. 16/093,495, Saeki el al., filed Oct. 12, 2018.
U.S. Appl. No. 16/061,429, Igawa el al., filed Jun. 12, 2018.
U.S. Appl. No. 16/318,883, Igawa el al., filed Jan. 18, 2019.
U.S. Appl. No. 16/536,385, filed Aug. 9, 2019, Hattori et al.
U.S. Appl. No. 11/910,836, Hattori el al., filed Jan. 12, 2009 (abandoned).
U.S. Appl. No. 14/921,590, Hattori el al., filed Oct. 23, 2015 (abandoned).
U.S. Appl. No. 15/402,580, Hattori el al., filed Jan. 10, 2017 (abandoned).
U.S. Appl. No. 15/132,996, Igawa el al., filed Apr. 19, 2016.
U.S. Appl. No. 16/496,089, filed Sep. 20, 2019, Shima et al.
U.S. Appl. 14/921,590, Hattori et al., filed Oct. 23, 2015 (abandoned).
U.S. Appl. No. 16/536,385, Hattori et al., filed Aug. 9, 2019 (abandoned).
U.S. Appl. No. 16/825,513, Hattori el al., filed Mar. 20, 2020.
U.S. Appl. No. 14/019,117, Igawa el al., filed Sep. 5, 2013 (abandoned).
U.S. Appl. No. 15/288,965, Igawa et al., filed Oct. 7, 2016.
U.S. Appl. No. 16/061,429, Igawa et al., filed Jun. 12, 2016.
U.S. Appl. No. 14/921,590, filed Oct. 23, 2015, Hattori et al.
U.S. Appl. No. 15/172,727, filed Jun. 3, 2016, Hattori et al.
U.S. Appl. No. 15/963,345, Apr. 26, 2018, Hattori et al.
U.S. Appl. No. 16/061,429, filed Jun. 12, 2018, Igawa et al.
U.S. Appl. No. 16/093,495, filed Oct. 12, 2018, Saeki et al.
U.S. Appl. No. 16/226,798, filed Dec. 20, 2018, Hattori et al.
[No Authors Listed], "Hemophilia and von Willebrand's Disease: 2. Management," Can Med Assoc J, Jul. 15, 1995, 153(2):147-57.
Amersdorfer et al., GenPept Accession No. AAC26541, 2001, 8.1.
Asselta et al., "Factor V Deficiency," Semin Thromb Hemost, Jun. 2009, 35(4):382-9.
Bajaj et al., "A Monoclonal Antibody to Factor IX That Inhibits the Factor VIII:Ca Potentiation of Factor X Activation," J Biol Chem, Sep. 25, 1985, 260(21):11574-80.
Baker et al., "Immunogenicity of protein therapeutics: The key causes, consequences and challenges," Self Nonself. Oct. 2010, 1(4):314-322.
Bebbington et al., "High-Level Expression of a Recombinant Antibody From Myeloma Cells Using a Glutamine Synthetase Gene as an Amplifiable Selectable Marker," Biotechnology (NY), Feb. 1992, 10(2):169-75.
Bessos et al., "The Characterization of a Panel of Monoclonal Antibodies to Human Coagulation Factor IX," Thromb Res, Dec. 15, 1985, 40(6):863-7.
Blazar et al., "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J Immunol, Oct. 15, 1996, 157(8):3250-9.

(56) References Cited

OTHER PUBLICATIONS

Bolton-Maggs et al., "Haemophilias A and B," Lancet, May 24, 2003, 361(9371):1801-9.
Borrebaeck et al., "Antibody evolution beyond Nature," Nat Biotechnol, Dec. 2002, 20(12):1189-90.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992, 11(1):41-51.
Bowen, "Haemophilia A and haemophilia B: molecular insights," Mol Pathol, Feb. 2002, 55(1):1-18.
Brandstetter et al., "X-ray structure of clotting factor IXa: Active site and module structure related to Xase activity and hemophilia B," Proc Natl Acad Sci USA, Oct. 10, 1995, 92(21):9796-800.
Brennan et al., "Preparation of Bispecific Antibodies by Chemical Recombination of Monoclonal Immunoglobulin G1 Fragments," Science, Jul. 5, 1985, 229(4708):81-3.
Brinkman et al., "Phospholipid-Binding Domain of Factor VIII Is Involved in Endothelial Cell-Mediated Activation of Factor X by Factor IXa," Arterioscler Thromb Vasc Biol, Mar. 1, 2002, 22(3):511-6.
Carter, "Bispecific human IgG by design," J Immunol Methods, Feb. 1, 2001, 248(1-2):7-15.
Chugai Seiyaku Kabushiki Kaisha's letter dated Jun. 12, 2013, regarding oral proceedings scheduled on Jun. 26, 2013, in EP 06730769.4, including Annex A.
Dahlback, "Blood coagulation," Lancet, May 6, 2000, 355(9215):1627-32.
Davie et al., "The Coagulation Cascade: Initiation, Maintenance, and Regulation," Biochemistry, Oct. 29, 1991, 30(43):10363-70.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-84.
Deng et al., "An Agonist Murine Monoclonal Antibody to the Human c-Mpl Receptor Stimulates Megakaryocytopoiesis," Blood, Sep. 15, 1998, 92(6):1981-8.
Edelman et al., "The Covalent Structure of an Entire γG Immunoglobulin Molecule," Proc Natl Acad Sci USA, May 1969, 63(1):78-85.
Ewert et al., "Stability improvement of antibodies for extracellular and intracellular applications: CDR grafting to stable frameworks and structure-based framework engineering," Methods, Oct. 2004, 34(2):184-99.
Fay, "Activation of factor VIII and mechanisms of cofactor action," Blood Rev, Mar. 2004, 18(1):1-15.
Fay et al., "Nonenzymatic cofactors: factor VIII," Comprehensive Biochemistry, vol. 13, 1986, pp. 35-37.
Fay et al., "The size of human factor VIII heterodimers and the effects produced by thrombin," Biochim. et Biophys. Acta., Jun. 1986, 23:871(3):268-78.
Figini et al., "In Vitro Assembly of Repertoires of Antibody Chains on the Surface of Phage by Renaturation," J Mol Biol, May 27, 1994, 239(1):68-78.
Francois et al., "Construction of a Bispecific Antibody Reacting with the α- and β-Chains of the Human IL-2 Receptor," J Immunol, May 15, 1993, 150(10):4610-9.
Gelderman et al., "The Inhibitory Effect of CD46, CD55, and CD59 on Complement Activation After Immunotherapeutic Treatment of Cervical Carcinoma Cells with Monoclonal Antibodies or Bispecific Monoclonal Antibodies," Lab Invest, Apr. 2002, 82(4):483-93.
Gonzales et al., "Minimizing the Immunogenicity of Antibodies for Clinical Application," Tumour Biol. Jan.-Feb. 2005;26(1):31-43.
Griffin et al., "Analysis of heavy and light chain sequences of conventional camelid antibodies from *Camelus dromedarius* and *Camelus bactrianus* species," J Immunol Methods, Mar. 2014, 405:35-46. doi: 10.1016/j.jim.2014.01.003. Epub Jan. 18, 2014.

Grosse-Hovest et al., "A recombinant bispecific single-chain antibody induces targeted, supra-agonistic CD28-stimulation and tumor cell killing," Eur J Immunol, May 2003, 33(5):1334-40.
Hammerling et al., "Use of Hybrid Antibody With Anti-KG and Anti-Ferritin Specificities in Locating Cell Surface Antigens by Electron Microscopy," J Exp Med, Dec. 1, 1968, 128(6):1461-73.
Helfrich et al., "A rapid and versatile method for harnessing scFv antibody fragments with various biological effector functions," J Immunol Methods, Apr. 3, 2000, 237(1-2):131-45.
Hoad et al., "Characterisation of monoclonal antibodies to human factor X/Xa Initial observations with a quantitative ELISA procedure," J Immunol Methods, Feb. 15, 1991, 136(2):269-78.
Holliger et al., "'Diabodies': Small bivalent and bispecific antibody fragments," Proc Natl Acad Sci USA, Jul. 15, 1993, 90(14):6444-8.
Hoyer, "The factor VIII complex: structure and function," Blood, Jul. 1981, 58(1):1-13.
Hsia et al., "Treatment of acquired factor X inhibitor by plasma exchange with concomitant intravenous immunoglobulin and corticosteroids," Am J Hematol, Apr. 2008, 83(4):318-20.
Hu et al., "Development and Characterization of a Novel Fusion Protein Composed of a Human IgG1 Heavy Chain Constant Region and a Single-Chain Fragment Variable Antibody against Venezuelan Equine Encephalitis Virus," J Biochem, Jan. 2003, 133(1):59-66.
Huse et al., "Generation of a Large Combinatorial Library of the Immunoglobulin Repertoire in Phage Lambda," Science, Dec. 8, 1989, 246(4935):1275-81.
Igawa, "Next Generation Antibody Therapeutics Using Bispecific Antibody Technology," The Pharmaceutical Society of Japan, Jul. 1, 2017, vol. 137(7), pp. 831-836 (with English translation).
Igawa, "Technological Development of Bispecific Antibodies and Creation of Pharmaceuticals," Experimental Medicine, Jul. 1, 2018, vol. 36, pp. 1823-1829, fig.3 (with English translation).
Igawa, "Innovative Technology to develop Bispecific Antibody," CSJ Current Review 30, Part II, Aug. 30, 2018, Chapter 17, pp. 157-163, fig. 17-3 (with English translation).
Iwahashi et al., "CDR substitutions of a humanized monoclonal antibody (CC49): contributions of individual CDRs to antigen binding and immunogenicity," Mol Immunol, Oct.-Nov. 1999, 36(15-16): 1079-91.
Janeway et al., Immunobiology, 3rd Edition, Garland Press, 1997, pp. 3:1-3:11.
Jirholt et al., "Exploiting sequence space: shuffling in vivo formed complementarity determining regions into a master framework," Gene, Jul. 30, 1998, 215(2):471-6.
Kang et al., "Linkage of recognition and replication functions by assembling combinatorial antibody Fab libraries along phage surfaces," Proc Natl Acad Sci USA, May 15, 1991, 88(10):4363-6.
Karpovsky et al., ., "Production of Target-Specific Effector Cells Using Hetero-Cross-Linked Aggregates Containing Anti-Target Cell and Anti-Fcγ Receptor Antibodies," J Exp Med, Dec. 1, 1984, ;160(6):1686-701.
Kerschbaumer et al., "An Antibody Specific for Coagulation Factor IX Enhances the Activity of the Intrinsic Factor X-activating Complex," J Biol Chem, Sep. 24, 2004, 279(39):40445-50. Epub Jul. 20, 2004.
Kim et al., "Mammalian type I interferon receptors consists of two subunits: IFNaR1 and IFNaR2," Gene, Sep. 1, 1997, 196(1-2):279-86.
Kitazawa et al., "A bispecific antibody to factors IXa and X restores factor VIII hemostatic activity in a hemophilia A model," Nat Med., Sep. 2012, 18(10):1570-4. doi: 10. 1038/nm.2942. Epub Sep. 30, 2012.
Kroesen et al., "Phase I study of intravenously applied bispecific antibody in renal cell cancer patients receiving subcutaneous interleukin 2," Br J Cancer, Oct. 1994, 70(4):652-61.
Kurokawa et al., "Enhanced Fibrinolysis by a Bispecific Monoclonal Antibody Reactive to Fibrin and Tissue Plasminogen Activator," Bio/Technology, Nov. 1989, 7:1163-7.
Lacroix-Desmazes et al., "Dynamics of factor VIII interactions determine its immunologic fate in hemophilia A," Blood, Jul. 15, 2008, 112(2):240-9. doi: 10.1182/blood-2008-02-124941. Epub May 9, 2008.

(56) References Cited

OTHER PUBLICATIONS

Lapan et al., "Interaction of the A1 Subunit of Factor VIIIa and the Serine Protease Domain of Factor X Identified by Zero-length Cross-linking," Thromb Haemost, Sep. 1998, 80(3):418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J Nucl Med. Oct. 1993;34(10):1662-71.
Lenting et al., "The Life Cycle of Coagulation Factor VIII in View of Its Structure and Function," Blood, Dec. 1, 1998, 92(11):3983-96.
Lindsay, Chapter 4 : Determination of the Kinetics and Mechanism of tg-FIX Activation by Factor XIa, 2004, pp. 49-75.
Link et al., "Production and Characterization of a Bispecific lgG Capable of Inducing T-Cell-Mediated Lysis of Malignant B Cells," Blood, Jun. 15, 1993, 81(12):3343-9.
Lofqvist et al., "Haemophilia prophylaxis in young patients—a long-term follow-up," J Intern Med, May 1997, 241(5):395-400.
Lu et al., "Fab-scFv fusion protein: an efficient approach to production of bispecific antibody fragments," J Immunol Methods, Sep. 15, 2002, 267(2):213-26.
Lu et al., "Di-diabody: a novel tetravalent bispecific antibody molecule by design," J Immunol Methods, Aug. 2003, 279(1-2):219-32.
Maeda et al., "Novel Antibody Modification Techniques and their Application to Antibody Therapeutics," Farumashia, 2015, vol. 51, pp. 424-428 (with English translation).
Massino et al., "Quantitative analysis of the products of IgG chain recombination in hybrid hybridomas based on affinity chromatography and radioimmunoassay," J J Immunol Methods, Feb. 14, 1997, 201(1):57-66.
McCafferty et al., ., "Phage antibodies: filamentous phage displaying antibody variable domains," Nature, Dec. 6, 1990, 348(6301):552-4.
Menegatti et al., "Factor X Deficiency," Semin Thromb Hemost, Jun. 2009, 35(4):407-15.
Merchant et al., "An efficient route to human bispecific IgG," Nat Biotechnol, Jul. 1998. 16(7):677-81.
Mertens et al., "Factor VIII-Factor IX Interactions: Molecular Sites Involved in Enzyme-Cofactor Complex Assembly," Thromb Haemost, Aug. 1999, 82(2):209-17.
Milstein et al., "Hybrid hybridomas and their use in immunohistochemistry," Nature, Oct. 6-12, 1983, 305(5934):537-40.
Miyazaki et al., "Generation of bispecific IgG, which mimics the cofactor function of blood coagulation factor VIII," Seikagaku, Poster sessions (2P-B-161), 2006.
Morrison, "Two heads are better than one," Nat Biotechnol, Nov. 2007, 25(11):1233-4.
Muto et al., "Anti-factor IXa/X bispecific antibody (ACE910): hemostatic potency against ongoing bleeds in a hemophilia A model and the possibility of routine supplementation," J Thromb Haemost., Feb. 2014, 12(2):206-213. doi: 10. 1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-71. doi: 10.1182/blood-2014-07-585737. Epub Oct. 1, 2014.
"National Haemophilia Foundation (NHF) Medical and Scientific Advisory Council (MASAC) Recommendations Concerning Prophylaxis," Medical Bulletin, No. 193, 1 page (1994).
Nilsson et al., "Induction of split tolerance and clinical cure in high-responding hemophiliacs with factor IX antibodies," Proc Natl Acad Sci USA, Dec. 1986, 83(23):9169-73.
Nilsson et al., "Twenty-five years' experience of prophylactic treatment in severe haemophilia A and B," J Intern Med, Jul. 1992, 232(1):25-32.
Nitta et al., "Preliminary trial of specific targeting therapy against malignant glioma," Lancet, Feb. 17, 1990, 335(8686):368-71.
Okubo et al., "The Production and Characterization of Four Monoclonal Antibodies to Human Factor X," J Nara Med Ass, 1987, 38(1):20-28.
Oldenburg et al., "Emicizumab Prophylaxis in Hemophilia A with Inhibitors," N Engl J Med, Aug. 31, 2017, 377(9):809-818. doi: 10.1056/NEJMoa1703068. Epub Jul. 10, 2017.
Panka et al., "Variable region framework differences result in decreased or increased affinity of variant anti-digoxin antibodies," Proc Natl Acad Sci USA, May 1988, 85(9):3080-4.
Paul, Fundamental Immunology, 3rd Edition, Raven Press, NY, 1993, Chapter 8: Immunogenicity and Antigen Structure, p. 242.
Piper et al., "Interferon Therapy in Primary Care," Prim Care Update Ob Gyns, Jul. 2001, 8(4):163-169.
Portolano et al., "Lack of Promiscuity in Autoantigen-Specific H and L Chain Combinations as Revealed by Human H and L Chain 'Roulette'," J Immunol, Feb. 1, 1993, 150(3):880-7.
Price et al., "Tissue factor and tissue factor pathway inhibitor," Anaesthesia, May 2004, 59(5):483-92.
Ridgway et al., "'Knobs-into-holes' engineering of antibody CH3 domains for heavy chain heterodimerization," Protein Eng, Jul. 1996, 9(7):617-21.
Rudikoff et al., "Single amino acid substitution altering antigen-binding specificity," Proc Natl Acad Sci USA, Mar. 1982, 79(6):1979-83.
Ruef et al., "A Bispecific Antifibrin-antiplatelet Urokinase Conjugate (BAAUC) Induces Enhanced Clot Lysis and Inhibits Platelet Aggregation," Thromb Haemost, Jul. 1999, 82(1):109-14.
Ruggeri et al., "von Willebrand Factor and von Willebrand Disease," Blood, Oct. 1987, 70(4):895-904.
Saito et al., "Factor VIII Mimetic Antibody: (1) Establishment and Characterization of Anti-factor IX/anti-factor X Bispecific Antibodies," International Society of Thrombosis and Haemostasis, 2005, vol. 3, Issue Supplement s1, p. #OR160.
Saito et al., "Establishment of Factor VIII Mimetic Antibodies and Their In Vitro Activities in Hemophilia A," National Hemophilia Foundation Symposia, 2006.
Sampei et al., "Identification and multidimensional optimization of an asymmetric bispecific IgG antibody mimicking the function of factor VIII cofactor activity," PLOS ONE, Feb. 2013, 8(2):e57479. doi: 10.1371/journal.pone.0057479. Epub Feb. 28, 2013.
Sampei et al., "Non-antigen-contacting region of an asymmetric bispecific antibody to factors IXa/X significantly affects factor VIII-mimetic activity," mAbs, Jan./Feb. 2015, 7(1):120-8.doi: 10.4161/19420862. 2015. 989028.
Sato et al., "Properties of Two VEGF Receptors, Flt-1 and KDR, in Signal Transduction," Ann NY Acad Sci, May 2000, 902:201-5; discussion 205-7.
Schmidt et al., Chapter 18, Section 18.6, "Hemostasis and Coagulation," Human Physiology, Second, Completely Revised Edition, Springer-Verlag, 1989, pp. 418-423 (with English translation).
Schmidt et al., Chapter 29, "Enzymes of the pancreatic juice," Human Physiology, Second, Completely Revised Edition, Springer-Verlag, 1989, p. 716 (with English translation).
Schmidt et al., "Structure—Function Relationships in Factor IX and Factor IXa," Trends Cardiovasc Med, Jan. 2003, 13(1):39-45.
Segal et al., "Introduction: bispecific antibodies," J Immunol Methods, Feb. 1, 2001, 248(1-2):1-6.
Shalaby et al., "Development of Humanized Bispecific Antibodies Reactive with Cytotoxic Lymphocytes and Tumor Cells Overexpressing the *HER2* Protooncogene," J Exp Med, Jan. 1, 1992, 175(1):217-25.
Shima, "Bispecific antibodies to coagulation factors IXa and X mimic the function of factor VIII," Haemophilia, 2006 World Federation of Haemophilia, 2006, 12 (Suppl. 2).
Shima et al., "Factor VIII Mimetic Antibody: (2) In Vitro Assessment of Cofactor Activity in Hemophilia A," Rinsho Ketsueki, Aug. 30, 2005, 46(8):777(#WS-36-5) (with English translation).
Shima et al., "Factor VIII Mimetic Antibody: (2) In Vitro Assessment of Cofactor Activity in Hemophilia A," International Society of Thrombosis and Haemostasis, 2005, vol. 3, Issue Supplement s1, p. #P0038.

(56) References Cited

OTHER PUBLICATIONS

Shima et al., "Factor VIII-Mimetic Function of Humanized Bispecific Antibody in Hemophilia A," N Engl J Med, May 26, 2016, 374(21):2044-53. doi: 10.1056/NEJMoa1511769.
Shirahata, "5. Future Prospects, 1) Direction for Improvement of Coagulation Factor Preparations," Iyaku (Medicine and Drug) Journal Co., Ltd., Jan. 15, 2009, 280-9 (with English translation).
Soeda et al., "Factor VIII Mimetic Antibody: (1) Establishment of Anti-FIXa/Fx Bispecific Antibodies," Rinsho Ketsueki, Aug. 30, 2005, 46(8):728(#PL-2-4) (with English translation).
Soeda et al., "FVIII-Mimetic Action of Anti-FIXa/Anti-Fx Bispecific Antibodies Produced by the Phage Library Method," Jpn J Thromb Hemost, Oct. 1, 2005, 16(5):526(#O-24) (with English translation).
Stickney et al., "Bifunctional Antibody: A Binary Radiopharmaceutical Delivery System for Imaging Colorectal Carcinoma," Cancer Res, Dec. 15, 1991, 51(24):6650-5.
Suresh et al., "Advantages of bispecific hybridomas in one-step immunocytochemistry and immunoassays," Methods Enzymol, 1986, 121:210-28.
Suresh et al., "Bispecific Monoclonal Antibodies from Hybrid Hybridomas," Proc Natl Acad Sci USA, Oct. 1986, 83(20):7989-93.
Taki, The Journal of Japanese Society on Thrombosis and Hemostasis, Feb. 2, 2002, 13(1):109-13 (with English translation).
Tamura et al., "Structural Correlates of an Anticarcinoma Antibody: Identification of Specificity-Determining Residues (SDRs) and Development of a Minimally Immunogenic Antibody Variant by Retention of SDRs Only," J Immunol, Feb. 1, 2000, 164(3):1432-41.
Uchida et al., "A first-in-human phase 1 study of ACE910, a novel factor VIII-mimetic bispecific antibody, in healthy subjects," Blood, Mar. 31, 2016, 127(13):1633-41. doi: 10.1182/blood-2015-06-650226. Epub Dec. 1, 2015.
Vaughan et al., "Human Antibodies with Sub-nanomolar Affinities Isolated from a Large Non-immunized Phage Display Library," Nat Biotechnol, Mar. 1996, 14(3):309-14.
Vehar et al., "Structure of human factor VIII," Nature, Nov. 22-28, 1984, 312(5992):337-42.
Weiner et al., "A Human Tumor Xenograft Model of Therapy with a Bispecific Monoclonal Antibody Targeting c-erbB-2 and CD16," Cancer Res, Jan. 1, 1993, 53(1):94-100.
Weiner et al., "The Role of T Cell Activation in Anti-CD3 x Antitumor Bispecific Antibody Therapy," J Immunol, Mar. 1, 1994, 152(5):2385-92.
Wood et al., "Expression of active human factor VIII from recombinant DNA clones," Nature, Nov. 22-28, 1984, 312(5992):330-7.
Xiang et al., "Production of Murine V-Human Cκ1 Chimeric Anti-Tag72 Antibody Using V Region cDNA Amplified by PCR," Mol Immunol, Aug. 1990, 27(8):809-17.
Yoneyama et al., "A Pharmacometric Approach to Substitute for a Conventional Dose-Finding Study in Rare Diseases: Example of Phase III Dose Selection for Emicizumab in Hemophilia A," Clin Pharmacokinet, Sep. 2018, 57(9):1123-1134. doi: 10.1007/s40262-017-0616-3.
Zuo et al., "An efficient route to the production of an IgG-like bispecific antibody," Protein Eng, May 2000, 13(5):361-7.
International Search Report for App. Ser. No. PCT/JP2018/035832, dated Dec. 11, 2018, 5 pages.
Schmidt et al., Human Physiology, Moscow, 1996, v. 2, pp. 431-436 (with English translation).
Schmidt et al., Human Physiology, Moscow, 1996, v. 3, p. 764 (with English translation).

\* cited by examiner

MULTISPECIFIC ANTIGEN-BINDING MOLECULES HAVING BLOOD COAGULATION FACTOR VIII (FVIII) COFACTOR FUNCTION-SUBSTITUTING ACTIVITY AND PHARMACEUTICAL FORMULATIONS CONTAINING SUCH A MOLECULE AS AN ACTIVE INGREDIENT

CROSS-REFERENCE TO RELATED APPLICATIONS

This application is the National Stage of International Application Serial No. PCT/JP2018/035832, filed on Sep. 27, 2018, which claims the benefit of Japanese Application Serial No. 2017-189647, filed on Sep. 29, 2017.

TECHNICAL FIELD

The present invention relates to multispecific antigen-binding molecules having an activity of substituting for the cofactor function of blood coagulation factor VIII (FVIII) and pharmaceutical formulations thereof. The invention also relates to antigen-binding molecules in which association between a heavy chain and a light chain is regulated, methods for producing an antigen-binding molecule in which association between a heavy chain and a light chain is regulated, and methods for regulating association between a heavy chain and a light chain of an antigen-binding molecule.

BACKGROUND ART

Hemophilia A is a bleeding abnormality caused by a hereditary decrease or deficiency of blood coagulation factor VIII (FVIII) function. Hemophilia A patients are generally administered with an FVIII formulation for the bleeding (on-demand administration). In recent years, FVIII formulations are also administered prophylactically to prevent bleeding events (preventive administration; Non-patent Documents 1 and 2). The half-life of FVIII formulations in blood is approximately 12 to 16 hours. Therefore, for continuous prevention, FVIII formulations are administered to patients three times a week (Non-patent Documents 3 and 4). In on-demand administrations, FVIII formulations are also additionally administered when necessary at regular intervals to prevent rebleeding. In addition, the administration of FVIII formulations is done intravenously. Therefore, there has been a strong need for pharmaceutical agents with a lesser burden than FVIII formulations.

Occasionally, anti-FVIII antibodies (inhibitors) develop in hemophilia patients. Such inhibitors cancel the effects of the FVIII formulations. For bleeding in patients who have developed inhibitors (inhibitor patients), bypass formulations are administered. Their action mechanisms are not dependent on FVIII function, that is, the function of catalyzing the activation of blood coagulation factor X (FX) by activated blood coagulation factor IX (FIXa). Therefore, in some cases, bypass formulations cannot sufficiently stop the bleeding. Accordingly, there has been a strong need for pharmaceutical agents that are not affected by the presence of inhibitors and which can functionally substitute for FVIII.

As a means for solving these problems, bispecific antibodies that substitute for the function of FVIII and their use have been reported (Patent Documents 1, 2, 3, and 4). Bispecific antibodies against FIXa and FX can substitute for the function of FVIII by positioning the two factors close to each other to exhibit FVIII cofactor function-substituting activity (Non-patent Document 5). It has been reported that the FVIII cofactor function-substituting activity of the antibodies can be improved by optimizing the affinity and orientation towards FIXa and FX (Non-patent Document 6). Furthermore, the FVIII cofactor function-substituting activity of the antibodies is known to be affected by the IgG isotype, disulfide bond pattern, amino acid sequence of the hinge region, and the presence or absence of sugar chains in the Fc region (Non-patent Document 7). ACE910 (Emicizumab) having high FVIII cofactor function-substituting activity, which is one of these antibodies, has been reported to exhibit hemostatic effects in monkey models of hemophilia (Non-patent Documents 8 and 9). Furthermore, in clinical trials on healthy subjects, ACE910 (Emicizumab) was confirmed to achieve excellent pharmacokinetics (long half-life) and tolerability (Non-patent Document 10), and in clinical trials on hemophilia A patients with or without inhibitors, ACE910 (Emicizumab) administration remarkably reduced the bleeding rates compared to before ACE910 (Emicizumab) administration (Non-patent Document 11).

As described above, the effects of reducing the bleeding rates have been observed for ACE910 (Emicizumab) in clinical trials. However, in in vitro thrombin generation assays using FVIII-deficient plasma, improvement effects by ACE910 (Emicizumab) on the maximum amount of thrombin generation (peak height) was lower than the amount generated in the presence of a normal level of FVIII which is 100 U/dL (Non-patent Document 8). Therefore, further enhancement of drug efficacy has been desired. In addition, considering convenience for hemophilia A patients, there has been a demand for bispecific antibodies having FVIII cofactor function-substituting activity which can further reduce the administered dose through improvement of specific activity, and such.

Generally, there are cases where an antibody pharmaceutical acts as an antigen to induce anti-antibody (ADA) production (Non-patent Document 12). Since continuous administration of ACE910 (Emicizumab) becomes difficult for hemophilia patients with occurrence of ADA (anti-ACE910 (Emicizumab) idiotype antibodies), there has been a demand for bispecific antibodies having FVIII cofactor function-substituting activity which can be administered to such patients.

ACE910 (Emicizumab) is a bispecific antibody which has been optimized from many aspects by introducing many amino acid substitutions into a lead antibody hBS1. The lead antibody hBS1 was obtained by humanizing a bispecific antibody acquired through animal immunization which recognizes FIX and/or FIXa, and FX. ACE910 (Emicizumab) has high FVIII cofactor function-substituting activity (Non-patent Document 6 and Patent Document 4). However, for enhancement of drug efficacy and improvement of specific activity, a bispecific antibody that substitutes for the function of FVIII is necessary, which antibody has higher maximum activity (maximum FVIII cofactor function-substituting activity) than ACE910 (Emicizumab) and can exhibit FVIII cofactor function-substituting activity at concentrations lower than that of ACE910 (Emicizumab). However, to date, there have been no reports of bispecific antibodies having remarkably high FVIII cofactor function-substituting activity compared to ACE910 (Emicizumab) from the viewpoint of concentration and maximum activity (Patent Documents 4 and 5).

Several methods have previously been reported as methods for preparing IgG-type bispecific antibodies having human constant regions (IgG-type antibodies having a human constant region that has binding specificity for an antigen A on one arm and binding specificity for an antigen B on the other arm). In general, IgG-type bispecific antibodies are composed of two types of H chains (namely, an H chain for antigen A and an H chain for antigen B) and two types of L chains (namely, an L chain for antigen A and an L chain for antigen B). When such IgG-type bispecific antibodies are expressed, 10 types of combinations are possible as combinations of H2L2 since two types of H chains and two types of L chains are expressed. Among these, there is one type of combination that has the desired binding specificity (IgG having binding specificity for antigen A on one arm and binding specificity for antigen B on the other arm). Consequently, in order to acquire the desired bispecific antibody, it is necessary to purify one type of antibody of interest from among ten types of antibodies, which is extremely low in efficiency and difficult.

Methods have been reported for solving this problem, which involve preferentially secreting IgG having a heterologous combination of an H chain for antigen A and an H chain for antigen B, by substituting amino acids in the CH3 region of the IgG H chain (Patent Documents 6, 7, 8 and 9, and Non-patent Documents 13 and 14). Among these, there have been reported methods that use physical obstacles in the form of a "knob" and "hole", and those that use electric charge repulsion.

A method has also been reported for efficiently obtaining a desired molecule, which uses a common L chain in which an L chain for antigen A and an L chain for antigen B are present on a same amino acid sequence (Patent Documents 10 and 11). However, since the use of a common L chain has the potential of considerably lowering the antigen affinity, this is not necessarily the optimum method. Consequently, in order for a bispecific antibody to bind to two antigens with high affinity, it is preferable that only the L chain and H chain for antigen A associate, and only the L chain and H chain for antigen B associate. Moreover, a method has been reported to allow the H chains and L chains for each antigen to associate irrespectively of the variable regions, which comprises substituting amino acids in the CH1 and CL domains which are constant regions, instead of those in the variable regions (Patent Documents 7, 12, and 13). However, this method leaves much to be improved for efficiently producing a bispecific antibody of interest.

CITATION LIST

Patent Documents

[Patent Document 1] WO 2005/035754
[Patent Document 2] WO 2005/035756
[Patent Document 3] WO 2006/109592
[Patent Document 4] WO 2012/067176
[Patent Document 5] WO 2017/110980
[Patent Document 6] WO 1996/027011
[Patent Document 7] WO 2006/106905
[Patent Document 8] WO 2009/089004
[Patent Document 9] WO 2010/129304
[Patent Document 10] WO 98/050431
[Patent Document 11] WO 2006/109592
[Patent Document 12] WO 2007/147901
[Patent Document 13] WO 2013/065708

Non-Patent Documents

[Non-patent Document 1] Blood 58, 1-13 (1981)
[Non-patent Document 2] Nature 312, 330-337 (1984)
[Non-patent Document 3] Nature 312, 337-342 (1984)
[Non-patent Document 4] Biochim. Biophys. Acta 871, 268-278 (1986)
[Non-patent Document 5] Nat. Med. 2012 October; 18 (10):1570-4.
[Non-patent Document 6] PLoS One. 2013; 8 (2):e57479.
[Non-patent Document 7] MAbs. 2015; 7 (1):120-8.
[Non-patent Document 8] J. Thromb. Haemost. 2014 February; 12 (2):206-213.
[Non-patent Document 9] Blood. 2014 Nov. 13; 124 (20): 3165-71.
[Non-patent Document 10] Blood. 2016, Vol. 127, 13
[Non-patent Document 11] New Eng. J. Med. 2016, 374; 21, 2044-2053
[Non-patent Document 12] Self/Nonself Volume 1, 2010—Issue 4
[Non-patent Document 13] Protein Engineering. 1996, Vol. 9:617-621
[Non-patent Document 14] Nature Biotechnology. 1998, Vol. 16:677-681

SUMMARY OF THE INVENTION

Problems to be Solved by the Invention

The present invention was achieved in view of the above circumstances. An objective of the present invention is to provide multispecific antigen-binding molecules having blood coagulation factor VIII (FVIII) cofactor function-substituting activity and pharmaceutical formulations containing such a molecule as an active ingredient.

Furthermore, the present invention was achieved in view of the above circumstances. Another objective of the present invention is to provide antibodies in which association between a heavy chain and a light chain is regulated, methods for producing an antibody in which association between a heavy chain and a light chain is regulated, and methods for regulating association between a heavy chain and a light chain of an antibody.

Means for Solving the Problems

To obtain bispecific antibodies with high specific activity and maximum FVIII cofactor function-substituting activity, the present inventors obtained from a human antibody library, novel light chains having sequences different from those of ACE910 (Emicizumab), which have FVIII cofactor function-substituting activity, and prepared bispecific antibodies in which amino acid substitutions have been introduced at various sites of the light chains and ACE910 (Emicizumab) heavy chains. Then, they found that blood coagulation factor IX (FIX) activation-inhibiting activity increases with increase in the FVIII cofactor function-substituting activity.

As a result of dedicated examination, the present inventors succeeded in finding bispecific antibodies whose FIX activation-inhibiting activity is not elevated and whose FVIII cofactor function-substituting activity is elevated.

Furthermore, the present inventors selected a heavy chain constant region CH1 and a light chain constant region (CL) as heavy-chain and light-chain regions to be subjected to association regulation, and conducted dedicated studies on the regulation of association between the CH1 and CL. As a result, the present inventors succeeded in discovering that undesirable CH1 and CL association can be suppressed by substituting specific amino acid residues present at the interface between CH1 and CL with amino acid residues which electrostatically repel each other, and that heterogeneous molecules are formed more efficiently than by using the above-described modifications that only introduce a knob and hole into CH3.

The present invention has been made based on such findings, and specifically provides

[1] to [25] below:

[1] a multispecific antigen-binding molecule which has a function to substitute for the function of blood coagulation factor VIII, wherein the molecule comprises a first antigen-binding site which binds to blood coagulation factor IX and/or activated blood coagulation factor IX, and a second antigen-binding site which binds to blood coagulation factor X, wherein the first antigen-binding site comprises a heavy chain variable domain and a light chain variable domain, wherein the heavy chain variable domain (Q499) comprises HVR-H1 comprising the amino acid sequence of SEQ ID NO: 1, HVR-H2 comprising the amino acid sequence of SEQ ID NO: 2, and HVR-H3 comprising the amino acid sequence of SEQ ID NO: 3, and the light chain variable domain (QNK131) comprises HVR-L1 comprising the amino acid sequence of SEQ ID NO: 162, HVR-L2 comprising the amino acid sequence of SEQ ID NO: 163, and HVR-L3 comprising the amino acid sequence of SEQ ID NO: 164; and wherein the second antigen-binding site comprises a heavy chain variable domain and a light chain variable domain, wherein the heavy chain variable domain (J327) comprises HVR-H1 comprising the amino acid sequence of SEQ ID NO: 4, HVR-H2 comprising the amino acid sequence of SEQ ID NO: 5, and HVR-H3 comprising the amino acid sequence of SEQ ID NO: 6, and the light chain variable domain (JNL095) comprises HVR-L1 comprising the amino acid sequence of SEQ ID NO: 165, HVR-L2 comprising the amino acid sequence of SEQ ID NO: 166, and HVR-L3 comprising the amino acid sequence of SEQ ID NO: 167;

wherein one or more amino acid residues are substituted with other amino acids, deleted, or inserted in at least one of the HVRs;

[2] the multispecific antigen-binding molecule of [1], wherein:

at least one amino acid residue selected from amino acid residues at positions 31, 34, 97, 98, 100, 100a, 100b, and 100e according to Kabat numbering is substituted with another amino acid or deleted in the heavy chain variable domain of the first antigen-binding site, at least one amino acid residue selected from amino acid residues at positions 26, 27, 30, 31, 32, 53, 55, 92, 93, 95, and 96 according to Kabat numbering is substituted with another amino acid or inserted in the light chain variable domain of the first antigen-binding site, at least one amino acid residue selected from amino acid residues at positions 31, 51, 56, 57, 59, 61, 62, 65, and 102 according to Kabat numbering is substituted with another amino acid in the heavy chain variable domain of the second antigen-binding site, at least one amino acid residue selected from amino acid residues at positions 24, 26, 27, 29, 30, 31, 32, 50, 92, 94, 95, 95a, and 96 according to Kabat numbering is substituted or deleted in the light chain variable domain of the second antigen-binding site;

[3] the multispecific antigen-binding molecule of [1] or [2], wherein:

in the heavy chain variable domain of the first antigen-binding site, the amino acid residue at position 31 is histidine, the amino acid residue at position 34 is alanine, the amino acid residue at position 97 is aspartic acid, the amino acid residue at position 98 is serine, the amino acid residue at position 100 is aspartic acid or glutamic acid, the amino acid residue at position 100a is aspartic acid or deleted, the amino acid residue at position 100b is alanine or histidine, or the amino acid residue at position 100e is histidine or isoleucine, said position being according to Kabat numbering;

in the light chain variable domain of the first antigen-binding site, the amino acid residue at position 26 is threonine, the amino acid residue at position 27 is arginine, the amino acid residue at position 30 is arginine, the amino acid residue at position 31 is arginine, the amino acid residue at position 32 is aspartic acid or glutamic acid, the amino acid residue at position 53 is arginine, the amino acid residue at position 55 is glutamic acid, the amino acid residue at position 92 is arginine, the amino acid residue at position 93 is serine or aspartic acid, the amino acid residue at position 95 is proline, or the amino acid residue at position 96 is glycine, said position being according to Kabat numbering;

in the heavy chain variable domain of the second antigen-binding site, the amino acid residue at position 31 is asparagine, glutamine, or histidine, the amino acid residue at position 51 is serine, the amino acid residue at position 56 is threonine or arginine, the amino acid residue at position 57 is valine, the amino acid residue at position 59 is serine, the amino acid residue at position 61 is arginine, the amino acid residue at position 62 is lysine, the amino acid residue at position 65 is asparagine or glutamine, or the amino acid residue at position 102 is valine, said position being according to Kabat numbering; and in the light chain variable domain of the second antigen-binding site, the amino acid residue at position 24 is threonine, the amino acid residue at position 26 is glutamic acid, the amino acid residue at position 27 is glutamine, the amino acid residue at position 29 is serine, the amino acid residue at position 30 is glutamine, serine, or glutamic acid, the amino acid residue at position 31 is arginine, the amino acid residue at position 32 is glutamine or glutamic acid, the amino acid residue at position 50 is glutamine, the amino acid residue at position 92 is alanine, the amino acid residue at position 94 is aspartic acid, the amino acid residue at position 95 is aspartic acid or alanine, the amino acid residue at position 95a is tyrosine or deleted, or the amino acid residue at position 96 is threonine, said position being according to Kabat numbering;

[4] the multispecific antigen-binding molecule of any one of [1] to [3], wherein the first antigen-binding site comprises a heavy chain variable domain and a light chain variable domain, wherein the heavy chain variable domain comprises:

1) HVR-H1 comprising the amino acid sequence of SEQ ID NO: 168, HVR-H2 comprising the amino acid sequence of SEQ ID NO: 169, and HVR-H3 comprising the amino acid sequence of SEQ ID NO: 170 (QH01);

2) HVR-H1 comprising the amino acid sequence of SEQ ID NO: 171, HVR-H2 comprising the amino acid sequence of SEQ ID NO: 172, and HVR-H3 comprising the amino acid sequence of SEQ ID NO: 173 (QH02);

3) HVR-H1 comprising the amino acid sequence of SEQ ID NO: 174, HVR-H2 comprising the amino acid sequence of SEQ ID NO: 175, and HVR-H3 comprising the amino acid sequence of SEQ ID NO: 176 (QH03);

4) HVR-H1 comprising the amino acid sequence of SEQ ID NO: 177, HVR-H2 comprising the amino acid sequence of SEQ ID NO: 178, and HVR-H3 comprising the amino acid sequence of SEQ ID NO: 179 (QH04);

5) HVR-H1 comprising the amino acid sequence of SEQ ID NO: 180, HVR-H2 comprising the amino acid sequence of SEQ ID NO: 181, and HVR-H3 comprising the amino acid sequence of SEQ ID NO: 182 (QH06); or
6) HVR-H1 comprising the amino acid sequence of SEQ ID NO: 183, HVR-H2 comprising the amino acid sequence of SEQ ID NO: 184, and HVR-H3 comprising the amino acid sequence of SEQ ID NO: 185 (QH07); and the light chain variable domain comprises:
1) HVR-L1 comprising the amino acid sequence of SEQ ID NO: 186, HVR-L2 comprising the amino acid sequence of SEQ ID NO: 187, and HVR-L3 comprising the amino acid sequence of SEQ ID NO: 188 (QL21);
2) HVR-L1 comprising the amino acid sequence of SEQ ID NO: 189, HVR-L2 comprising the amino acid sequence of SEQ ID NO: 190, and HVR-L3 comprising the amino acid sequence of SEQ ID NO: 191 (QL22);
3) HVR-L1 comprising the amino acid sequence of SEQ ID NO: 192, HVR-L2 comprising the amino acid sequence of SEQ ID NO: 193, and HVR-L3 comprising the amino acid sequence of SEQ ID NO: 194 (QL23);
4) HVR-L1 comprising the amino acid sequence of SEQ ID NO: 195, HVR-L2 comprising the amino acid sequence of SEQ ID NO: 196, and HVR-L3 comprising the amino acid sequence of SEQ ID NO: 197 (QL24);
5) HVR-L1 comprising the amino acid sequence of SEQ ID NO: 198, HVR-L2 comprising the amino acid sequence of SEQ ID NO: 199, and HVR-L3 comprising the amino acid sequence of SEQ ID NO: 200 (QL25);
6) HVR-L1 comprising the amino acid sequence of SEQ ID NO: 201, HVR-L2 comprising the amino acid sequence of SEQ ID NO: 202, and HVR-L3 comprising the amino acid sequence of SEQ ID NO: 203 (QL26);
7) HVR-L1 comprising the amino acid sequence of SEQ ID NO: 204, HVR-L2 comprising the amino acid sequence of SEQ ID NO: 205, and HVR-L3 comprising the amino acid sequence of SEQ ID NO: 206 (QL28);
8) HVR-L1 comprising the amino acid sequence of SEQ ID NO: 207, HVR-L2 comprising the amino acid sequence of SEQ ID NO: 208, and HVR-L3 comprising the amino acid sequence of SEQ ID NO: 209 (QL29);
9) HVR-L1 comprising the amino acid sequence of SEQ ID NO: 210, HVR-L2 comprising the amino acid sequence of SEQ ID NO: 211, and HVR-L3 comprising the amino acid sequence of SEQ ID NO: 212 (QL30);
10) HVR-L1 comprising the amino acid sequence of SEQ ID NO: 213, HVR-L2 comprising the amino acid sequence of SEQ ID NO: 214, and HVR-L3 comprising the amino acid sequence of SEQ ID NO: 215 (QL31);
11) HVR-L1 comprising the amino acid sequence of SEQ ID NO: 216, HVR-L2 comprising the amino acid sequence of SEQ ID NO: 217, and HVR-L3 comprising the amino acid sequence of SEQ ID NO: 218 (QL32); or
12) HVR-L1 comprising the amino acid sequence of SEQ ID NO: 219, HVR-L2 comprising the amino acid sequence of SEQ ID NO: 220, and HVR-L3 comprising the amino acid sequence of SEQ ID NO: 221 (QL33), and
wherein the second antigen-binding site comprises a heavy chain variable domain and a light chain variable domain, wherein the heavy chain variable domain comprises:
1) HVR-H1 comprising the amino acid sequence of SEQ ID NO: 222, HVR-H2 comprising the amino acid sequence of SEQ ID NO: 223, and HVR-H3 comprising the amino acid sequence of SEQ ID NO: 224 (JH01);
2) HVR-H1 comprising the amino acid sequence of SEQ ID NO: 225, HVR-H2 comprising the amino acid sequence of SEQ ID NO: 226, and HVR-H3 comprising the amino acid sequence of SEQ ID NO: 227 (JH02);
3) HVR-H1 comprising the amino acid sequence of SEQ ID NO: 228, HVR-H2 comprising the amino acid sequence of SEQ ID NO: 229, and HVR-H3 comprising the amino acid sequence of SEQ ID NO: 230 (JH03);
4) HVR-H1 comprising the amino acid sequence of SEQ ID NO: 231, HVR-H2 comprising the amino acid sequence of SEQ ID NO: 232, and HVR-H3 comprising the amino acid sequence of SEQ ID NO: 233 (JH04);
5) HVR-H1 comprising the amino acid sequence of SEQ ID NO: 234, HVR-H2 comprising the amino acid sequence of SEQ ID NO: 235, and HVR-H3 comprising the amino acid sequence of SEQ ID NO: 236 (JH05);
6) HVR-H1 comprising the amino acid sequence of SEQ ID NO: 237, HVR-H2 comprising the amino acid sequence of SEQ ID NO: 238, and HVR-H3 comprising the amino acid sequence of SEQ ID NO: 239 (JH06);
7) HVR-H1 comprising the amino acid sequence of SEQ ID NO: 240, HVR-H2 comprising the amino acid sequence of SEQ ID NO: 241, and HVR-H3 comprising the amino acid sequence of SEQ ID NO: 242 (JH07);
8) HVR-H1 comprising the amino acid sequence of SEQ ID NO: 243, HVR-H2 comprising the amino acid sequence of SEQ ID NO: 244, and HVR-H3 comprising the amino acid sequence of SEQ ID NO: 245 (JH08);
9) HVR-H1 comprising the amino acid sequence of SEQ ID NO: 246, HVR-H2 comprising the amino acid sequence of SEQ ID NO: 247, and HVR-H3 comprising the amino acid sequence of SEQ ID NO: 248 (JH09);
10) HVR-H1 comprising the amino acid sequence of SEQ ID NO: 249, HVR-H2 comprising the amino acid sequence of SEQ ID NO: 250, and HVR-H3 comprising the amino acid sequence of SEQ ID NO: 251 (JH10); or
11) HVR-H1 comprising the amino acid sequence of SEQ ID NO: 252, HVR-H2 comprising the amino acid sequence of SEQ ID NO: 253, and HVR-H3 comprising the amino acid sequence of SEQ ID NO: 254 (JH11), and
the light chain variable domain comprises:
1) HVR-L1 comprising the amino acid sequence of SEQ ID NO: 255, HVR-L2 comprising the amino acid sequence of SEQ ID NO: 256, and HVR-L3 comprising the amino acid sequence of SEQ ID NO: 257 (JL01);
2) HVR-L1 comprising the amino acid sequence of SEQ ID NO: 258, HVR-L2 comprising the amino acid sequence of SEQ ID NO: 259, and HVR-L3 comprising the amino acid sequence of SEQ ID NO: 260 (JL02);
3) HVR-L1 comprising the amino acid sequence of SEQ ID NO: 261, HVR-L2 comprising the amino acid sequence of SEQ ID NO: 262, and HVR-L3 comprising the amino acid sequence of SEQ ID NO: 263 (JL03);
4) HVR-L1 comprising the amino acid sequence of SEQ ID NO: 264, HVR-L2 comprising the amino acid sequence of SEQ ID NO: 265, and HVR-L3 comprising the amino acid sequence of SEQ ID NO: 266 (JL04);
5) HVR-L1 comprising the amino acid sequence of SEQ ID NO: 267, HVR-L2 comprising the amino acid sequence of SEQ ID NO: 268, and HVR-L3 comprising the amino acid sequence of SEQ ID NO: 269 (JL05);
6) HVR-L1 comprising the amino acid sequence of SEQ ID NO: 270, HVR-L2 comprising the amino acid sequence of SEQ ID NO: 271, and HVR-L3 comprising the amino acid sequence of SEQ ID NO: 272 (JL06);
7) HVR-L1 comprising the amino acid sequence of SEQ ID NO: 273, HVR-L2 comprising the amino acid sequence of SEQ ID NO: 274, and HVR-L3 comprising the amino acid sequence of SEQ ID NO: 275 (JL07);

8) HVR-L1 comprising the amino acid sequence of SEQ ID NO: 276, HVR-L2 comprising the amino acid sequence of SEQ ID NO: 277, and HVR-L3 comprising the amino acid sequence of SEQ ID NO: 278 (JL08);
9) HVR-L1 comprising the amino acid sequence of SEQ ID NO: 279, HVR-L2 comprising the amino acid sequence of SEQ ID NO: 280, and HVR-L3 comprising the amino acid sequence of SEQ ID NO: 281 (JL09);
10) HVR-L1 comprising the amino acid sequence of SEQ ID NO: 282, HVR-L2 comprising the amino acid sequence of SEQ ID NO: 283, and HVR-L3 comprising the amino acid sequence of SEQ ID NO: 284 (JL10); or
11) HVR-L1 comprising the amino acid sequence of SEQ ID NO: 285, HVR-L2 comprising the amino acid sequence of SEQ ID NO: 286, and HVR-L3 comprising the amino acid sequence of SEQ ID NO: 287 (JL11);

[5] the multispecific antigen-binding molecule of [1], wherein the first antigen-binding site comprises a heavy chain variable domain of SEQ ID NO: 45 (Q499) and a light chain variable domain of SEQ ID NO: 13 (QNK131), and the second antigen-binding site comprises a heavy chain variable domain of SEQ ID NO: 46 (J327) and a light chain variable domain of SEQ ID NO: 31 (JNL095),
wherein one or more amino acid residues are substituted with other amino acids, deleted, or inserted in at least one of the heavy chain variable domains or the light chain variable domains;

[6] the multispecific antigen-binding molecule of [5], wherein:
at least one amino acid residue selected from amino acid residues at positions 31, 34, 39, 97, 98, 100, 100a, 100b, and 100e according to Kabat numbering is substituted with another amino acid or deleted in the heavy chain variable domain of the first antigen-binding site,
at least one amino acid residue selected from amino acid residues at positions 26, 27, 30, 31, 32, 38, 45, 53, 55, 60, 70, 76, 79, 80, 83, 85, 92, 93, 95, and 96 according to Kabat numbering is substituted with another amino acid or inserted in the light chain variable domain of the first antigen-binding site,
at least one amino acid residue selected from amino acid residues at positions 28, 31, 39, 51, 56, 57, 59, 61, 62, 65, 67, 73, 82b, and 102 according to Kabat numbering is substituted with another amino acid in the heavy chain variable domain of the second antigen-binding site, and
at least one amino acid residue selected from amino acid residues at positions 3, 8, 15, 24, 26, 27, 29, 30, 31, 32, 38, 48, 49, 50, 79, 92, 94, 95, 95a, and 96 according to Kabat numbering is substituted with another amino acid or deleted in the light chain variable domain of the second antigen-binding site;

[7] the multispecific antigen-binding molecule of [5] or [6], wherein:
in the heavy chain variable domain of the first antigen-binding site, the amino acid residue at position 31 is histidine, the amino acid residue at position 34 is alanine, the amino acid residue at position 39 is glutamic acid, the amino acid residue at position 97 is aspartic acid, the amino acid residue at position 98 is serine, the amino acid residue at position 100 is aspartic acid or glutamic acid, the amino acid residue at position 100a is aspartic acid or deleted, the amino acid residue at position 100b is alanine or histidine, or the amino acid residue at position 100e is histidine or isoleucine, said position being according to Kabat numbering,
in the light chain variable domain of the first antigen-binding site, the amino acid residue at position 26 is threonine, the amino acid residue at position 27 is arginine, the amino acid residue at position 30 is arginine, the amino acid residue at position 31 is arginine, the amino acid residue at position 32 is aspartic acid or glutamic acid, the amino acid residue at position 38 is lysine, the amino acid residue at position 45 is glutamic acid, the amino acid residue at position 53 is arginine, the amino acid residue at position 55 is glutamic acid, the amino acid residue at position 60 is aspartic acid, the amino acid residue at position 70 is aspartic acid, the amino acid residue at position 76 is asparagine, the amino acid residue at position 79 is glutamic acid, the amino acid residue at position 80 is proline or alanine, the amino acid residue at position 83 is methionine or alanine, the amino acid residue at position 85 is threonine, the amino acid residue at position 92 is arginine, the amino acid residue at position 93 is serine or aspartic acid, the amino acid residue at position 95 is proline, or the amino acid residue at position 96 is glycine, said position being according to Kabat numbering,
in the heavy chain variable domain of the second antigen-binding site, the amino acid residue at position 28 is glutamic acid, the amino acid residue at position 31 is asparagine, glutamine, or histidine, the amino acid residue at position 39 is lysine, the amino acid residue at position 51 is serine, the amino acid residue at position 56 is threonine or arginine, the amino acid residue at position 57 is valine, the amino acid residue at position 59 is serine, the amino acid residue at position 61 is arginine, the amino acid residue at position 62 is lysine, the amino acid residue at position 65 is asparagine or glutamine, the amino acid residue at position 67 is leucine, the amino acid residue at position 73 is isoleucine, the amino acid residue at position 82b is glutamic acid, or the amino acid residue at position 102 is valine, said position being according to Kabat numbering, and
in the light chain variable domain of the second antigen-binding site, the amino acid residue at position 3 is glutamic acid, the amino acid residue at position 8 is proline, the amino acid residue at position 15 is leucine, the amino acid residue at position 24 is threonine, the amino acid residue at position 26 is glutamic acid, the amino acid residue at position 27 is glutamine, the amino acid residue at position 29 is serine, the amino acid residue at position 30 is glutamine, serine, or glutamic acid, the amino acid residue at position 31 is arginine, the amino acid residue at position 32 is glutamine or glutamic acid, the amino acid residue at position 38 is glutamic acid, the amino acid residue at position 48 is isoleucine, the amino acid residue at position 49 is tyrosine, the amino acid residue at position 50 is glutamine, the amino acid residue at position 79 is glutamic acid, the amino acid residue at position 92 is alanine, the amino acid residue at position 94 is aspartic acid, the amino acid residue at position 95 is aspartic acid or alanine, the amino acid residue at position 95a is tyrosine or deleted, or the amino acid residue at position 96 is threonine, said position being according to Kabat numbering;

[8] the multispecific antigen-binding molecule of any one of [1] to [7], wherein
the first antigen-binding site comprises:
a heavy chain variable domain (QH) comprising the amino acid sequence of SEQ ID NO: 56, SEQ ID NO: 57, SEQ ID NO: 58, SEQ ID NO: 59, or SEQ ID NO: 60, and a light chain variable domain (QL) comprising the amino acid sequence of SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71 or SEQ ID NO: 72; and the second antigen-binding site comprises:
  a heavy chain variable domain (JH) comprising the amino acid sequence of SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, and
  a light chain variable domain (JL) comprising the amino acid sequence of SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94;
[9] the multispecific antigen-binding molecule of any one of [1] to [8], wherein the first antigen-binding site comprises constant regions comprising the amino acid sequences set forth in (1) or (2) below, and the second antigen-binding site comprises constant regions comprising the amino acid sequences set forth in (1) or (2) below which are different from the constant regions comprised in the first antigen-binding site:
(1) SEQ ID NO: 119 as a heavy chain constant region and SEQ ID NO: 100 as a light chain constant region
(2) SEQ ID NO: 118 as a heavy chain constant region and SEQ ID NO: 102 as a light chain constant region;
[10] the multispecific antigen-binding molecule of any one of [1] to [9], which is a multispecific antibody or a bispecific antibody;
[11] a bispecific antibody comprising a first antibody heavy chain and a first antibody light chain which bind to blood coagulation factor IX and/or activated blood coagulation factor IX, and a second antibody heavy chain and a second antibody light chain which bind to blood coagulation factor X, wherein the bispecific antibody is any of (a) to (v) below:
(a) a bispecific antibody which comprises a first antibody heavy chain comprising the amino acid sequence of SEQ ID NO: 120, a first antibody light chain comprising the amino acid sequence of SEQ ID NO: 126, a second antibody heavy chain comprising the amino acid sequence of SEQ ID NO: 138, and a second antibody light chain comprising the amino acid sequence of SEQ ID NO: 149 (QH01/QL21//JH01/JL01);
(b) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 138, and a second antibody light chain comprising the amino acid sequence of SEQ ID NO: 149 (QH02/QL22//JH01/JL01);
(c) a bispecific antibody which comprises a first antibody heavy chain comprising the amino acid sequence of SEQ ID NO: 122, a first antibody light chain comprising the amino acid sequence of SEQ ID NO: 128, a second antibody heavy chain comprising the amino acid sequence of SEQ ID NO: 139, and a second antibody light chain comprising the amino acid sequence of SEQ ID NO: 150 (QH03/QL23//JH02/JL02);
(d) a bispecific antibody which comprises a first antibody heavy chain comprising the amino acid sequence of SEQ ID NO: 122, a first antibody light chain comprising the amino acid sequence of SEQ ID NO: 129, a second antibody heavy chain comprising the amino acid sequence of SEQ ID NO: 139, and a second antibody light chain comprising the amino acid sequence of SEQ ID NO: 150 (QH03/QL24//JH02/JL02);
(e) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 140, and a second antibody light chain comprising the amino acid sequence of SEQ ID NO: 151 (QH02/QL22//JH03/JL03);
(f) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 141, and a second antibody light chain comprising the amino acid sequence of SEQ ID NO: 152 (QH02/QL22//JH04/JL04);
(g) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 139, and a second antibody light chain comprising the amino acid sequence of SEQ ID NO: 150 (QH02/QL22//JH02/JL02);
(h) a bispecific antibody which comprises a first antibody heavy chain comprising the amino acid sequence of SEQ ID NO: 123, a first antibody light chain comprising the amino acid sequence of SEQ ID NO: 130, a second antibody heavy chain comprising the amino acid sequence of SEQ ID NO: 139, and a second antibody light chain comprising the amino acid sequence of SEQ ID NO: 150 (QH04/QL25//JH02/JL02);
(i) a bispecific antibody which comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 139, and a second antibody light chain comprising the amino acid sequence of SEQ ID NO: 150 (QH04/QL26//JH02/JL02);
(j) a bispecific antibody which comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 142, and a second antibody light chain comprising the amino acid sequence of SEQ ID NO: 153 (QH04/QL26//JH05/JL05);
(k) a bispecific antibody which comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 142, and a second antibody light chain comprising the amino acid sequence of SEQ ID NO: 153 (QH04/QL28//JH05/JL05);
(l) a bispecific antibody which comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 143, and a second antibody light chain comprising the amino acid sequence of SEQ ID NO: 154 (QH04/QL28//JH06/JL06);
(m) a bispecific antibody which comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 142, and a second antibody light chain comprising the amino acid sequence of SEQ ID NO: 153 (QH04/QL29//JH05/JL05);

(n) a bispecific antibody which comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 143, and a second antibody light chain comprising the amino acid sequence of SEQ ID NO: 154 (QH04/QL29//JH06/JL06);

(o) a bispecific antibody which comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 144, and a second antibody light chain comprising the amino acid sequence of SEQ ID NO: 155 (QH06/QL30//JH07/JL07);

(p) a bispecific antibody which comprises a first antibody heavy chain comprising the amino acid sequence of SEQ ID NO: 123, a first antibody light chain comprising the amino acid sequence of SEQ ID NO: 135, a second antibody heavy chain comprising the amino acid sequence of SEQ ID NO: 145, and a second antibody light chain comprising the amino acid sequence of SEQ ID NO: 156 (QH04/QL31//JH08/JL08);

(q) a bispecific antibody which comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 144, and a second antibody light chain comprising the amino acid sequence of SEQ ID NO: 155 (QH06/QL32//JH07/JL07);

(r) a bispecific antibody which comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 146, and a second antibody light chain comprising the amino acid sequence of SEQ ID NO: 157 (QH06/QL32//JH09/JL09);

(s) a bispecific antibody which comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 147, and a second antibody light chain comprising the amino acid sequence of SEQ ID NO: 158 (QH06/QL30//JH10/JL10);

(t) a bispecific antibody which comprises a first antibody heavy chain comprising the amino acid sequence of SEQ ID NO: 125, a first antibody light chain comprising the amino acid sequence of SEQ ID NO: 137, a second antibody heavy chain comprising the amino acid sequence of SEQ ID NO: 148, and a second antibody light chain comprising the amino acid sequence of SEQ ID NO: 159 (QH07/QL33//JH11/JL11);

(u) a bispecific antibody which binds to epitopes identical with both an epitope in blood coagulation factor IX and/or activated blood coagulation factor IX and an epitope in blood coagulation factor X which are recognized by any of the antibodies of (a) to (t); (v) a bispecific antibody which competes for binding to both an epitope in blood coagulation factor IX and/or activated blood coagulation factor IX and an epitope in blood coagulation factor X which are recognized by any of the antibodies of (a) to (t);

[12] an antigen-binding molecule in which association between a heavy chain and a light chain is regulated, wherein one set or two or more sets of amino acid residues selected from the group consisting of the sets of amino acid residues shown in (a) to (c) below in the heavy chain and the light chain of the antigen-binding molecule are amino acid residues which electrostatically repel each other:

(a) an amino acid residue in a heavy chain constant region (CH1) which is at position 175 according to EU numbering, and an amino acid residue in a light chain constant region (CL) which is at position 180 according to Kabat numbering, (b) an amino acid residue in CH1 which is at position 175 according to EU numbering, and an amino acid residue in CL which is at position 131 according to Kabat numbering, (c) amino acid residues in CH1 which are at positions 147 and 175 according to EU numbering, and amino acid residues in CL which are at positions 131 and 180 according to Kabat numbering;

[13] the antigen-binding molecule of [12], wherein further two or more amino acid residues that form an interface between a heavy chain variable region and a light chain variable region are amino acid residues which electrostatically repel each other;

[14] the antigen-binding molecule of [13], wherein the amino acid residues which electrostatically repel each other are one or two sets of amino acid residues selected from the group consisting of the sets of amino acid residues shown in (a) or (b) below:

(a) an amino acid residue in the heavy chain variable region which is at position 39 according to Kabat numbering, and an amino acid residue in the light chain variable region which is at position 38 according to Kabat numbering, (b) an amino acid residue in the heavy chain variable region which is at position 45 according to Kabat numbering, and an amino acid residue in the light chain variable region which is at position 44 according to Kabat numbering;

[15] the antigen-binding molecule of any one of [12] to [14], wherein the amino acid residues which electrostatically repel each other are selected from the amino acid residues included in either set of (X) or (Y) below:

(X) glutamic acid (E), aspartic acid (D),
(Y) lysine (K), arginine (R), histidine (H);

[16] the antigen-binding molecule of any one of [12] to [15], which is a bispecific antibody; [17] a method for producing an antigen-binding molecule in which association between a heavy chain and a light chain is regulated, wherein the method comprises the steps of (1) to (3) below: (1) modifying a nucleic acid(s) encoding a heavy chain constant region (CH1) and a light chain constant region (CL) such that one set or two or more sets of amino acid residues selected from the group consisting of the sets of amino acid residues shown in (a) to (c) below electrostatically repel each other:

(a) an amino acid residue in CH1 which is at position 175 according to EU numbering, and an amino acid residue in CL which is at position 180 according to Kabat numbering, (b) an amino acid residue in CH1 which is at position 175 according to EU numbering, and an amino acid residue in CL which is at position 131 according to Kabat numbering, (c) amino acid residues in CH1 which are at positions 147 and 175 according to EU numbering, and amino acid residues in CL which are at positions 131 and 180 according to Kabat numbering;

(2) introducing the modified nucleic acid(s) into a host cell and culturing the host cell such that the nucleic acid(s) are expressed.

(3) collecting an antigen-binding molecule from the culture of the host cell;

[18] a method for regulating association between a heavy chain and a light chain in an antigen-binding molecule, wherein the method comprises modifying a nucleic acid such that one set or two or more sets of amino acid residues selected from the group consisting of the sets of amino acid residues shown in (a) to (c) below are amino acid residues that electrostatically repel each other:

(a) an amino acid residue in CH1 which is at position 175 according to EU numbering, and an amino acid residue in CL which is at position 180 according to Kabat numbering, (b) an amino acid residue in CH1 which is at position 175 according to EU numbering, and an amino acid residue in CL which is at position 131 according to Kabat numbering, (c) amino acid residues in CH1 which are at positions 147 and 175 according to EU numbering, and amino acid residues in CL which are at positions 131 and 180 according to Kabat numbering;

[19] an isolated nucleic acid which encodes the multispecific antigen-binding molecule of any one of [1] to [9], the multispecific antibody of [10], the bispecific antibody of [10], [11], or [16], or the antigen-binding molecule of any one of [12] to [15];

[20] a host cell which comprises the nucleic acid of [19];

[21] a method for producing a multispecific antigen-binding molecule, a multispecific antibody, a bispecific antibody, or an antigen-binding molecule, wherein the method comprises culturing the host cell of [20] such that a multispecific antigen-binding molecule, a multispecific antibody, a bispecific antibody, or an antigen-binding molecule is produced;

[22] a pharmaceutical formulation which comprises the multispecific antigen-binding molecule of any one of [1] to [9], the multispecific antibody of [10], the bispecific antibody of [10], [11], or [16], or the antigen-binding molecule of any one of [12] to [15], and a pharmaceutically acceptable carrier;

[23] the pharmaceutical formulation of [22], which is for use in prevention and/or treatment of bleeding, a disease involving bleeding, or a disease caused by bleeding;

[24] the pharmaceutical formulation of [23], wherein the bleeding, the disease involving bleeding, or the disease caused by bleeding is a disease which develops and/or progresses due to a decrease or deficiency in the activity of blood coagulation factor VIII and/or activated blood coagulation factor VIII;

[25] the pharmaceutical formulation of [24], wherein the disease which develops and/or progresses due to a decrease or deficiency in the activity of blood coagulation factor VIII and/or activated blood coagulation factor VIII is hemophilia A, a disease with emergence of an inhibitor against blood coagulation factor VIII and/or activated blood coagulation factor VIII, acquired hemophilia, or von Willebrand disease.

Furthermore, the present invention relates to the following:

[26] the multispecific antigen-binding molecule of any one of [1] to [9], the multispecific antibody of [10], the bispecific antibody of [10], [11], or [16], or the antigen-binding molecule of any one of [12] to [15], which is for use as a medicament;

[27] the multispecific antigen-binding molecule of any one of [1] to [9], the multispecific antibody of [10], or the bispecific antibody of [10] or [11], which is for use in prevention and/or treatment of bleeding, a disease involving bleeding, or a disease caused by bleeding;

[28] the multispecific antigen-binding molecule of any one of [1] to [9], the multispecific antibody of [10], or the bispecific antibody of [10] or [11], which is for use in substituting for the cofactor function of FVIII;

[29] use of the multispecific antigen-binding molecule of any one of [1] to [9], the multispecific antibody of [10], or the bispecific antibody of [10] or [11] in the manufacture of a medicament for treating bleeding, a disease involving bleeding, or a disease caused by bleeding;

[30] use of the multispecific antigen-binding molecule of any one of [1] to [9], the multispecific antibody of [10], or the bispecific antibody of [10] or [11] in the manufacture of a medicament for substituting for the cofactor function of FVIII;

[31] a method for treating an individual with bleeding, a disease involving bleeding, or a disease caused by bleeding, wherein the method comprises administering to the individual an effective amount of the multispecific antigen-binding molecule of any one of [1] to [9], the multispecific antibody of [10], or the bispecific antibody of [10] or [11]; and

[32] a method for substituting for the cofactor function of FVIII in an individual, wherein the method comprises the step of administering to the individual an effective amount of the multispecific antigen-binding molecule of any one of [1] to [9], the multispecific antibody of [10], or the bispecific antibody of [10] or [11] for substituting for the cofactor function of FVIII.

Furthermore, the present invention relates to the following:

[33] the antigen-binding molecule production method of [17], which comprises in step (1), the step of modifying a nucleic acid such that the amino acid residues which electrostatically repel each other are selected from the amino acid residues included in either group of (X) or (Y) below:

(X) glutamic acid (E) and aspartic acid (D); and
(Y) lysine (K), arginine (R), and histidine (H);

[34] the antigen-binding molecule production method of [17] or [33], which further comprises in step (1), the step of modifying a nucleic acid such that two or more amino acid residues that form an interface between a heavy chain variable region and a light chain variable region are amino acid residues which electrostatically repel each other;

[35] the antigen-binding molecule production method of [34], wherein the amino acid residues which electrostatically repel each other are any one set of amino acid residues selected from the group consisting of the sets of amino acid residues shown in (a) or (b) below:

(a) an amino acid residue in the heavy chain variable region which is at position 39 according to Kabat numbering, and an amino acid residue in the light chain variable region which is at position 38 according to Kabat numbering; and (b) an amino acid residue in the heavy chain variable region which is at position 45 according to Kabat numbering, and an amino acid residue in the light chain variable region which is at position 44 according to Kabat numbering;

[36] the antigen-binding molecule production method of [34] or [35], wherein the amino acid residues which electrostatically repel each other are selected from the amino acid residues included in either set of (X) or (Y) below:

(X) glutamic acid (E) and aspartic acid (D); and
(Y) lysine (K), arginine (R), and histidine (H);

[37] the method of [18], wherein the amino acid residues which electrostatically repel each other are selected from the amino acid residues included in either set of (X) or (Y) below:

(X) glutamic acid (E) and aspartic acid (D); and
(Y) lysine (K), arginine (R), and histidine (H);

[38] the method of [18] or [37], wherein further two or more amino acid residues that form an interface between a heavy chain variable region and a light chain variable region are amino acid residues which electrostatically repel each other;

[39] the method of [38], wherein the amino acid residues which electrostatically repel each other are any one set of amino acid residues selected from the group consisting of the sets of amino acid residues shown in (a) or (b) below:

(a) an amino acid residue in the heavy chain variable region which is at position 39 according to Kabat numbering, and an amino acid residue in the light chain variable region which is at position 38 according to Kabat numbering; and
(b) an amino acid residue in the heavy chain variable region which is at position 45 according to Kabat numbering, and an amino acid residue in the light chain variable region which is at position 44 according to Kabat numbering; and

[40] the method of [38] or [39], wherein the amino acid residues which electrostatically repel each other are selected from the amino acid residues included in either set of (X) or (Y) below:

(X) glutamic acid (E) and aspartic acid (D); and
(Y) lysine (K), arginine (R), and histidine (H).

Furthermore, the present invention relates to the following:

[41] the multispecific antigen-binding molecule of any one of [1] to [7], which is any of (a) to (v) below:

(a) a multispecific antigen-binding molecule which comprises a first antibody heavy chain variable domain comprising the amino acid sequence of SEQ ID NO: 56, a first antibody light chain variable domain comprising the amino acid sequence of SEQ ID NO: 61, a second antibody heavy chain variable domain comprising the amino acid sequence of SEQ ID NO: 73, and a second antibody light chain variable domain comprising the amino acid sequence of SEQ ID NO: 84 (QH01/QL21//JH01/JL01);

(b) a multispecific antigen-binding molecule which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 73, and a second antibody light chain variable domain comprising the amino acid sequence of SEQ ID NO: 84 (QH02/QL22//JH01/JL01);

(c) a multispecific antigen-binding molecule which comprises a first antibody heavy chain variable domain comprising the amino acid sequence of SEQ ID NO: 58, a first antibody light chain variable domain comprising the amino acid sequence of SEQ ID NO: 63, a second antibody heavy chain variable domain comprising the amino acid sequence of SEQ ID NO: 74, and a second antibody light chain variable domain comprising the amino acid sequence of SEQ ID NO: 85 (QH03/QL23//JH02/JL02);

(d) a multispecific antigen-binding molecule which comprises a first antibody heavy chain variable domain comprising the amino acid sequence of SEQ ID NO: 58, a first antibody light chain variable domain comprising the amino acid sequence of SEQ ID NO: 64, a second antibody heavy chain variable domain comprising the amino acid sequence of SEQ ID NO: 74, and a second antibody light chain variable domain comprising the amino acid sequence of SEQ ID NO: 85 (QH03/QL24//JH02/JL02);

(e) a multispecific antigen-binding molecule which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 75, and a second antibody light chain variable domain comprising the amino acid sequence of SEQ ID NO: 86 (QH02/QL22//JH03/JL03);

(f) a multispecific antigen-binding molecule which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 76, and a second antibody light chain variable domain comprising the amino acid sequence of SEQ ID NO: 87 (QH02/QL22//JH04/JL04);

(g) a multispecific antigen-binding molecule which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 74, and a second antibody light chain variable domain comprising the amino acid sequence of SEQ ID NO: 85 (QH02/QL22//JH02/JL02);

(h) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 65, a second antibody heavy chain variable domain comprising the amino acid sequence of SEQ ID NO: 74, and a second antibody light chain variable domain comprising the amino acid sequence of SEQ ID NO: 85 (QH04/QL25//JH02/JL02);

(i) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 74, and a second antibody light chain variable domain comprising the amino acid sequence of SEQ ID NO: 85 (QH04/QL26//JH02/JL02);

(j) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 77, and a second antibody light chain variable domain comprising the amino acid sequence of SEQ ID NO: 88 (QH04/QL26//JH05/JL05);

(k) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 77, and a second antibody light chain variable domain comprising the amino acid sequence of SEQ ID NO: 88 (QH04/QL28//JH05/JL05);

(l) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 78, and a second antibody light chain variable domain comprising the amino acid sequence of SEQ ID NO: 89 (QH04/QL28//JH06/JL06);

(m) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 77, and a second antibody light chain variable domain comprising the amino acid sequence of SEQ ID NO: 88 (QH04/QL29//JH05/JL05);

(n) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 78, and a second antibody light chain variable domain comprising the amino acid sequence of SEQ ID NO: 89 (QH04/QL29//JH06/JL06);

(o) a multispecific antigen-binding molecule which comprises a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 79, and a second antibody light chain variable domain comprising the amino acid sequence of SEQ ID NO: 90 (QH06/QL30//JH07/JL07);

(p) a multispecific antigen-binding molecule which comprises a first antibody heavy chain variable domain comprising the amino acid sequence of SEQ ID NO: 59, a first antibody light chain variable domain comprising the amino acid sequence of SEQ ID NO: 70, a second antibody heavy chain variable domain comprising the amino acid sequence of SEQ ID NO: 80, and a second antibody light chain variable domain comprising the amino acid sequence of SEQ ID NO: 91 (QH04/QL31//JH08/JL08);

(q) a multispecific antigen-binding molecule which comprises a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 79, and a second antibody light chain variable domain comprising the amino acid sequence of SEQ ID NO: 90 (QH06/QL32//JH07/JL07);

(r) a multispecific antigen-binding molecule which comprises a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 81, and a second antibody light chain variable domain comprising the amino acid sequence of SEQ ID NO: 92 (QH06/QL32//JH09/JL09);

(s) a multispecific antigen-binding molecule which comprises a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 82, and a second antibody light chain variable domain comprising the amino acid sequence of SEQ ID NO: 93 (QH06/QL30//JH10/JL10);

(t) a multispecific antigen-binding molecule which comprises a first antibody heavy chain variable domain comprising the amino acid sequence of SEQ ID NO: 105, a first antibody light chain variable domain comprising the amino acid sequence of SEQ ID NO: 72, a second antibody heavy chain variable domain comprising the amino acid sequence of SEQ ID NO: 83, and a second antibody light chain variable domain comprising the amino acid sequence of SEQ ID NO: 94 (QH07/QL33//JH11/JL11);

(u) a multispecific antigen-binding molecule which binds to epitopes identical with both an epitope in blood coagulation factor IX and/or activated blood coagulation factor IX and an epitope in blood coagulation factor X which are recognized by any of the antibodies of (a) to (t); and (v) a multispecific antigen-binding molecule which competes for binding to both an epitope in blood coagulation factor IX and/or activated blood coagulation factor IX and an epitope in blood coagulation factor X which are recognized by any of the antibodies of (a) to (t); and

[42] a bispecific antibody comprising a first antibody heavy chain variable domain and a first antibody light chain variable domain which bind to blood coagulation factor IX and/or activated blood coagulation factor IX, and a second antibody heavy chain variable domain and a second antibody light chain variable domain which bind to blood coagulation factor X, wherein the bispecific antibody is any of (a) to (v) below:

(a) a bispecific antibody which comprises a first antibody heavy chain variable domain comprising the amino acid sequence of SEQ ID NO: 56, a first antibody light chain variable domain comprising the amino acid sequence of SEQ ID NO: 61, a second antibody heavy chain variable domain comprising the amino acid sequence of SEQ ID NO: 73, and a second antibody light chain variable domain comprising the amino acid sequence of SEQ ID NO: 84 (QH01/QL21//JH01/JL01);

(b) a bispecific antibody which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 73, and a second antibody light chain variable domain comprising the amino acid sequence of SEQ ID NO: 84 (QH02/QL22//JH01/JL01);

(c) a bispecific antibody which comprises a first antibody heavy chain variable domain comprising the amino acid sequence of SEQ ID NO: 58, a first antibody light chain variable domain comprising the amino acid sequence of SEQ ID NO: 63, a second antibody heavy chain variable domain comprising the amino acid sequence of SEQ ID NO: 74, and a second antibody light chain variable domain comprising the amino acid sequence of SEQ ID NO: 85 (QH03/QL23//JH02/JL02);

(d) a bispecific antibody which comprises a first antibody heavy chain variable domain comprising the amino acid sequence of SEQ ID NO: 58, a first antibody light chain variable domain comprising the amino acid sequence of SEQ ID NO: 64, a second antibody heavy chain variable domain comprising the amino acid sequence of SEQ ID NO: 74, and a second antibody light chain variable domain comprising the amino acid sequence of SEQ ID NO: 85 (QH03/QL24//JH02/JL02);

(e) a bispecific antibody which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 75, and a second antibody light chain variable domain comprising the amino acid sequence of SEQ ID NO: 86 (QH02/QL22//JH03/JL03);

(f) a bispecific antibody which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 76, and a second antibody light chain variable domain comprising the amino acid sequence of SEQ ID NO: 87 (QH02/QL22//JH04/JL04);

(g) a bispecific antibody which comprises a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 74, and a second antibody light chain variable domain comprising the amino acid sequence of SEQ ID NO: 85 (QH02/QL22//JH02/JL02);

(h) a bispecific antibody which comprises a first antibody heavy chain variable domain comprising the amino acid sequence of SEQ ID NO: 59, a first antibody light chain variable domain comprising the amino acid sequence of SEQ ID NO: 65, a second antibody heavy chain variable domain comprising the amino acid sequence of SEQ ID NO: 74, and a second antibody light chain variable domain comprising the amino acid sequence of SEQ ID NO: 85 (QH04/QL25//JH02/JL02);

(i) a bispecific antibody which comprises a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 74, and a second antibody light chain variable domain comprising the amino acid sequence of SEQ ID NO: 85 (QH04/QL26//JH02/JL02);

(j) a bispecific antibody which comprises a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 77, and a second antibody light chain variable domain comprising the amino acid sequence of SEQ ID NO: 88 (QH04/QL26//JH05/JL05);

(k) a bispecific antibody which comprises a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 77, and a second antibody light chain variable domain comprising the amino acid sequence of SEQ ID NO: 88 (QH04/QL28//JH05/JL05);

(l) a bispecific antibody which comprises a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 78, and a second antibody light chain variable domain comprising the amino acid sequence of SEQ ID NO: 89 (QH04/QL28//JH06/JL06);

(m) a bispecific antibody which comprises a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 77, and a second antibody light chain variable domain comprising the amino acid sequence of SEQ ID NO: 88 (QH04/QL29//JH05/JL05);

(n) a bispecific antibody which comprises a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 78, and a second antibody light chain variable domain comprising the amino acid sequence of SEQ ID NO: 89 (QH04/QL29//JH06/JL06);

(o) a bispecific antibody which comprises a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 79, and a second antibody light chain variable domain comprising the amino acid sequence of SEQ ID NO: 90 (QH06/QL30//JH07/JL07);

(p) a bispecific antibody which comprises a first antibody heavy chain variable domain comprising the amino acid sequence of SEQ ID NO: 59, a first antibody light chain variable domain comprising the amino acid sequence of SEQ ID NO: 70, a second antibody heavy chain variable domain comprising the amino acid sequence of SEQ ID NO: 80, and a second antibody light chain variable domain comprising the amino acid sequence of SEQ ID NO: 91 (QH04/QL31//JH08/JL08);

(q) a bispecific antibody which comprises a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 79, and a second antibody light chain variable domain comprising the amino acid sequence of SEQ ID NO: 90 (QH06/QL32//JH07/JL07);

(r) a bispecific antibody which comprises a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 81, and a second antibody light chain variable domain comprising the amino acid sequence of SEQ ID NO: 92 (QH06/QL32//JH09/JL09);

(s) a bispecific antibody which comprises a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 82, and a second antibody light chain variable domain comprising the amino acid sequence of SEQ ID NO: 93 (QH06/QL30//JH10/JL10);

(t) a bispecific antibody which comprises a first antibody heavy chain variable domain comprising the amino acid sequence of SEQ ID NO: 105, a first antibody light chain variable domain comprising the amino acid sequence of SEQ ID NO: 72, a second antibody heavy chain variable domain comprising the amino acid sequence of SEQ ID NO: 83, and a second antibody light chain variable domain comprising the amino acid sequence of SEQ ID NO: 94 (QH07/QL33//JH11/JL11);

(u) a bispecific antibody which binds to epitopes identical with both an epitope in blood coagulation factor IX and/or activated blood coagulation factor IX and an epitope in blood coagulation factor X which are recognized by any of the antibodies of (a) to (t); and (v) a bispecific antibody which competes for binding to both an epitope in blood coagulation factor IX and/or activated blood coagulation factor IX and an epitope in blood coagulation factor X which are recognized by any of the antibodies of (a) to (t).

BRIEF DESCRIPTION OF THE DRAWINGS

FIG. 4-1 shows the concentration dependency of the FVIII cofactor function-substituting activity in bispecific antibodies having a combination of H-chain and L-chain modifications.

FIG. 4-2 shows the concentration dependency of the FVIII cofactor function-substituting activity in bispecific antibodies having a combination of H-chain and L-chain modifications.

FIG. 9-1 shows the data from CIEX analysis of a prepared bispecific antibody.

FIG. 9-2 shows the data from CIEX analysis of a prepared bispecific antibody.

FIG. 9-3 shows the data from CIEX analysis of a prepared bispecific antibody.

FIG. 9-4 shows the data from CIEX analysis of a prepared bispecific antibody.

FIG. 9-5 shows the data from CIEX analysis of a prepared bispecific antibody.

FIG. 9-6 shows the data from CIEX analysis of a prepared bispecific antibody.

FIG. 9-7 shows the data from CIEX analysis of a prepared bispecific antibody.

FIG. 9-8 shows the data from CIEX analysis of a prepared bispecific antibody.

FIG. 9-9 shows the data from CIEX analysis of a prepared bispecific antibody.

FIG. 9-10 shows the data from CIEX analysis of a prepared bispecific antibody.

FIG. 9-11 shows the data from CIEX analysis of a prepared bispecific antibody.

FIG. 9-12 shows the data from CIEX analysis of a prepared bispecific antibody.

FIG. 9-13 shows the data from CIEX analysis of a prepared bispecific antibody.

FIG. 9-14 shows the data from CIEX analysis of a prepared bispecific antibody.

FIG. 9-15 shows the data from CIEX analysis of a prepared bispecific antibody.

FIG. 9-16 shows the data from CIEX analysis of a prepared bispecific antibody.

FIG. 9-17 shows the data from CIEX analysis of a prepared bispecific antibody.

FIG. 9-18 shows the data from CIEX analysis of a prepared bispecific antibody.

FIG. 9-19 shows the data from CIEX analysis of a prepared bispecific antibody.

FIG. 9-20 shows the data from CIEX analysis of a prepared bispecific antibody.

FIG. 10 shows the results of measuring the FVIII cofactor function-substituting activity of bispecific antibodies having novel L chains.

MODE FOR CARRYING OUT THE INVENTION

I. Definitions

Figure 1:
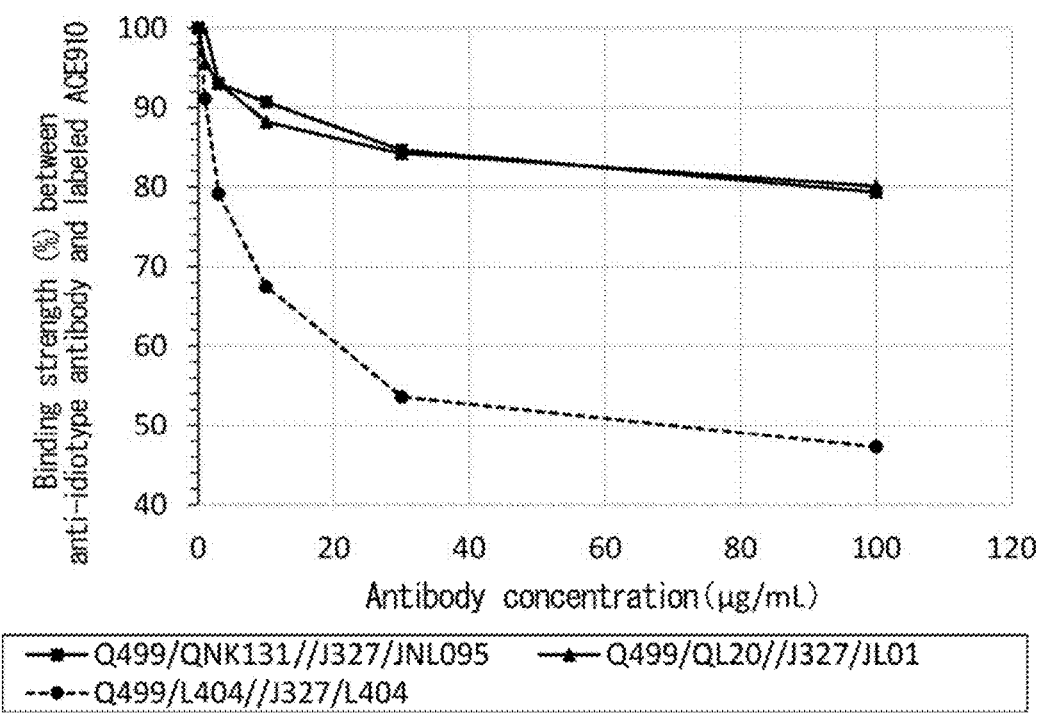
FIG. 1 shows the reactivities with an anti-ACE910 (Emicizumab) idiotype antibody for bispecific antibodies having novel L chains.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

Multispecific antigen-binding molecules described herein comprise a first antigen-binding site and a second antigen-binding site that can specifically bind to at least two different types of antigens.

In one embodiment, the first antigen-binding site and the second antigen-binding site are only required to have an activity to bind to blood coagulation factor IX (FIX) and/or activated blood coagulation factor IX (FIXa), and blood coagulation factor X (FX), respectively, and examples include sites necessary for binding with antigens, such as antibodies, scaffold molecules (antibody-like molecules), or peptides, or fragments containing such sites. Scaffold molecules are molecules that exhibit function by binding to target molecules, and any polypeptide may be used as long as they are conformationally stable polypeptides that can bind to at least one target antigen. Examples of such polypeptides include antibody variable regions, fibronectin (WO 2002/032925), protein A domain (WO 1995/001937), LDL receptor A domain (WO 2004/044011, WO 2005/040229), ankyrin (WO 2002/020565), and such, and also molecules described in documents by Nygren et al. (Current Opinion in Structural Biology, 7: 463-469 (1997); and Journal of Immunol Methods, 290: 3-28 (2004)), Binz et al. (Nature Biotech. 23: 1257-1266 (2005)), and Hosse et al. (Protein Science 15: 14-27 (2006)). Furthermore, as mentioned in Curr. Opin. Mol. Ther. 2010 August; 12(4): 487-95 and Drugs. 2008; 68(7): 901-12, peptide molecules that can bind to target antigens may be used.

Polypeptides in the present invention generally refer to proteins and peptides having a length of approximately ten amino acids or longer. Polypeptides are ordinarily derived from organisms, but are not particularly limited thereto, and for example, they may be composed of an artificially designed sequence. They may also be any naturally occurring polypeptides, or synthetic polypeptides, recombinant polypeptides, or such. Additionally, the fragments of the above-mentioned polypeptides are also included in the polypeptides of the present invention.

In one embodiment, examples of multispecific antigen-binding molecules include multispecific antibodies that can bind specifically to at least two different antigens or two different epitopes on the same antigen.

In one embodiment, multispecific antibodies of the present invention are bispecific antibodies (BsAbs) (they may also be called dual specific antibodies).

Herein, the terms "FVIII cofactor function-substituting activity", "FVIII substituting activity", and "an activity of substituting for the function of FVIII" are used synonymously and refer to an activity of binding to FIX and/or FIXa, and FX to promote the activation of FX (promoting activated blood coagulation factor X (FXa) generation).

In one embodiment, multispecific antigen-binding molecules having FVIII cofactor function-substituting activity are multispecific antigen-binding molecules that bind to FIX and/or FIXa, and FX.

In certain embodiments, multispecific antigen-binding molecules having FVIII cofactor function-substituting activity are multispecific antibodies that bind to FIX and/or FIXa, and FX. In another specific embodiment, multispecific antibodies that bind to FIX and/or FIXa, and FX are bispecific antibodies that bind to FIX and/or FIXa, and FX.

The term "bispecific antibodies that bind to FIX and/or FIXa, and FX" refers to a bispecific antibody that can bind to FIX and/or FIXa, and FX with sufficient affinity, such that the antibody is useful as a diagnostic and/or therapeutic agent in targeting FIX and/or FIXa, and FX. In one embodiment, the extent of binding of an FIX and/or FIXa-binding and FX-binding bispecific antibody to an unrelated, non-FIX protein, non-FIXa protein, or non-FX protein is less than 10% of the binding of the antibody to FIX and/or FIXa, and FX as measured (for example by a radioimmunoassay (RIA)). In certain embodiments, an FIX and/or FIXa-binding and FX-binding antibody has a dissociation constant (Kd) of 100 µM or less, 10 µM or less, 1 µM or less, 100 nM or less, 10 nM or less, 1 nM or less, 0.1 nM or less, 0.01 nM or less, or 0.001 nM or less (for example, $10^{-5}$ M or less, for example from $10^{-5}$ M to $10^{-10}$ M, for example, from $10^{-6}$ M to $10^{-10}$ M). In certain embodiments, a bispecific antibody binding to FIX and/or FIXa, and FX, binds to epitopes in FIX, FIXa, and FX which are conserved among FIX, among FIXa, and among FX from different species, respectively.

In the present invention, in certain embodiments, the term "antibody" is used synonymously with "antigen-binding molecule". In the present invention, the terms "antibody" and "antigen-binding molecule" are used in the broadest sense, and include monoclonal antibodies, polyclonal antibodies, and antibody variants (such as chimeric antibodies, humanized antibodies, minibodies (low molecular weight antibodies) (including antibody fragments to which other molecules may be added arbitrarily), and multispecific antibodies), as long as they exhibit the desired antigen-binding activity or biological activity. Examples of an "antibody" or "antigen-binding molecule" in the present invention include a molecule in which an HAS-binding scaffold has been added to Fab (an antibody in which only the Fab portion is normal). In addition, in the present invention, an "antibody" may also be a polypeptide or a heteromeric multimer. Preferred antibodies are monoclonal antibodies, chimeric antibodies, humanized antibodies, human antibodies, Fc-fusion antibodies, and minibodies such as antibody fragments.

As used herein, the term "antibody" refers to a binding protein comprising an antigen-binding site. The terms "binding site" and "antigen-binding site" as used herein refer to a region of an antibody molecule to which an antigen actually binds. The term "antigen-binding site" includes an antibody heavy chain variable domain (VH) and an antibody light chain variable domain (VL) (a VH/VL pair).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (Gly446-Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antibody that binds to FIX and/or FIXa, and FX" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "FIX", "FIXa", and "FX", as used herein, refer to any native "FIX", native "FIXa", and native "FX", respectively, from any vertebrate source, including mammals such as primates (e.g. humans) and rodents (e.g., mice and rats), unless otherwise indicated. The terms encompass "full-length" unprocessed "FIX", "FIXa", and "FX" as well as any form of "FIX", "FIXa", and "FX" that result from processing in the cell. The terms also encompass naturally occurring variants of "FIX", "FIXa", and "FX", e.g., splice variants or allelic variants.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology, 6$^{th}$* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the present invention is based, in part, on multispecific antigen-binding molecules having FVIII cofactor function-substituting activity. In certain embodiments, multispecific antigen-binding molecules that bind to FIX and/or FIXa, and FX are provided. The multispecific antigen-binding molecules of the present invention are useful, for example, for treating bleeding, a disease involving bleeding, or a disease caused by bleeding.

A. Exemplary Multispecific Antigen-Binding Molecules that Bind to FIX and/or FIXa, and FX.

In one aspect, the present invention provides isolated multispecific antigen-binding molecules that bind to FIX and/or FIXa, and FX. In certain embodiments, the multispecific antigen-binding molecules are bispecific antibodies that bind to FIX and/or FIXa, and FX, and such bispecific antibodies have FVIII cofactor function-substituting activity.

A bispecific antibody that binds to FIX and/or FIXa, and FX, ACE910 (emicizumab) is an antibody described in a patent document (WO 2012/067176) and described below.

The antibody is a bispecific antibody in which a first polypeptide and a third polypeptide are associated and a second polypeptide and a fourth polypeptide are associated, the bispecific antibody comprising a first polypeptide which is an H chain containing HVR-H1, HVR-H2, and HVR-H3 amino acid sequences of SEQ ID NOs: 1, 2, and 3 (H-chain CDRs of Q499), respectively; a second polypeptide which is an H chain containing HVR-H1, HVR-H2, and HVR-H3 amino acid sequences of SEQ ID NOs: 4, 5, and 6 (H-chain CDRs of J327), respectively; and a third and fourth polypeptide which are a commonly shared L chain containing HVR-L1, HVR-L2, and HVR-L3 amino acid sequences of SEQ ID NOs: 7, 8, and 9 (L-chain CDRs of L404), respectively.

More specifically, the antibody is a bispecific antibody in which a first polypeptide and a third polypeptide are associated and a second polypeptide and a fourth polypeptide are associated, the bispecific antibody comprising a first polypeptide which is an H chain containing the H chain variable region amino acid sequence of SEQ ID NO: 45; a second polypeptide which is an H chain containing the H chain variable region amino acid sequence of SEQ ID NO: 46; and a third and fourth polypeptide which are a commonly shared L chain containing the L chain variable region amino acid sequence of SEQ ID NO: 47.

More specifically the antibody is a bispecific antibody in which a first polypeptide and a third polypeptide are associated and a second polypeptide and a fourth polypeptide are associated, the bispecific antibody comprising a first polypeptide which is an H chain consisting of the amino acid sequence of SEQ ID NO: 10; a second polypeptide which is an H chain consisting of the amino acid sequence of SEQ ID NO: 11; and a third and fourth polypeptide which are a commonly shared L chain consisting of the amino acid sequence of SEQ ID NO: 12 (Q499-z121/J327-z119/L404-k).

Multispecific antigen-binding molecules of the present invention are multispecific antigen-binding molecules which has a function to substitute for the function of FVIII, wherein the molecules comprise a first antigen-binding site which binds to FIX and/or FIXa, and a second antigen-binding site which binds to FX, wherein the first antigen-binding site comprises a heavy chain variable domain and a light chain variable domain, wherein the heavy chain variable domain (Q499) comprises HVR-H1 comprising the amino acid sequence of SEQ ID NO: 1, HVR-H2 comprising the amino acid sequence of SEQ ID NO: 2, and HVR-H3 comprising the amino acid sequence of SEQ ID NO: 3, and the light chain variable domain (QNK131) comprises HVR-L1 comprising the amino acid sequence of SEQ ID NO: 162, HVR-L2 comprising the amino acid sequence of SEQ ID NO: 163, and HVR-L3 comprising the amino acid sequence of SEQ ID NO: 164, and wherein the second antigen-binding site comprises a heavy chain variable domain and a light chain variable domain, wherein the heavy chain variable domain (J327) comprises HVR-H1 comprising the amino acid sequence of SEQ ID NO: 4, HVR-H2 comprising the amino acid sequence of SEQ ID NO: 5, and HVR-H3 comprising the amino acid sequence of SEQ ID NO: 6, and the light chain variable domain (JNL095) comprises HVR-L1 comprising the amino acid sequence of SEQ ID NO: 165, HVR-L2 comprising the amino acid sequence of SEQ ID NO: 166, and HVR-L3 comprising the amino acid sequence of SEQ ID NO: 167;

wherein one or more amino acid residues are substituted with other amino acids, deleted, or inserted in at least one of the HVRs.

In certain embodiments, multispecific antigen-binding molecules of the present invention are multispecific antigen-binding molecules which have a function to substitute for the function of FVIII.

Furthermore, in other embodiments, multispecific antigen-binding molecules of the present invention are multispecific antigen-binding molecules having decreased reactivity with an anti-ACE910 (Emicizumab) idiotype antibody compared to ACE910 (Emicizumab). Herein, the phrase "having decreased reactivity with an anti-ACE910 (Emicizumab) idiotype antibody compared to ACE910 (Emicizumab)" means that when the binding strength (%) between the anti-idiotype antibody and labeled ACE910 is measured using the method described in Example 1, and if the concentration of the antibody to be measured is 100 μg/mL, the binding strength is preferably decreased by 10% or more, more preferably decreased by 20% or more, and still more preferably decreased by 30% or more.

Furthermore, in other embodiments, the multispecific antigen-binding molecules are multispecific antigen-binding molecules which has an enhanced FVIII cofactor function-substituting activity and a higher activity even at a low antibody concentration compared to ACE910 (Emicizumab).

In other embodiments, the multispecific antigen-binding molecules have substantially no FIX activation-inhibiting activity and have an increased FVIII cofactor function-substituting activity compared to ACE910 (Emicizumab). Herein, "having substantially no FIX activation-inhibiting activity" means that when OD values are measured using a method shown in the Examples, the decrease in an OD value compared to the control OD value is 0.025 or less, preferably 0.02 or less, and more preferably 0.01 or less.

In one embodiment, the heavy chain variable domain of the first antigen-binding site of a multispecific antigen-binding molecule of the present invention is a heavy chain variable domain of the first antigen-binding site, wherein at least one amino acid residue selected from amino acid residues at positions 31, 34, 97, 98, 100, 100a, 100b, and 100e according to Kabat numbering is substituted with another amino acid or deleted in the heavy chain variable domain of the first antigen-binding site.

In one embodiment, the light chain variable domain of the first antigen-binding site of the present invention is a light chain variable domain of the first antigen-binding site, wherein at least one amino acid residue selected from amino acid residues at positions 26, 27, 30, 31, 32, 53, 55, 92, 93, 95, and 96 according to Kabat numbering is substituted with another amino acid or inserted in the light chain variable domain of the first antigen-binding site.

In one embodiment, the heavy chain variable domain of the second antigen-binding site of the present invention is a heavy chain variable domain of the second antigen-binding site, wherein at least one amino acid residue selected from amino acid residues at positions 31, 51, 56, 57, 59, 61, 62, 65, and 102 according to Kabat numbering is substituted with another amino acid in the heavy chain variable domain of the second antigen-binding site.

In one embodiment, the light chain variable domain of the second antigen-binding site of the present invention is a light chain variable domain of the second antigen-binding site, wherein at least one amino acid residue selected from amino acid residues at positions 24, 26, 27, 29, 30, 31, 32, 50, 92, 94, 95, 95a, and 96 according to Kabat numbering is substituted with another amino acid or deleted in the light chain variable domain of the second antigen-binding site.

In one embodiment, the multispecific antigen-binding molecule of the present invention is a multispecific antigen-binding molecule, wherein:

at least one amino acid residue selected from amino acid residues at positions 31, 34, 97, 98, 100, 100a, 100b, and 100e according to Kabat numbering is substituted with another amino acid or deleted in the heavy chain variable domain of the first antigen-binding site, at least one amino acid residue selected from amino acid residues at positions 26, 27, 30, 31, 32, 53, 55, 92, 93, 95, and 96 according to Kabat numbering is substituted with another amino acid or inserted in the light chain variable domain of the first antigen-binding site, at least one amino acid residue selected from amino acid residues at positions 31, 51, 56, 57, 59, 61, 62, 65, and 102 according to Kabat numbering is substituted with another amino acid in the heavy chain variable domain of the second antigen-binding site, and at least one amino acid residue selected from amino acid residues at positions 24, 26, 27, 29, 30, 31, 32, 50, 92, 94, 95, 95a, and 96 according to Kabat numbering is substituted with another amino acid or deleted in the light chain variable domain of the second antigen-binding site.

In one embodiment, the heavy chain variable domain of the first antigen-binding site of the multispecific antigen-binding molecule of the present invention is a heavy chain variable domain of the first antigen-binding site, wherein:

in the heavy chain variable domain of the first antigen-binding site, the amino acid residue at position 31 is histidine, the amino acid residue at position 34 is alanine, the amino acid residue at position 97 is aspartic acid, the amino acid residue at position 98 is serine, the amino acid residue at position 100 is aspartic acid or glutamic acid, the amino acid residue at position 100a is aspartic acid or deleted, the amino acid residue at position 100b is alanine or histidine, or the amino acid residue at position 100e is histidine or isoleucine, said position being according to Kabat numbering.

In one embodiment, the light chain variable domain of the first antigen-binding site of the present invention is a light chain variable domain of the first antigen-binding site, wherein:

in the light chain variable domain of the first antigen-binding site, the amino acid residue at position 26 is threonine, the amino acid residue at position 27 is arginine, the amino acid residue at position 30 is arginine, the amino acid residue at position 31 is arginine, the amino acid residue at position 32 is aspartic acid or glutamic acid, the amino acid residue at position 53 is arginine, the amino acid residue at position 55 is glutamic acid, the amino acid residue at position 92 is arginine, the amino acid residue at position 93 is serine or aspartic acid, the amino acid residue at position 95 is proline, or the amino acid residue at position 96 is glycine, said position being according to Kabat numbering.

In one embodiment, the heavy chain variable domain of the second antigen-binding site of the present invention is a heavy chain variable domain of the second antigen-binding site, wherein:

in the heavy chain variable domain of the second antigen-binding site, the amino acid residue at position 31 is asparagine, glutamine, or histidine, the amino acid residue at position 51 is serine, the amino acid residue at position 56 is threonine or arginine, the amino acid residue at position 57 is valine, the amino acid residue at position 59 is serine, the amino acid residue at position 61 is arginine, the amino acid residue at position 62 is lysine, the amino acid residue at position 65 is asparagine or glutamine, or the amino acid residue at position 102 is valine, said position being according to Kabat numbering.

In one embodiment, the light chain variable domain of the second antigen-binding site of the present invention is a light chain variable domain of the second antigen-binding site, wherein:

in the light chain variable domain of the second antigen-binding site, the amino acid residue at position 24 is threonine, the amino acid residue at position 26 is glutamic acid, the amino acid residue at position 27 is glutamine, the amino acid residue at position 29 is serine, the amino acid residue at position 30 is glutamine, serine, or glutamic acid, the amino acid residue at position 31 is arginine, the amino acid residue at position 32 is glutamine or glutamic acid, the amino acid residue at position 50 is glutamine, the amino acid residue at position 92 is alanine, the amino acid residue at position 94 is aspartic acid, the amino acid residue at position 95 is aspartic acid or alanine, the amino acid residue at position 95a is tyrosine or deleted, or the amino acid residue at position 96 is threonine, said position being according to Kabat numbering.

In one embodiment, the multispecific antigen-binding molecule of the present invention is a multispecific antigen-binding molecule, wherein:

in the heavy chain variable domain of the first antigen-binding site, the amino acid residue at position 31 is histidine, the amino acid residue at position 34 is alanine, the amino acid residue at position 97 is aspartic acid, the amino acid residue at position 98 is serine, the amino acid residue at position 100 is aspartic acid or glutamic acid, the amino acid residue at position 100a is aspartic acid or deleted, the amino acid residue at position 100b is alanine or histidine, or the amino acid residue at position 100e is histidine or isoleucine, said position being according to Kabat numbering;

in the light chain variable domain of the first antigen-binding site, the amino acid residue at position 26 is threonine, the amino acid residue at position 27 is arginine, the amino acid residue at position 30 is arginine, the amino acid residue at position 31 is arginine, the amino acid residue at position 32 is aspartic acid or glutamic acid, the amino acid residue at position 53 is arginine, the amino acid residue at position 55 is glutamic acid, the amino acid residue at position 92 is arginine, the amino acid residue at position 93 is serine or aspartic acid, the amino acid residue at position 95 is proline, or the amino acid residue at position 96 is glycine, said position being according to Kabat numbering;

in the heavy chain variable domain of the second antigen-binding site, the amino acid residue at position 31 is asparagine, glutamine, or histidine, the amino acid residue at position 51 is serine, the amino acid residue at position 56 is threonine or arginine, the amino acid residue at position 57 is valine, the amino acid residue at position 59 is serine, the amino acid residue at position 61 is arginine, the amino acid residue at position 62 is lysine, the amino acid residue at position 65 is asparagine or glutamine, or the amino acid residue at position 102 is valine, said position being according to Kabat numbering; and in the light chain variable domain of the second antigen-binding site, the amino acid residue at position 24 is threonine, the amino acid residue at position 26 is glutamic acid, the amino acid residue at position 27 is glutamine, the amino acid residue at position 29 is serine, the amino acid residue at position 30 is glutamine, serine, or glutamic acid, the amino acid residue at position 31 is arginine, the amino acid residue at position 32 is glutamine or glutamic acid, the amino acid residue at position 50 is glutamine, the amino acid residue at position 92 is alanine, the amino acid residue at position 94 is aspartic acid, the amino acid residue at position 95 is aspartic acid or alanine, the amino acid residue at position 95a is tyrosine or deleted, or the amino acid residue at position 96 is threonine, said position being according to Kabat numbering.

In one embodiment, the heavy chain variable domain of the first antigen-binding site of the multispecific antigen-binding molecule of the present invention is a heavy chain variable domain which comprises:
1) HVR-H1 comprising the amino acid sequence of SEQ ID NO: 168, HVR-H2 comprising the amino acid sequence of SEQ ID NO: 169, and HVR-H3 comprising the amino acid sequence of SEQ ID NO: 170 (QH01);
2) HVR-H1 comprising the amino acid sequence of SEQ ID NO: 171, HVR-H2 comprising the amino acid sequence of SEQ ID NO: 172, and HVR-H3 comprising the amino acid sequence of SEQ ID NO: 173 (QH02);
3) HVR-H1 comprising the amino acid sequence of SEQ ID NO: 174, HVR-H2 comprising the amino acid sequence of SEQ ID NO: 175, and HVR-H3 comprising the amino acid sequence of SEQ ID NO: 176 (QH03);
4) HVR-H1 comprising the amino acid sequence of SEQ ID NO: 177, HVR-H2 comprising the amino acid sequence of SEQ ID NO: 178, and HVR-H3 comprising the amino acid sequence of SEQ ID NO: 179 (QH04);
5) HVR-H1 comprising the amino acid sequence of SEQ ID NO: 180, HVR-H2 comprising the amino acid sequence of SEQ ID NO: 181, and HVR-H3 comprising the amino acid sequence of SEQ ID NO: 182 (QH06); or
6) HVR-H1 comprising the amino acid sequence of SEQ ID NO: 183, HVR-H2 comprising the amino acid sequence of SEQ ID NO: 184, and HVR-H3 comprising the amino acid sequence of SEQ ID NO: 185 (QH07).

In one embodiment, the light chain variable domain of the first antigen-binding site of a multispecific antigen-binding molecule of the present invention is a light chain variable domain which comprises:
1) HVR-L1 comprising the amino acid sequence of SEQ ID NO: 186, HVR-L2 comprising the amino acid sequence of SEQ ID NO: 187, and HVR-L3 comprising the amino acid sequence of SEQ ID NO: 188 (QL21);
2) HVR-L1 comprising the amino acid sequence of SEQ ID NO: 189, HVR-L2 comprising the amino acid sequence of SEQ ID NO: 190, and HVR-L3 comprising the amino acid sequence of SEQ ID NO: 191 (QL22);
3) HVR-L1 comprising the amino acid sequence of SEQ ID NO: 192, HVR-L2 comprising the amino acid sequence of SEQ ID NO: 193, and HVR-L3 comprising the amino acid sequence of SEQ ID NO: 194 (QL23);
4) HVR-L1 comprising the amino acid sequence of SEQ ID NO: 195, HVR-L2 comprising the amino acid sequence of SEQ ID NO: 196, and HVR-L3 comprising the amino acid sequence of SEQ ID NO: 197 (QL24);

5) HVR-L1 comprising the amino acid sequence of SEQ ID NO: 198, HVR-L2 comprising the amino acid sequence of SEQ ID NO: 199, and HVR-L3 comprising the amino acid sequence of SEQ ID NO: 200 (QL25);

6) HVR-L1 comprising the amino acid sequence of SEQ ID NO: 201, HVR-L2 comprising the amino acid sequence of SEQ ID NO: 202, and HVR-L3 comprising the amino acid sequence of SEQ ID NO: 203 (QL26);

7) HVR-L1 comprising the amino acid sequence of SEQ ID NO: 204, HVR-L2 comprising the amino acid sequence of SEQ ID NO: 205, and HVR-L3 comprising the amino acid sequence of SEQ ID NO: 206 (QL28);

8) HVR-L1 comprising the amino acid sequence of SEQ ID NO: 207, HVR-L2 comprising the amino acid sequence of SEQ ID NO: 208, and HVR-L3 comprising the amino acid sequence of SEQ ID NO: 209 (QL29);

9) HVR-L1 comprising the amino acid sequence of SEQ ID NO: 210, HVR-L2 comprising the amino acid sequence of SEQ ID NO: 211, and HVR-L3 comprising the amino acid sequence of SEQ ID NO: 212 (QL30);

10) HVR-L1 comprising the amino acid sequence of SEQ ID NO: 213, HVR-L2 comprising the amino acid sequence of SEQ ID NO: 214, and HVR-L3 comprising the amino acid sequence of SEQ ID NO: 215 (QL31);

11) HVR-L1 comprising the amino acid sequence of SEQ ID NO: 216, HVR-L2 comprising the amino acid sequence of SEQ ID NO: 217, and HVR-L3 comprising the amino acid sequence of SEQ ID NO: 218 (QL32); or 12) HVR-L1 comprising the amino acid sequence of SEQ ID NO: 219, HVR-L2 comprising the amino acid sequence of SEQ ID NO: 220, and HVR-L3 comprising the amino acid sequence of SEQ ID NO: 221 (QL33).

In one embodiment, the heavy chain variable domain of the second antigen-binding site of the multispecific antigen-binding molecule of the present invention is a heavy chain variable domain which comprises:

1) HVR-H1 comprising the amino acid sequence of SEQ ID NO: 222, HVR-H2 comprising the amino acid sequence of SEQ ID NO: 223, and HVR-H3 comprising the amino acid sequence of SEQ ID NO: 224 (JH01);

2) HVR-H1 comprising the amino acid sequence of SEQ ID NO: 225, HVR-H2 comprising the amino acid sequence of SEQ ID NO: 226, and HVR-H3 comprising the amino acid sequence of SEQ ID NO: 227 (JH02);

3) HVR-H1 comprising the amino acid sequence of SEQ ID NO: 228, HVR-H2 comprising the amino acid sequence of SEQ ID NO: 229, and HVR-H3 comprising the amino acid sequence of SEQ ID NO: 230 (JH03);

4) HVR-H1 comprising the amino acid sequence of SEQ ID NO: 231, HVR-H2 comprising the amino acid sequence of SEQ ID NO: 232, and HVR-H3 comprising the amino acid sequence of SEQ ID NO: 233 (JH04);

5) HVR-H1 comprising the amino acid sequence of SEQ ID NO: 234, HVR-H2 comprising the amino acid sequence of SEQ ID NO: 235, and HVR-H3 comprising the amino acid sequence of SEQ ID NO: 236 (JH05);

6) HVR-H1 comprising the amino acid sequence of SEQ ID NO: 237, HVR-H2 comprising the amino acid sequence of SEQ ID NO: 238, and HVR-H3 comprising the amino acid sequence of SEQ ID NO: 239 (JH06);

7) HVR-H1 comprising the amino acid sequence of SEQ ID NO: 240, HVR-H2 comprising the amino acid sequence of SEQ ID NO: 241, and HVR-H3 comprising the amino acid sequence of SEQ ID NO: 242 (JH07);

8) HVR-H1 comprising the amino acid sequence of SEQ ID NO: 243, HVR-H2 comprising the amino acid sequence of SEQ ID NO: 244, and HVR-H3 comprising the amino acid sequence of SEQ ID NO: 245 (JH08);

9) HVR-H1 comprising the amino acid sequence of SEQ ID NO: 246, HVR-H2 comprising the amino acid sequence of SEQ ID NO: 247, and HVR-H3 comprising the amino acid sequence of SEQ ID NO: 248 (JH09);

10) HVR-H1 comprising the amino acid sequence of SEQ ID NO: 249, HVR-H2 comprising the amino acid sequence of SEQ ID NO: 250, and HVR-H3 comprising the amino acid sequence of SEQ ID NO: 251 (JH10); or 11) HVR-H1 comprising the amino acid sequence of SEQ ID NO: 252, HVR-H2 comprising the amino acid sequence of SEQ ID NO: 253, and HVR-H3 comprising the amino acid sequence of SEQ ID NO: 254 (JH11).

In one embodiment, the light chain variable domain of the second antigen-binding site of the multispecific antigen-binding molecule of the present invention is a light chain variable domain which comprises:

1) HVR-L1 comprising the amino acid sequence of SEQ ID NO: 255, HVR-L2 comprising the amino acid sequence of SEQ ID NO: 256, and HVR-L3 comprising the amino acid sequence of SEQ ID NO: 257 (JL01);

2) HVR-L1 comprising the amino acid sequence of SEQ ID NO: 258, HVR-L2 comprising the amino acid sequence of SEQ ID NO: 259, and HVR-L3 comprising the amino acid sequence of SEQ ID NO: 260 (JL02);

3) HVR-L1 comprising the amino acid sequence of SEQ ID NO: 261, HVR-L2 comprising the amino acid sequence of SEQ ID NO: 262, and HVR-L3 comprising the amino acid sequence of SEQ ID NO: 263 (JL03);

4) HVR-L1 comprising the amino acid sequence of SEQ ID NO: 264, HVR-L2 comprising the amino acid sequence of SEQ ID NO: 265, and HVR-L3 comprising the amino acid sequence of SEQ ID NO: 266 (JL04);

5) HVR-L1 comprising the amino acid sequence of SEQ ID NO: 267, HVR-L2 comprising the amino acid sequence of SEQ ID NO: 268, and HVR-L3 comprising the amino acid sequence of SEQ ID NO: 269 (JL05);

6) HVR-L1 comprising the amino acid sequence of SEQ ID NO: 270, HVR-L2 comprising the amino acid sequence of SEQ ID NO: 271, and HVR-L3 comprising the amino acid sequence of SEQ ID NO: 272 (JL06);

7) HVR-L1 comprising the amino acid sequence of SEQ ID NO: 273, HVR-L2 comprising the amino acid sequence of SEQ ID NO: 274, and HVR-L3 comprising the amino acid sequence of SEQ ID NO: 275 (JL07);

8) HVR-L1 comprising the amino acid sequence of SEQ ID NO: 276, HVR-L2 comprising the amino acid sequence of SEQ ID NO: 277, and HVR-L3 comprising the amino acid sequence of SEQ ID NO: 278 (JL08);

9) HVR-L1 comprising the amino acid sequence of SEQ ID NO: 279, HVR-L2 comprising the amino acid sequence of SEQ ID NO: 280, and HVR-L3 comprising the amino acid sequence of SEQ ID NO: 281 (JL09);

10) HVR-L1 comprising the amino acid sequence of SEQ ID NO: 282, HVR-L2 comprising the amino acid sequence of SEQ ID NO: 283, and HVR-L3 comprising the amino acid sequence of SEQ ID NO: 284 (JL10); or 11) HVR-L1 comprising the amino acid sequence of SEQ ID NO: 285, HVR-L2 comprising the amino acid sequence of SEQ ID NO: 286, and HVR-L3 comprising the amino acid sequence of SEQ ID NO: 287 (JL11).

In one embodiment, the multispecific antigen-binding molecule of the present invention is a multispecific antigen-binding molecule, wherein the first antigen-binding site comprises a heavy chain variable domain and a light chain variable domain, wherein the heavy chain variable domain comprises:
1) HVR-H1 comprising the amino acid sequence of SEQ ID NO: 168, HVR-H2 comprising the amino acid sequence of SEQ ID NO: 169, and HVR-H3 comprising the amino acid sequence of SEQ ID NO: 170 (QH01);
2) HVR-H1 comprising the amino acid sequence of SEQ ID NO: 171, HVR-H2 comprising the amino acid sequence of SEQ ID NO: 172, and HVR-H3 comprising the amino acid sequence of SEQ ID NO: 173 (QH02);
3) HVR-H1 comprising the amino acid sequence of SEQ ID NO: 174, HVR-H2 comprising the amino acid sequence of SEQ ID NO: 175, and HVR-H3 comprising the amino acid sequence of SEQ ID NO: 176 (QH03);
4) HVR-H1 comprising the amino acid sequence of SEQ ID NO: 177, HVR-H2 comprising the amino acid sequence of SEQ ID NO: 178, and HVR-H3 comprising the amino acid sequence of SEQ ID NO: 179 (QH04);
5) HVR-H1 comprising the amino acid sequence of SEQ ID NO: 180, HVR-H2 comprising the amino acid sequence of SEQ ID NO: 181, and HVR-H3 comprising the amino acid sequence of SEQ ID NO: 182 (QH06); or
6) HVR-H1 comprising the amino acid sequence of SEQ ID NO: 183, HVR-H2 comprising the amino acid sequence of SEQ ID NO: 184, and HVR-H3 comprising the amino acid sequence of SEQ ID NO: 185 (QH07); and
the light chain variable domain comprises:
1) HVR-L1 comprising the amino acid sequence of SEQ ID NO: 186, HVR-L2 comprising the amino acid sequence of SEQ ID NO: 187, and HVR-L3 comprising the amino acid sequence of SEQ ID NO: 188 (QL21);
2) HVR-L1 comprising the amino acid sequence of SEQ ID NO: 189, HVR-L2 comprising the amino acid sequence of SEQ ID NO: 190, and HVR-L3 comprising the amino acid sequence of SEQ ID NO: 191 (QL22);
3) HVR-L1 comprising the amino acid sequence of SEQ ID NO: 192, HVR-L2 comprising the amino acid sequence of SEQ ID NO: 193, and HVR-L3 comprising the amino acid sequence of SEQ ID NO: 194 (QL23);
4) HVR-L1 comprising the amino acid sequence of SEQ ID NO: 195, HVR-L2 comprising the amino acid sequence of SEQ ID NO: 196, and HVR-L3 comprising the amino acid sequence of SEQ ID NO: 197 (QL24);
5) HVR-L1 comprising the amino acid sequence of SEQ ID NO: 198, HVR-L2 comprising the amino acid sequence of SEQ ID NO: 199, and HVR-L3 comprising the amino acid sequence of SEQ ID NO: 200 (QL25);
6) HVR-L1 comprising the amino acid sequence of SEQ ID NO: 201, HVR-L2 comprising the amino acid sequence of SEQ ID NO: 202, and HVR-L3 comprising the amino acid sequence of SEQ ID NO: 203 (QL26);
7) HVR-L1 comprising the amino acid sequence of SEQ ID NO: 204, HVR-L2 comprising the amino acid sequence of SEQ ID NO: 205, and HVR-L3 comprising the amino acid sequence of SEQ ID NO: 206 (QL28);
8) HVR-L1 comprising the amino acid sequence of SEQ ID NO: 207, HVR-L2 comprising the amino acid sequence of SEQ ID NO: 208, and HVR-L3 comprising the amino acid sequence of SEQ ID NO: 209 (QL29);
9) HVR-L1 comprising the amino acid sequence of SEQ ID NO: 210, HVR-L2 comprising the amino acid sequence of SEQ ID NO: 211, and HVR-L3 comprising the amino acid sequence of SEQ ID NO: 212 (QL30);
10) HVR-L1 comprising the amino acid sequence of SEQ ID NO: 213, HVR-L2 comprising the amino acid sequence of SEQ ID NO: 214, and HVR-L3 comprising the amino acid sequence of SEQ ID NO: 215 (QL31);
11) HVR-L1 comprising the amino acid sequence of SEQ ID NO: 216, HVR-L2 comprising the amino acid sequence of SEQ ID NO: 217, and HVR-L3 comprising the amino acid sequence of SEQ ID NO: 218 (QL32); or
12) HVR-L1 comprising the amino acid sequence of SEQ ID NO: 219, HVR-L2 comprising the amino acid sequence of SEQ ID NO: 220, and HVR-L3 comprising the amino acid sequence of SEQ ID NO: 221 (QL33); and
wherein the second antigen-binding site comprises a heavy chain variable domain and a light chain variable domain, wherein the heavy chain variable domain comprises:
1) HVR-H1 comprising the amino acid sequence of SEQ ID NO: 222, HVR-H2 comprising the amino acid sequence of SEQ ID NO: 223, and HVR-H3 comprising the amino acid sequence of SEQ ID NO: 224 (JH01);
2) HVR-H1 comprising the amino acid sequence of SEQ ID NO: 225, HVR-H2 comprising the amino acid sequence of SEQ ID NO: 226, and HVR-H3 comprising the amino acid sequence of SEQ ID NO: 227 (JH02);
3) HVR-H1 comprising the amino acid sequence of SEQ ID NO: 228, HVR-H2 comprising the amino acid sequence of SEQ ID NO: 229, and HVR-H3 comprising the amino acid sequence of SEQ ID NO: 230 (JH03);
4) HVR-H1 comprising the amino acid sequence of SEQ ID NO: 231, HVR-H2 comprising the amino acid sequence of SEQ ID NO: 232, and HVR-H3 comprising the amino acid sequence of SEQ ID NO: 233 (JH04);
5) HVR-H1 comprising the amino acid sequence of SEQ ID NO: 234, HVR-H2 comprising the amino acid sequence of SEQ ID NO: 235, and HVR-H3 comprising the amino acid sequence of SEQ ID NO: 236 (JH05);
6) HVR-H1 comprising the amino acid sequence of SEQ ID NO: 237, HVR-H2 comprising the amino acid sequence of SEQ ID NO: 238, and HVR-H3 comprising the amino acid sequence of SEQ ID NO: 239 (JH06);
7) HVR-H1 comprising the amino acid sequence of SEQ ID NO: 240, HVR-H2 comprising the amino acid sequence of SEQ ID NO: 241, and HVR-H3 comprising the amino acid sequence of SEQ ID NO: 242 (JH07);
8) HVR-H1 comprising the amino acid sequence of SEQ ID NO: 243, HVR-H2 comprising the amino acid sequence of SEQ ID NO: 244, and HVR-H3 comprising the amino acid sequence of SEQ ID NO: 245 (JH08);
9) HVR-H1 comprising the amino acid sequence of SEQ ID NO: 246, HVR-H2 comprising the amino acid sequence of SEQ ID NO: 247, and HVR-H3 comprising the amino acid sequence of SEQ ID NO: 248 (JH09);
10) HVR-H1 comprising the amino acid sequence of SEQ ID NO: 249, HVR-H2 comprising the amino acid sequence of SEQ ID NO: 250, and HVR-H3 comprising the amino acid sequence of SEQ ID NO: 251 (JH10); or
11) HVR-H1 comprising the amino acid sequence of SEQ ID NO: 252, HVR-H2 comprising the amino acid sequence of SEQ ID NO: 253, and HVR-H3 comprising the amino acid sequence of SEQ ID NO: 254 (JH11); and
the light chain variable domain comprises:
1) HVR-L1 comprising the amino acid sequence of SEQ ID NO: 255, HVR-L2 comprising the amino acid sequence of SEQ ID NO: 256, and HVR-L3 comprising the amino acid sequence of SEQ ID NO: 257 (JL01);
2) HVR-L1 comprising the amino acid sequence of SEQ ID NO: 258, HVR-L2 comprising the amino acid sequence of SEQ ID NO: 259, and HVR-L3 comprising the amino acid sequence of SEQ ID NO: 260 (JL02);

3) HVR-L1 comprising the amino acid sequence of SEQ ID NO: 261, HVR-L2 comprising the amino acid sequence of SEQ ID NO: 262, and HVR-L3 comprising the amino acid sequence of SEQ ID NO: 263 (JL03);
4) HVR-L1 comprising the amino acid sequence of SEQ ID NO: 264, HVR-L2 comprising the amino acid sequence of SEQ ID NO: 265, and HVR-L3 comprising the amino acid sequence of SEQ ID NO: 266 (JL04);
5) HVR-L1 comprising the amino acid sequence of SEQ ID NO: 267, HVR-L2 comprising the amino acid sequence of SEQ ID NO: 268, and HVR-L3 comprising the amino acid sequence of SEQ ID NO: 269 (JL05);
6) HVR-L1 comprising the amino acid sequence of SEQ ID NO: 270, HVR-L2 comprising the amino acid sequence of SEQ ID NO: 271, and HVR-L3 comprising the amino acid sequence of SEQ ID NO: 272 (JL06);
7) HVR-L1 comprising the amino acid sequence of SEQ ID NO: 273, HVR-L2 comprising the amino acid sequence of SEQ ID NO: 274, and HVR-L3 comprising the amino acid sequence of SEQ ID NO: 275 (JL07);
8) HVR-L1 comprising the amino acid sequence of SEQ ID NO: 276, HVR-L2 comprising the amino acid sequence of SEQ ID NO: 277, and HVR-L3 comprising the amino acid sequence of SEQ ID NO: 278 (JL08);
9) HVR-L1 comprising the amino acid sequence of SEQ ID NO: 279, HVR-L2 comprising the amino acid sequence of SEQ ID NO: 280, and HVR-L3 comprising the amino acid sequence of SEQ ID NO: 281 (JL09);
10) HVR-L1 comprising the amino acid sequence of SEQ ID NO: 282, HVR-L2 comprising the amino acid sequence of SEQ ID NO: 283, and HVR-L3 comprising the amino acid sequence of SEQ ID NO: 284 (JL10); or
11) HVR-L1 comprising the amino acid sequence of SEQ ID NO: 285, HVR-L2 comprising the amino acid sequence of SEQ ID NO: 286, and HVR-L3 comprising the amino acid sequence of SEQ ID NO: 287 (JL11).

In one embodiment of the present invention, the multispecific antigen-binding molecule of the present invention is a multispecific antigen-binding molecule having a function to substitute for the function of blood coagulation factor VIII, wherein the molecules comprises a first antigen-binding site that binds to blood coagulation factor IX and/or activated blood coagulation factor IX, and a second antigen-binding site that binds to blood coagulation factor X, wherein the first antigen-binding site comprises the heavy chain variable domain (Q499) of SEQ ID NO: 45 and the light chain variable domain (QNK131) of SEQ ID NO: 13, and the second antigen-binding site comprises the heavy chain variable domain (J327) of SEQ ID NO: 46 and the light chain variable domain (JNL095) of SEQ ID NO: 31, and wherein one or more amino acid residues are substituted with other amino acids or deleted in at least one of the heavy chain variable domains or the light chain variable domains.

In an embodiment, in a heavy chain variable domain of a first antigen-binding site of the present invention, at least one amino acid residue selected from the amino acid residues at positions 31, 34, 39, 97, 98, 100, 100a, 100b, and 100e, according to Kabat numbering, is substituted with another amino acid or deleted in the above heavy chain variable domain of the first antigen-binding site.

In an embodiment, in a light chain variable domain of a first antigen-binding site of the present invention, at least one amino acid residue selected from the amino acid residues at positions 26, 27, 30, 31, 32, 38, 45, 53, 55, 60, 70, 76, 79, 80, 83, 85, 92, 93, 95, and 96, according to Kabat numbering, is substituted with another amino acid or inserted in the above light chain variable domain of the first antigen-binding site.

In an embodiment, in a heavy chain variable domain of a second antigen-binding site of the present invention, at least one amino acid residue selected from the amino acid residues at positions 28, 31, 39, 51, 56, 57, 59, 61, 62, 65, 67, 73, 82b, and 102, according to Kabat numbering, is substituted with another amino acid in the above heavy chain variable domain of the second antigen-binding site.

In an embodiment, in a light chain variable domain of a second antigen-binding site of the present invention, at least one amino acid residue selected from the amino acid residues at positions 3, 8, 15, 24, 26, 27, 29, 30, 31, 32, 38, 48, 49, 50, 79, 92, 94, 95, 95a, and 96, according to Kabat numbering, is substituted with another amino acid or deleted in the above light chain variable domain of the second antigen-binding site.

In an embodiment, in a multispecific antigen-binding molecule of the present invention: at least one amino acid residue selected from the amino acid residues at positions 31, 34, 39, 97, 98, 100, 100a, 100b, and 100e, according to Kabat numbering, is substituted with another amino acid or deleted in the above heavy chain variable domain of the first antigen-binding site; at least one amino acid residue selected from the amino acid residues at positions 26, 27, 30, 31, 32, 38, 45, 53, 55, 60, 70, 76, 79, 80, 83, 85, 92, 93, 95, and 96, according to Kabat numbering, is substituted with another amino acid or inserted in the above light chain variable domain of the first antigen-binding site;
at least one amino acid residue selected from the amino acid residues at positions 28, 31, 39, 51, 56, 57, 59, 61, 62, 65, 67, 73, 82b, and 102, according to Kabat numbering, is substituted with another amino acid in the above heavy chain variable domain of the second antigen-binding site; and
at least one amino acid residue selected from the amino acid residues at positions 3, 8, 15, 24, 26, 27, 29, 30, 31, 32, 38, 48, 49, 50, 79, 92, 94, 95, 95a, and 96, according to Kabat numbering, is substituted with another amino acid or deleted in the above light chain variable domain of the second antigen-binding site.

In an embodiment, in a heavy chain variable domain of a first antigen-binding site of the present invention, the amino acid residue at position 31 (according to Kabat numbering; the same applies to the following) is histidine; the amino acid residue at position 34 is alanine; the amino acid residue at position 39 is glutamic acid; the amino acid residue at position 97 is aspartic acid; the amino acid residue at position 98 is serine; the amino acid residue at position 100 is aspartic acid or glutamic acid; the amino acid residue at position 100a is aspartic acid or deleted; the amino acid residue at position 100b is alanine or histidine; and the amino acid residue at position 100e is histidine or isoleucine, in the above heavy chain variable domain of the first antigen-binding site.

In an embodiment, in a light chain variable domain of a first antigen-binding site of the present invention, the amino acid residue at position 26 (according to Kabat numbering; the same applies to the following) is threonine; the amino acid residue at position 27 is arginine; the amino acid residue at position 30 is arginine; the amino acid residue at position 31 is arginine; the amino acid residue at position 32 is aspartic acid or glutamic acid; the amino acid residue at position 38 is lysine; the amino acid residue at position 45 is glutamic acid; the amino acid residue at position 53 is arginine; the amino acid residue at position 55 is glutamic acid; the amino acid residue at position 60 is aspartic acid; the amino acid residue at position 70 is aspartic acid; the amino acid residue at position 76 is asparagine; the amino acid residue at position 79 is glutamic acid; the amino acid residue at position 80 is proline or alanine; the amino acid residue at position 83 is methionine or alanine; the amino acid residue at position 85 is threonine; the amino acid residue at position 92 is arginine; the amino acid residue at position 93 is serine or aspartic acid; the amino acid residue at position 95 is proline; or the amino acid residue at position 96 is glycine, in the above light chain variable domain of the first antigen-binding site.

In an embodiment, in a heavy chain variable domain of a second antigen-binding site of the present invention, the amino acid residue at position 28 (according to Kabat numbering; the same applies to the following) is glutamic acid; the amino acid residue at position 31 is asparagine, glutamine, or histidine; the amino acid residue at position 39 is lysine; the amino acid residue at position 51 is serine; the amino acid residue at position 56 is threonine or arginine; the amino acid residue at position 57 is valine; the amino acid residue at position 59 is serine; the amino acid residue at position 61 is arginine; the amino acid residue at position 62 is lysine; the amino acid residue at position 65 is asparagine or glutamine; the amino acid residue at position 67 is leucine; the amino acid residue at position 73 is isoleucine; the amino acid residue at position 82b is glutamic acid; or the amino acid residue at position 102 is valine, in the above heavy chain variable domain of the second antigen-binding site.

In an embodiment, in a light chain variable domain of a second antigen-binding site of the present invention, the amino acid residue at position 3 (according to Kabat numbering; the same applies to the following) is glutamic acid; the amino acid residue at position 8 is proline; the amino acid residue at position 15 is leucine; the amino acid residue at position 24 is threonine; the amino acid residue at position 26 is glutamic acid; the amino acid residue at position 27 is glutamine; the amino acid residue at position 29 is serine; the amino acid residue at position 30 is glutamine, serine, or glutamic acid; the amino acid residue at position 31 is arginine; the amino acid residue at position 32 is glutamine or glutamic acid; the amino acid residue at position 38 is glutamic acid; the amino acid residue at position 48 is isoleucine; the amino acid residue at position 49 is tyrosine; the amino acid residue at position 50 is glutamine; the amino acid residue at position 79 is glutamic acid; the amino acid residue at position 92 is alanine; the amino acid residue at position 94 is aspartic acid; the amino acid residue at position 95 is aspartic acid or alanine; the amino acid residue at position 95a is tyrosine or deleted; or the amino acid residue at position 96 is threonine, in the above light chain variable domain of the second antigen-binding site.

In an embodiment, in a multispecific antigen-binding molecule of the present invention:

the amino acid residue at position 31 (according to Kabat numbering; the same applies to the following) is histidine; the amino acid residue at position 34 is alanine; the amino acid residue at position 39 is glutamic acid; the amino acid residue at position 97 is aspartic acid; the amino acid residue at position 98 is serine; the amino acid residue at position 100 is aspartic acid or glutamic acid; the amino acid residue at position 100a is aspartic acid or deleted; the amino acid residue at position 100b is alanine or histidine; and the amino acid residue at position 100e is histidine or isoleucine, in the above heavy chain variable domain of the first antigen-binding site;

the amino acid residue at position 26 (according to Kabat numbering; the same applies to the following) is threonine; the amino acid residue at position 27 is arginine; the amino acid residue at position 30 is arginine; the amino acid residue at position 31 is arginine; the amino acid residue at position 32 is aspartic acid or glutamic acid; the amino acid residue at position 38 is lysine; the amino acid residue at position 45 is glutamic acid; the amino acid residue at position 53 is arginine; the amino acid residue at position 55 is glutamic acid; the amino acid residue at position 60 is aspartic acid; the amino acid residue at position 70 is aspartic acid; the amino acid residue at position 76 is asparagine; the amino acid residue at position 79 is glutamic acid; the amino acid residue at position 80 is proline or alanine; the amino acid residue at position 83 is methionine or alanine; the amino acid residue at position 85 is threonine; the amino acid residue at position 92 is arginine; the amino acid residue at position 93 is serine or aspartic acid; the amino acid residue at position 95 is proline; or the amino acid residue at position 96 is glycine, in the above light chain variable domain of the first antigen-binding site;

the amino acid residue at position 28 (according to Kabat numbering; the same applies to the following) is glutamic acid; the amino acid residue at position 31 is asparagine, glutamine, or histidine; the amino acid residue at position 39 is lysine; the amino acid residue at position 51 is serine; the amino acid residue at position 56 is threonine or arginine; the amino acid residue at position 57 is valine; the amino acid residue at position 59 is serine; the amino acid residue at position 61 is arginine; the amino acid residue at position 62 is lysine; the amino acid residue at position 65 is asparagine or glutamine; the amino acid residue at position 67 is leucine; the amino acid residue at position 73 is isoleucine; the amino acid residue at position 82b is glutamic acid; or the amino acid residue at position 102 is valine, in the above heavy chain variable domain of the second antigen-binding site;

the amino acid residue at position 3 (according to Kabat numbering; the same applies to the following) is glutamic acid; the amino acid residue at position 8 is proline; the amino acid residue at position 15 is leucine; the amino acid residue at position 24 is threonine; the amino acid residue at position 26 is glutamic acid; the amino acid residue at position 27 is glutamine; the amino acid residue at position 29 is serine; the amino acid residue at position 30 is glutamine, serine, or glutamic acid; the amino acid residue at position 31 is arginine; the amino acid residue at position 32 is glutamine or glutamic acid; the amino acid residue at position 38 is glutamic acid; the amino acid residue at position 48 is isoleucine; the amino acid residue at position 49 is tyrosine; the amino acid residue at position 50 is glutamine; the amino acid residue at position 79 is glutamic acid; the amino acid residue at position 92 is alanine; the amino acid residue at position 94 is aspartic acid; the amino acid residue at position 95 is aspartic acid or alanine; the amino acid residue at position 95a is tyrosine or deleted; or the amino acid residue at position 96 is threonine, in the above light chain variable domain of the second antigen-binding site.

In an embodiment, the heavy chain variable domain of the first antigen-binding site of the multispecific antigen-binding molecule of the present invention is a heavy chain variable domain comprising an amino acid sequence of SEQ ID NO: 56, SEQ ID NO: 57, SEQ ID NO: 58, SEQ ID NO: 59, or SEQ ID NO: 60.

In an embodiment, the light chain variable domain of the first antigen-binding site of the multispecific antigen-binding molecule of the present invention is a light chain variable domain comprising an amino acid sequence of SEQ ID NO: 61, SEQ ID NO: 62, SEQ ID NO: 63, SEQ ID NO: 64, or SEQ ID NO: 65, SEQ ID NO: 66, SEQ ID NO: 67, SEQ ID NO: 68, SEQ ID NO: 69, SEQ ID NO: 70, SEQ ID NO: 71, or SEQ ID NO: 72.

In an embodiment, the heavy chain variable domain of the second antigen-binding site of the multispecific antigen-binding molecule of the present invention is a heavy chain variable domain comprising an amino acid sequence of SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, or SEQ ID NO: 83.

In an embodiment, the light chain variable domain of the second antigen-binding site of the multispecific antigen-binding molecule of the present invention is a light chain variable domain comprising an amino acid sequence of SEQ ID NO: 84, SEQ ID NO: 85, SEQ ID NO: 86, SEQ ID NO: 87, or SEQ ID NO: 88, SEQ ID NO: 89, SEQ ID NO: 90, SEQ ID NO: 91, SEQ ID NO: 92, SEQ ID NO: 93, or SEQ ID NO: 94.

In an embodiment, the multispecific antigen-binding molecule of the present invention is a multispecific antigen-binding molecule, wherein the first antigen-binding site comprises:
a heavy chain variable domain (QH) of SEQ ID NO: 56, SEQ ID NO: 57, SEQ ID NO: 58, SEQ ID NO: 59, or SEQ ID NO: 60; and
a light chain variable domain (QL) of SEQ ID NO: 61, SEQ ID NO: 62, SEQ ID NO: 63, SEQ ID NO: 64, or SEQ ID NO: 65, SEQ ID NO: 66, SEQ ID NO: 67, SEQ ID NO: 68, SEQ ID NO: 69, SEQ ID NO: 70, SEQ ID NO: 71, or SEQ ID NO: 72, and wherein the second antigen-binding site comprises:
a heavy chain variable domain (JH) of SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, or SEQ ID NO: 83; and
a light chain variable domain (JL) of SEQ ID NO: 84, SEQ ID NO: 85, SEQ ID NO: 86, SEQ ID NO: 87, or SEQ ID NO: 88, SEQ ID NO: 89, SEQ ID NO: 90, SEQ ID NO: 91, SEQ ID NO: 92, SEQ ID NO: 93, or SEQ ID NO: 94.

In an embodiment, the present invention provides a multispecific antigen-binding molecule comprising a first antibody heavy chain variable domain and antibody light chain variable domain that bind to FIX and/or FIXa, and a second antibody heavy chain variable domain and antibody light chain variable domain that bind to FX, which is any one of (a) to (v) below:

(a) a multispecific antigen-binding molecule (QH01/QL21//JH01/JL01) comprising a first antibody heavy chain variable domain comprising the amino acid sequence of SEQ ID NO: 56, a first antibody light chain variable domain comprising the amino acid sequence of SEQ ID NO: 61, a second antibody heavy chain variable domain comprising the amino acid sequence of SEQ ID NO: 73, and a second antibody light chain variable domain comprising the amino acid sequence of SEQ ID NO: 84;

(b) a multispecific antigen-binding molecule (QH02/QL22//JH01/JL01) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 73, and a second antibody light chain variable domain comprising the amino acid sequence of SEQ ID NO: 84;

(c) a multispecific antigen-binding molecule (QH03/QL23//JH02/JL02) comprising a first antibody heavy chain variable domain comprising the amino acid sequence of SEQ ID NO: 58, a first antibody light chain variable domain comprising the amino acid sequence of SEQ ID NO: 63, a second antibody heavy chain variable domain comprising the amino acid sequence of SEQ ID NO: 74, and a second antibody light chain variable domain comprising the amino acid sequence of SEQ ID NO: 85;

(d) a multispecific antigen-binding molecule (QH03/QL24//JH02/JL02) comprising a first antibody heavy chain variable domain comprising the amino acid sequence of SEQ ID NO: 58, a first antibody light chain variable domain comprising the amino acid sequence of SEQ ID NO: 64, a second antibody heavy chain variable domain comprising the amino acid sequence of SEQ ID NO: 74, and a second antibody light chain variable domain comprising the amino acid sequence of SEQ ID NO: 85;

(e) a multispecific antigen-binding molecule (QH02/QL228JH03/JL03) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 75, and a second antibody light chain variable domain comprising the amino acid sequence of SEQ ID NO: 86;

(f) a multispecific antigen-binding molecule (QH02/QL228JH04/JL04) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 76, and a second antibody light chain variable domain comprising the amino acid sequence of SEQ ID NO: 87;

(g) a multispecific antigen-binding molecule (QH02/QL22//JH02/JL02) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 74, and a second antibody light chain variable domain comprising the amino acid sequence of SEQ ID NO: 85;

(h) a multispecific antigen-binding molecule (QH04/QL25//JH02/JL02) comprising a first antibody heavy chain variable domain comprising the amino acid sequence of SEQ ID NO: 59, a first antibody light chain variable domain comprising the amino acid sequence of SEQ ID NO: 65, a second antibody heavy chain variable domain comprising the amino acid sequence of SEQ ID NO: 74, and a second antibody light chain variable domain comprising the amino acid sequence of SEQ ID NO: 85;

(i) a multispecific antigen-binding molecule (QH04/QL268JH02/JL02) comprising a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 74, and a second antibody light chain variable domain comprising the amino acid sequence of SEQ ID NO: 85;

(j) a multispecific antigen-binding molecule (QH04/QL26//JH05/JL05) comprising a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 77, and a second antibody light chain variable domain comprising the amino acid sequence of SEQ ID NO: 88;

(k) a multispecific antigen-binding molecule (QH04/QL28//JH05/JL05) comprising a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 77, and a second antibody light chain variable domain comprising the amino acid sequence of SEQ ID NO: 88;

(l) a multispecific antigen-binding molecule (QH04/QL28//JH06/JL06) comprising a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 78, and a second antibody light chain variable domain comprising the amino acid sequence of SEQ ID NO: 89;

(m) a multispecific antigen-binding molecule (QH04/QL29//JH05/JL05) comprising a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 77, and a second antibody light chain variable domain comprising the amino acid sequence of SEQ ID NO: 88;

(n) a multispecific antigen-binding molecule (QH04/QL29//JH06/JL06) comprising a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 78, and a second antibody light chain variable domain comprising the amino acid sequence of SEQ ID NO: 89;

(o) a multispecific antigen-binding molecule (QH06/QL30//JH07/JL07) comprising a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 79, and a second antibody light chain variable domain comprising the amino acid sequence of SEQ ID NO: 90;

(p) a multispecific antigen-binding molecule (QH04/QL31//JH08/JL08) comprising a first antibody heavy chain variable domain comprising the amino acid sequence of SEQ ID NO: 59, a first antibody light chain variable domain comprising the amino acid sequence of SEQ ID NO: 70, a second antibody heavy chain variable domain comprising the amino acid sequence of SEQ ID NO: 80, and a second antibody light chain variable domain comprising the amino acid sequence of SEQ ID NO: 91;

(q) a multispecific antigen-binding molecule (QH06/QL32//JH07/JL07) comprising a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 79, and a second antibody light chain variable domain comprising the amino acid sequence of SEQ ID NO: 90;

(r) a multispecific antigen-binding molecule (QH06/QL32//JH09/JL09) comprising a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 81, and a second antibody light chain variable domain comprising the amino acid sequence of SEQ ID NO: 92;

(s) a multispecific antigen-binding molecule (QH06/QL30//JH10/JL10) comprising a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 82, and a second antibody light chain variable domain comprising the amino acid sequence of SEQ ID NO: 93;

(t) a multispecific antigen-binding molecule (QH07/QL33//JH11/JL11) comprising a first antibody heavy chain variable domain comprising the amino acid sequence of SEQ ID NO: 105, a first antibody light chain variable domain comprising the amino acid sequence of SEQ ID NO: 72, a second antibody heavy chain variable domain comprising the amino acid sequence of SEQ ID NO: 83, and a second antibody light chain variable domain comprising the amino acid sequence of SEQ ID NO: 94;

(u) a multispecific antigen-binding molecule that binds to epitopes identical with both an epitope in FIX and/or FIXa and an epitope in FX which are recognized by any one of the antibodies of (a) to (t).

(v) a multispecific antigen-binding molecule that competes for binding to both an epitope in FIX and/or FIXa and an epitope in FX which are recognized by any one of the antibodies of (a) to (t).

In an embodiment, the heavy chain constant region of the multispecific antigen-binding molecule of the present invention is a heavy chain constant region comprising the amino acid sequence of SEQ ID NO: 118 or SEQ ID NO: 119.

In an embodiment, the light chain constant region of the multispecific antigen-binding molecule of the present invention is a light chain constant region comprising the amino acid sequence of SEQ ID NO: 100 or SEQ ID NO: 102.

In an embodiment, the multispecific antigen-binding molecule of the present invention is a multispecific antigen-binding molecule, wherein the first antigen-binding site comprises the constant region of (1) or (2) below, and the second antigen-binding site comprises the constant region of (1) or (2) below which is not the constant region comprised in the first antigen-binding site:

(1) SEQ ID NO: 119 for the heavy chain constant region and SEQ ID NO: 100 for the light chain constant region;
(2) SEQ ID NO: 118 for the heavy chain constant region and SEQ ID NO: 102 for the light chain constant region.

In an embodiment, the multispecific antigen-binding molecule of the present invention is a multispecific antibody. In a further embodiment, the multispecific antibody of the present invention is a bispecific antibody.

In an embodiment, the present invention provides a bispecific antibody comprising a first antibody heavy chain variable domain and antibody light chain variable domain that bind to FIX and/or FIXa, and a second antibody heavy chain variable domain and antibody light chain variable domain that bind to FX, which is any one of (a) to (v) below:

(a) a bispecific antibody (QH01/QL21//JH01/JL01) comprising a first antibody heavy chain variable domain comprising the amino acid sequence of SEQ ID NO: 56, a first antibody light chain variable domain comprising the amino acid sequence of SEQ ID NO: 61, a second antibody heavy chain variable domain comprising the amino acid sequence of SEQ ID NO: 73, and a second antibody light chain variable domain comprising the amino acid sequence of SEQ ID NO: 84;

(b) a bispecific antibody (QH02/QL22//JH01/JL01) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 73, and a second antibody light chain variable domain comprising the amino acid sequence of SEQ ID NO: 84;

(c) a bispecific antibody (QH03/QL23//JH02/JL02) comprising a first antibody heavy chain variable domain comprising the amino acid sequence of SEQ ID NO: 58, a first antibody light chain variable domain comprising the amino acid sequence of SEQ ID NO: 63, a second antibody heavy chain variable domain comprising the amino acid sequence of SEQ ID NO: 74, and a second antibody light chain variable domain comprising the amino acid sequence of SEQ ID NO: 85;

(d) a bispecific antibody (QH03/QL24//JH02/JL02) comprising a first antibody heavy chain variable domain comprising the amino acid sequence of SEQ ID NO: 58, a first antibody light chain variable domain comprising the amino acid sequence of SEQ ID NO: 64, a second antibody heavy chain variable domain comprising the amino acid sequence of SEQ ID NO: 74, and a second antibody light chain variable domain comprising the amino acid sequence of SEQ ID NO: 85;

(e) a bispecific antibody (QH02/QL22//JH03/JL03) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 75, and a second antibody light chain variable domain comprising the amino acid sequence of SEQ ID NO: 86;

(f) a bispecific antibody (QH02/QL22//JH04/JL04) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 76, and a second antibody light chain variable domain comprising the amino acid sequence of SEQ ID NO: 87;

(g) a bispecific antibody (QH02/QL22//JH02/JL02) comprising a first antibody heavy chain variable domain comprising the amino acid sequence of SEQ ID NO: 57, a first antibody light chain variable domain comprising the amino acid sequence of SEQ ID NO: 62, a second antibody heavy chain variable domain comprising the amino acid sequence of SEQ ID NO: 74, and a second antibody light chain variable domain comprising the amino acid sequence of SEQ ID NO: 85;

(h) a bispecific antibody (QH04/QL25//JH02/JL02) comprising a first antibody heavy chain variable domain comprising the amino acid sequence of SEQ ID NO: 59, a first antibody light chain variable domain comprising the amino acid sequence of SEQ ID NO: 65, a second antibody heavy chain variable domain comprising the amino acid sequence of SEQ ID NO: 74, and a second antibody light chain variable domain comprising the amino acid sequence of SEQ ID NO: 85;

(i) a bispecific antibody (QH04/QL26//JH02/JL02) comprising a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 74, and a second antibody light chain variable domain comprising the amino acid sequence of SEQ ID NO: 85;

(j) a bispecific antibody (QH04/QL26//JH05/JL05) comprising a first antibody heavy chain variable domain comprising the amino acid sequence of SEQ ID NO: 59, a first antibody light chain variable domain comprising the amino acid sequence of SEQ ID NO: 66, a second antibody heavy chain variable domain comprising the amino acid sequence of SEQ ID NO: 77, and a second antibody light chain variable domain comprising the amino acid sequence of SEQ ID NO: 88;

(k) a bispecific antibody (QH04/QL28//JH05/JL05) comprising a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 77, and a second antibody light chain variable domain comprising the amino acid sequence of SEQ ID NO: 88;

(l) a bispecific antibody (QH04/QL28//JH06/JL06) comprising a first antibody heavy chain variable domain comprising the amino acid sequence of SEQ ID NO: 59, a first antibody light chain variable domain comprising the amino acid sequence of SEQ ID NO: 67, a second antibody heavy chain variable domain comprising the amino acid sequence of SEQ ID NO: 78, and a second antibody light chain variable domain comprising the amino acid sequence of SEQ ID NO: 89;

(m) a bispecific antibody (QH04/QL29//JH05/JL05) comprising a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 77, and a second antibody light chain variable domain comprising the amino acid sequence of SEQ ID NO: 88;

(n) a bispecific antibody (QH04/QL29//JH06/JL06) comprising a first antibody heavy chain variable domain comprising the amino acid sequence of SEQ ID NO: 59, a first antibody light chain variable domain comprising the amino acid sequence of SEQ ID NO: 68, a second antibody heavy chain variable domain comprising the amino acid sequence of SEQ ID NO: 78, and a second antibody light chain variable domain comprising the amino acid sequence of SEQ ID NO: 89;

(o) a bispecific antibody (QH06/QL30//JH07/JL07) comprising a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 79, and a second antibody light chain variable domain comprising the amino acid sequence of SEQ ID NO: 90;

(p) a bispecific antibody (QH04/QL31//JH08/JL08) comprising a first antibody heavy chain variable domain comprising the amino acid sequence of SEQ ID NO: 59, a first antibody light chain variable domain comprising the amino acid sequence of SEQ ID NO: 70, a second antibody heavy chain variable domain comprising the amino acid sequence of SEQ ID NO: 80, and a second antibody light chain variable domain comprising the amino acid sequence of SEQ ID NO: 91;

(q) a bispecific antibody (QH06/QL32//JH07/JL07) comprising a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 79, and a second antibody light chain variable domain comprising the amino acid sequence of SEQ ID NO: 90;

(r) a bispecific antibody (QH06/QL32//JH09/JL09) comprising a first antibody heavy chain variable domain comprising the amino acid sequence of SEQ ID NO: 60, a first antibody light chain variable domain comprising the amino acid sequence of SEQ ID NO: 71, a second antibody heavy chain variable domain comprising the amino acid sequence of SEQ ID NO: 81, and a second antibody light chain variable domain comprising the amino acid sequence of SEQ ID NO: 92;

(s) a bispecific antibody (QH06/QL30//JH10/JL10) comprising a first antibody heavy chain variable domain comprising the amino acid sequence of SEQ ID NO: 60, a first antibody light chain variable domain comprising the amino acid sequence of SEQ ID NO: 69, a second antibody heavy chain variable domain comprising the amino acid sequence of SEQ ID NO: 82, and a second antibody light chain variable domain comprising the amino acid sequence of SEQ ID NO: 93;

(t) a bispecific antibody (QH07/QL33//JH11/JL11) comprising a first antibody heavy chain variable domain comprising the amino acid sequence of SEQ ID NO: 105, a first antibody light chain variable domain comprising the amino acid sequence of SEQ ID NO: 72, a second antibody heavy chain variable domain comprising the amino acid sequence of SEQ ID NO: 83, and a second antibody light chain variable domain comprising the amino acid sequence of SEQ ID NO: 94;

(u) a bispecific antibody that binds to epitopes identical with both an epitope in blood coagulation factor IX and/or activated blood coagulation factor IX and an epitope in blood coagulation factor X which are recognized by any one of the antibodies of (a) to (t).

(v) a multispecific antigen-binding molecule that competes for binding to both an epitope in blood coagulation factor IX and/or activated blood coagulation factor IX and an epitope in blood coagulation factor X which are recognized by any one of the antibodies of (a) to (t).

In an embodiment, the present invention provides a bispecific antibody comprising a first antibody heavy chain and antibody light chain that bind to FIX and/or FIXa, and a second antibody heavy chain and antibody light chain that bind to FX, which is any one of (a) to (v) below:

(a) a bispecific antibody (QH01/QL21//JH01/JL01) comprising a first antibody heavy chain comprising the amino acid sequence of SEQ ID NO: 120, a first antibody light chain comprising the amino acid sequence of SEQ ID NO: 126, a second antibody heavy chain comprising the amino acid sequence of SEQ ID NO: 138, and a second antibody light chain comprising the amino acid sequence of SEQ ID NO: 149;

(b) a bispecific antibody (QH02/QL22//JH01/JL01) comprising a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 138, and a second antibody light chain comprising the amino acid sequence of SEQ ID NO: 149;

(c) a bispecific antibody (QH03/QL23//JH02/JL02) comprising a first antibody heavy chain comprising the amino acid sequence of SEQ ID NO: 122, a first antibody light chain comprising the amino acid sequence of SEQ ID NO: 128, a second antibody heavy chain comprising the amino acid sequence of SEQ ID NO: 139, and a second antibody light chain comprising the amino acid sequence of SEQ ID NO: 150;

(d) a bispecific antibody (QH03/QL24//JH02/JL02) comprising a first antibody heavy chain comprising the amino acid sequence of SEQ ID NO: 122, a first antibody light chain comprising the amino acid sequence of SEQ ID NO: 129, a second antibody heavy chain comprising the amino acid sequence of SEQ ID NO: 139, and a second antibody light chain comprising the amino acid sequence of SEQ ID NO: 150;

(e) a bispecific antibody (QH02/QL22//JH03/JL03) comprising a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 140, and a second antibody light chain comprising the amino acid sequence of SEQ ID NO: 151;

(f) a bispecific antibody (QH02/QL22//JH04/JL04) comprising a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 141, and a second antibody light chain comprising the amino acid sequence of SEQ ID NO: 152;

(g) a bispecific antibody (QH02/QL22//JH02/JL02) comprising a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 139, and a second antibody light chain comprising the amino acid sequence of SEQ ID NO: 150;

(h) a bispecific antibody (QH04/QL25//JH02/JL02) comprising a first antibody heavy chain comprising the amino acid sequence of SEQ ID NO: 123, a first antibody light chain comprising the amino acid sequence of SEQ ID NO: 130, a second antibody heavy chain comprising the amino acid sequence of SEQ ID NO: 139, and a second antibody light chain comprising the amino acid sequence of SEQ ID NO: 150;

(i) a bispecific antibody (QH04/QL26//JH02/JL02) comprising a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 139, and a second antibody light chain comprising the amino acid sequence of SEQ ID NO: 150;

(j) a bispecific antibody (QH04/QL26//JH05/JL05) comprising a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 142, and a second antibody light chain comprising the amino acid sequence of SEQ ID NO: 153;

(k) a bispecific antibody (QH04/QL28//JH05/JL05) comprising a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 142, and a second antibody light chain comprising the amino acid sequence of SEQ ID NO: 153;

(l) a bispecific antibody (QH04/QL28//JH06/JL06) comprising a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 143, and a second antibody light chain comprising the amino acid sequence of SEQ ID NO: 154;

(m) a bispecific antibody (QH04/QL29//JH05/JL05) comprising a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 142, and a second antibody light chain comprising the amino acid sequence of SEQ ID NO: 153;

(n) a bispecific antibody (QH04/QL29//JH06/JL06) comprising a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 143, and a second antibody light chain comprising the amino acid sequence of SEQ ID NO: 154;

(o) a bispecific antibody (QH06/QL30//JH07/JL07) comprising a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 144, and a second antibody light chain comprising the amino acid sequence of SEQ ID NO: 155;

(p) a bispecific antibody (QH04/QL31//JH08/JL08) comprising a first antibody heavy chain comprising the amino acid sequence of SEQ ID NO: 123, a first antibody light chain comprising the amino acid sequence of SEQ ID NO: 135, a second antibody heavy chain comprising the amino acid sequence of SEQ ID NO: 145, and a second antibody light chain comprising the amino acid sequence of SEQ ID NO: 156;

(q) a bispecific antibody (QH06/QL32//JH07/JL07) comprising a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 144, and a second antibody light chain comprising the amino acid sequence of SEQ ID NO: 155;

(r) a bispecific antibody (QH06/QL32//JH09/JL09) comprising a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 146, and a second antibody light chain comprising the amino acid sequence of SEQ ID NO: 157;

(s) a bispecific antibody (QH06/QL30//JH10/JL10) comprising a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 147, and a second antibody light chain comprising the amino acid sequence of SEQ ID NO: 158;

(t) a bispecific antibody (QH07/QL33//JH11/JL11) comprising a first antibody heavy chain comprising the amino acid sequence of SEQ ID NO: 125, a first antibody light chain comprising the amino acid sequence of SEQ ID NO: 137, a second antibody heavy chain comprising the amino acid sequence of SEQ ID NO: 148, and a second antibody light chain comprising the amino acid sequence of SEQ ID NO: 159;

(u) a bispecific antibody that binds to epitopes identical with both an epitope in FIX and/or FIXa and an epitope in FX which are recognized by any one of the antibodies of (a) to (t).

(v) a multispecific antigen-binding molecule that competes for binding to both an epitope in FIX and/or FIXa and an epitope in FX which are recognized by any one of the antibodies of (a) to (t).

In an embodiment, the present invention further provides a multispecific antigen-binding molecule having a function of substituting for the function of blood coagulation factor VIII, which comprises a first antigen-binding site that binds to blood coagulation factor IX and/or activated blood coagulation factor IX, and a second antigen-binding site that binds to blood coagulation factor X, wherein the first antigen-binding site comprises a heavy chain variable domain and a light chain variable domain, wherein the heavy chain variable domain (Q499) comprises HVR-H1 comprising the amino acid sequence of SEQ ID NO: 1, HVR-H2 comprising the amino acid sequence of SEQ ID NO: 2, and HVR-H3 comprising the amino acid sequence of SEQ ID NO: 3, wherein the light chain variable domain (QNK131) comprises HVR-L1 comprising the amino acid sequence of SEQ ID NO: 162, HVR-L2 comprising the amino acid sequence of SEQ ID NO: 163, and HVR-L3 comprising the amino acid sequence of SEQ ID NO: 164, and wherein the second antigen-binding site comprises a heavy chain variable domain and a light chain variable domain, wherein the heavy chain variable domain (J327) comprises HVR-H1 comprising the amino acid sequence of SEQ ID NO: 4, HVR-H2 comprising the amino acid sequence of SEQ ID NO: 5, and HVR-H3 comprising the amino acid sequence of SEQ ID NO: 6, wherein the light chain variable domain (JNL095) comprises HVR-L1 comprising the amino acid sequence of SEQ ID NO: 165, HVR-L2 comprising the amino acid sequence of SEQ ID NO: 166, and HVR-L3 comprising the amino acid sequence of SEQ ID NO: 167.

In certain embodiments, the antibodies of (a) to (v) above are antibodies that have a function of substituting for the function of FVIII.

In other embodiments, the antibodies of (a) to (v) above are antibodies in which the reactivity to the anti-ACE910 (Emicizumab) idiotype antibody is decreased compared to ACE910 (Emicizumab). Herein, the phrase "the reactivity to the anti-ACE910 (Emicizumab) idiotype antibody is decreased compared to ACE910 (Emicizumab)" means that, when the binding strength (%) between the anti-idiotype antibody and labelled ACE910 is measured using the methods described herein, and if the test substance is added at a concentration of 100 µg/mL, the reactivity is preferably decreased by 10% or more, more preferably decreased by 20% or more, still more preferably decreased by 30% or more.

Anti-ACE910 (Emicizumab) idiotype antibodies can be obtained by, for example, the following method. F(ab')$_2$ of Q499/L404 that recognizes FIX(a) and F(ab')$_2$ of J327/L404 that recognizes FX of ACE910 (Emicizumab) are administered into rabbits, and anti-Q499/L404 F(ab')$_2$ rabbit serum and anti-J327/L404 F(ab')$_2$ rabbit serum are obtained. Ammonium sulfate fractions of these serums are applied to a column to remove human IgG-reactive antibodies. Next, affinity purification is conducted using a Q499/L404 (J327/L404)-bound column, and J327/L404 (Q499/L404)-reactive antibodies are removed using a J327/L404 (Q499/L404)-bound column, and thus polyclonal anti-idiotype antibodies that specifically bind to Q499/L404 (J327/L404) are obtained.

The binding strength (%) of the anti-idiotype antibody towards labelled ACE910 (Emicizumab) can be measured by, for example, electrochemical luminescence immunoassay, and this can assess binding inhibition by a test substance. When the anti-idiotype antibodies obtained as mentioned above are used, a test substance (bispecific antibody) is added at a concentration of 0, 1, 3, 10, 30, or 100 µg/mL to a mixture of the anti-Q499/L404 idiotype antibody, the anti-J327/L404 idiotype antibody, biotin-labelled ACE910 (Emicizumab), and SULFO-TAG-labelled ACE910 (Emicizumab), and the resulting mixed solution is incubated overnight under refrigeration. Then, the mixed solution is added to a 96-well plate, and the place is washed, and then the binding strength is measured by an electrochemical luminescence method.

In other embodiments, compared to ACE910 (Emicizumab), the antibodies of (a) to (v) above have an enhanced FVIII cofactor function-substituting activity and a higher activity at a low antibody concentration.

In other embodiments, the antibodies of (a) to (v) above have substantially no FIX activation-inhibiting activity, and have an increased FVIII cofactor function-substituting activity compared to ACE910 (Emicizumab). Herein, the phrase "having substantially no FIX activation-inhibiting activity" means that, when the OD value is measured by the method shown in this specification, the decrease in the OD value compared to the control OD value is 0.025 or less, preferably 0.02 or less, more preferably 0.01 or less.

Amino acids contained in the amino acid sequences described herein may undergo post-translational modification (for example, modification of N-terminal glutamine into pyroglutamic acid by pyroglutamylation is well-known to those skilled in the art). Naturally, such sequences with post-translationally modified amino acids are also included in the amino acid sequences described herein.

In a further aspect, the invention provides a multispecific antigen-binding molecule or bispecific antibody that binds to the same epitope as the multispecific antigen-binding molecule or bispecific antibody that binds to FIX and/or FIXa, and FX provided herein. For example, in certain embodiments, a multispecific antigen-binding molecule or bispecific antibody is provided that binds to the same epitope as the multispecific antigen-binding molecule or bispecific antibody recited in (a) to (t) above.

In a further aspect of the invention, a bispecific antibody that binds to FIX and/or FIXa, and FX according to any of the above embodiments is a monoclonal antibody, including a chimeric, humanized or human antibody. In one embodiment, a bispecific antibody that binds to FIX and/or FIXa, and FX is an antibody fragment, e.g., (scFv)$_2$, diabody, or F(ab')$_2$ fragment. In another embodiment, the antibody is a full length antibody, e.g., an intact IgG4 antibody or other antibody class or isotype as defined herein.

In a further aspect, a bispecific antibody that binds to FIX and/or FIXa, and FX according to any of the above embodiments may incorporate any of the features, singly or in combination, as described in Sections 1-7 below:

1. Antibody Affinity

In certain embodiments, an antibody provided herein has a dissociation constant (Kd) of 100 micro M or less, 10 micro M or less, 1 micro M or less, 100 nM or less, 10 nM or less, 1 nM or less, 0.1 nM or less, 0.01 nM or less, or 0.001 nM or less (e.g. $10^{-5}$ M or less, e.g. from $10^{-5}$ M to $10^{-10}$ M, e.g., from $10^{-6}$ M to $10^{-10}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro l/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, N.J.) is performed at 25 degrees C. with immobilized antigen CMS chips at ~10 response units (RU). In one embodiment, carboxymethylated dextran biosensor chips (CM5, BIA-CORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro 1/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro 1/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINC6[114] spectrophotometer (ThermoSpectronic) with a stirred cuvette.

2. Antibody Fragments

In certain embodiments, an antibody provided herein is an antibody fragment. Antibody fragments include, but are not limited to, (scFv)₂, diabody, or F(ab')₂, and other fragments described below. For a review of certain antibody fragments, see Hudson et al. *Nat. Med.* 9:129-134 (2003). For a review of scFv fragments, see, e.g., Pluckthtin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of F(ab')₂ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., *Proc. Natl. Acad. Sci. USA* 90: 6444-6448 (1993).

Antibody fragments can be made by various techniques, including but not limited to proteolytic digestion of an intact antibody as well as production by recombinant host cells (e.g. E. colt or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl. Acad. Sci. USA* 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE technology; U.S. Pat. No. 5,770,429 describing HuMAB® technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., Monoclonal Antibody Production Techniques and Applications, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific antibody

In the context of the present invention, the term "multispecific antibody" refers to an antibody that may bind specifically to different types of epitopes. More specifically, multispecific antibodies are antibodies having specificity to at least two different types of epitopes, and, in addition to antibodies recognizing different antigens, antibodies recognizing different epitopes on the same antigen are also included. (For example, when the antigens are heterologous receptors, multispecific antibodies bind to different domains constituting the heterologous receptors; alternatively, when the antigens are monomers, multispecific antibodies bind to multiple sites on the monomer antigens.) Ordinarily, such molecules bind to two antigens (bispecific antibodies), but they may even have specificity toward more antigens (for example, three types). In specific embodiments, one of the antigens is FIX and/or FIXa, and the other is FX. A bispecific antibody can be prepared as a whole antibody or an antibody fragment.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (scFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96 (registered trademark) non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Certain antibody variants with increased or decreased binding to FcRs are described. (See, e.g., U.S. Pat. No. 6,737,056; WO 2004/056312, and Shields et al., *J. Biol. Chem.* 9(2): 6591-6604 (2001).)

Antibodies with increased half lives and increased binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions:

Antibodies may be produced using recombinant methods and compositions, e.g., as described in U.S. Pat. No. 4,816,567. In one embodiment, isolated nucleic acid encoding a multispecific antibody that binds to FIX and/or FIXa, and FX described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp2/0 cell). In one embodiment, a method of making a multispecific antibody that binds to FIX and/or FIXa, and FX is provided, wherein the method comprises culturing a host cell comprising a nucleic acid encoding the antibody, as provided above, under conditions suitable for expression of the multispecific antibody that binds to FIX and/or FIXa, and FX, and optionally recovering the antibody from the host cell (or host cell culture medium).

For recombinant production of a multispecific antibody that binds to FIX and/or FIXa, and FX, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES$^{Tm}$ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen. Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Multispecific antigen-binding molecules that bind to FIX and/or FIXa, and FX provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with any of the multispecific antibodies that bind to FIX and/or FIXa, and FX described herein, for binding to FIX and/or FIXa, and FX. In certain embodiments, such a competing antibody binds to the same epitope (e.g., a linear or a conformational epitope) that is bound by the multispecific antibody that binds to FIX and/or FIXa, and FX described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized FIX, FIXa, or FX is incubated in a solution comprising a first labeled antibody that binds to FIX, FIXa, or FX (e.g., any of the antibodies described herein) and a second unlabeled antibody that is being tested for its ability to compete with the first antibody for binding to FIX, FIXa, or FX. The second antibody may be present in a hybridoma supernatant. As a control, immobilized FIX, FIXa, or FX is incubated in a solution comprising the first labeled antibody but not the second unlabeled antibody. After incubation under conditions permissive for binding of the first antibody to FIX, FIXa, or FX, excess unbound antibody is removed, and the amount of label associated with immobilized FIX, FIXa, or FX is measured. If the amount of label associated with immobilized FIX, FIXa, or FX is substantially reduced in the test sample relative to the control sample, then that indicates that the second antibody is competing with the first antibody for binding to FIX, FIXa, or FX. See Harlow and Lane (1988) *Antibodies: A Laboratory Manual* ch.14 (Cold Spring Harbor Laboratory, Cold Spring Harbor, N.Y.).

2. Activity Assays

In one aspect, assays are provided for identifying biological activity of a multispecific antigen-binding molecule that binds to FIX and/or FIXa, and FX and has biological activity. Biological activity may include, e.g., activity to promote FXa generation. Multispecific antigen-binding molecules having such biological activity in vivo and/or in vitro are also provided.

In certain embodiments, an antibody of the invention is tested for such biological activity. The "FVIII cofactor function-substituting activity" means, for example, the activity to increase the absorbance in a test of FX activation reaction by FIXa using a colorimetric quantification method, and the activity to increase the amount of thrombin generation calculated in a thrombin generation test using hemophilia A serum.

Using colorimetric quantification methods, the FVIII cofactor function-substituting activity can be evaluated, specifically, by assessing it in a measurement system comprising the multispecific antigen-binding molecule of the present invention and, for example, FIXa, FX, synthetic substrate S-2222 (synthetic substrate of FXa), and phospholipid. For example, the measurement can be performed by the following method. All of the reactions are conducted at room temperature. 54 of antibody solution diluted with Tris-buffered physiological saline containing 0.1% bovine serum albumin (hereinafter, referred to as TBSB) is mixed with 5 μL of 150 ng/mL human Factor IXa beta (Enzyme Research Laboratories), and this is incubated in a 384-well plate for 30 minutes at room temperature. The enzyme reaction in this mixture is initiated by adding 5 μL of 24.7 μg/mL human Factor X (Enzyme Research Laboratories), and after four minutes, terminated by adding 5 μL of 0.5 M EDTA. The chromogenic reaction is initiated by adding 5 μL of chromogenic substrate solution. After 30 minutes of chromogenic reaction, the change in absorbance at 405 nm is measured using SpectroMax 340PC384 (Molecular Devices). The solvent of human Factor IXa beta and human Factor X is TBSB containing 4.0 μM phospholipid solution (SYSMEX CO.) and 1.5 mM $CaCl_2$. S-2222 (SEKISUI MEDICAL) is dissolved in purified water to provide a chromogenic substrate solution at 1.47 mg/mL, and this is used in this assay. This measurement system shows a correlation with the disease severity and clinical symptom in hemophilia A cases (Rosen S, Andersson M, Blomback M et al. Clinical applications of a chromogenic substrate method for determination of FVIII activity. Thromb Haemost 1985; 54: 811-23).

Using thrombin generation test, the FVIII cofactor function-substituting activity can be evaluated, specifically, by using a measurement system comprising the multispecific antigen-binding molecule of the present invention and, for example, FVIII-deficient plasma, activated blood coagulation factor XI, phospholipid, Fluo-buffer, and Fluo-Substrate (FluCa-Kit; synthetic substrate of thrombin). For example, the measurement can be conducted by the following method. 8 μL of bispecific antibody diluted with TBSB is added to 72 μL of FVIII-deficient plasma (George King), and this is incubated for 30 minutes or more at room temperature. Subsequently, 20 μL of trigger solution containing 20 μM phospholipid and 5 ng/mL human Factor XIa (Enzyme Research Laboratories) is added. Then, coagulation reaction is initiated by adding 20 μL of a mixed solution of Fluo-buffer and Fluo-Substrate of FluCa-Kit (Thrombinoscope). The amount of thrombin generation can be assessed using a thrombin generation fluorescence measurement and analysis system (Thrombinoscope). The thrombin generation test using hemophilia A plasma shows general coagulation activity in a hemophilia A case, and a correlation with the clinical symptom of the disease (Shima M, Matsumoto T & Ogiwara K. New assays for monitoring haemophilia treatment. Haemophilia 2008; 14: 83-92).

The term "FIX activation-inhibiting activity" refers to a decrease in the absorbance in FIX activation reaction by FXIa using a colorimetric quantification method. Specifically, the following method is conducted. 5 μL of antibody solution diluted with TBSB is mixed with 5 μL of 3 U/mL human Factor IX (Christmassin M, Japan Blood Products Organization), and this is incubated in a 384-well plate for 30 minutes at room temperature. The enzyme reaction in this mixture is initiated by adding 5 μL of 90 ng/mL human Factor XIa (Enzyme Research Laboratories), and after 60 minutes, terminated by adding 5 μL of 0.5 M EDTA. The chromogenic reaction is initiated by adding 10 μL of chromogenic substrate solution. After 60 minutes of chromogenic reaction, the change in absorbance at 405 nm is measured using SpectroMax 340PC384 (Molecular Devices). The solvent of human Factor IX and human Factor XIa is TBSB containing 6.0 μM phospholipid solution (SYSMEX CO.) and 1.5 mM $CaCl_2$. Spectrozyme FIXa (Sekisui Diagnostics) is dissolved in purified water to provide a chromogenic substrate solution at 6.7 mM, and this is mixed with ethylene glycol at 5:8 and used in this assay.

Referring to US 2014/0080153 (WO 2012/093704), the binding of an antibody to ECM (extracellular matrix) can be assessed by the following procedure. ECM Phenol red free (BD Matrigel #6137013) is diluted with TBS at 2 mg/mL, and 5 μL of this dilution is dropped on the center of each well of a plate for ECL measurement (L15XB-6, MSD high bind) chilled on ice. Then, this is sealed with a plate seal and let stand overnight at 4° C. Next, an antibody sample is diluted to 9 μg/mL with ACES-T (20 mM ACES, 150 mM NaCl, pH 7.4 or pH 5.8 supplemented with 0.01% Tween 20). A secondary antibody is diluted to 2 μg/mL with ECLDB (ACES supplemented with 0.1% BSA and 0.01% Tween 20). 25 μL of antibody solution is added to a round bottom plate where 50 μL of ECLDB is aliquoted in each well. ECL Blocking Buffer is removed by tilting from an ECM plate containing the ECL Blocking Buffer, and 50 μL of each antibody solution mentioned above is added to the plate. Then, this is agitated for an hour at room temperature. After removing the sample by tilting, 50 μL of 0.25% gluteraldehyde (prepared with ACES-T) is added to each well, and this is let stand for 10 minutes at room temperature. Each well is washed three times with PBS-T (PBS supplemented with 0.05% Tween 20), and 50 μL of secondary antibody diluted to 1 μg/mL with ECLDB is added to each well, and this is agitated for an hour at room temperature without light exposure. Then, 150 μL of READ buffer (MSD) is added to each well, and light emission signal by sulfo-tag is detected using MESO SECTOR 5600 (Meso Scale Discovery).

F. Pharmaceutical Formulations

Pharmaceutical formulations of a multispecific antigen-binding molecule that binds to FIX and/or FIXa, and FX as described herein are prepared by mixing such a multispecific antigen-binding molecule having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide FVIII, FVII, FIX, TFPI inhibitor, siRNA targeting antithrombin; more specifically, Advate, Adynovate, Feiba, NovoSeven, NovoEight, N8-GP, N9-GP, Concizumab, Elocta, and Fitusiran. Such active ingredients are suitably present in combination in amounts that are effective for the purpose intended. FVIII, FVII, and FIX may include Fc fusions and PEG fusions thereof.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the multispecific antigen-binding molecule, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the multispecific antigen-binding molecule that binds to FIX and/or FIXa, and FX provided herein may be used in therapeutic methods.

In one aspect, a multispecific antigen-binding molecule that binds to FIX and/or FIXa, and FX for use as a medicament is provided. In further aspects, a multispecific antigen-binding molecule that binds to FIX and/or FIXa, and FX for use in treating bleeding, a disease involving bleeding, or a disease caused by bleeding, is provided. In certain embodiments, a multispecific antigen-binding molecule that binds to FIX and/or FIXa, and FX for use in a method of treatment is provided. In certain embodiments, the invention provides a multispecific antigen-binding molecule that binds to FIX and/or FIXa, and FX for use in a method of treating an individual having bleeding, a disease involving bleeding, or a disease caused by bleeding, comprising administering to the individual an effective amount of the multispecific antigen-binding molecule that binds to FIX and/or FIXa, and FX. In one such embodiment, the method further comprises administering to the individual an effective amount of at least one additional therapeutic agent, e.g., as described below. In further embodiments, the invention provides a multispecific antigen-binding molecule that binds to FIX and/or FIXa, and FX for use in the substitution for FVIII cofactor function. In certain embodiments, the invention provides a multispecific antigen-binding molecule that binds to FIX and/or FIXa, and FX for use in a method of substituting for FVIII cofactor function in an individual comprising administering to the individual an effective of the multispecific antigen-binding molecule that binds to FIX and/or FIXa, and FX to substitute for FVIII cofactor function. An "individual" according to any of the above embodiments is preferably a human. In the present invention, "bleeding, a disease involving bleeding, or a disease caused by bleeding" is preferably a disease that develops and/or progresses due to a decrease or deficiency in the activity of FVIII and/or activated blood coagulation factor VIII (FVIIIa). Such a disease includes the above-mentioned hemophilia A, hemophilia B, hemophilia C, a disease with emergence of an inhibitor against FVIII/FVIIIa, acquired hemophilia, and von Willebrand disease, but is not particularly limited thereto.

In a further aspect, the invention provides for the use of a multispecific antigen-binding molecule that binds to FIX and/or FIXa, and FX in the manufacture or preparation of a medicament. In one embodiment, the medicament is for treatment of bleeding, a disease involving bleeding, or a disease caused by bleeding. In a further embodiment, the medicament is for use in a method of treating bleeding, a disease involving bleeding, or a disease caused by bleeding, comprising administering to an individual having bleeding, a disease involving bleeding, or a disease caused by bleeding an effective amount of the medicament. In one such embodiment, the method further comprises administering to the individual an effective amount of at least one additional therapeutic agent, e.g., as described below. In a further embodiment, the medicament is for substituting for FVIII cofactor function. In a further embodiment, the medicament is for use in a method of substituting for FVIII cofactor function in an individual comprising administering to the individual an amount effective of the medicament to substitute for FVIII cofactor function. An "individual" according to any of the above embodiments may be a human. In the present invention, "bleeding, a disease involving bleeding, or a disease caused by bleeding" is preferably a disease that develops and/or progresses due to a decrease or deficiency in the activity of FVIII and/or FVIIIa. Such a disease includes the above-mentioned hemophilia A, hemophilia B, hemophilia C, a disease with emergence of an inhibitor against FVIII/FVIIIa, acquired hemophilia, and von Willebrand disease, but is not particularly limited thereto.

In a further aspect, the invention provides a method for treating bleeding, a disease involving bleeding, or a disease caused by bleeding. In one embodiment, the method comprises administering to an individual having bleeding, a disease involving bleeding, or a disease caused by bleeding an effective amount of a multispecific antigen-binding molecule that binds to FIX and/or FIXa, and FX. In one such embodiment, the method further comprises administering to the individual an effective amount of at least one additional therapeutic agent, as described below. An "individual" according to any of the above embodiments may be a human. In a further aspect, the invention provides a method for substituting for FVIII cofactor function in an individual. In one embodiment, the method comprises administering to the individual an effective amount of a multispecific antigen-binding molecule that binds to FIX and/or FIXa, and FX to substitute for FVIII cofactor function. In one embodiment, an "individual" is a human.

In a further aspect, the invention provides pharmaceutical formulations comprising any of the multispecific antigen-binding molecules that bind to FIX and/or FIXa, and FX provided herein, e.g., for use in any of the above therapeutic methods. In one embodiment, a pharmaceutical formulation comprises any of the multispecific antigen-binding molecules that bind to FIX and/or FIXa, and FX provided herein and a pharmaceutically acceptable carrier. In another embodiment, a pharmaceutical formulation comprises any of the multispecific antigen-binding molecules that bind to FIX and/or FIXa, and FX provided herein and at least one additional therapeutic agent, e.g., as described below.

A multispecific antigen-binding molecule of the invention can be used either alone or in combination with other agents in a therapy. For instance, an antibody of the invention may be co-administered with at least one additional therapeutic agent. In certain embodiments, an additional therapeutic agent is, for example, FVIII, FVII, FIX, TFPI inhibitor, siRNA targeting antithrombin; more specifically, Advate, Adynovate, Feiba, NovoSeven, NovoEight, N8-GP, N9-GP, Concizumab, Elocta, and Fitusiran. FVIII, FVII, and FIX may be Fc fusions and PEG fusions thereof.

Such combination therapies noted above encompass combined administration (where two or more therapeutic agents are included in the same or separate formulations), and separate administration, in which case, administration of the multispecific antigen-binding molecule of the invention can occur prior to, simultaneously, and/or following, administration of the additional therapeutic agent or agents. In one embodiment, administration of the multispecific antigen-binding molecule that binds to FIX and/or FIXa, and FX and administration of an additional therapeutic agent occur within about one month, two months, three months, four months, five months, or six months, or within about one, two or three weeks, or within about one, two, three, four, five, or six days, of each other.

A multispecific antigen-binding molecule of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Multispecific antigen-binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The multispecific antigen-binding molecule need not be, but is optionally formulated with one or more agents currently used to prevent or treat the disorder in question. The effective amount of such other agents depends on the amount of the multispecific antigen-binding molecule present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a multispecific antigen-binding molecule of the invention (when used alone or in combination with one or more other additional therapeutic agents) will depend on the type of disease to be treated, the type of multispecific antigen-binding molecule, the severity and course of the disease, whether the multispecific antigen-binding molecule is administered for preventive or therapeutic purposes, previous therapy, the patient's clinical history and response to the antibody, and the discretion of the attending physician. The multispecific antigen-binding molecule is suitably administered to the patient at one time or over a series of treatments. Depending on the type and severity of the disease, about 1 micro g/kg to 15 mg/kg (e.g. 0.1 mg/kg-10 mg/kg) of multispecific antigen-binding molecule can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the multispecific antigen-binding molecule would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the multispecific antigen-binding molecule). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a multispecific antigen-binding molecule that binds to FIX and/or FIXa, and FX.

H. Articles of Manufacture

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is a multispecific antigen-binding molecule of the invention. The label or package insert indicates that the composition is used for treating the condition of choice. Moreover, the article of manufacture may comprise (a) a first container with a composition contained therein, wherein the composition comprises a multispecific antigen-binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Another embodiment of the present invention relates to an antigen-binding molecule in which the association of the heavy chain and light chain is regulated, a method of manufacturing an antigen-binding molecule in which the association of the heavy chain and light chain is regulated, and a method of regulating the association of the heavy chain and light chain in an antigen-binding molecule.

The antigen-binding molecule of the present invention relates to an antigen-binding molecule in which the association of the heavy chain and light chain is regulated, in which the heavy chain and light chain constituting the antigen-binding molecule are a combination of heavy chain and light chain of interest, and in which the amino acid residues at given locations in the constant region of the heavy chain (CH1) and the constant region of the light chain (CL) are mutually electrically repelling amino acid residues (having the same charge).

In the present invention, by making amino acid residues at given locations in CH1 and CL of an undesired combination of heavy chain and light chain into amino acid residues that mutually repel electrically (i.e., that have the same charge), the formation of undesired combinations of heavy chain and light chain can be prevented by utilizing this charge repulsion, and as a result, the desired combination of heavy chain and light chain can be formed.

In the present invention, the phrases "to regulate association" and "association is regulated" refer to regulating to achieve a desired association condition, and more specifically refers to regulating so that undesirable associations are not formed between the heavy chain and light chain.

In the present invention, the term "interface" generally refers to the association surface that results from association (interaction), and amino acid residues that form the interface are ordinarily one or more amino acid residues included in the polypeptide regions which participate in the association, and are more preferably amino acid residues that approach each other during association and are involved in the interaction. More specifically, this interaction includes, for example, instances where the amino acid residues come close during the association to form hydrogen bonds, electrostatic interactions, or salt bridges with each other.

In the present invention, the phrase, "amino acid residues forming an interface" more specifically refers to amino acid residues included in the polypeptide region that constitutes the interface. For example, polypeptide regions constituting the interface refer to polypeptide regions responsible for selective binding between molecules such as in antigen-binding molecules (e.g., antibodies), ligands, receptors, or substrates. More specifically, in antigen-binding molecules, such examples include heavy chain constant regions, heavy chain variable regions, light chain constant regions, and light chain variable regions.

"Modification" of amino acid residues in the present invention specifically refers to substituting original amino acid residue(s) for other amino acid residue(s), deleting original amino acid residue(s), adding new amino acid residue(s), and such, but preferably refers to substituting one or more original amino acid residues for other amino acid residues.

In a preferred embodiment of the antigen-binding molecule of the present invention, the antigen-binding molecule has amino acid residues at given locations in CH1 and CL of an undesired combination of heavy chain and light chain before association regulation which electrically repel (which have the same charge).

By modifying amino acid residues in the aforementioned antigen-binding molecule into amino acid residues that mutually repel electrically (have the same charge), association of these amino acid residues is thought to be inhibited by the repulsive force of electrical charges.

Thus, in the aforementioned antigen-binding molecule, the modified amino acid residues are preferably amino acid residues that approach each other at association, in the polypeptide regions forming the interface.

The amino acid residues that approach during association can be determined by, for example, analyzing the three-dimensional structure of a polypeptide, and investigating the amino acid sequences of the polypeptide regions that form an interface during polypeptide association. Amino acid residues at the interface that mutually approach each other are preferable targets of "modification" in the antigen-binding molecule of the present invention.

Some amino acids are known to be electrically charged. In general, lysine (K), arginine (R) and histidine (H) are known to be amino acids having a positive charge (positively charged amino acids). Aspartic acid (D), glutamic acid (E), and such are known to be amino acids having a negative charge (negatively charged amino acids). In addition, alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), and the like are known to be amino acids that do not have a charge, or nonpolar amino acids.

Thus, amino acids that mutually repel electrically (have the same charge) in the present invention refer to:
(1) amino acids in which one of the amino acids is a positively charged amine acid and the other amino acid is also a positively charged amino acid, and (2) amino acids in which one of the amino acids is a negatively charged amino acid and the other amino acid is also a negatively charged amino acid.

Amino acids can be modified according to various methods known in the field of the art. Examples of these methods include, but are not limited to site-directed mutagenesis (Hashimoto-Gotoh, T., Mizuno, T., Ogasahara, Y. and Nakagawa, M. (1995) An oligodeoxyribonucleotide-directed dual amber method for site-directed mutagenesis, Gene 152, 271-275; Zoller, M. J. and Smith, M. (1983) Oligonucleotide-directed mutagenesis of DNA fragments cloned into M13 vectors, Methods Enzymol. 100, 468-500; Kramer, W., Drutsa, V., Jansen, H. W., Kramer, B., Pflugfelder, M. and Fritz, H. J. (1984) The gapped duplex DNA approach to oligonucleotide-directed mutation construction, Nucleic Acids Res. 12, 9441-9456; Kramer, W. and Fritz, H. J. (1987) Oligonucleotide-directed construction of mutations via gapped duplex DNA, Methods Enzymol. 154, 350-367; Kunkel, T. A. (1985) Rapid and efficient site-specific mutagenesis without phenotypic selection, Proc. Natl. Acad. Sci. USA 82, 488-492), PCR mutagenesis, cassette mutagenesis, etc.

Examples of amino acid modifications include modification of an uncharged amino acid or a nonpolar amino acid into a positively charged amino acid, modification of an uncharged amino acid or a nonpolar amino acid into a negatively charged amino acid, modification of a positively charged amino acid into a negatively charged amino acid, and modification of a negatively charged amino acid into a positively charged amino acid. Furthermore, modification of an uncharged amino acid or a nonpolar amino acid into a different uncharged or nonpolar amino acid, modification of a positively charged amino acid into a different positively charged amino acid, and modification of a negatively charged amino acid into a different negatively charged amino acid are also included in the amino acid modifications of the present invention.

Modifying amino acids in the present invention includes making one modification in each of the heavy and light chain, or making multiple modifications to each of the heavy and light chain. In addition, the number of modifications added to the heavy chain and light chain may be the same or different.

Modifying amino acids in the present invention includes making multiple modifications into positively charged amino acids on either the heavy chain or light chain, and making multiple modifications into negatively charged amino acids on the other chain. Moreover, multiple modifications into positively charged amino acids as well as multiple modifications into negatively charged amino acids may be made on the same heavy chain or light chain. In these modifications, modifications into uncharged amino acids or nonpolar amino acids as well as modifications of uncharged amino acids or nonpolar amino acids may also be suitably combined.

In the modifications of the present invention, for example, the amino acids on one of the chains can be used as they are without being modified, and in such cases, the heavy chain and light chain do not need to be both modified, and only one of the chains may be modified.

Although there are no particular limitations to the number of amino acid residues subjected to modification in the antigen-binding molecule of the present invention, for example, when modifying the constant region of the antibody, in order not to reduce the binding activity toward the antigen and not to increase immunogenicity, it is preferable to modify as few amino acid residues as possible. The aforementioned "few" refers to, for example, a number of about 1 to 30, preferably a number of about 1 to 20, even more preferably a number of about 1 to 15, and most preferably a number of 1 to 5.

The light chain constant region of the antigen-binding molecule of the present invention is preferably a human light chain constant region. Examples of antibody light chain constant region include IgK (Kappa), IgL1, IgL2, IgL3, IgL6 and IgL7 (Lambda) type constant regions. The light chain constant region of the antigen-binding molecule of the present invention is not particularly limited; when using multiple types of light chains, the light chains may be different types of light chains, for example, Kappa and Lambda. Several allotype sequences obtained by genetic polymorphism are described in Sequences of Proteins of Immunological Interest, NIH Publication No. 91-3242 as human IgK (Kappa) constant region and human IgL7 (Lambda) constant region, and any of these may be used in the present invention.

Antibody constant regions, in particular, heavy chain constant regions, may be modified as necessary in order to improve the function or stability of an antigen-binding molecule. Examples of modifications for improving the function of an antigen-binding molecule include modifications that strengthen or weaken the binding between an antigen-binding molecule and an Fcγ receptor (FcγR), modifications that strengthen or weaken the binding between an antigen-binding molecule and FcRn, modifications that strengthen or weaken the cytotoxic activity (such as ADCC activity and CDC activity) of an antigen-binding molecule, and such. In addition, modifications that improve the heterogeneity of an antigen-binding molecule and modifications that improve the immunogenicity and/or pharmacokinetics may also be included.

Moreover, as the heterogeneity of the heavy chain C-terminal sequence of the IgG antibody, amidation of the C-terminal carboxyl group by deletion of the C-terminal amino acid, lysine residue, or by deletion of the two C-terminal amino acids, glycine and lysine, has been reported the (Anal. Biochem. 2007 Jan. 1;360(1):75-83).

Thus, in the present invention, to lower heterogeneity of the heavy chain C terminus, it is preferable to use an IgG in which the C-terminal lysine or the C-terminal lysine and glycine have been deleted.

Since their antigenicity in the human body has been attenuated, chimeric and humanized antibodies using human-derived sequences are expected to be useful when administered to humans for therapeutic purposes or such.

A preferred example of the antigen-binding molecule of the present invention is a heteromeric multimer having two or more types of CH1 and two or more types of CL. This heteromeric multimer preferably binds to two or more types of epitopes, and an example thereof is a multispecific antibody.

A preferred example of a multispecific antibody of the present invention is a bispecific antibody. Thus, an example of a preferred embodiment of the antigen-binding molecule of the present invention is a bispecific antibody composed of two types of heavy chains (a first heavy chain and a second heavy chain) and two types of light chains (a first light chain and a second light chain).

Describing the "bispecific antibodies" of the preferred embodiments of the antigen-binding molecules of the present invention more precisely, the above-mentioned "first heavy chain" refers to one of the two heavy chains (H chains) forming the antibody, and the "second H chain" refers to the other H chain that is different from the first H chain. That is, of the two H chains, one of them can be arbitrarily defined as the first H chain and the other can be defined as the second H chain. Similarly, the "first light chain" refers to one of the two light chains (L chains) forming the bispecific antibody, and the "second L chain" refers to the other L chain that is different from the first L chain. Of the two L chains, one of them can be arbitrarily defined as the first L chain and the other can be defined as the second L chain. Ordinarily, the first L chain and the first H chain are derived from a same antibody that binds to a certain antigen (or epitope), and the second L chain and the second H chain are also derived from a same antibody that binds to a certain antigen (or epitope). Herein, the L chain-H chain pair formed by the first H chain and L chain is called the first pair, and the L chain-H chain pair formed by the second H chain and L chain is called the second pair. The antigen (or epitope) used to produce the antibody from which the second pair derives is preferably different from the antigen used to produce the antibody from which the first pair derives. More specifically, antigens recognized by the first pair and the second pair may be the same, but preferably, the pairs bind to different antigens (or epitopes). In this case, the H chains and L chains of the first pair and second pair preferably have amino acid sequences that differ from each other. When the first pair and the second pair bind to different epitopes, the first pair and the second pair may recognize a completely different antigen, or they may recognize different sites (different epitopes) on the same antigen. Furthermore, one of them may recognize an antigen such as a protein, peptide, gene, or sugar, and the other may recognize cytotoxic substances such as radioactive substances, chemotherapeutic agents, or cell-derived toxins. However, when one wishes to produce an antibody having pairs formed by specific combinations of H chains and L chains, those specific H chains and L chains may be arbitrary determined to be the first pair and second pair.

A more detailed explanation is provided below on the case of an IgG-type bispecific antibody having two types of heavy chain constant regions CH1 (CH1-A and CH1-B) and two types of light chain constant regions (CL-A and CL-B); however, the present invention can be similarly applied to other antibodies as well.

When one wishes to obtain a bispecific antibody that would recognize one epitope by the first CH1-A and the first CL-A, and bind to another epitope by the second CH1-B and the second CL-B, theoretically there is the possibility that 10 types of antibody molecules may be produced when each of the four types of chains is expressed for producing that antibody.

In this case, desired antibody molecules can be preferentially acquired if, for example, the association is regulated so that association of CH1-A and CL-B and/or between CH1-B and CL-A is inhibited.

An example is modifying amino acid residues forming an interface between CH1-A and CL-B into positively charged amino acid residues and modifying amino acid residues forming an interface between CH1-B and CL-A into negatively charged amino acid residues. As a result of these modifications, unintended association between CH1-A and CL-B is inhibited since the amino acid residues forming the interface are both positively charged, and association between CH1-B and CL-A is also inhibited since the amino acid residues forming the interface are both negatively charged. Thus, the unintended association between CH1-A and CL-B and association between CH1-B and CL-A are inhibited because the amino acid residues forming the interfaces mutually have the same charge. As a result, antibodies having the intended association between CH1-A and CL-A, and the intended association between CH1-B and CL-B can be acquired efficiently. Moreover, the intended association between CH1-A and CL-A is promoted since the amino acid residues forming the interface have different types of charges from each other; and the intended association between CH1-B and CL-B is also promoted since the amino acid residues forming the interface have different types of charges from each other. Consequently, antibodies with intended association can be efficiently obtained.

Another example is modifying the amino acid residues forming the interface between CH1-A and CL-B into positively charged amino acid residues, when the amino acid residues forming the interface between CL-A and CH1-B are mutually uncharged or nonpolar amino acids. As a result of this modification, the unintended association between CH1-A and CL-B is inhibited because the amino acid residues forming the interface are both positively charged. On the other hand, since the amino acid residues forming the interfaces are amino acids that do not mutually repel electrically, the intended association between CH1-A and CL-A, and the intended association between CH1-B and CL-B will occur more easily than in the case where the amino acids repel electrically. Consequently, antibodies having the intended association between CH1-A and CL-A, and the intended association between CH1-B and CL-B can be efficiently obtained. Meanwhile, in this example, in the case that the amino acid residues forming the interface between CL-A and CH1-B are not mutually uncharged or nonpolar amino acids, they may be modified so as to become mutually uncharged or nonpolar amino acids.

Moreover, in another example, when the amino acid residues forming the interface between CL-B and CH1-B are uncharged or nonpolar amino acids in CH1-B, one of the amino acid residues forming the interface between CH1-A and CL-A is modified into a positively charged amino acid residue while the other is modified into a negatively charged amino acid residue; and amino acid residues forming the interface between CL-B and CH1-B in CL-B are modified so as to have the same charge as the modification made to CH1-A. As a result of this modification, while the intended association between CH1-A and CL-A is promoted because the amino acid residues forming the interface are a combination of positive charge and negative charge, the intended association between CH1-B and CL-B is not inhibited because the amino acid residues forming the interface are amino acids that do not mutually repel electrically. As a result, one can efficiently obtain an antibody having intended association between CH1-A and CL-A, and intended association between CH1-B and CL-B. Meanwhile, in this example, when the amino acid residues forming the interface between CL-B and CH1-B are not uncharged or nonpolar amino acids in CH1-B, they may be modified so as to become uncharged or nonpolar amino acids.

In addition, use of the association regulation of the present invention makes it possible to suppress association between CHls (CH1-A and CH1-B), or association between CLs (CL-A and CL-B).

Those skilled in the art would be able to suitably determine the types of amino acid residues that come close during association at the CH1 and CL interface in a desired polypeptide for which regulation of association by the present invention is desired.

Further, those skilled in the art can also suitably acquire sequences that can be used as CH1 or CL of an antibody in an organism such as a human, monkey, mouse, rabbit, and the like by using a public database and such. More specifically, the amino acid sequence information of CH1 or CL can be acquired by means described in the Examples described below.

For example, with respect to the bispecific antibodies described in the Examples below, specific examples of amino acid residues that come close (that face or are in contact) at the interface of CH1 and CL upon association include the combinations shown below:

glutamine (Q) at position 175 according to EU numbering in CH1 and the facing (contacting) threonine (T) or serine (S) at position 180 according to Kabat numbering in CL;

glutamine (Q) at position 175 according to EU numbering in CH1 and the facing (contacting) threonine (T) or serine (S) at position 131 according to Kabat numbering in CL;

glutamine (Q) at position 175 according to EU numbering in CH1 and the facing (contacting) serine (S) or threonine (T) at position 131 and serine (S) or threonine (T) at position 180 according to Kabat numbering in CL; and, lysine (K) at position 147 and glutamine (Q) at position 175 according to EU numbering in CH1 and the facing (contacting) serine (S) or threonine (T) at position 131 and serine (S) or threonine (T) at position 180 according to Kabat numbering in CL.

The numbers described in EU numbering in the present invention are indicated in accordance with EU numbering (Sequences of proteins of immunological interest, NIH Publication No. 91-3242). In the present invention, the phrases "an amino acid residue at position X according to EU numbering" and "an amino acid at position X according to EU numbering" (where X is an arbitrary number) can also be read as "an amino acid residue that corresponds to position X according to EU numbering" and "an amino acid that corresponds to position X according to EU numbering". As indicated in the Examples described below, desired antigen-binding molecules can be preferentially acquired by modifying these amino acid residues and carrying out the methods of the present invention.

In an embodiment, the present invention provides an antigen-binding molecule in which association of the heavy chain and light chain is regulated, wherein one or two or more sets of amino acid residues selected from the group consisting of the sets of amino acid residues shown in (a) to (c) below in the heavy chain and light chain of the antigen-binding molecule are amino acid residues that mutually repel electrically:

(a) the amino acid residue contained in CH1 at position 175 according to EU numbering, and the amino acid residue contained in CL at position 180 according to Kabat numbering;

(b) the amino acid residue contained in CH1 at position 175 according to EU numbering, and the amino acid residue contained in CL at position 131 according to Kabat numbering; and (c) the amino acid residues contained in CH1 at positions 147 and 175 according to EU numbering, and the amino acid residues contained in CL at positions 131 and 180 according to Kabat numbering.

In the aforementioned antigen-binding molecule, the "amino acid residues that mutually repel electrically" or "amino acid residues having the same charge" are preferably selected from amino acid residues contained in, for example, either of the set of (X) or (Y) below:

(X) glutamic acid (E) or aspartic acid (D); or
(Y) lysine (K), arginine (R), or histidine (H).

In the aforementioned antigen-binding molecule, specific examples of the sets of the amino acid residues that mutually repel electrically include the sets of the amino acid residues below:

(a) the amino acid residue contained in CH1 at position 175 according to EU numbering, and the amino acid residue contained in CL at position 180 according to EU numbering;

(b) the amino acid residue contained in CH1 at position 175 according to EU numbering, and the amino acid residue contained in CL at position 131 according to Kabat numbering;

(c) the amino acid residues contained in CH1 at positions 147 and 175 according to EU numbering, and the amino acid residues contained in CL at positions 131 and 180 according to Kabat numbering;

(d) the amino acid residue contained in CH1 at position 175 according to EU numbering, and the amino acid residues contained in CL at positions 131 and 180 according to Kabat numbering.

The present invention provides an antigen-binding molecule in which one or two or more sets of amino acid residues selected from the group consisting of the sets of amino acid residues shown in (a1) to (c2) below in the heavy chain and light chain of the antigen-binding molecule are amino acid residues that mutually repel electrically:

(a1) the amino acid residue contained in CH1 at position 175 according to EU numbering which is glutamic acid (E) or aspartic acid (D), and the amino acid residue contained in CL at position 180 according to EU numbering which is glutamic acid (E) or aspartic acid (D);

(a2) the amino acid residue contained in CH1 at position 175 according to EU numbering which is lysine (K), histidine (H), or arginine (R), and the amino acid residue contained in CL at position 180 according to EU numbering which is lysine (K), histidine (H), or arginine (R);

(b1) the amino acid residue contained in CH1 at position 175 according to EU numbering which is glutamic acid (E) or aspartic acid (D), and the amino acid residue contained in CL at position 131 according to EU numbering which is glutamic acid (E) or aspartic acid (D);

(b2) the amino acid residue contained in CH1 at position 175 according to EU numbering which is lysine (K), histidine (H), or arginine (R), and the amino acid residue contained in CL at position 131 according to EU numbering which is lysine (K), histidine (H), or arginine (R);

(c1) the amino acid residues contained in CH1 at positions 147 and 175 according to EU numbering which are each glutamic acid (E) or aspartic acid (D), and the amino acid residues contained in CL at positions 131 and 180 according to EU numbering which are each glutamic acid (E) or aspartic acid (D);

(c2) the amino acid residues contained in CH1 at positions 147 and 175 according to EU numbering which are each lysine (K), histidine (H), or arginine (R), and the amino acid residues contained in CL at positions 131 and 180 according to EU numbering which are each lysine (K), histidine (H), or arginine (R).

In the aforementioned antigen-binding molecule, specific examples of amino acid residues that mutually repel electrically include the amino acid residues below:

(a1) the amino acid residue contained in CH1 at position 175 according to EU numbering which is glutamic acid (E) or aspartic acid (D), and the amino acid residue contained in CL at position 180 according to EU numbering which is glutamic acid (E) or aspartic acid (D);

(a2) the amino acid residue contained in CH1 at position 175 according to EU numbering which is lysine (K), histidine (H), or arginine (R), and the amino acid residue contained in CL at position 180 according to EU numbering which is lysine (K), histidine (H), or arginine (R);

(b1) the amino acid residue contained in CH1 at position 175 according to EU numbering which is glutamic acid (E) or aspartic acid (D), and the amino acid residue contained in CL at position 131 according to EU numbering which is glutamic acid (E) or aspartic acid (D);

(b2) the amino acid residue contained in CH1 at position 175 according to EU numbering which is lysine (K), histidine (H), or arginine (R), and the amino acid residue contained in CL at position 131 according to EU numbering which is lysine (K), histidine (H), or arginine (R);

(c1) the amino acid residues contained in CH1 at positions 147 and 175 according to EU numbering which are each glutamic acid (E) or aspartic acid (D), and the amino acid residues contained in CL at positions 131 and 180 according to EU numbering which are each glutamic acid (E) or aspartic acid (D);

(c2) the amino acid residues contained in CH1 at positions 147 and 175 according to EU numbering which are each lysine (K), histidine (H), or arginine (R), and the amino acid residues contained in CL at positions 131 and 180 according to EU numbering which are each lysine (K), histidine (H), or arginine (R);

(d1) the amino acid residue contained in CH1 at position 175 according to EU numbering which is glutamic acid (E) or aspartic acid (D), and the amino acid residues contained in CL at positions 131 and 180 according to EU numbering which are each glutamic acid (E) or aspartic acid (D);

(d2) the amino acid residue contained in CH1 at position 175 according to EU numbering which is lysine (K), histidine (H), or arginine (R), and the amino acid residues contained in CL at positions 131 and 180 according to EU numbering which are each lysine (K), histidine (H), or arginine (R).

In addition to the above, the technique for inhibiting the CH1/CL associated of no interest by introducing electric charge repulsion on the interface between CH1 and CL (WO 2013/065708) can be further applied to the antigen-binding molecule of the present invention. More specifically, the present invention provides an antigen-binding molecule having CH1 and CL, wherein one or two or more sets of amino acid residues selected from the group consisting of the sets of amino acid residues shown in (a) to (d) below mutually repel electrically:

(a) the amino acid residue contained in the heavy chain constant region (CH1) at position 147 according to EU numbering, and the amino acid residue contained in the light chain constant region (CL) at position 180 according to EU numbering;

(b) the amino acid residue contained in CH1 at position 147 according to EU numbering, and the amino acid residue contained in CL at position 131 according to EU numbering;

(c) the amino acid residue contained in CH1 at position 175 according to EU numbering, and the amino acid residue contained in CL at position 160 according to EU numbering;

(d) the amino acid residue contained in CH1 at position 213 according to EU numbering, and the amino acid residue contained in CL at position 123 according to EU numbering.

A technique for introducing electrical repulsion into the interface of the second constant region of the heavy chain (CH2) or the third constant region of the heavy chain (CH3) to suppress undesired association between heavy chains, a technique for introducing electrical repulsion into the interface of the heavy chain variable region and light chain variable region to suppress unintended association between the heavy chain and light chain, or a technique for modifying amino acid residues forming a hydrophobic core present at the interface of the heavy chain variable region and light chain variable region into polar amino acids having an electrical charge to suppress unintended association between the heavy chain and light chain can be further applied to the antigen-binding molecules of the present invention (see WO 2006/106905).

In the technique that suppresses unintended association between heavy chains by introducing electrical repulsion at the interface of CH2 or CH3, examples of amino acid residues that are in contact at the interface of other constant regions of the heavy chain include regions corresponding to position 356 (EU numbering) and position 439 (EU numbering), position 357 (EU numbering) and position 370 (EU numbering), and position 399 (EU numbering) and position 409 (EU numbering) in the CH3 region. For the numbering of the antibody constant regions, one may refer to the publication by Kabat et al. (Kabat, E. A., et al., 1991, Sequences of Proteins of Immunological Interest, NIH); and for the numbering of the heavy chain constant regions, the EU numbering are shown.

More specifically, for example, in an antigen-binding molecule containing two types of heavy chain CH3 regions, one to three sets of amino acid residues in the first heavy chain CH3 region, which are selected from the sets of amino acid residues of (1) to (3) below, may be made to mutually repel electrically:

(1) the amino acid residues contained in the heavy chain CH3 region at position 356 and position 439 according to EU numbering;

(2) the amino acid residues contained in the heavy chain CH3 region at position 357 and position 370 according to EU numbering; and (3) the amino acid residues contained in the heavy chain CH3 region at position 399 and position 409 according to EU numbering.

Moreover, the antibody can be an antibody having a set of amino acid residues in the second heavy chain CH3 region distinct from the aforementioned first heavy chain CH3 region, wherein the set of amino acid residues is selected from the sets of amino acid residues shown in (1) to (3) above, and wherein the one to three sets of amino acid residues that correspond to the sets of amino acid residues shown in (1) to (3) above, which mutually repel electrically in the first heavy chain CH3 region, do not electrically repel from the corresponding amino acid residues in the first heavy chain CH3 region.

The amino acid residues described in (1) to (3) above approach each other upon association. Those skilled in the art would be able to find sites corresponding to the amino acid residues described in (1) to (3) mentioned above for a desired heavy chain CH3 region or heavy chain constant region by homology modeling and such using commercially available software, and to suitably modify the amino acid residues at those sites.

In the aforementioned antigen-binding molecule, "electrically repelling" or "having a same charge" means that, for example, any two or more amino acid residues have amino acid residues that are contained in either one group of (X) and (Y) mentioned above.

In a preferred embodiment of the aforementioned antigen-binding molecule, the first heavy chain CH3 region and the second heavy chain CH3 region may be cross-linked by disulfide bonds.

In the present invention, an amino acid residue subjected to "modification" is not limited to an amino acid residue of the antigen-binding molecule variable region or antibody constant region mentioned above. Those skilled in the art would be able to find amino acid residues that form an interface in a polypeptide variant or heteromeric multimer by homology modeling and the like using commercially available software, and to modify amino acid residues at those sites so as to regulate association. Homology modeling is a technique for predicting the three-dimensional structure of a protein using commercially available software. When constructing the structure of a protein with unknown three-dimensional structure, one first searches for a protein that has been determined to have a highly homologous three-dimensional structure to the protein. Next, using this three-dimensional structure as a template, one constructs the structure of the protein with unknown structure, and the structure is further optimized by molecular dynamics methods and the like to predict the three-dimensional structure of the unknown protein.

In the technique for introducing electrical repulsion into the interface of the heavy chain variable region and light chain variable region to suppress undesired association of the heavy chain and light chain, examples of amino acid residues that are in contact at the interface of the heavy chain variable region (VH) and light chain variable region (VL) include glutamine (Q) at position 39 according to Kabat numbering in the VH (FR2 region) and the facing (contacting) glutamine (Q) at position 38 according to Kabat numbering in the VL (FR2 region). Moreover, a preferable example is leucine (L) at position 45 according to the Kabat numbering in the VH (FR2) and the facing proline (P) at position 44 according to the Kabat numbering in the VL (FR2). The publication by Kabat, et al. (Kabat, E. A., et al., 1991, Sequence of Proteins of Immunological Interest, NIH) was referred to for the numbering of these sites.

Since these amino acid residues are known to be highly conserved in humans and mice (J. Mol. Recognit. 2003; 16: 113-120), association of the variable regions of antigen-binding molecules can be regulated for VH-VL association of antigen-binding molecules other than those indicated in the Examples by modifying amino acid residues corresponding to the above-mentioned amino acid residues.

A specific example is an antigen-binding molecule in which two or more amino acid residues forming the interface of the VH and VL are amino acid residues that mutually repel electrically. More specifically, examples include an antigen-binding molecule with one set or two sets of amino acid residues selected from the group consisting of the sets of amino acid residues shown in (a) or (b) below:
(a) the amino acid residue contained in the VH at position 39 according to Kabat numbering and, the amino acid residue contained in the VL at position 38 according to Kabat numbering; or
(b) the amino acid residue contained in the VH at position 45 according to Kabat numbering, and the amino acid residue contained in the VL at position 44 according to Kabat numbering.

Each of the amino acid residues described in the aforementioned (a) or (b) approaches each other upon association. Those skilled in the art would be able to find sites that correspond to the amino acid residues described in the aforementioned (a) or (b) in a desired VH or VL by homology modeling and the like using commercially available software, and to suitably modify the amino acid residues at those sites.

In the aforementioned antigen-binding molecule, "amino acid residues that mutually repel electrically" are preferably selected from amino acid residues contained in, for example, either of the sets (X) and (Y) below:
(X) glutamic acid (E) or aspartic acid (D); or
(Y) lysine (K), arginine (R), or histidine (H).

In the technique for modifying amino acid residues forming a hydrophobic core present at the interface of the VH and VL into polar amino acids having an electrical charge to suppress unintended association of the heavy chain and light chain, preferable examples of amino acid residues which are able to form a hydrophobic core at the interface of the VH and VL include leucine (L) at position 45 according to Kabat numbering in the VH (FR2), and the facing proline (P) at position 44 according to Kabat numbering in the VL (FR2). For the numbering of these sites, Kabat, et al. (Kabat, E. A., et al., 1991, Sequences of Proteins of Immunological Interest, NIH) was used as a reference.

In general, the term "hydrophobic core" refers to a part that is formed by an assembly of hydrophobic amino acid side chains at the interior of associated polypeptides. Examples of hydrophobic amino acids include alanine, isoleucine, leucine, methionine, phenylalanine, proline, tryptophan, and valine. Furthermore, amino acid residues other than hydrophobic amino acids (for example tyrosine) may be involved in the formation of a hydrophobic core. This hydrophobic core together with a hydrophilic surface, in which hydrophilic amino acid side chains are exposed to the exterior, becomes a driving force for promoting association of water-soluble polypeptides. When hydrophobic amino acids of two different domains are present on a molecular surface and are exposed to water molecules, the entropy will increase and the free energy will increase. Accordingly, the two domains will associate with each other to decrease the free energy and become stable, and hydrophobic amino acids at the interface will be buried into the interior of the molecule to form a hydrophobic core.

It is thought that when polypeptide association occurs, formation of a hydrophobic core is inhibited by modifying hydrophobic amino acids forming the hydrophobic core to polar amino acids having an electrical charge; and consequently, polypeptide association is thought to be inhibited.

Those skilled in the art would be able to recognize the presence or absence of a hydrophobic core, the formation site (region), and the like by analyzing amino acid sequences for a desired antigen-binding molecule. Namely, the antigen-binding molecule of the present invention is an antigen-binding molecule characterized in that amino acid residues capable of forming a hydrophobic core at an interface are modified to amino acid residues having an electrical charge. More specifically, examples include an antigen-binding molecule in which the amino acid residues shown in either (1) or (2) below are amino acid residues having an electrical charge. Side chains of the amino acid residues shown in (1) and (2) below are adjacent to each other, and can form a hydrophobic core:
(1) the amino acid residue contained in the VH at position 45 according to Kabat numbering; and
(2) the amino acid residue contained in the VL at position 44 according to Kabat numbering. Preferable examples of amino acid residues having an electrical charge in the aforementioned antigen-binding molecule include glutamic acid (E), aspartic acid (D), lysine (K), arginine (R) and histidine (H). More preferable examples include glutamic acid (E) and lysine (K).

Generally, the amino acid residues described in the aforementioned (1) and (2) in humans and mice are respectively:
(1) leucine (L), and
(2) proline (P).

Thus, in a preferred embodiment of the present invention, these amino acid residues are subjected to modification (such as substitution with amino acids having an electrical charge). Furthermore, the types of the aforementioned amino acid residues of (1) and (2) are not necessarily limited to the aforementioned amino acid residues, but may also be other amino acids equivalent to these amino acid residues.

Other known techniques can be applied to the antigen-binding molecules of the present invention. For example, in order to promote association of the first VH (VH1) and the first VL (VL1) and/or the second VH (VH2) and the second VL (VL2), an amino acid side chain present in the variable region of one of the H chains can be substituted with a larger side chain (knob), and an amino acid side chain present in the opposing variable region of the other H chain can be substituted with a smaller side chain (hole), so that the knob may be arranged in the hole, and association of VH1 and VL1 and/or VH2 and VL2 is promoted; and consequently, association of VH1 and VL2 and/or VH2 and VL1 can be further suppressed (WO 1996/027011; Ridgway, J. B., et al., Protein Engineering (1996) 9, 617-621; Merchant, A. M., et al., Nature Biotechnology (1998) 16, 677-681).

For example, in the case of human IgG1, in order to make an amino acid side chain in the CH3 region of one H chain a larger side chain (knob), the modifications of Y349C and T366W are made, and in order to make an amino acid side chain in the CH3 region of the other H chain a smaller side chain, the modifications of D356C, T336S, L368A and Y407V are made.

Still other known techniques can be applied to the antigen-binding molecules of the present invention. A target antigen-binding molecule can be efficiently prepared by complementary association of CH3 using strand-exchange engineered domain CH3, in which a portion of CH3 of one H chain of an antigen-binding molecule is changed to a sequence derived from IgA corresponding to that portion, and a complementary portion of CH3 of the other H chain is introduced with a sequence derived from IgA corresponding to that portion (Protein Engineering Design & Selection, 23: 195-202, 2010).

Still other known techniques can be applied to the antigen-binding molecules of the present invention. When producing bispecific antibodies, a target bispecific antibody can be prepared by, for example, imparting a difference in isoelectric point by making different amino acid modifications to each of the variable regions of the two types of H chains, and utilizing that difference in isoelectric point for purification by ion exchange chromatography (WO 2007/114325).

The technique of modifying the amino acid residue at position 435 according to EU numbering, which is a site related to binding between IgG and Protein A, to an amino acid having a different binding strength toward Protein A, such as Arg, may also be used on the antigen-binding molecule of the present invention in combination with the aforementioned techniques. By using this technique, the interaction between the H chain and Protein A can be changed, and only heterodimeric antigen-binding molecules can be efficiently purified using a Protein A column. This technique can also be used independently without combining with the aforementioned techniques.

The modifications of the present invention can be used on antigen-binding molecules such as the one below, for example, an antigen-binding molecule having a structure in which, to promote association of a first VH (VH1) and a first VL (VL1) and/or a second VH (VH2) and a second VL (VL2), VH1 is linked to an Fc region through a first CH1 and VL1 is linked to a first CL, and VH2 is linked to another Fc region through a second CL and VL2 is linked to a second CH1 (WO 09/80254).

A plurality, for example, two or more of the aforementioned known techniques can be used in combination for the antigen-binding molecule of the present invention. Furthermore, the antigen-binding molecule of the present invention may be prepared based on an antibody to which modifications of the aforementioned known techniques have been made.

The below-mentioned methods of the present invention for regulating association allow, for example, for the efficient production of antigen-binding molecules that are active. Examples of such activities include binding activity, neutralizing activity, cytotoxic activity, agonist activity, antagonist activity, and enzyme activity and such. Agonist activity is an activity that induces some kind of changes in physiological activity through binding of an antigen-binding molecule to an antigen, such as a receptor, which causes signal transduction or such in cells. Examples of the physiological activity include growth activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity and such, but are not limited thereto.

Antigen-binding molecules that bind to the desired antigens or bind to the desired receptors can be produced efficiently by the methods of the present invention.

The antigens of the present invention are not particularly limited, and any type of antigen can be used. Examples of antigens include receptors or their fragments, cancer antigens, MHC antigens, and differentiation antigens and the like, but are not particularly limited thereto.

Examples of the receptors of the present invention include receptors belonging to the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, adhesion factor family, hormone receptor family, and such. Reports on the receptors belonging to these receptor families and their characteristics can be found in various sources of documents, for example, in Cooke B A., King R J B., van der Molen H J. ed. New Comprehensive Biochemistry Vol. 18B "Hormones and their Actions Part II" pp.1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; Miyasaka M. ed. Cell Technology, Handbook Series "Handbook for adhesion factors" (1994) Shujunsha, Tokyo, Japan; and such. Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α or β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644.; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN α/β R: Uze, G. et al. (1990) Cell 60, 225-234; and Novick, D. et al. (1994) Cell 77, 391-400).

Cancer antigens are antigens that are expressed following malignant transformation of a cell, and are also referred to as tumor specific antigens. In addition, abnormal sugar chains which appear on a cell surface or on a protein molecule when the cell has become cancerous are also cancer antigens, and they are also referred to as cancer sugar chain antigens. Examples of cancer antigens include EpCAM, which is expressed in multiple cancers including lung cancer (Proc. Natl. Acad. Sci. USA (1989) 86 (1), 27-31) (the polynucleotide sequence thereof is indicated as RefSeq Accession No. NM_002354.2 and the polypeptide sequence thereof is indicated as RefSeq Accession No. NP_002345.2), CA19-9, CA15-3, sialyl SSEA-1 (SLX), etc.

MHC antigens can be classified broadly into MHC class I antigens and MHC class II antigens: MHC class I antigens include HLA-A, -B, -C, -E, -F, -G, and -H; and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The antigen-binding molecule of the present invention may be a bispecific antibody; and in that case, two antigens (or epitopes) recognized by that antibody can be arbitrarily selected from the aforementioned receptors or fragments thereof, cancer antigens, MHC antigens, differentiation antigens and the like. For example, two antigens may be selected from receptors or fragments thereof, two may be selected from cancer antigens, two may be selected from MHC antigens, or two may be selected from differentiation antigens. In addition, one antigen each may be selected from two antigens arbitrarily selected from, for example, receptors or fragments thereof, cancer antigens, MHC antigens, and differentiation antigens.

In addition, the present invention provides a method for producing an antigen-binding molecule in which association between a heavy chain and a light chain is regulated. A preferred embodiment of the production method of the present invention is a method for producing an antigen-binding molecule in which association between a heavy chain and a light chain is regulated, comprising:

(1) modifying nucleic acids encoding CH1 and CL such that one set or two or more sets of amino acid residues selected from the group consisting of the sets of amino acid residues shown in (a) to (c) below are amino acid residues that electrostatically repel each other:

(a) an amino acid residue in CH1 that is at position 175 according to EU numbering, and an amino acid residue in CL that is at position 180 according to Kabat numbering, (b) an amino acid residue in CH1 that is at position 175 according to EU numbering, and an amino acid residue in CL that is at position 131 according to Kabat numbering, and (c) amino acid residues in CH1 that are at positions 147 and 175 according to EU numbering, and amino acid residues in CL that are at positions 131 and 180 according to Kabat numbering;

(2) introducing the modified nucleic acids into a host cell and culturing the host cell such that the nucleic acids are expressed; and (3) collecting an antigen-binding molecule from a cell culture of the host cell.

In addition, the present invention relates to a production method comprising, in the aforementioned step (1), modifying the nucleic acids so that the amino acid residues that electrically repel each other are selected from among the amino acid residues contained in either of the groups of the aforementioned (X) and (Y).

Moreover, the present invention relates to a production method comprising in the aforementioned step (1), modifying the nucleic acids so that two or more amino acid residues that form the interface of the VH and VL are amino acid residues that electrically repel each other. Preferably, the amino acid residues that electrically repel each other are any set of amino acid residues selected from the group consisting of, for example, the sets of amino acid residues shown in (a) and (b) below:

(a) the amino acid residue contained in the VH at position 39 according to Kabat numbering, and the amino acid residue contained in the VL at position 38 according to Kabat numbering; or (b) the amino acid residue contained in the VH at position 45 according to Kabat numbering, and the amino acid residue contained in the VL at position 44 according to Kabat numbering.

The aforementioned amino acid residues which electrically repel each other are preferably selected from the amino acid residues contained in either set of the aforementioned (X) and (Y).

In addition, the present invention provides a method for regulating association of heavy and light chains of an antigen-binding molecule. A preferred embodiment of the method for regulating association of the present invention is a method for regulating association of heavy and light chains of an antigen-binding molecule, comprising modifying nucleic acids such that one set or two or more sets of amino acid residues selected from the group consisting of the sets of amino acid residues shown in (a) to (c) below are amino acid residues that electrostatically repel each other:

(a) an amino acid residue in CH1 that is at position 175 according to EU numbering, and an amino acid residue in CL that is at position 180 according to EU numbering, (b) an amino acid residue in CH1 that is at position 175 according to EU numbering, and an amino acid residue in CL that is at position 131 according to EU numbering, and (c) amino acid residues in CH1 that are at positions 147 and 175 according to EU numbering, and amino acid residues in CL that are at positions 131 and 180 according to EU numbering.

In addition, the present invention relates to a method for regulating association comprising, in the aforementioned step (1), modifying the nucleic acids such that the amino acid residues that electrically repel each other are selected from the amino acid residues included in the aforementioned group of either (X) or (Y).

Moreover, the present invention relates to a method for regulating association comprising, in the aforementioned step (1), modifying the nucleic acids such that two or more amino acid residues that form a VH-VL interface are amino acid residues that electrostatically repel each other. Here, the amino acid residues that electrostatically repel each other are preferably any one set of amino acid residues selected from the group consisting of, for example, the sets of amino acid residues shown in (a) and (b) below:

(a) an amino acid residue in VH that is at position 39 according to Kabat numbering, and an amino acid residue in VL that is at position 38 according to Kabat numbering, (b) an amino acid residue in VH that is at position 45 according to Kabat numbering, and an amino acid residue in VL that is at position 44 according to Kabat numbering.

According to the method for regulating association of the present invention, a desired bispecific antibody can be obtained preferentially and efficiently as previously described. Namely, a desired heteromeric multimer in the form of a bispecific antibody can be efficiently formed from a monomer mixture.

The phrase "modify nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing gene manipulations or mutation treatment that would result in at least one nucleotide insertion, deletion, or substitution to the original nucleic acid so that codons encoding amino acid residues of interest is formed. More specifically, codons encoding the original amino acid residues are substituted with codons encoding the amino acid residues that are to be introduced by the modification. Such nucleic acid modification can be performed suitably by those skilled in the art using known techniques such as site-specific mutagenesis and PCR mutagenesis.

In addition, the present invention provides nucleic acids that encode an antigen-binding molecule of the present invention. Moreover, vectors carrying the nucleic acids are also included in the present invention.

Moreover, the present invention relates to pharmaceutical formulations comprising an antigen-binding molecule of the present invention and a pharmaceutically acceptable carrier. In the present invention, pharmaceutical formulations ordinarily refer to pharmaceutical agents for treating or preventing, or testing and diagnosing diseases.

The pharmaceutical formulations of the present invention can be formulated by methods known to those skilled in the art. Moreover, the antigen-binding molecule of the present invention can be formulated in combination with other pharmaceutical substances, as required. For example, they can be used parenterally in the form of an injection of a sterile solution or suspension with water or another pharmaceutically acceptable liquid. For example, they may be formulated as unit doses that meet the requirements for the preparation of pharmaceuticals by appropriately combining with pharmaceutically acceptable carriers or media, specifically with sterile water, physiological saline, a vegetable oil, emulsifier, suspension, detergent, stabilizer, flavoring agent, excipient, vehicle, preservative, binder, or such. In such preparations, the amount of active ingredient is adjusted such that the dose falls within an appropriately pre-determined range.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in the present specification are incorporated herein by reference.

EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Obtainment of Novel L Chains Compatible with Each H Chain of ACE910 (Emicizumab)

ACE910 (Emicizumab) is a humanized IgG4 antibody which consists of anti-FIX(a) and anti-FX, and shows an activity of substituting for the cofactor function of FVIII. It is composed of two different heavy chains (Q499 and J327) binding to FIX(a) and FX, respectively, and a common L chain (L404) (heavy chains: SEQ ID NOs: 10 and 11; light chain: SEQ ID NO: 12). A possible method for reducing the reactivity with an anti-ACE910 (Emicizumab) idiotype antibody and improving the activity of substituting for the cofactor function of FVIII was to obtain from a human antibody library a novel L chain with a sequence totally different from the common L chain, with respect to each of the H chains of the anti-FIX(a) antibody and the anti-FX antibody (Q499 and J327). Thus, the present inventors obtained novel L chains as shown in FIG. 10 and Table 7 in accordance with Reference Example 1. In the present Examples, FIX(a) refers to FIX and/or FIXa.

These antibodies were examined for reactivity with an anti-ACE910 (Emicizumab) idiotype antibody. An anti-ACE910 (Emicizumab) idiotype antibody was obtained by the following method. First, the F(ab')$_2$ of Q499/L404 and the F(ab')$_2$ of J327/L404 from ACE910(Emicizumab), which recognize FIX(a) and FX, respectively, were administered to rabbits, and anti-Q499/L404 F(ab')$_2$ rabbit serum and anti-J327/L404 F(ab')$_2$ rabbit serum were obtained. Ammonium sulfate fractions of these sera were flowed through a human IgG-bound column to remove human IgG-reactive antibodies. Next, affinity purification was performed using a Q499/L404 (or J327/L404)-bound column, and then treatment with a J327/L404 (or Q499/L404)-bound column was performed to remove J327/L404 (or Q499/L404)-reactive antibodies so that a polyclonal anti-idiotype antibody specifically binding to Q499/L404 (or J327/L404) was obtained.

The obtained anti-idiotype antibody was used to measure the strength of its binding with labeled ACE910 (Emicizumab) by electrochemiluminescence immunoassay, whereby inhibition of the binding by a test substance was evaluated. First, a test substance (bispecific antibody) was added at a concentration of 0, 1, 3, 10, 30, or 100 pg/mL to a mixture of the Q499/L404 idiotype antibody, the anti-J327/L404 idiotype antibody, biotin-labeled ACE910 (Emicizumab), and SULFO-TAG-labeled ACE910 (Emicizumab). The resulting mixture was incubated overnight in a refrigerator. The mixture was then added to a 96-well plate. After the plate was washed, the binding strength was measured by the electrochemiluminescence method.

As an example, the result for bispecific antibody Q499/QNK131/J327/JNL095 (variable regions: SEQ ID NOs: 45/13//46/31; constant regions: SEQ ID NOs: 95/99//97/101) shown in Table 2 and the result for Q499/QL20//J327/JL01 (variable regions: SEQ ID NOs: 45/43//46/44; constant regions: SEQ ID NOs: 95/99//97/101) prepared in Example 3 are shown in FIG. 1. ACE910 (Emicizumab) lowered the strength of binding between labeled-ACE910 (Emicizumab) and the anti-idiotype antibody in a manner dependent on the concentration of the added antibody, thus showing an inhibitory effect. On the other hand, the antibodies with the novel L chains were found to show significantly reduced binding with the anti-ACE910 (Emicizumab) idiotype antibody.

Thus, the present inventors successfully obtained novel L chains which, even when they are paired with the same H chains of ACE910 (Emicizumab) (SEQ ID NOs: 45 and 46), show significantly reduced binding with the anti-ACE910 (Emicizumab) idiotype antibody and have an activity of substituting for the cofactor function of FVIII. Therefore, it is expected that these bispecific antibodies can be administered even to hemophilia A patients in whom an anti-ACE910 (Emicizumab) idiotype antibody has been induced.

TABLE 2

Bispecific antibodies examined for reactivity with anti-ACE910 (Emicizumab) idiotype antibody

| Clone name | Heavy chain 1 variable region SEQ ID NO | Light chain 1 variable region SEQ ID NO | Heavy chain 2 variable region SEQ ID NO | Light chain 2 variable region SEQ ID NO |
|---|---|---|---|---|
| Q499/QNK131//J327/JNL095 | 45 | 13 | 46 | 31 |
| Q499/QL20//J327/JL01 | 45 | 43 | 46 | 44 |

Example 2

Production of Variants and H Chain Variants of the Bispecific Antibodies Having the Novel L Chains In order to improve the FVIII cofactor function-substituting activity of the bispecific antibodies having the novel L chains obtained in Reference Example 1, QNK131 (SEQ ID NO: 13), a novel L chain for the anti-FIX(a) antibody, and JNL095 (SEQ ID NO: 31), a novel L chain for the anti-FX antibody, were selected, and their amino acids were comprehensively mutated by methods known to the person skilled in the art such as PCR. The mutants were subjected to large-scale screening for the FVIII cofactor function-substituting activity, and thereby amino acid substitution variants with improved FVIII cofactor function-substituting activity were produced.

At the same time, using the obtained novel L chains, substitution variants were produced in which all CDRs of Q499 and J327 were comprehensively mutated by substitution with all amino acids except cysteine. The variants were subjected to large-scale screening for the FVIII cofactor function-substituting activity to find amino acid substitutions that improved the FVIII cofactor function-substituting activity.

Figure 2:
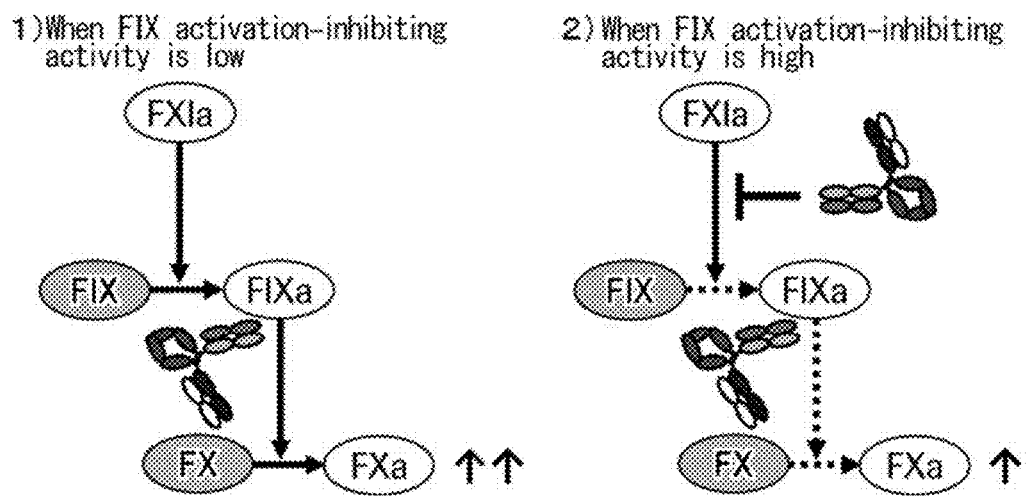
FIG. 2 shows the effects that FIX activation-inhibiting activity may have on FX activation.
Figure 3:
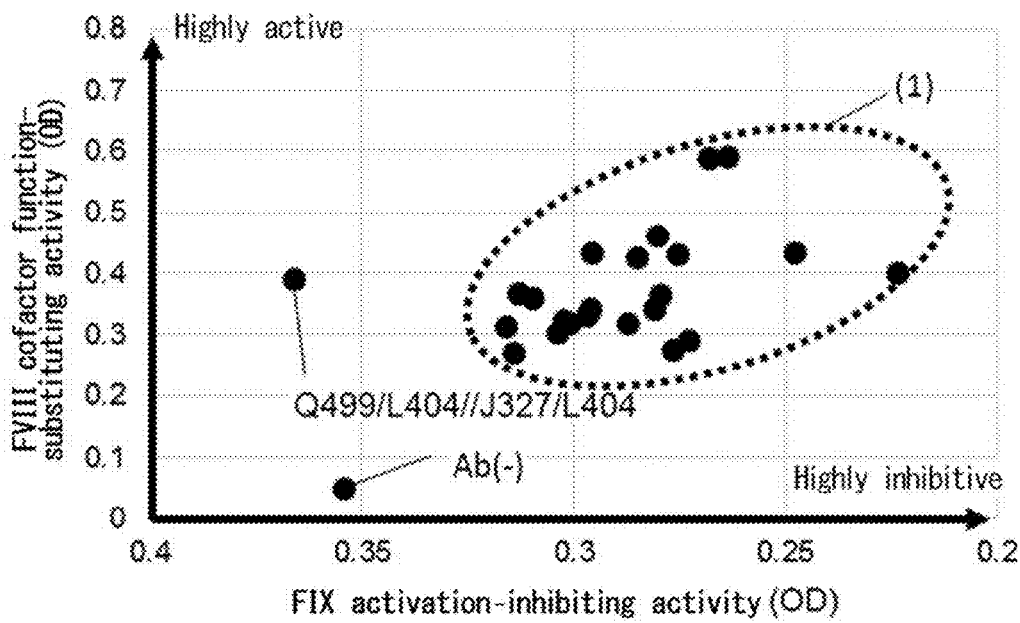
FIG. 3 shows graphs plotted with FIX activation-inhibiting activity against FVIII cofactor function-substituting activity, which result from novel L-chain modifications and H-chain modifications.
Figure 3:
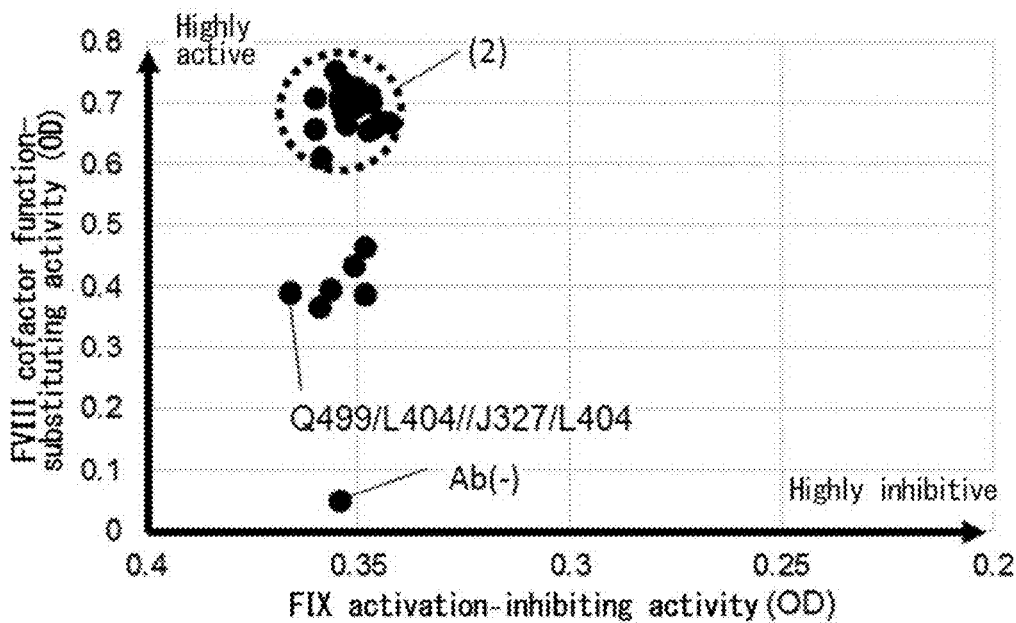

In WO2012/067176, bispecific antibodies whose FVIII cofactor function-substituting activity is increased but whose inhibitory effect on the reaction of FIXa to activate FX using FVIIIa as a cofactor is not enhanced have successfully been obtained. The present optimization process also improved the FVIII cofactor function-substituting activity without enhancing the inhibitory effect on the reaction of FIXa to activate FX using FVIIIa as a cofactor, but was newly found to affect the activation of FIX by FXIa (FIG. 3(1)). The FVIII cofactor function-substituting activity shown in FIG. 3(1), FIG. 3(2), and FIG. 4 was measured by the method described in Reference Example 1 except that the concentration of Human Factor X was changed to 22.9 pg/mL, and the concentration of phospholipid to 6.0 μM. In addition, the activity of inhibiting FIX activation refers to reduced absorbance in the activation reaction of FIX by FXIa as determined using colorimetry. Specifically, the measurement was performed by the following method. Five pL of an antibody solution diluted with TBSB was mixed with 5 μL of 3 U/mL Human Factor IX (Christmassin M, Japan Blood Products Organization), and incubated in a 384-well plate at room temperature for 30 minutes. Enzymatic reaction in this mixture was initiated by adding 5 μL of 90 ng/mL Human Factor XIa (Enzyme Research Laboratories). After 60 minutes, the reaction was ceased by adding 5 μL of 0.5M EDTA. Coloring reaction was initiated by adding 10 μL of a coloring substrate solution. After 60 minutes of the coloring reaction, a change in absorbance at 405 nm was measured using SpectroMax 340PC384 (Molecular Devices). The solvent of Human Factor IX and Human Factor XIa was TBSB containing 6.0 μM phospholipid solution (SYSMEX CO.) and 1.5 mM $CaCl_2$. The coloring substrate solution, Spectrozyme FIX (Sekisui Diagnostics), was used for this assay after being dissolved in purified water to yield a 6.7 mM solution and then mixed with ethylene glycol at a ratio of 5:8. As a result, the above samples showed a decrease in the OD value as compared to the no-antibody condition, indicating that the production of FIXa was reduced. In the FVIII cofactor function-substituting activity and the FIX activation-inhibiting activity as shown in FIG. 3, the final concentration of antibody was 100 pg/mL. The final concentration of antibody refers to a concentration in the mixed solution of the antibody solution, Human Factor IX, and Human Factor XIa. In the intrinsic coagulation reaction in vivo, FIXa is produced via activation of FIX by FXIa. Therefore, inhibition of this activation process results in decreased production of FIXa, which further has a negative impact on the magnitude of increase in the FIXa-mediated activation of FX with a bispecific antibody having a FVIII cofactor function-substituting activity (FIG. 2). Hence, in order to aim at obtaining a bispecific antibody with a higher FVIII cofactor function-substituting activity, it is preferable for the FIX activation-inhibiting activity to be as low as possible.

Accordingly, based on the results of the above-mentioned large-scale screening for FVIII cofactor function-substituting activity, the present inventors found a plurality of amino acid modifications that significantly elevate the FVIII cofactor function-substituting activity as compared to the elevation of the FIX activation-inhibiting activity. Specifically, they are S30R, S31R, T53R (all Kabat numbering), etc. These modifications were multiply introduced into QNK131 (SEQ ID NO: 13) to produce QL20 (QAL201) (SEQ ID NO: 43). Further, amino acid substitution variants were produced by comprehensively introducing multiple CDR amino acid substitutions into a variant having QL20 as an L chain for the anti-FIX(a) antibody. The variants were subjected to large-scale screening measuring FVIII cofactor function-substituting activity and FIX activation-inhibiting activity. As a result, combinations of modifications were found which lowered the FIX activation-inhibiting activity while maintaining the FVIII cofactor function-substituting activity. Specifically, they were combinations of basic and acidic residues, such as S30R/S31R/N32D, S30R/S31R/N32E, and Q27R/R93D (all Kabat numbering), in the L chain of the anti-FIX(a) antibody.

In addition, amino acid substitution variants were also produced by comprehensively introducing amino acid substitutions into the FRs, non-antigen contact sites, and subjected to activity screening. As a result, a plurality of modifications were found which further elevated the FVIII cofactor function-substituting activity while maintaining the FIX activation-inhibiting activity. Specifically, amino acid substitution variants in which Phe83 in the L chain of the anti-FIX(a) antibody was substituted with a Met residue, Ala residue, or such, or Arg45 with a Glu residue, showed increased FVIII cofactor function-substituting activity.

To optimize the combination of the above-mentioned modifications and also the balance of the antigen binding affinity (association and dissociation) of both the anti-FIX(a) arm and the anti-FX arm, exhaustive pairings of anti-FIX(a) and anti-FX antibodies were made. Specifically, for the anti-FIX(a) antibody, the H chain was modified by introducing Y100E, Y100eI, or deletion of G100a, or a combination of these, the L chain was modified by introducing A55E, K92R, insertion of Pro at position 95, or L96G, or a combination of these. For the anti-FX antibody, the H chain was modified by introducing T28E/D31H or D31N/Q, 1515, G56T/R, S57V, Y59S, E61R, E62K, D65N/Q, V67L, K731, S82bE, E102V, or a combination of these modifications, and, for the L chain, JNL095 (SEQ ID NO: 31) was modified by introducing E24T, N26E, H27Q, G29S, D30S/Q/E, K31R, H32E/Q, R50Q, D92A, S94D, S95D/A, A95aY, V96T, or a combination of these modifications (all Kabat numbering), thereby optimizing the antigen binding affinity.

Figures 1, 4:
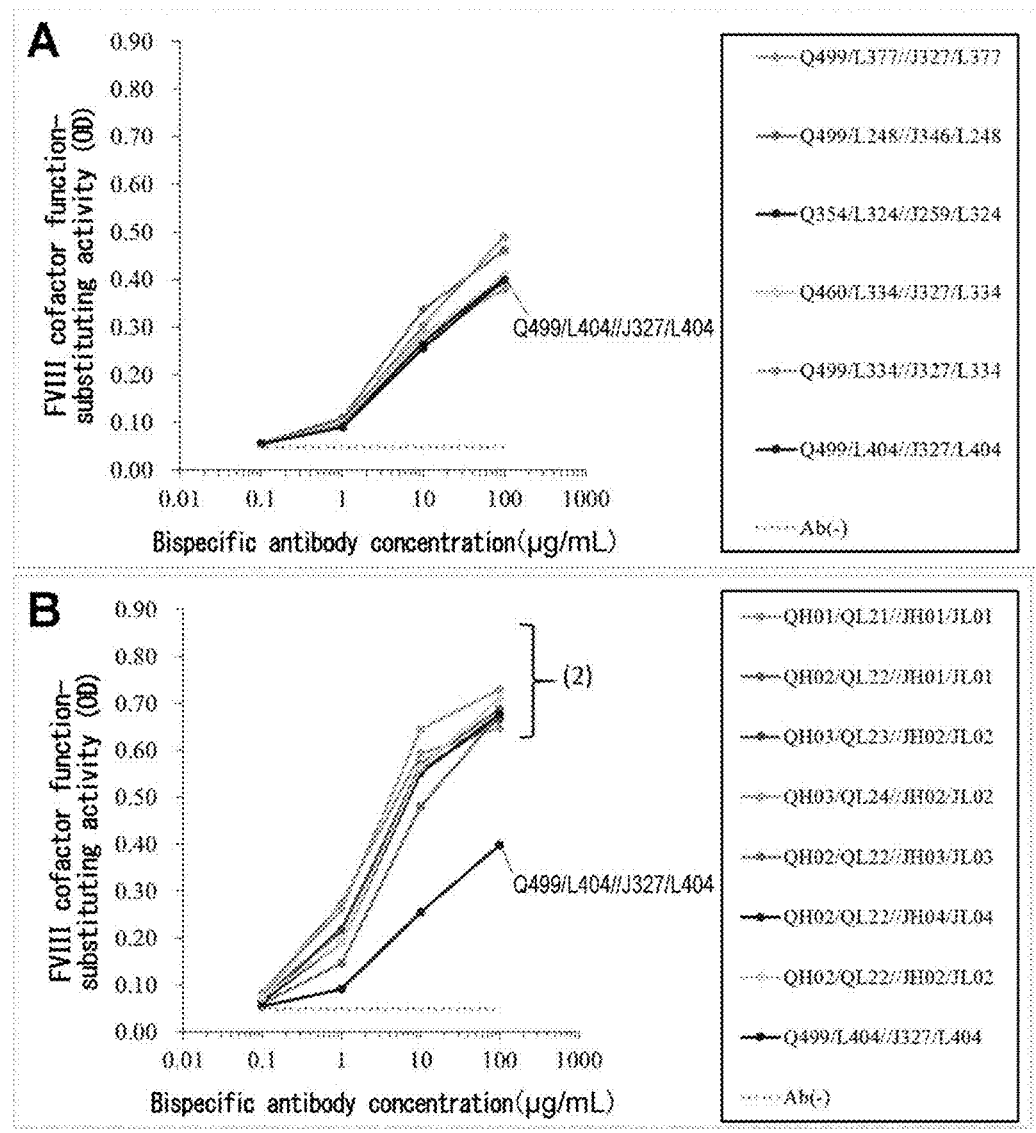
Figures 2, 4:
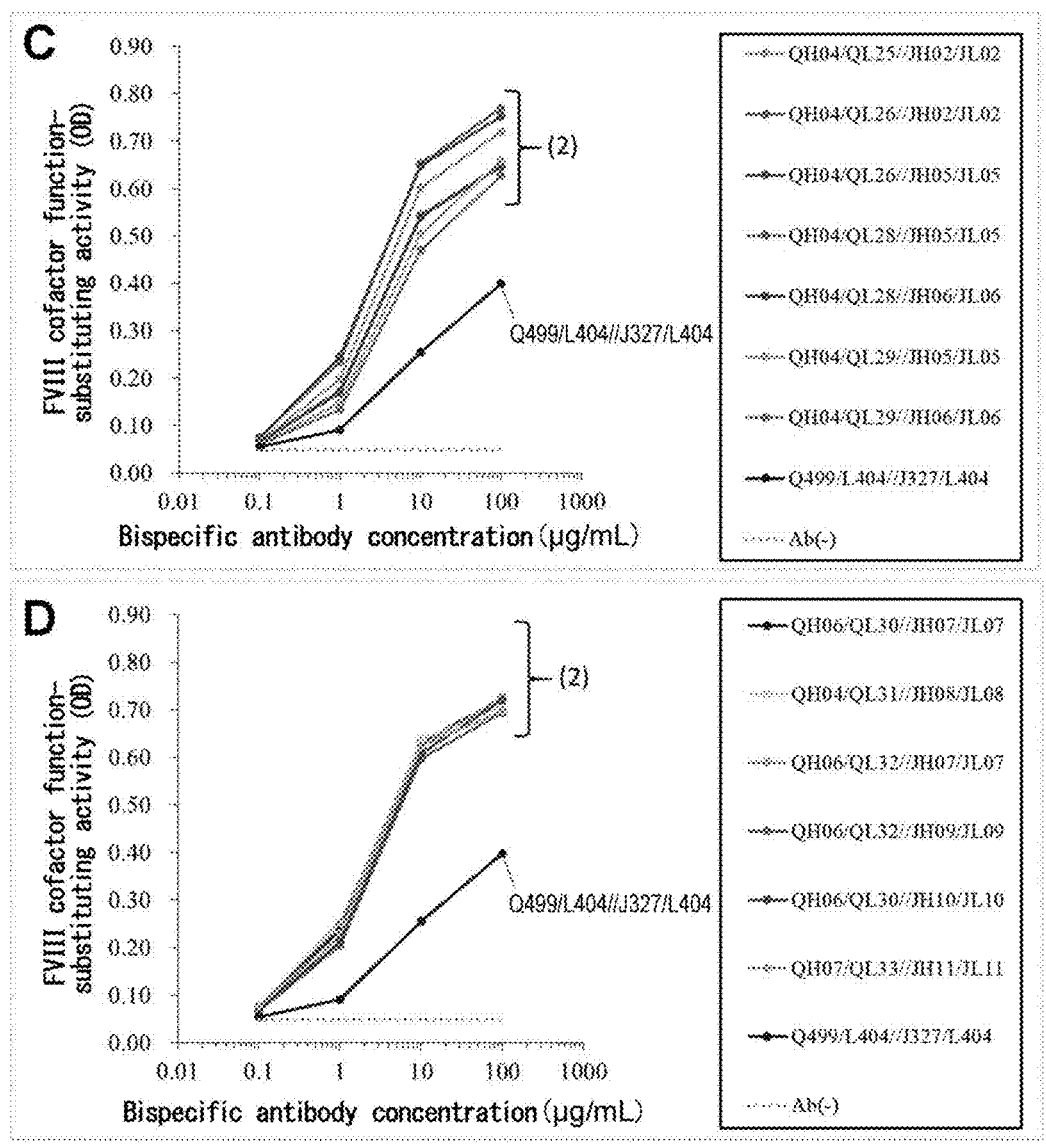

As a result, the present inventors successfully produced variants whose FIX activation-inhibiting activity was not elevated but whose FVIII cofactor function-substituting activity was dramatically improved (bispecific antibodies consisting of a combination of an H chain constant region of any of SEQ ID NOs: 95-98 and an L chain constant region of any of SEQ ID NOs: 99-104, and a combination of variable regions shown in Table 4) as compared to ACE910 (Emicizumab) and as compared to the variants that had been demonstrated in WO2012067176 to have higher FVIII cofactor function-substituting activity than ACE910 (Emicizumab) (bispecific antibodies consisting of an H chain constant region of SEQ ID NO: 95 or 97, an L chain constant region of SEQ ID NO: 99, and a combination of variable regions shown in Table 3) (FIG. 3(2)). Moreover, as shown in FIG. 4, these variants were found to have remarkably improved maximum activity and specific activity compared to ACE910 (Emicizumab). The FVIII cofactor function-substituting activity shown in FIG. 4 was measured by the method described in Reference Example 1 except that the concentration of Human Factor X was changed to 22.9 μg/mL, and the concentration of phospholipid to 6.0 ∞M.

Figure 5:
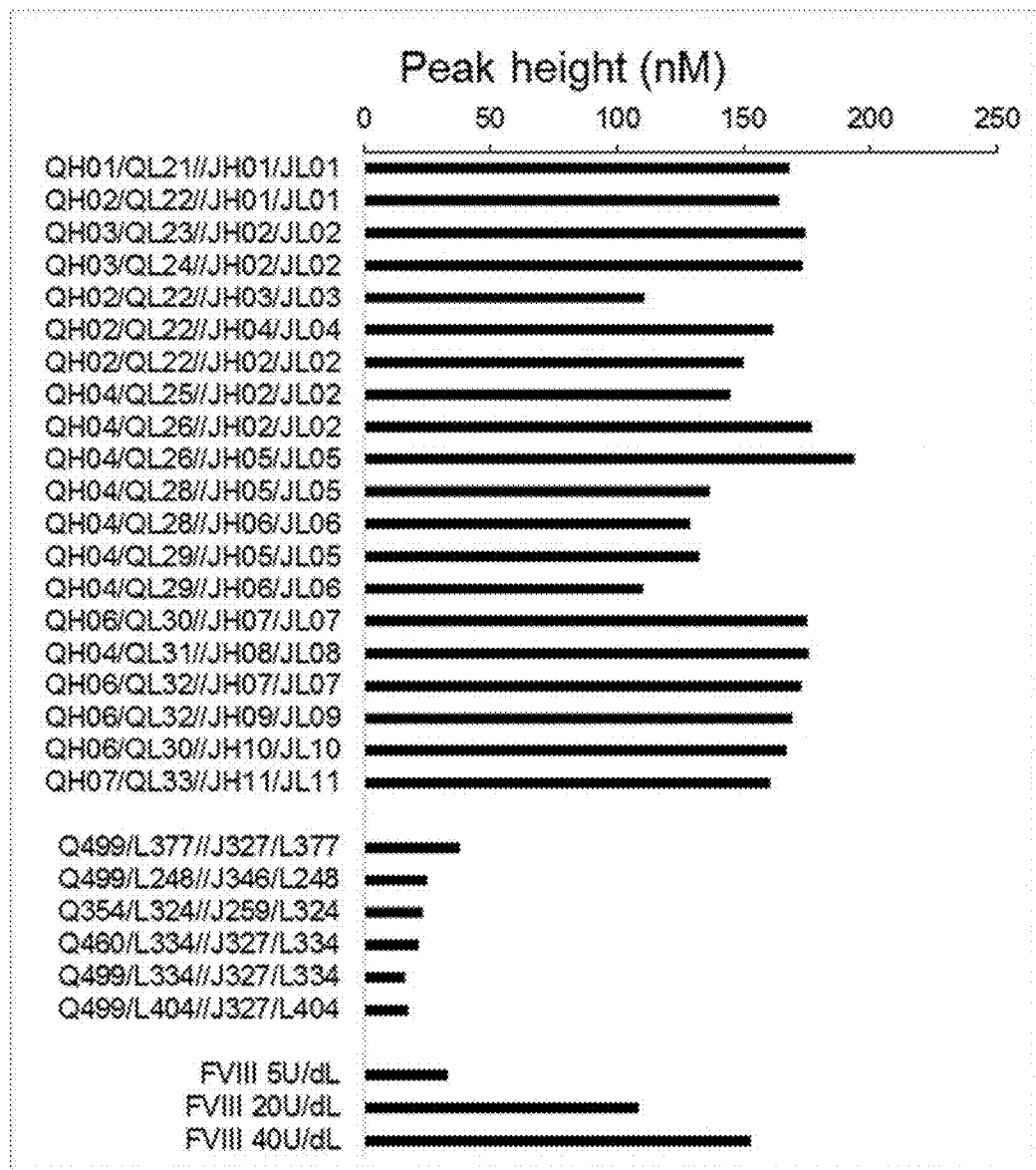
FIG. 5 shows the maximum amounts of thrombin generation (peak heights) for the bispecific antibodies having a combination of H-chain and L-chain modifications in thrombin generation assays.

Furthermore, to confirm that the FVIII cofactor function-substituting activity promotes generation of thrombin in plasma, a thrombin generation test was performed by a method known to the person skilled in the art. Specifically, 8 μL of a bispecific antibody diluted with TBSB was added to 72 μL of FVIII deficient plasma (George King), and incubated at room temperature for 30 minutes or longer. Next, 20 pL of a trigger reagent containing 20 μL of phospholipid and 5 ng/mL of Human Factor XIa (Enzyme Research Laboratories) was added. Further, 20 μL of a mixed solution of Fluo-Buffer and Fluo-Substrate from FluCa-Kit (Thrombinoscope) was added to initiate coagulation reaction. The amount of thrombin generated was assessed using a thrombin generation fluorimetry/analysis system (Thrombinoscope). The antibody was added to give a final concentration of 10 pg/mL. The final concentration of antibody refers to a concentration in the mixture of FVIII deficient plasma and the antibody solution. When the peak height at the time of antibody addition was used as an index of the level of thrombin generation, the result showed that all bispecific antibodies in Table 5 showed a further increase in the level of thrombin generation as compared to ACE910 (Emicizumab, Q499/L404//J327/L404). Moreover, when compared with FVIII added as a positive control (Kogenate-FS BIO-SET; Bayer), a number of variants (QH01/QL21//JH01/JL01, QH02/QL22//JH01/JL01, QH03/QL23//JH02/JL02, QH03/QL24//JH02/JL02, QH02/QL22//JH04/JL04, QH04/QL26//JH02/JL02, QH04/QL26//JH05/JL05, QH06/QL30//JH07/JL07, QH04/QL31//JH08/JL08, QH06/QL32//JH07/JL07, QH06/QL32//JH09/JL09, QH06/QL30//JH10/JL10, QH07/QL33//JH11/JL11) showed a higher thrombin generation level than that when 40 U/dL of FVIII was added, which is the level of healthy persons (FIG. 5).

TABLE 3

Combinations of variable regions of ACE910 (Emicizumab) and the variants demonstrated in WO2012067176 to have higher FVIII cofactor function-substituting activity than ACE910 (Emicizumab)

| | Anti-FIX(a) antibody | | Anti-FX antibody | |
|---|---|---|---|---|
| Clone name | Heavy chain variable region SEQ ID NO | Light chain variable region SEQ ID NO | Heavy chain variable region SEQ ID NO | Light chain variable region SEQ ID NO |
| Q499/L377//J327/L377 | 45 | 52 | 46 | 52 |
| Q499/L248//J346/L248 | 45 | 53 | 50 | 53 |
| Q354/L324//J259/L324 | 49 | 54 | 51 | 54 |
| Q460/L334//J327/L334 | 48 | 55 | 46 | 55 |
| Q499/L334//J327/L334 | 45 | 55 | 46 | 55 |

TABLE 4

Variants in which only the FVIII cofactor function-substituting activity was dramatically improved

| | Anti-FIX(a) antibody | | Anti-FX antibody | |
|---|---|---|---|---|
| Clone name | Heavy chain variable region SEQ ID NO | Light chain variable region SEQ ID NO | Heavy chain variable region SEQ ID NO | Light chain variable region SEQ ID NO |
| QH01/QL21//JH01/JL01 | 56 | 61 | 73 | 84 |
| QH02/QL22//JH01/JL01 | 57 | 62 | 73 | 84 |

TABLE 4-continued

Variants in which only the FVIII cofactor function-substituting activity was dramatically improved

| | Anti-FIX(a) antibody | | Anti-FX antibody | |
|---|---|---|---|---|
| Clone name | Heavy chain variable region SEQ ID NO | Light chain variable region SEQ ID NO | Heavy chain variable region SEQ ID NO | Light chain variable region SEQ ID NO |
| QH03/QL23//JH02/JL02 | 58 | 63 | 74 | 85 |
| QH03/QL24//JH02/JL02 | 58 | 64 | 74 | 85 |
| QH02/QL22//JH03/JL03 | 57 | 62 | 75 | 86 |
| QH02/QL22//JH04/JL04 | 57 | 62 | 76 | 87 |
| QH02/QL22//JH02/JL02 | 57 | 62 | 74 | 85 |
| QH04/QL25//JH02/JL02 | 59 | 65 | 74 | 85 |
| QH04/QL26//JH02/JL02 | 59 | 66 | 74 | 85 |
| QH04/QL26//JH05/JL05 | 59 | 66 | 77 | 88 |
| QH04/QL28//JH05/JL05 | 59 | 67 | 77 | 88 |
| QH04/QL28//JH06/JL06 | 59 | 67 | 78 | 89 |
| QH04/QL29//JH05/JL05 | 59 | 68 | 77 | 88 |
| QH04/QL29//JH06/JL06 | 59 | 68 | 78 | 89 |
| QH06/QL30//JH07/JL07 | 60 | 69 | 79 | 90 |
| QH04/QL31//JH08/JL08 | 59 | 70 | 80 | 91 |
| QH06/QL32//JH07/JL07 | 60 | 71 | 79 | 90 |
| QH06/QL32//JH09/JL09 | 60 | 71 | 81 | 92 |
| QH06/QL30//JH10/JL10 | 60 | 69 | 82 | 93 |
| QH07/QL33//JH11/JL11 | 105 | 72 | 83 | 94 |

Example 3

Antibody PK (Pharmacokinetics) of the Produced Bispecific Antibodies

For convenience in medication treatment of hemophilia A patients, it is preferred that an antibody to be administered have a longer half-life in order to reduce the frequency of administration. The major methods for improving antibody PK (pharmacokinetics) include a method of increasing recycling into blood via FcRn, and a method of decreasing cellular uptake via non-specific binding (ADME and Translational Pharmacokinetics/Pharmacodynamics of Therapeutic Proteins (2015) p25-37).

As demonstrated in Example 2, the present inventors successfully produced bispecific antibodies with dramatically improved FVIII cofactor function-substituting activity while preventing an increase in their FIX activation-inhibiting activity. In the process of creating these antibodies, the inventors also made an attempt to ameliorate the non-specific binding, which could affect the PK of the antibodies.

Figure 6:
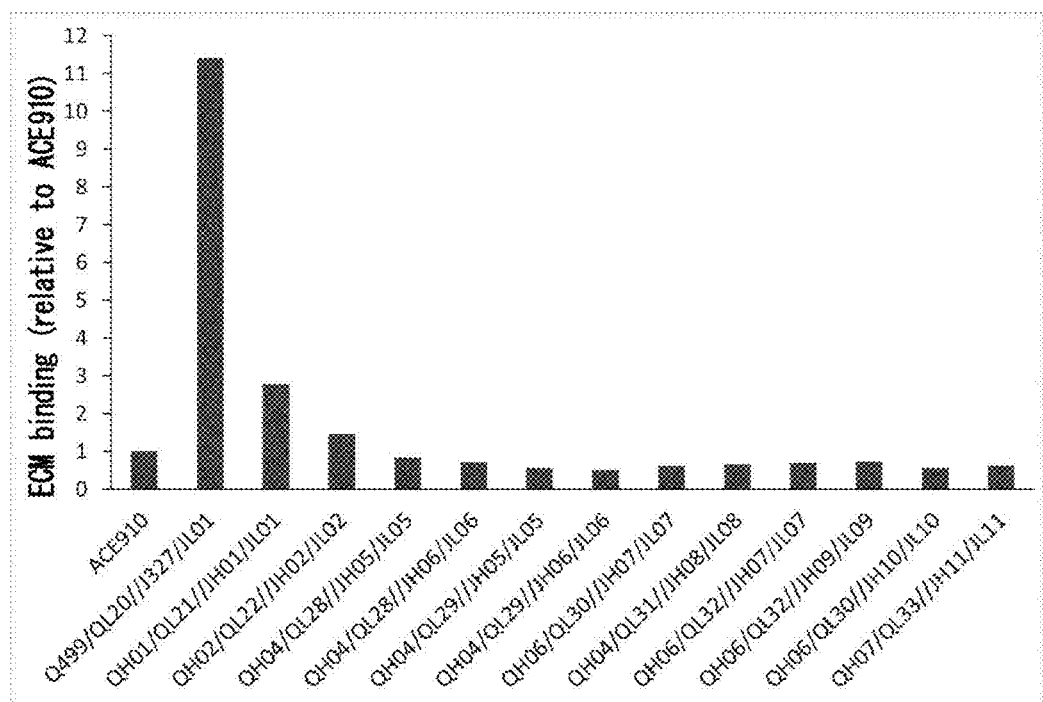
FIG. 6 shows the ECM binding of the prepared bispecific antibodies.

Specifically, a system of assaying the binding to extracellular matrix (ECM), which is known as a system of evaluating non-specific binding in vitro, was used to evaluate the antibodies (US patent 2014/0080153). As a result, the ECM binding of variant Q499/QL20//J327/JL01 (variable regions: SEQ ID NOs: 45/43/46/44), which showed a high FVIII cofactor function-substituting activity in Example 2, was very high when compared to ACE910 (Emicizumab). However, for variants in which the H chain of the anti-FIX (a) antibody was modified by G97D, Y100D, Y100E, and such, and the L chain of the anti-FIX(a) antibody was modified by N32D, N32E, A55E, and such (consisting of a combination of a Hch constant region of any of SEQ ID NOs: 95-98 and a Lch constant region of any of SEQ ID NOs: 99-104, and a combination of variable regions shown in Table 5), the ECM binding was successfully remarkably reduced (FIG. 6).

Figure 7:
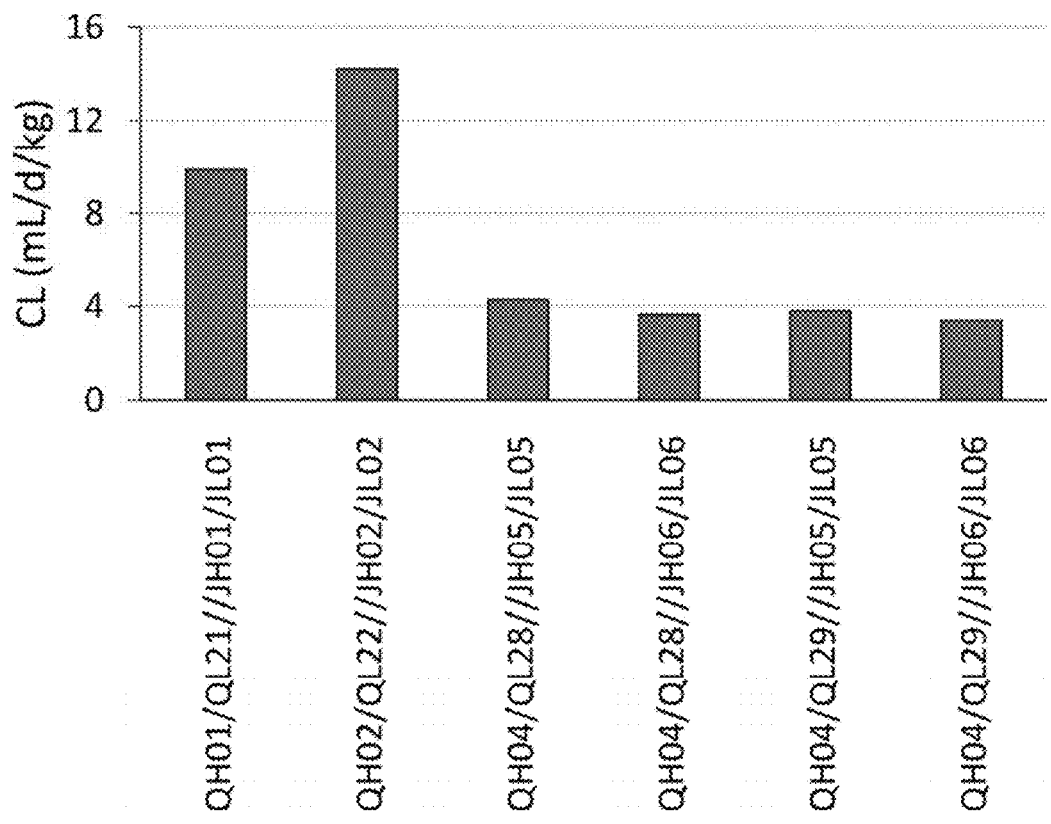
FIG. 7 shows the antibody PK of the prepared bispecific antibodies.

Further, variants made by introducing the ACT-Fc modification (Mabs, (2017) Vol. 9, No. 5, 844-853), which improves recycling into the blood via FcRn, into the antibody constant regions of the above variants, were subjected to a mouse intravenous administration test. After antibody administration, blood was sampled over time and plasma was obtained. Then the concentration of the administered antibody in plasma was measured by the LC-MS/MS method. Time-course data of the antibody concentration in plasma were analyzed with WinNonlin ver 7.0 (Certara) to calculate antibody clearance (CL). As a result, when compared with the variant without the ACT-Fc modification, i.e. QH01/QL21//JH01/JL01 (variable regions: SEQ ID NOs: 56/61//73/84) or QH02/QL22//JH02/JL02 (variable regions: SEQ ID NOs: 57/62//74/85), the antibody PK (clearance: CL) was successfully remarkably improved in the variants with the ACT-Fc modification, namely, QH04/QL28//JH05/JL05 (variable regions: SEQ ID NOs: 59/67//77/88), QH04/QL28//JH06/JL06 (variable regions: SEQ ID NOs: 59/67//78/89), QH04/QL29//JH05/JL05 (variable regions: SEQ ID NOs: 59/68//77/88), and QH04/QL29//JH06/JL06 (variable regions: SEQ ID NOs: 59/68//78/89) (FIG. 7).

TABLE 5

Combinations of variable regions of the bispecific antibodies showing low binding affinity for ECM

| | Anti-FIX(a) antibody | | Anti-FX antibody | |
|---|---|---|---|---|
| Clone name | Heavy chain variable region SEQ ID NO | Light chain variable region SEQ ID NO | Heavy chain variable region SEQ ID NO | Light chain variable region SEQ ID NO |
| QH01/QL21//JH01/JL01 | 56 | 61 | 73 | 84 |
| QH02/QL22//JH02/JL02 | 57 | 62 | 74 | 85 |
| QH04/QL28//JH05/JL05 | 59 | 67 | 77 | 88 |
| QH04/QL28//JH06/JL06 | 59 | 67 | 78 | 89 |
| QH04/QL29//JH05/JL05 | 59 | 68 | 77 | 88 |
| QH04/QL29//JH06/JL06 | 59 | 68 | 78 | 89 |
| QH06/QL30//JH07/JL07 | 60 | 69 | 79 | 90 |
| QH04/QL31//JH08/JL08 | 59 | 70 | 80 | 91 |
| QH06/QL32//JH07/JL07 | 60 | 71 | 79 | 90 |
| QH06/QL32//JH09/JL09 | 60 | 71 | 81 | 92 |
| QH06/QL30//JH10/JL10 | 60 | 69 | 82 | 93 |
| QH07/QL33//JH11/JL11 | 105 | 72 | 83 | 94 |

Example 4

Production of Bispecific Antibodies

As described above, the present inventors introduced modifications into the two different heavy chains (H chains) and the two different light chains (L chains) of bispecific antibodies to create antibodies with advantageous efficacy and properties.

When a bispecific antibody is expressed, two different H chains and two different L chains are expressed. Therefore, 10 different combinations are possible. Since only one of these combinations has bispecificity of interest, obtaining a bispecific antibody of interest requires purifying one antibody of interest from 10 different antibodies, which is highly inefficient and difficult. As means to solve this problem, there is a known method in which amino acid substitutions are introduced into the CH3 domain of IgG H chains so that IgG with two different H chains combined is preferentially secreted, and, to further efficiently obtain a molecule of interest, there are known amino acid substitutions and combinations thereof in the variable regions and the CH1-CL domain interface for promoting desired H chain-L chain association (WO2013065708). However, new pairs of modifications were also examined.

Antibodies Produced and Production Methods

In the description below, the heavy chain and light chain on the anti-FIX(a) antibody side are denoted as Q and κ, respectively, and the heavy chain and light chain on the anti-FX antibody side are denoted as J and λ, respectively.

Bispecific Antibody Q1014-G4T1k.LG.A5/AL869AE.F83M-kT0//J1494-G4T1h.LG.A5/YL681K27Q-lam1NL95 (variable regions: SEQ ID NOs: 106/108//109/111, constant regions: SEQ ID NOs: 107/99//110/101) was used as a template sequence. Combinations of modifications shown in Table 6 were introduced into this antibody to produce variants.

Figure 8:
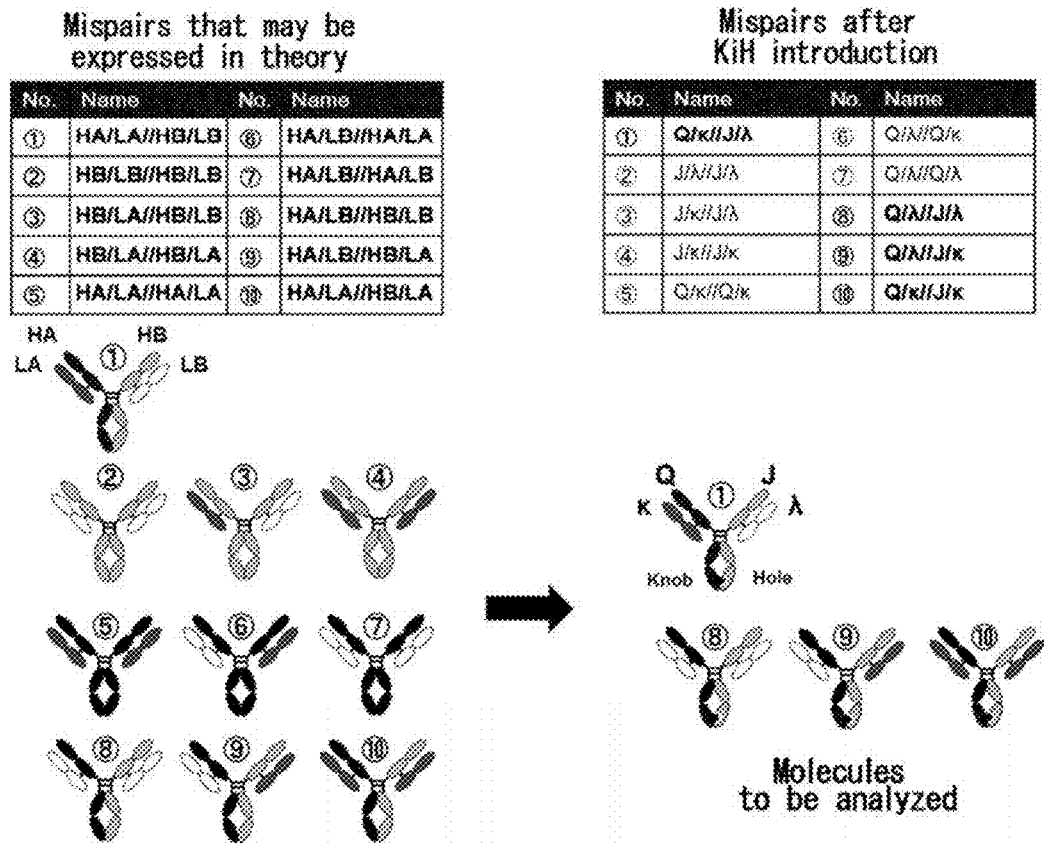
FIG. 8 shows the types of mispairs that may be expressed.

The purpose of this experiment is to assess regulation of heavy chain-light chain association. However, when one heavy chain has a constant region that makes homologous association occur easily, all nine types of mispaired molecules, including not only those with two different heavy chains associated heterologously as shown in FIG. 8(8)-(10) but also those shown in FIG. 8(2)-(7), are expressed. This makes it difficult to analyze and assess the molecule of interest (FIG. 8(1)). Therefore, in order to prevent one heavy chain from causing homologous association, "Knob" and "Hole" modifications (KiH: Knobs into Hole) were introduced into the constant regions of the heavy chains (Q and J), respectively (SEQ ID NOs: 107 and 110) so that the antibodies to be potentially expressed as mispairs would be reduced from 9 types to 3 types (FIG. 8(8)-(10)), and the assay was performed.

At the time of transfection, the four chains were expressed at three plasmid amount ratios (Q:κ:J:λ=1:3:1:1, 1:1:1:1, and 1:1:1:3), and purified by methods known to the person skilled in the art. When these chains are expressed under the conditions where a light chain is excessive, insufficient regulation between the heavy and light chains will promote formation of mispairs. Conversely, if the bispecific antibody of interest is formed at a high rate under all three conditions, the introduced modification pair can be considered as having a higher regulation capability.

In addition, as reference standards of the mispairs used in CIEX (Cation Exchange Chromatography) analysis, reference standards with a common light chain (Q/κ/J/κ and Q/λ/J/λ) were prepared by expression of three chains of Q/κ/J or Q/λ/J.

Assay and Analysis Methods

The produced antibodies were assayed by the CIEX method using Alliance system (Waters). Two-liquid gradient method was performed using YMC-BioPro SP-F, 4.6×100 mm as the assay column, CX-1 pH Gradient Buffer A, pH 5.6 (Thermo) as mobile phase A, and CX-1 pH Gradient Buffer B, pH 10.2 (Thermo) as mobile phase B. Measurement was performed at a wavelength of 280 nm. Data were analyzed using Empower3 (Waters), and the proportion of each detected peak was calculated. In cases where only a single peak was observed when the four chains were expressed, this peak was assigned as the main peak, i.e. peak of the bispecific antibody. When multiple peaks were observed, a peak that did not overlap the peaks of the reference standards of the mispairs having a common light chain was assigned as the main peak.

Results and Discussion

Figures 1, 9:
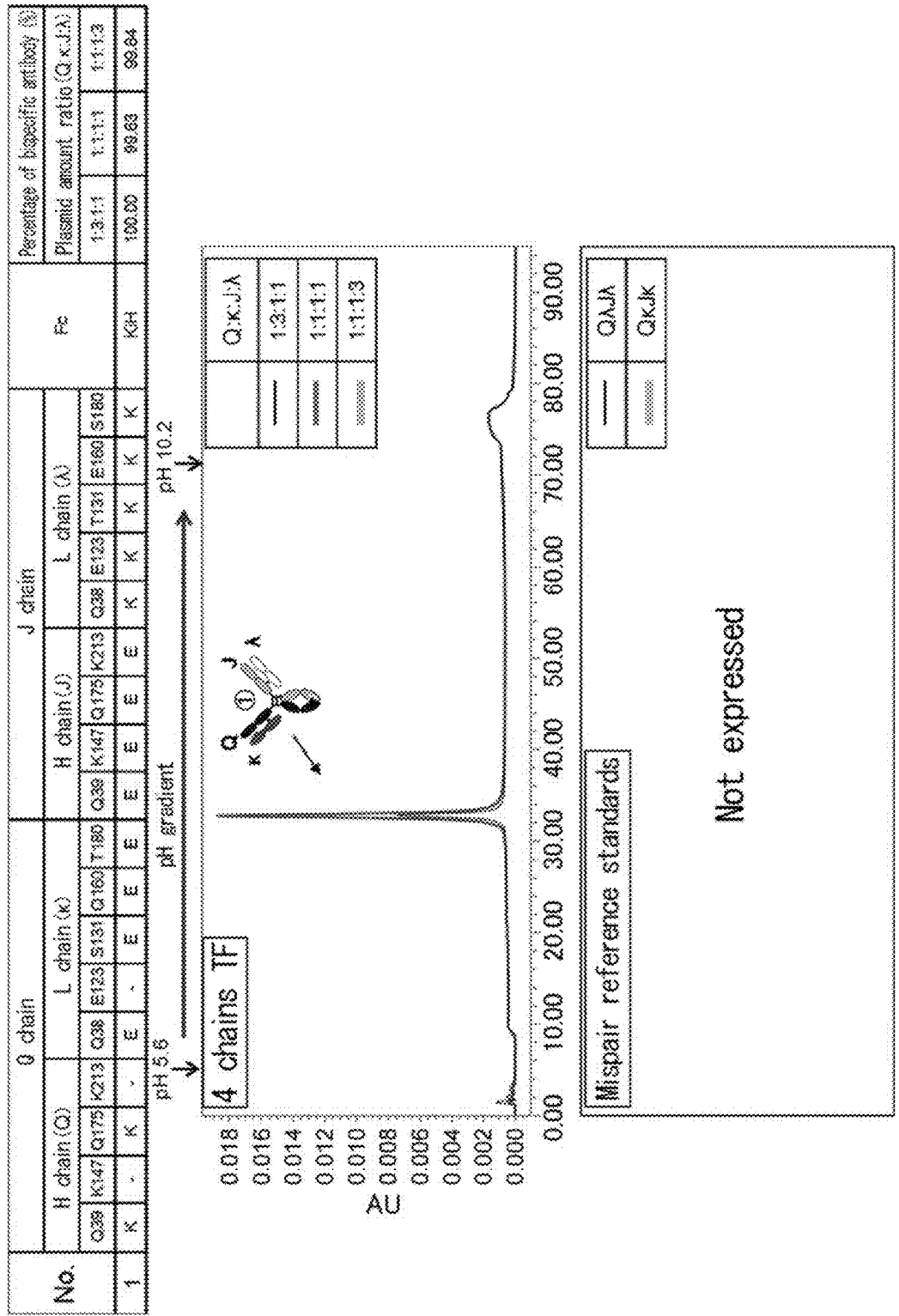
Figures 2, 9:
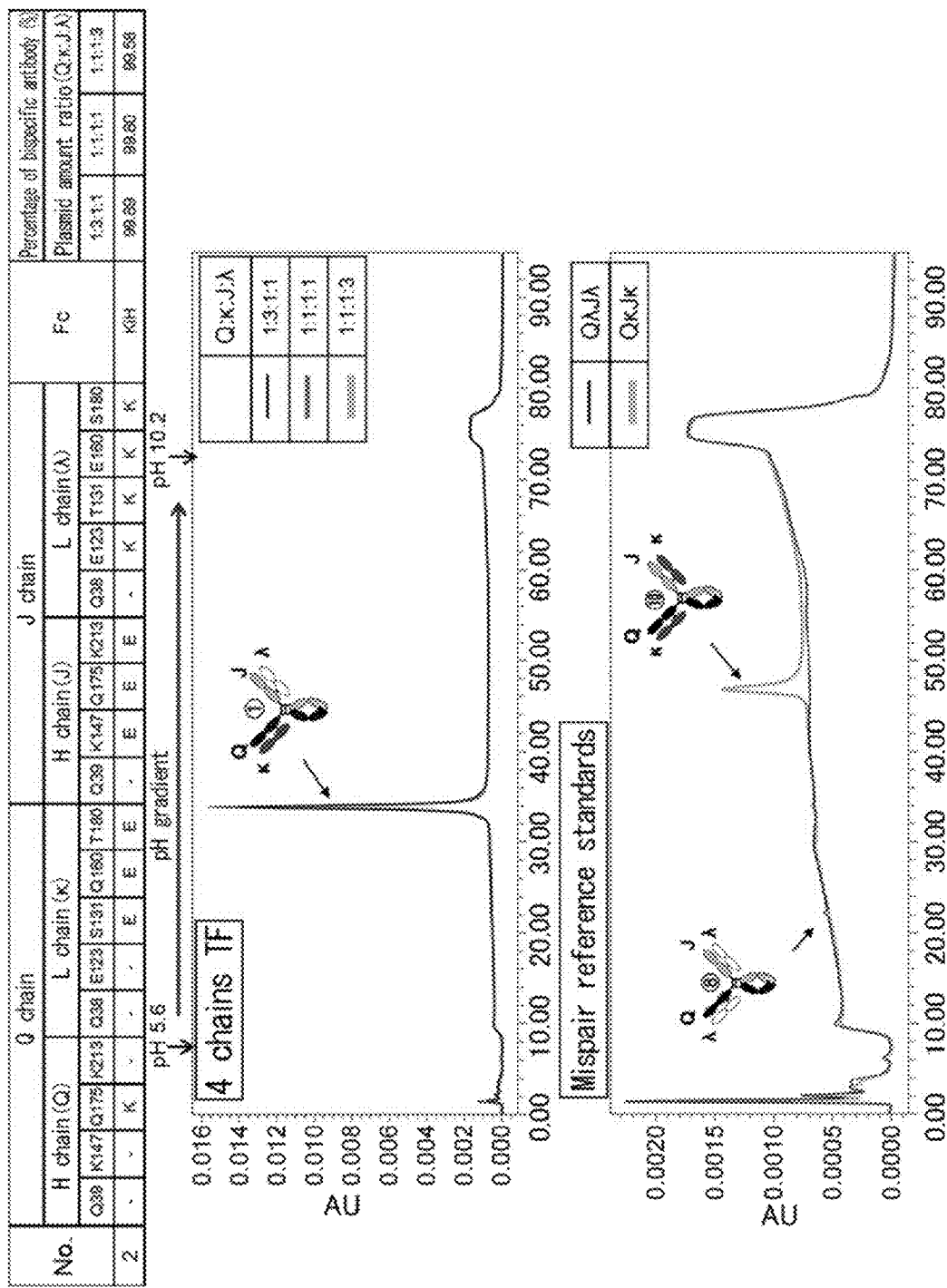
Figures 3, 9:
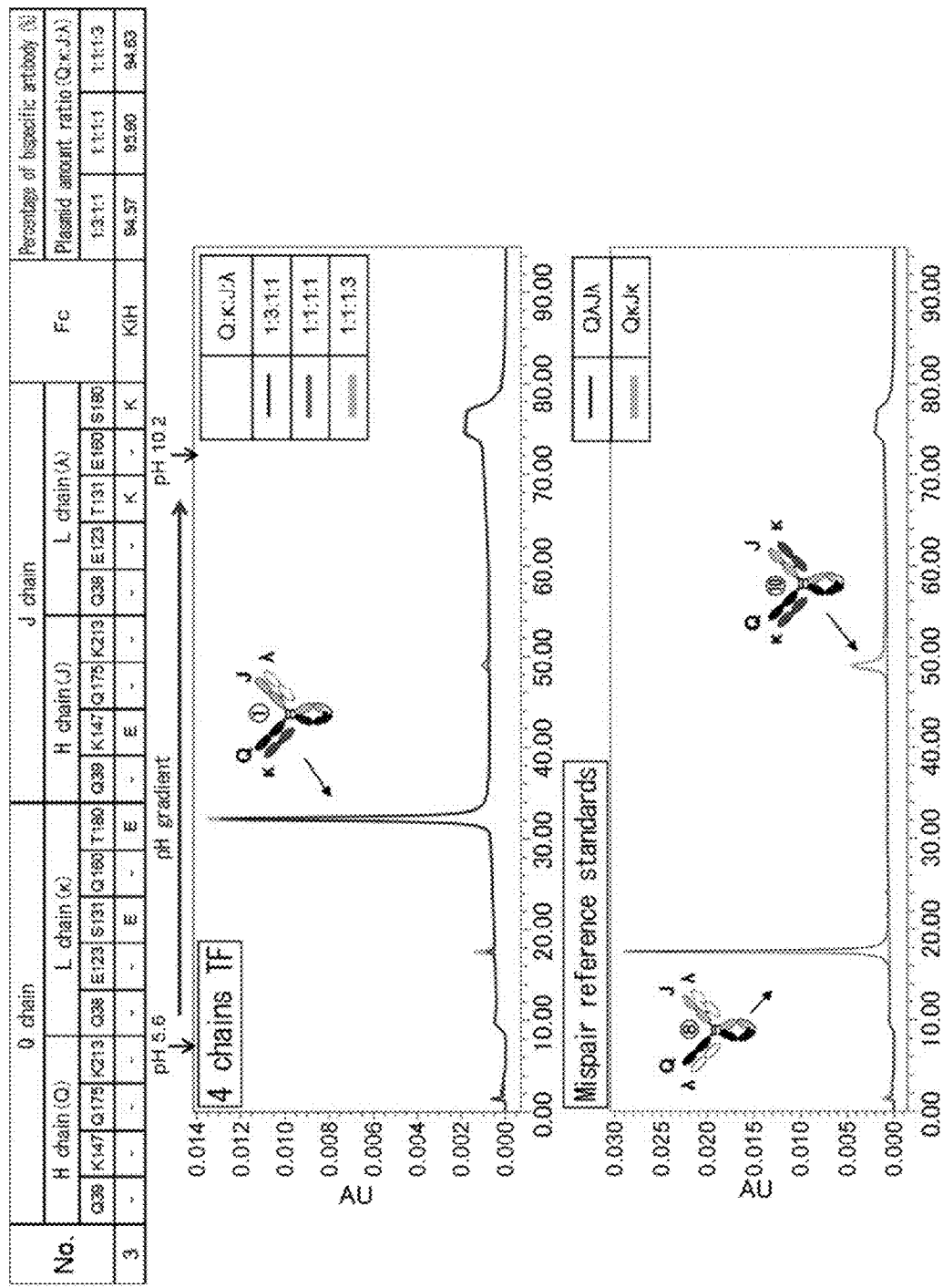
Figures 4, 9:
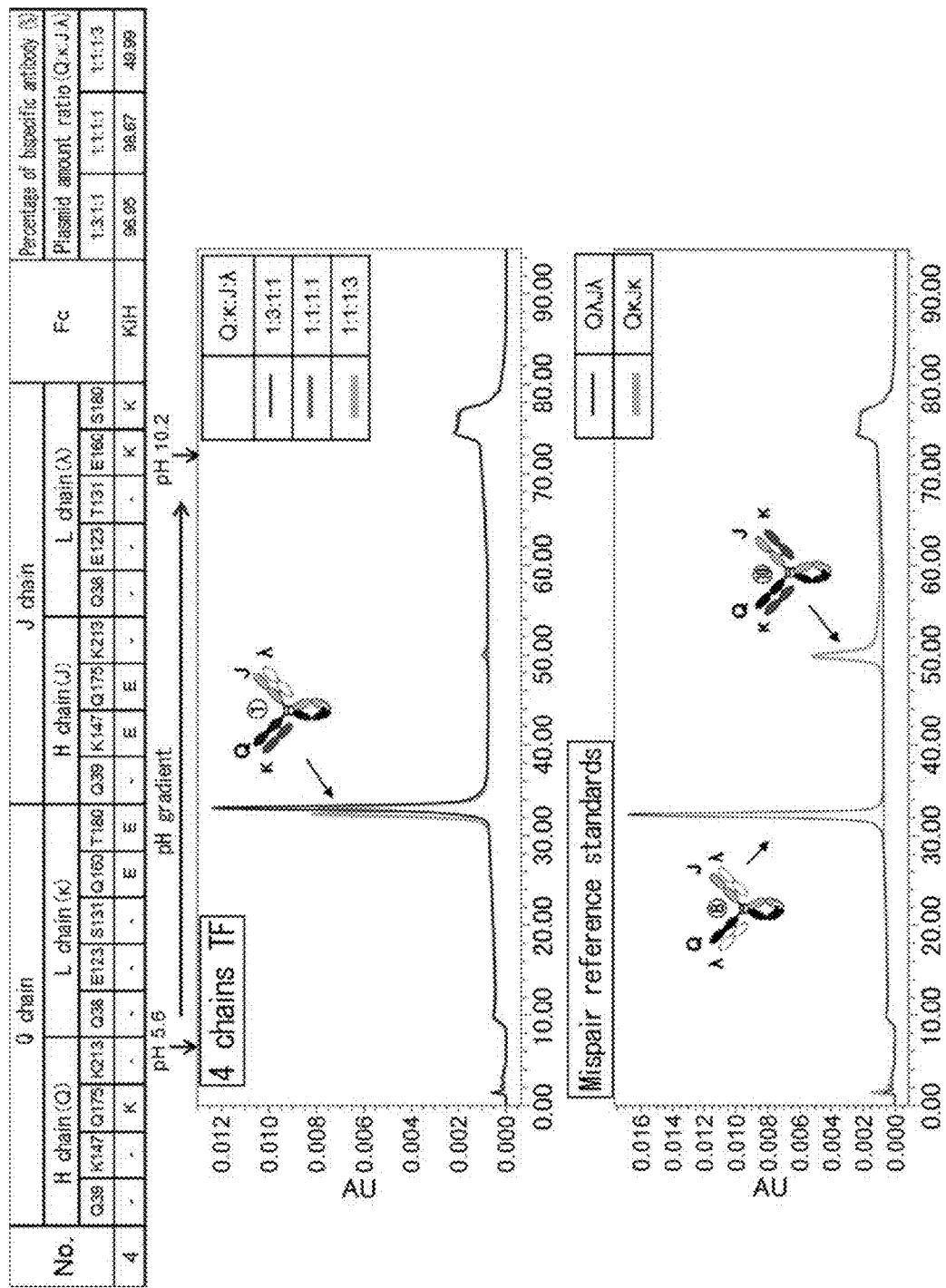
Figures 5, 9:
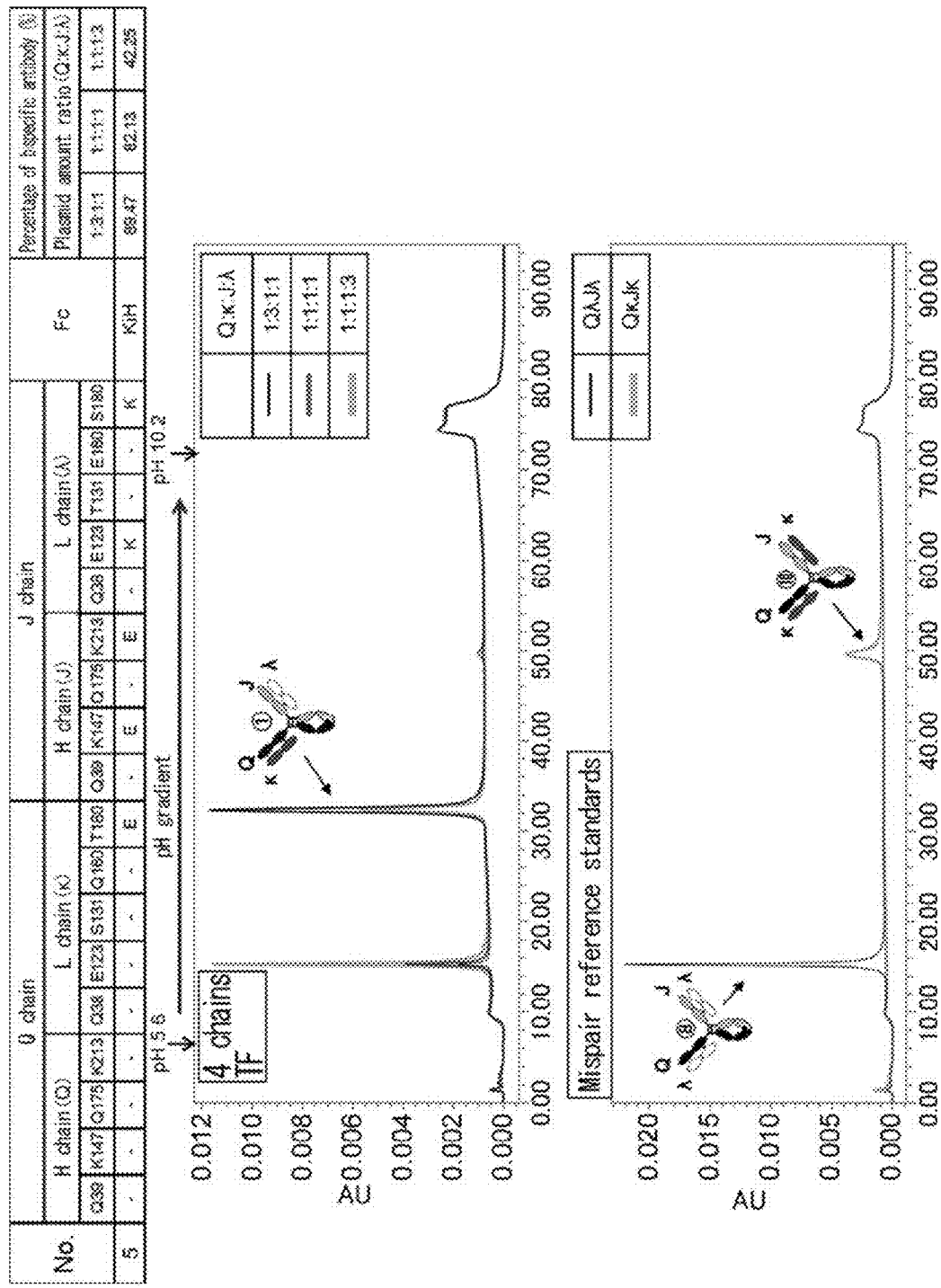
Figures 6, 9:
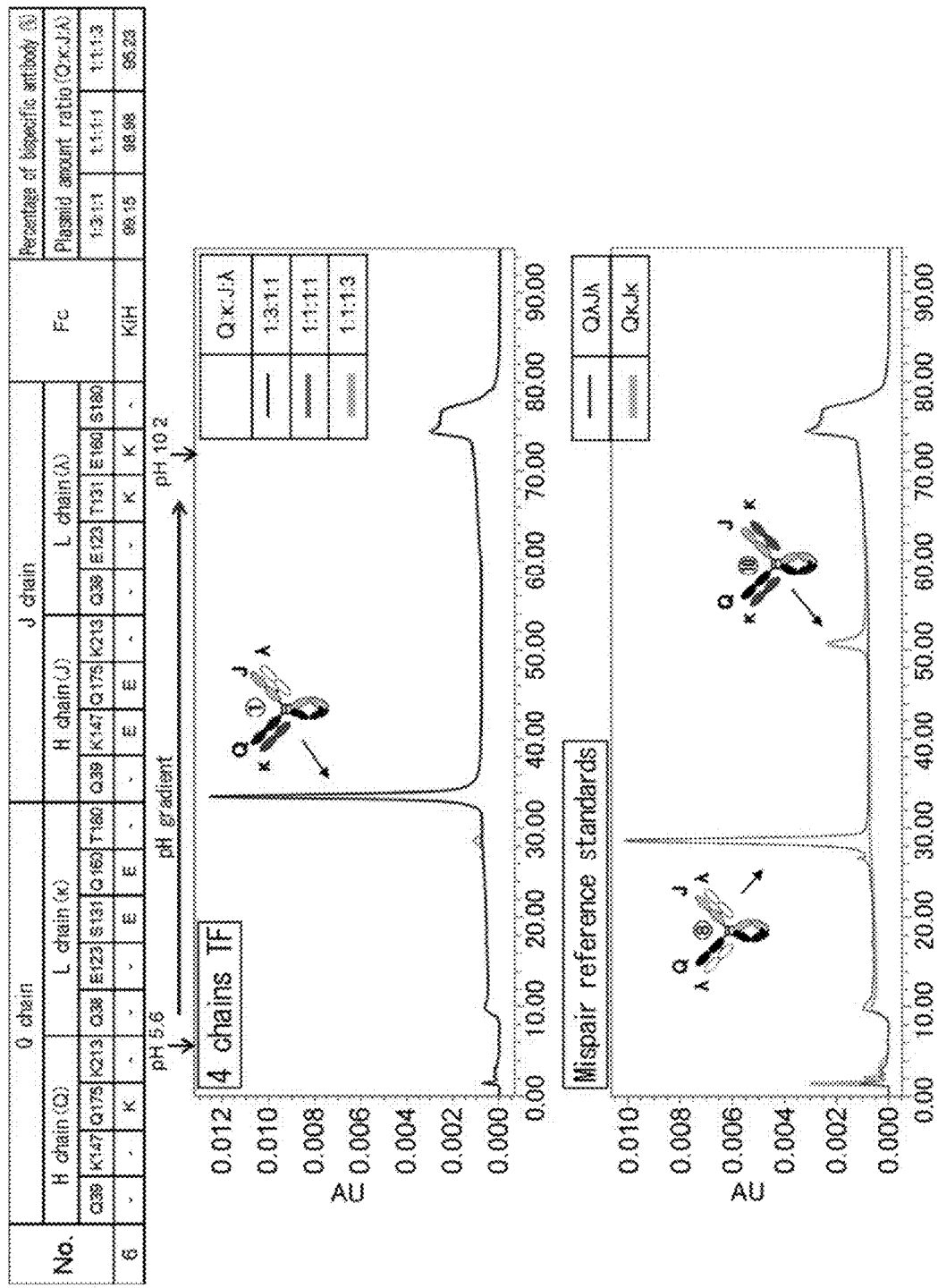
Figures 7, 9:
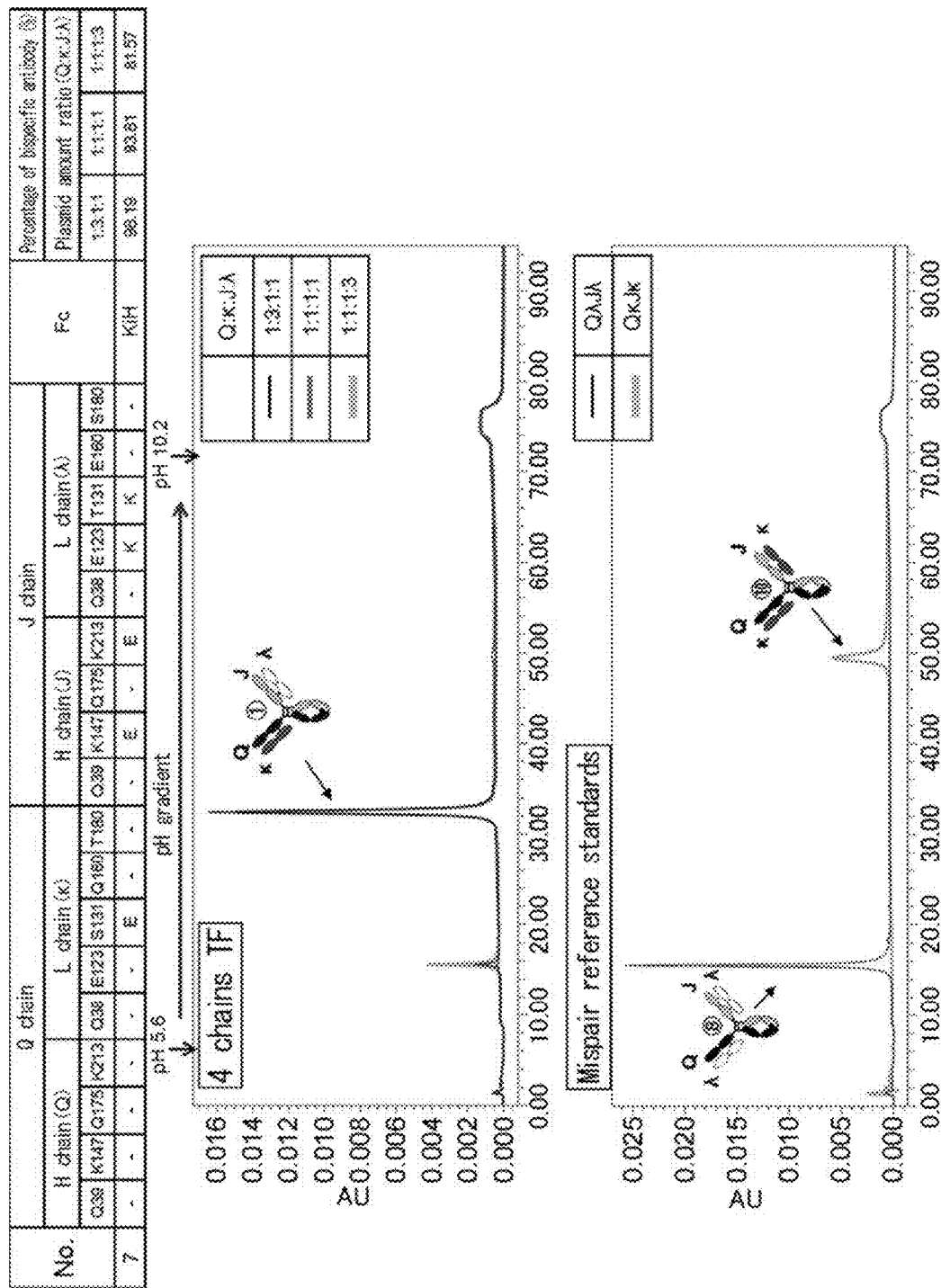
Figures 8, 9:
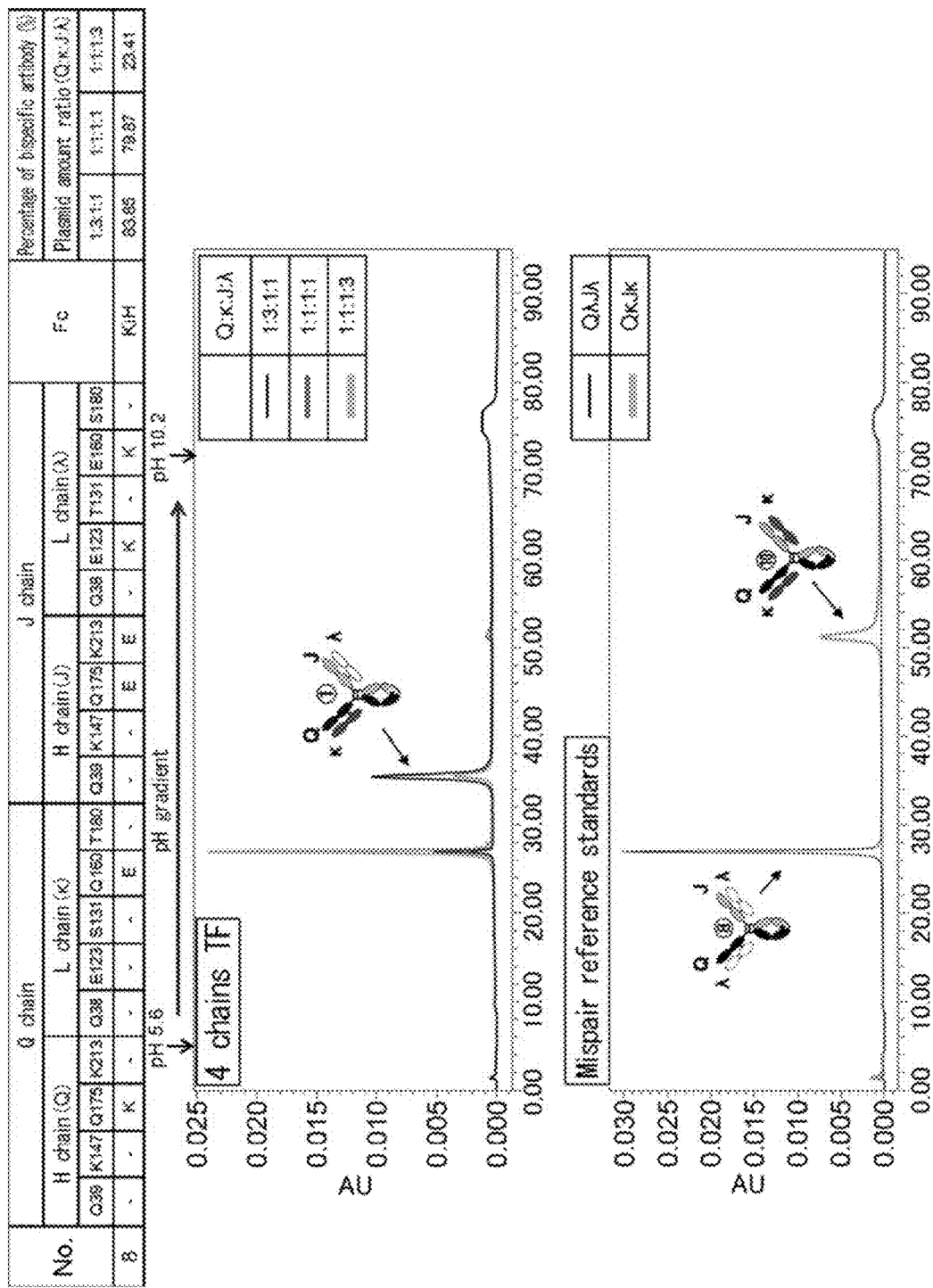
Figure 9:
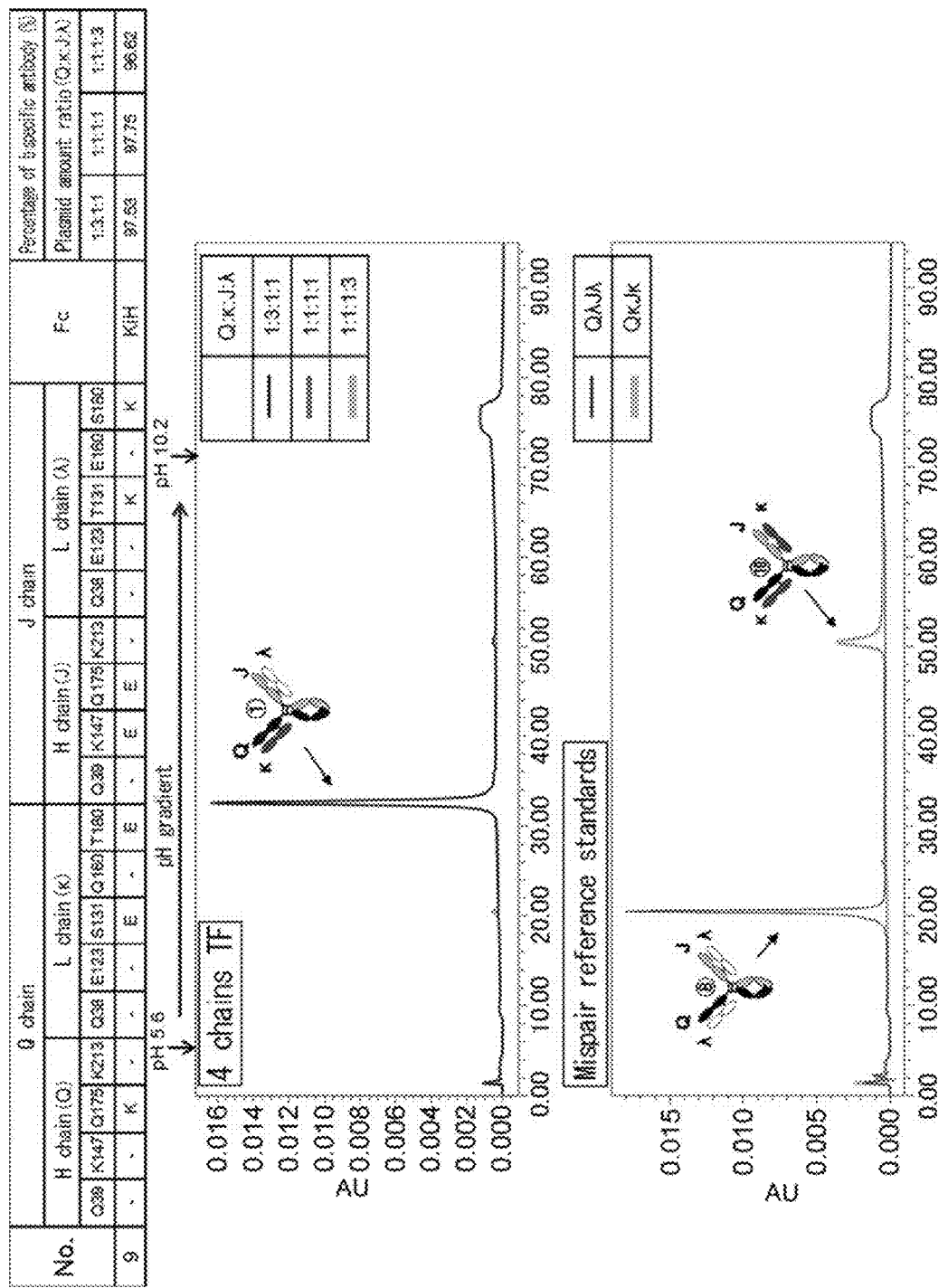
Figures 9, 10:
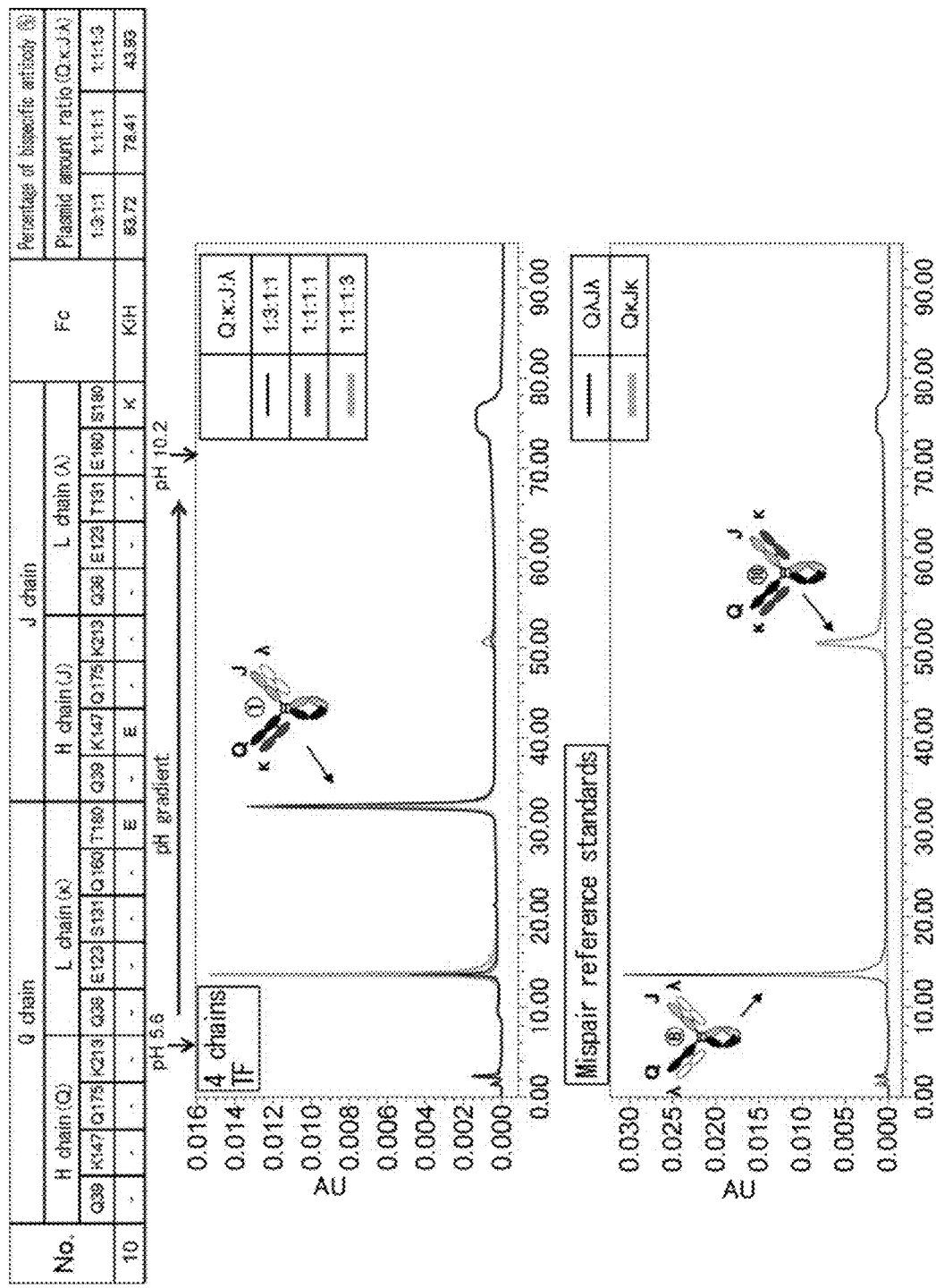
Figures 9, 10, 11:
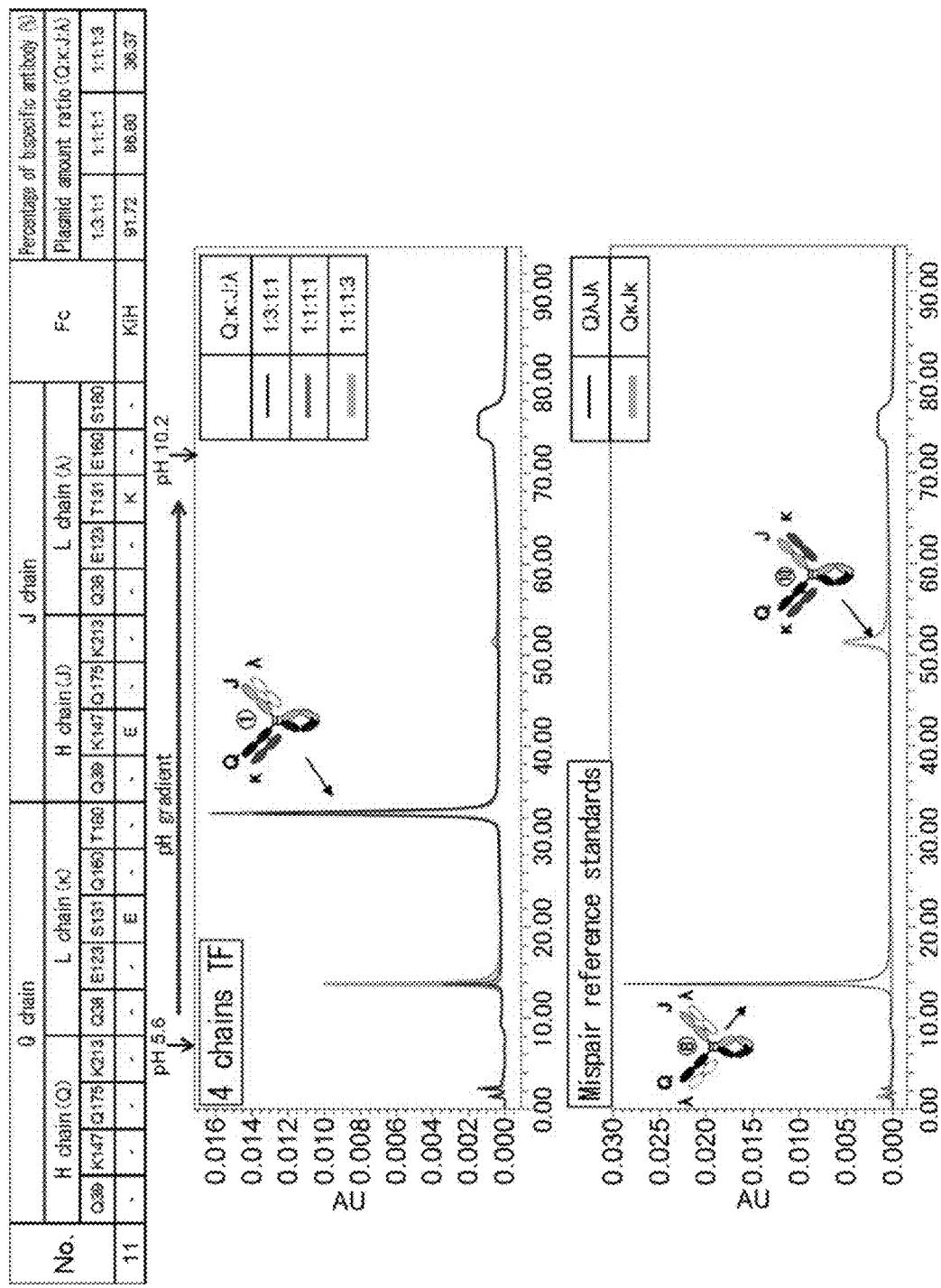
Figures 9, 10, 11, 12:
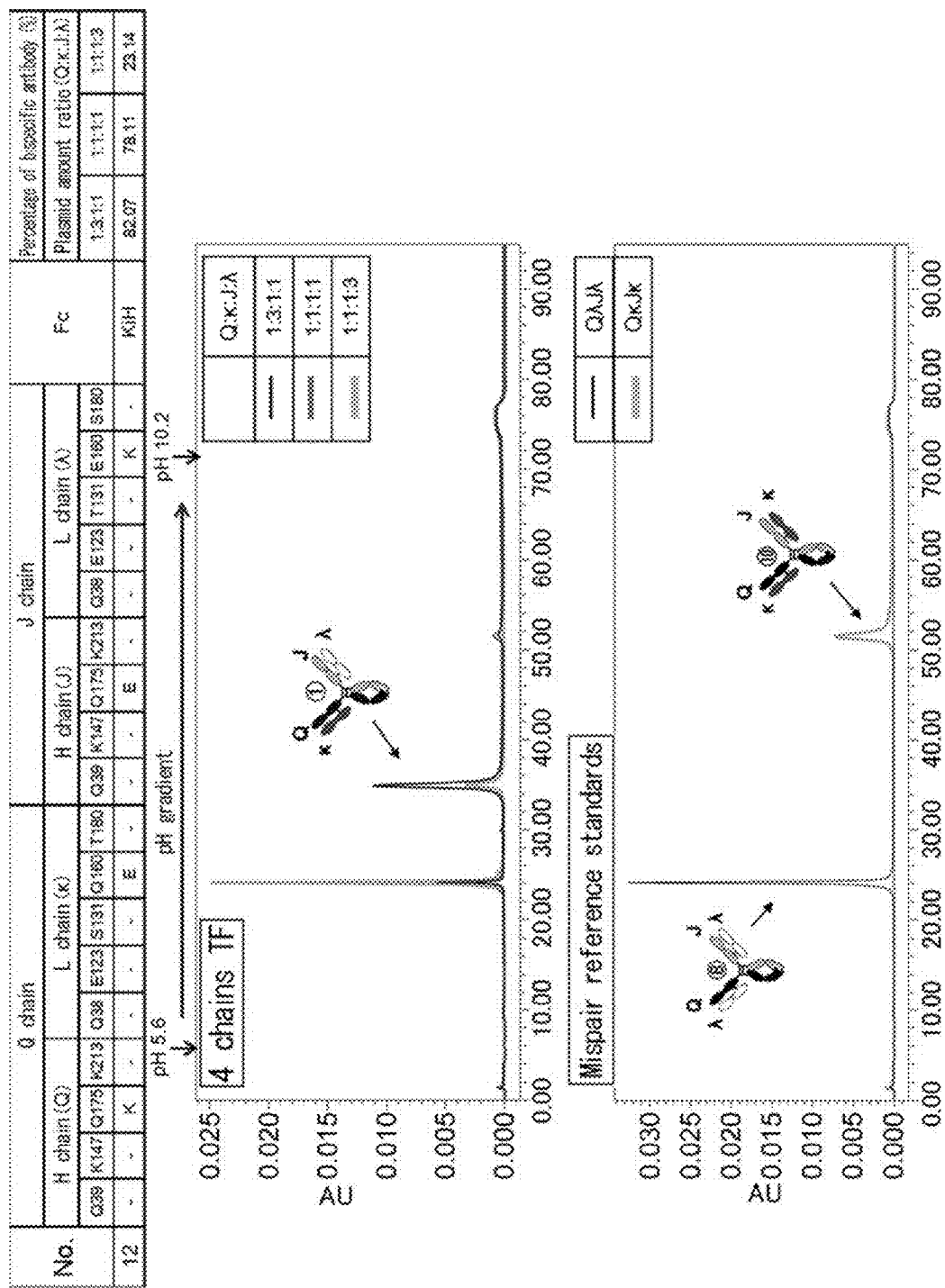
Figures 9, 10, 11, 12, 13:
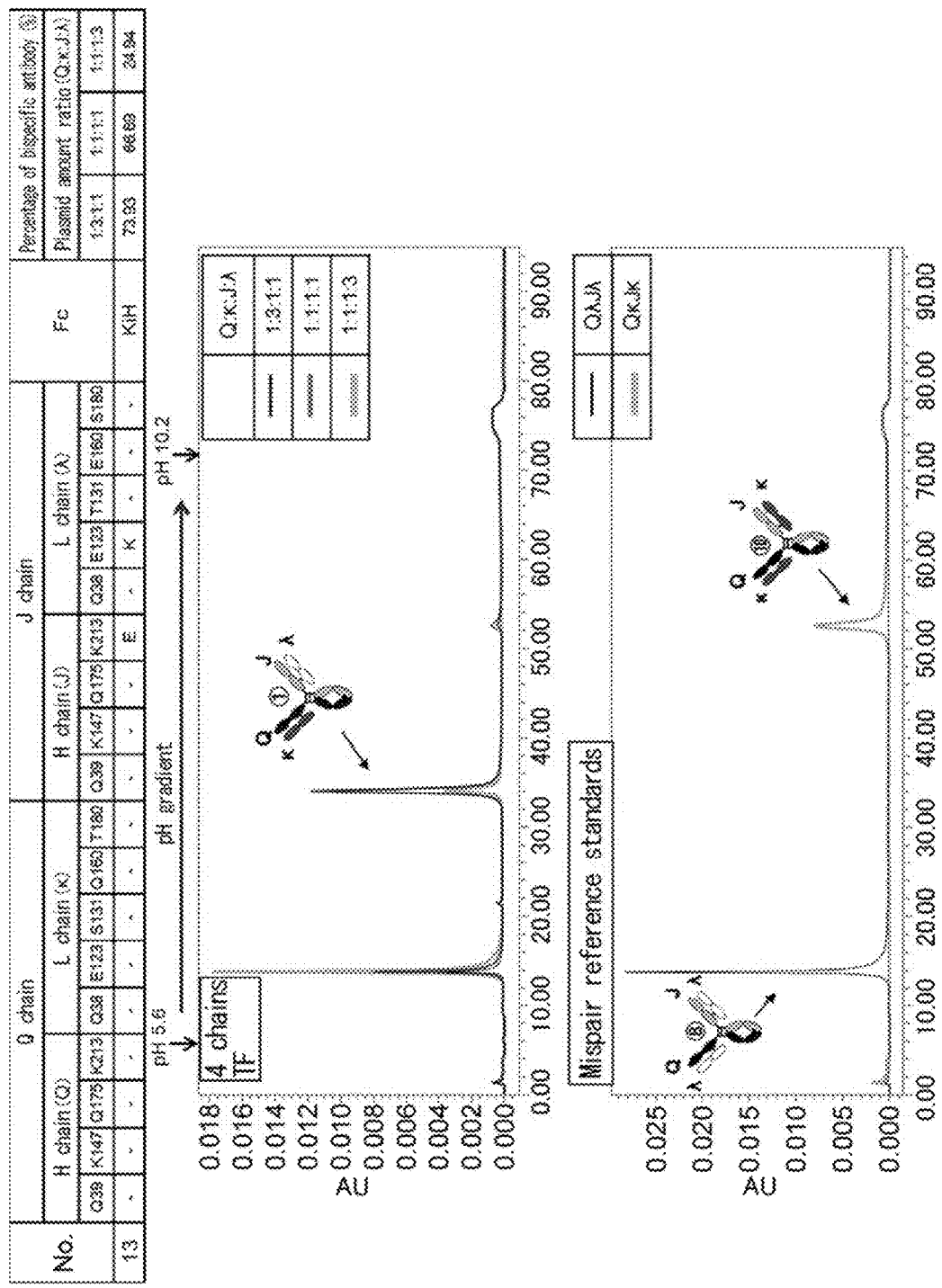
Figures 9, 10, 11, 12, 13, 14:
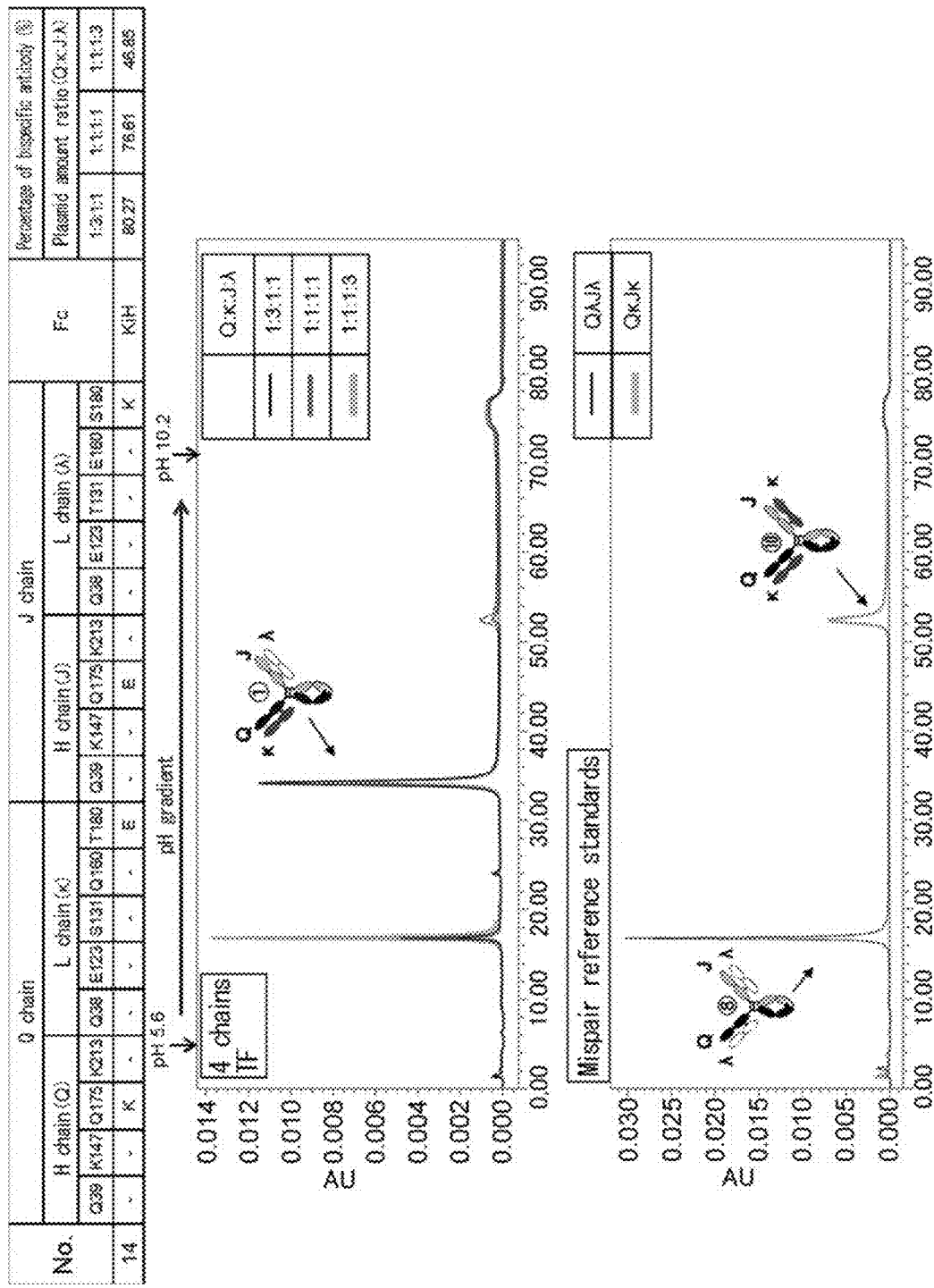
Figures 9, 10, 11, 12, 13, 14, 15:
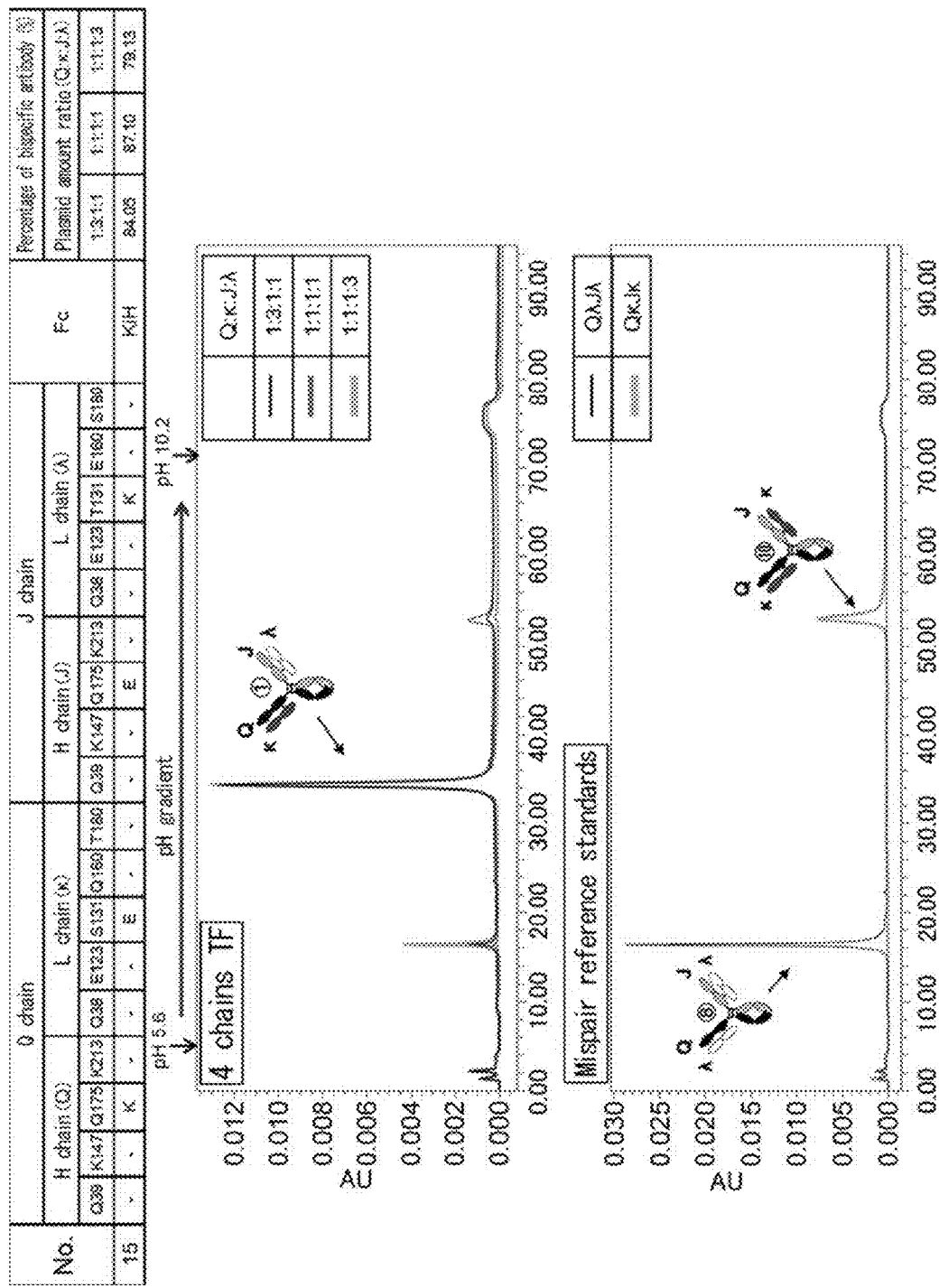
Figures 9, 10, 11, 12, 13, 14, 15, 16:
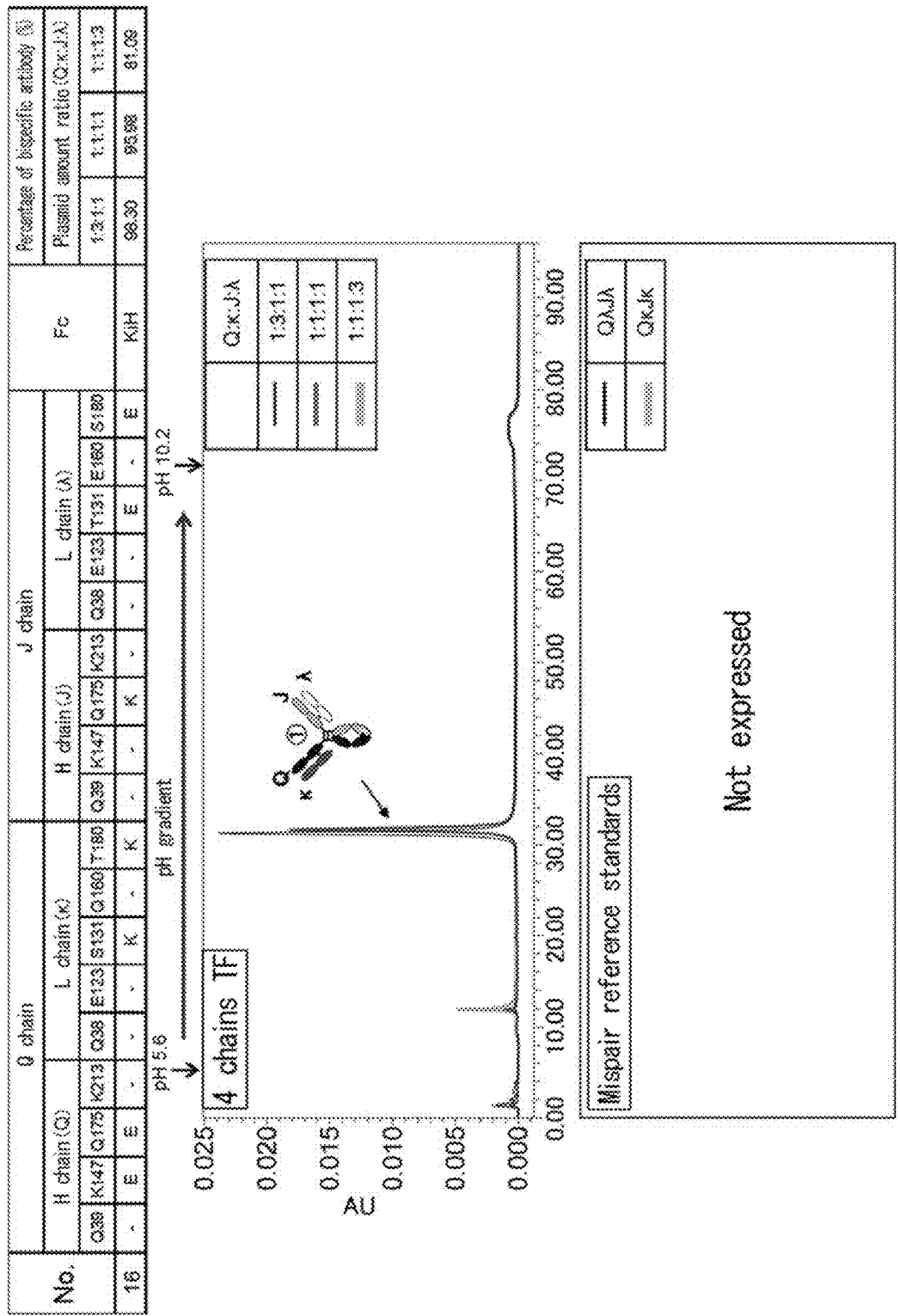
Figures 9, 10, 11, 12, 13, 14, 15, 16, 17:
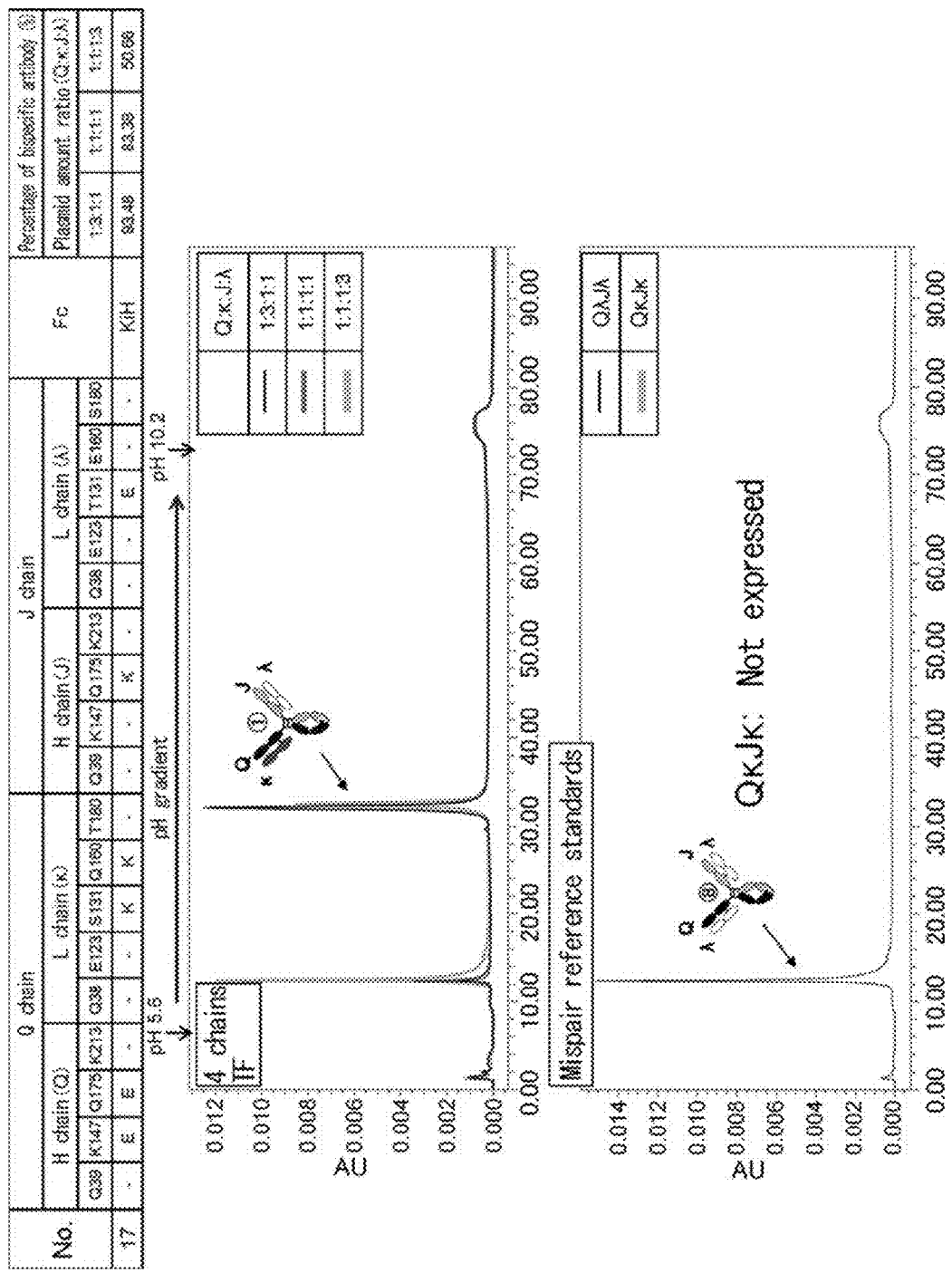
Figures 9, 10, 11, 12, 13, 14, 15, 16, 17, 18:
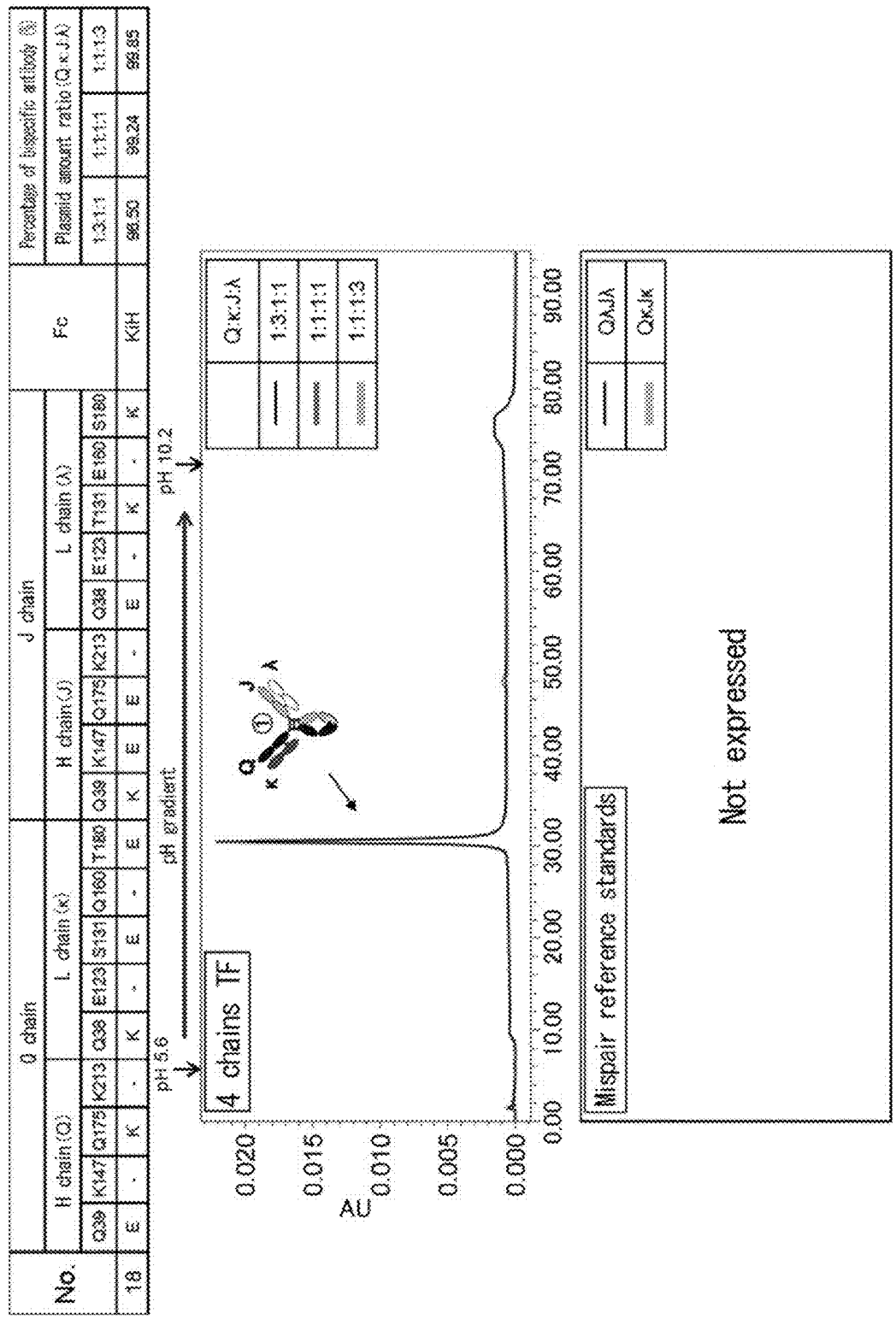
Figures 9, 10, 11, 12, 13, 14, 15, 16, 17, 18, 19:
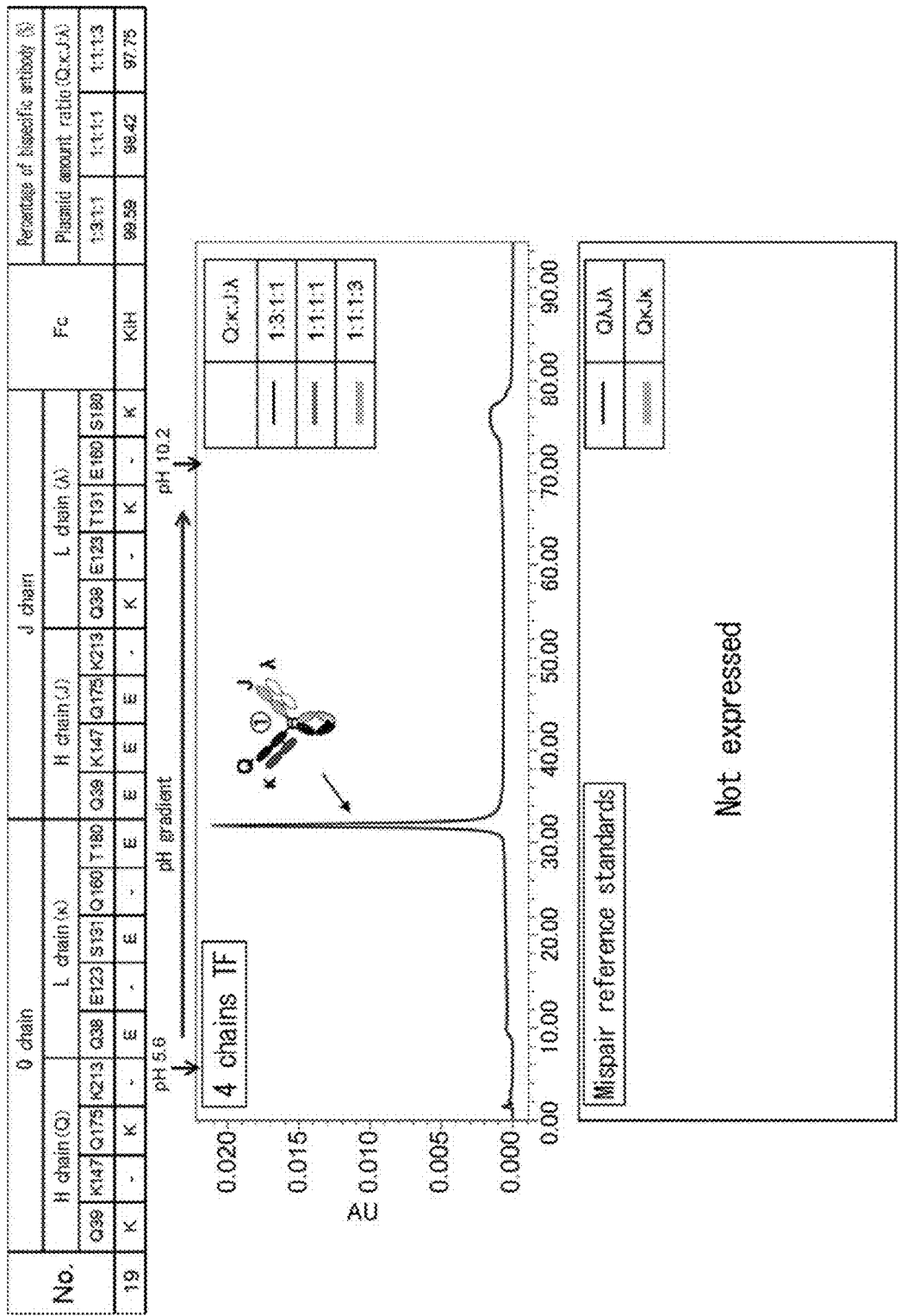
Figures 9, 10, 11, 12, 13, 14, 15, 16, 17, 18, 19, 20:
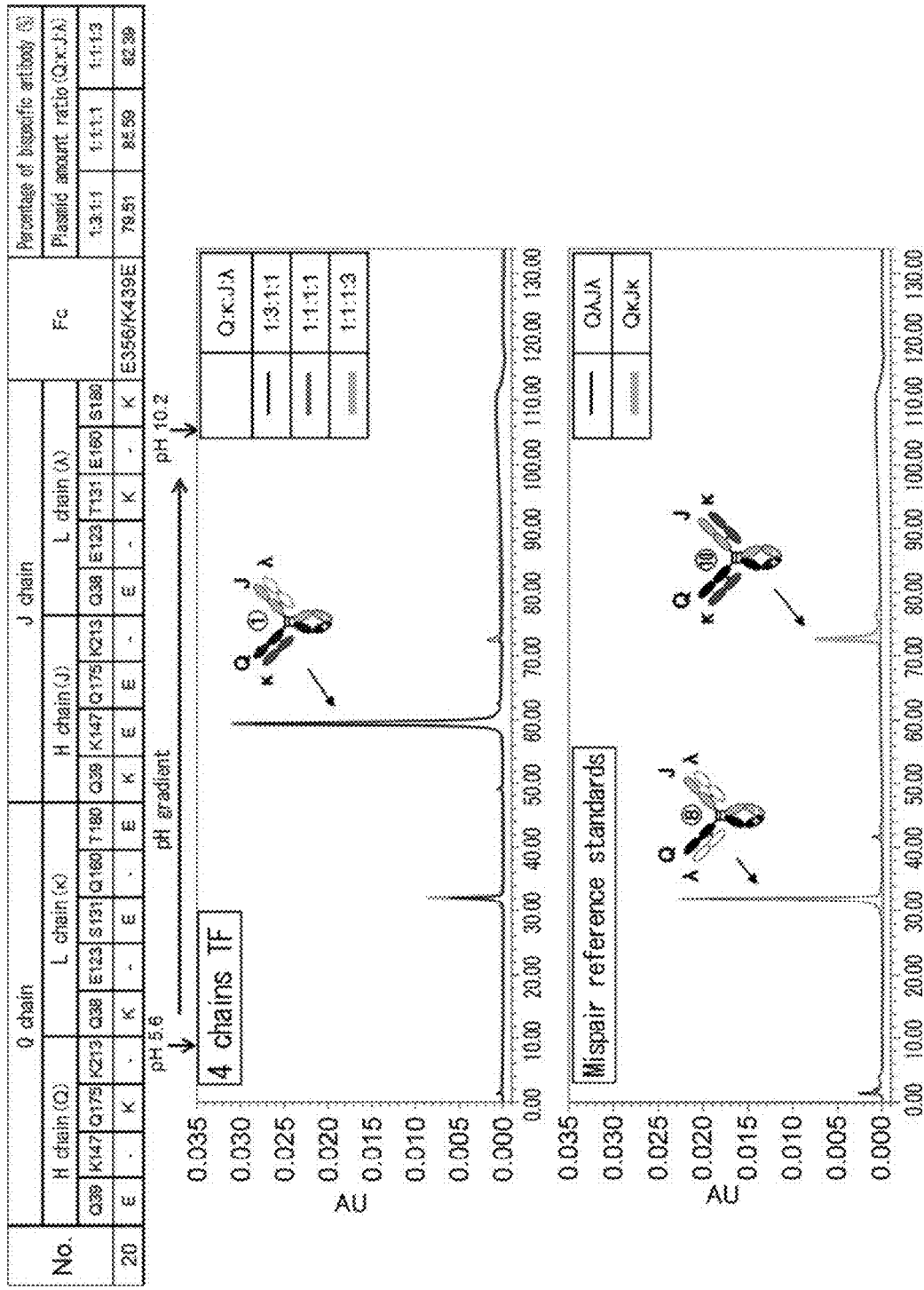
Figure 10:
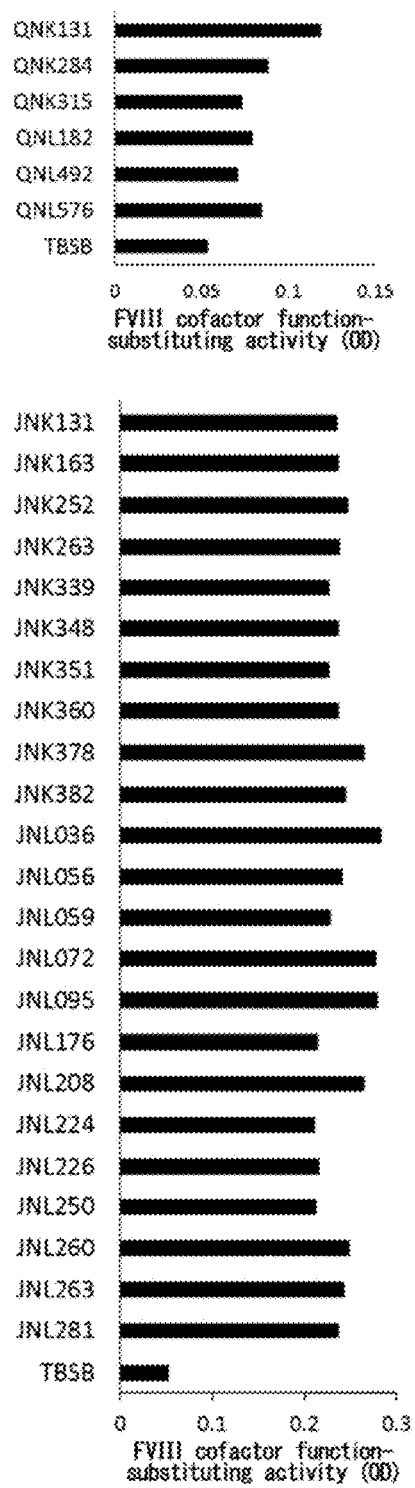

The peak proportion of the bispecific antibody calculated from the assay data is shown in Table 6, and each chromatogram was shown in FIG. 9.

New modification pairs No. 14 (the pair of the amino acid residue at position 175 (EU numbering) in CH1 and the amino acid residue at position 180 (Kabat numbering) in CL) and No. 15 (the pair of the amino acid residue at position 175 (EU numbering) in CH1 and the amino acid residue at position 131 (Kabat numbering) in CL), were found which exhibited regulation capability comparable to that of No. 10 (the pair of the amino acid residue at position 147 (EU numbering) in CH1 and the amino acid residue at position 180 (Kabat numbering) in CL) and No. 11 (the pair of the amino acid residue at position 147 (EU numbering) in CH1 and the amino acid residue at position 131 (Kabat numbering) in CL), which are among the known modifications in WO2013065708.

Moreover, new modification pair No. 9 (the pair of the amino acid residues at position 147 (EU numbering) and position 175 (EU numbering) in CH1 and the amino acid residues at position 131 (Kabat numbering) and position 180 (Kabat numbering) in CL) was found which exhibited as high regulation capability as the known combination of No. 6 (the pair of the amino acid residues at position 147 (EU numbering) and position 175 (EU numbering) in CH1 and the amino acid residues at position 131 (Kabat numbering) and position 160 (Kabat numbering) in CL).

Further, it is known that specific association between heavy and light chains is promoted by the modification pair of the amino acid residue at position 39 (Kabat numbering) in VH and the amino acid residue at position 38 (Kabat numbering) in VL (WO2013065708). Therefore, this modification pair was introduced into No. 9 to produce No. 18 and No. 19, and these were assessed. As a result, it was observed that all modifications resulted in high regulation capability.

In addition, when the modification pair of No. 9, newly found in the present invention, was applied to a template having a pair of modifications (E356K-K439E) for promoted H-chain association different from KiH (Q1014Q39E-G4T1A5LG409K.E356K/AL869Q38KAE.F83M-kT0//J1494Q39K-G4T1A5LG409K.K439E/YL681.K27Q.Q38E-lam1NL95 (variable regions: SEQ ID NOs: 112/113//114/115, constant regions: SEQ ID NOs: 117/99//116/101)), high regulation capability was also observed (No. 20: Q1014Q39E-G4T1th2A5LG409K.E356K/AL869Q38KAE.F83M-kOMTt117E160Q//J1494Q39 K-G4T1th13A5LG409K.K439E/YL681.K27Q.Q38E-lam1p9 (variable regions: SEQ ID NOs: 112/113//114/115, constant regions: SEQ ID NOs: 119/100//118/102).

TABLE 6

Introduced modifications, and percentage of bispecific antibody under each expression condition (%)

| | Q chain | | | | | | | | | J chain | |
|---|---|---|---|---|---|---|---|---|---|---|---|
| | H chain (Q) | | | | L chain (κ) | | | | | H chain (J) | |
| No. | Q39 | K147 | Q175 | K213 | Q38 | E123 | S131 | Q160 | T180 | Q39 | K147 |
| 1 | K | — | K | — | E | — | E | E | E | E | E |
| 2 | — | — | K | — | — | — | E | E | E | — | E |
| 3 | — | — | — | — | — | — | E | — | E | — | E |

TABLE 6-continued

Introduced modifications, and percentage of bispecific antibody under each expression condition (%)

| | | | | | | | | | | | |
|---|---|---|---|---|---|---|---|---|---|---|---|
| 4 | — | — | K | — | — | — | — | E | E | — | E |
| 5 | — | — | — | — | — | — | — | — | E | — | E |
| 6 | — | — | K | — | — | — | E | E | — | — | E |
| 7 | — | — | — | — | — | — | E | — | — | — | E |
| 8 | — | — | K | — | — | — | — | E | — | — | — |
| 9 | — | — | K | — | — | — | E | — | E | — | E |
| 10 | — | — | — | — | — | — | — | — | E | — | E |
| 11 | — | — | — | — | — | — | E | — | — | — | E |
| 12 | — | — | K | — | — | — | — | E | — | — | — |
| 13 | — | — | — | — | — | — | — | — | — | — | — |
| 14 | — | — | K | — | — | — | — | — | E | — | — |
| 15 | — | — | K | — | — | — | E | — | — | — | — |
| 16 | — | E | E | — | — | — | K | — | K | — | — |
| 17 | — | E | E | — | — | — | K | K | — | — | — |
| 18 | E | — | K | — | K | — | E | — | E | K | E |
| 19 | K | — | K | — | E | — | E | — | E | E | E |
| 20 | E | — | K | — | K | — | E | — | E | K | E |

| | H chain (J) | | L chain (λ) | | | | | | Percentage of bispecific antbody (%) Plasmid amount ratio(Q:κ:J:λ) | | |
|---|---|---|---|---|---|---|---|---|---|---|---|
| No. | Q175 | K213 | Q38 | E123 | T131 | E160 | S180 | Fc | 1:3:1:1 | 1:1:1:1 | 1:1:1:3 |
| 1 | E | E | K | K | K | K | K | KiH | 100.00 | 99.63 | 99.84 |
| 2 | E | E | — | K | K | K | K | KiH | 99.89 | 99.80 | 99.58 |
| 3 | — | — | — | — | K | — | K | KiH | 94.57 | 95.90 | 94.63 |
| 4 | E | — | — | — | — | K | K | KiH | 96.95 | 98.67 | 49.99 |
| 5 | — | E | — | K | — | — | K | KiH | 89.47 | 82.13 | 42.25 |
| 6 | E | — | — | — | K | K | — | KiH | 99.15 | 98.98 | 95.23 |
| 7 | — | E | — | K | K | — | — | KiH | 98.19 | 93.81 | 81.57 |
| 8 | E | E | — | K | — | K | — | KiH | 83.85 | 79.87 | 23.41 |
| 9 | E | — | — | — | K | — | K | KiH | 97.53 | 97.75 | 96.62 |
| 10 | — | — | — | — | — | — | K | KiH | 83.72 | 78.41 | 43.93 |
| 11 | — | — | — | — | K | — | — | KiH | 91.72 | 86.80 | 36.37 |
| 12 | E | — | — | — | — | K | — | KiH | 82.07 | 78.11 | 23.14 |
| 13 | — | E | — | K | — | — | — | KiH | 73.93 | 66.69 | 24.94 |
| 14 | E | — | — | — | — | — | K | KiH | 80.27 | 76.61 | 46.85 |
| 15 | E | — | — | — | K | — | — | KiH | 84.05 | 87.10 | 79.13 |
| 16 | K | — | — | — | E | — | E | KiH | 98.30 | 95.98 | 81.09 |
| 17 | K | — | — | — | E | — | — | KiH | 93.48 | 83.38 | 50.66 |
| 18 | E | — | E | — | K | — | K | KiH | 96.50 | 99.24 | 99.85 |
| 19 | E | — | K | — | K | — | K | KiH | 99.59 | 98.42 | 97.75 |
| 20 | E | — | E | — | K | — | K | E356K/K439E | 79.51 | 85.59 | 82.39 |

"—" indicates that no modification was introduced. The number of each residue is indicated by Kabat numbering for H chain variable region, L chain variable region, and L chain constant region, and by EU numbering for H chain constant region.

The present invention discovered novel light chains that reduce reactivity with anti-ACE910 (Emicizumab) idiotype antibody and exhibit FVIII cofactor function-substituting activity, and discovered amino acid substitutions and combinations thereof for heavy and light chains that improve the FVIII cofactor function-substituting activity of bispecific antibodies having those light chains while not increasing their FIX activation-inhibiting activity. These amino acid substitutions and combinations thereof are useful to create bispecific antibodies that have a superior FVIII cofactor function-substituting activity to that of ACE910 (Emicizumab).

Reference Example 1

A possible method for improving the activity of ACE910 to substitute for the cofactor function of FVIII was to obtain from a human antibody library a novel L chain with a sequence totally different from the common L chain, with respect to each of the H chains of the anti-FIX(a) antibody and the anti-FX antibody (Q499 and J327).

Referring to methods known to the person skilled in the art, specifically, Biochemical and Biophysical Research Communications, (2000), 275, 2, 553-557 and such, the present inventors produced a new library by replacing the L chain of an anti-ACE910 (Emicizumab) idiotype antibody with a human L-chain library, and performed panning against biotin-labeled human FIXa or biotin-labeled human FX to obtain antibodies with novel light chains that have a FVIII cofactor function-substituting activity.

As a result, QNK131 (SEQ ID NO: 13), QNK284 (SEQ ID NO: 14), QNK315 (SEQ ID NO: 15), QNL182 (SEQ ID NO: 16), QNL492 (SEQ ID NO: 17), and QNL576 (SEQ ID NO: 18) were found as L chain variable regions for the anti-human FIX(a) antibody of bispecific antibodies having a FVIII cofactor function-substituting activity, and JNK131 (SEQ ID NO: 19), JNK163 (SEQ ID NO: 20), JNK252 (SEQ ID NO: 21), JNK263 (SEQ ID NO: 22), JNK339(SEQ ID NO: 23), (SEQ ID NO: 24), JNK351 (SEQ ID NO: 25), JNK360 (SEQ ID NO: 26), JNK378 (SEQ ID NO: 27), JNK382 (SEQ ID NO: 28), JNL036 (SEQ ID NO: 29), JNL072 (SEQ ID NO: 30), JNL095 (SEQ ID NO: 31), JNL176 (SEQ ID NO: 32), JNL208 (SEQ ID NO: 33), JNL224 (SEQ ID NO: 34), JNL260 (SEQ ID NO: 35), JNL056 (SEQ ID NO: 36), JNL059 (SEQ ID NO: 37), JNL226 (SEQ ID NO: 38), JNL250 (SEQ ID NO: 39), JNL263 (SEQ ID NO: 40), and JNL281 (SEQ ID NO: 41) were found as L chain variable regions for the anti-human FX antibody.

Various bispecific antibodies having these novel L chains were expressed and purified by methods known to the person skilled in the art. The prepared antibodies are shown in Table 7 (clone names, SEQ ID NOs for heavy chain variable regions, and SEQ ID NOs for light chain variable regions are shown). A novel L chain variable region was used for only one of the chains. For the other chain, variable region L404, the common L chain of ACE910 (SEQ ID NO: 45), was used. For the H chain, variable region Q499 (SEQ ID NO: 45) and variable region J327 (SEQ ID NO: 46) were used. For the sake of convenience, the names of the novel L chains were used as clone names. For the anti-FIX(a) antibody, QC1 (SEQ ID NO: 95) and CL1 (SEQ ID NO: 99) were used as H chain and L chain constant regions, respectively. For the anti-FX antibody, JC1 (SEQ ID NO: 97) and CL3 (SEQ ID NO: 101) were used as H chain and L chain constant regions, respectively.

Each purified bispecific antibody was used to evaluate the FVIII cofactor function-substituting activity by a method known to the person skilled in the art. Specifically, the measurement was performed by the following method. All reactions were performed at room temperature. Five pt of the antibody solution diluted with Tris-buffered saline containing 0.1% bovine serum albumin (hereinafter abbreviated as TBSB) was mixed with 5 μL of 150 ng/mL Human Factor IXa beta (Enzyme Research Laboratories), and incubated in a 384-well plate at room temperature for 30 minutes. Enzymatic reaction in this mixture was initiated by adding 5 μL of 24.7 μg/mL Human Factor X (Enzyme Research Laboratories). After 4 minutes, the reaction was ceased by adding 5 μL of 0.5M EDTA. Coloring reaction was initiated by adding 5 μL of a coloring substrate solution. After 30 minutes of the coloring reaction, a change in absorbance at 405 nm was measured using SpectroMax 340PC384 (Molecular Devices). The solvent of Human Factor IXa beta and Human Factor X was TBSB containing 4.0 μM phospholipid solution (SYSMEX CO.) and 1.5 mM $CaCl_2$. The coloring substrate solution, S-2222 (SEKISUI MEDICAL), was dissolved with purified water to 1.47 mg/mL and used for this assay. The results of measuring the FVIII cofactor function-substituting activity of each purified bispecific antibody were shown in FIG. 10. The final concentration of antibody used in measuring the FVIII cofactor function-substituting activity shown in FIG. 10 was 66.7 μg/mL for antibodies formed with a novel anti-FIX(a) light chain, or 100 μg/mL for antibodies formed with a novel anti-FX light chain. The final concentration of antibody refers to a concentration in the mixture of the antibody solution, Human Factor IXa beta, and Human Factor X. All bispecific antibodies formed with any of the novel L chains were found to have a FVIII cofactor function-substituting activity.

TABLE 7

Bispecific antibodies having novel L chains that have been prepared

| Clone name | Heavy chain variable region SEQ ID NO | Light chain variable region SEQ ID NO |
| --- | --- | --- |
| QNK131 | 45 | 13 |
| QNK284 | 45 | 14 |
| QNK315 | 45 | 15 |
| QNL182 | 45 | 16 |
| QNL492 | 45 | 17 |
| QNL576 | 45 | 18 |

TABLE 7-continued

Bispecific antibodies having novel L chains that have been prepared

| Clone name | Heavy chain variable region SEQ ID NO | Light chain variable region SEQ ID NO |
| --- | --- | --- |
| JNK131 | 46 | 19 |
| JNK163 | 46 | 20 |
| JNK252 | 46 | 21 |
| JNK263 | 46 | 22 |
| JNK339 | 46 | 23 |
| JNK348 | 46 | 24 |
| JNK351 | 46 | 25 |
| JNK360 | 46 | 26 |
| JNK378 | 46 | 27 |
| JNK382 | 46 | 28 |
| JNL036 | 46 | 29 |
| JNL072 | 46 | 30 |
| JNL095 | 46 | 31 |
| JNL176 | 46 | 32 |
| JNL208 | 46 | 33 |
| JNL224 | 46 | 34 |
| JNL260 | 46 | 35 |
| JNL056 | 46 | 36 |
| JNL059 | 46 | 37 |
| JNL226 | 46 | 38 |
| JNL250 | 46 | 39 |
| JNL263 | 46 | 40 |
| JNL281 | 46 | 41 |

Reference Example 2

Substitution variants were produced in which all CDRs of Q499 and J327, the H chains of ACE910, were exhaustively mutated by substitution with all amino acids except cysteine. Using these variants and the novel L chains obtained in Reference Example 1, large-scale screening for the FVIII cofactor function-substituting activity was carried out to find amino acid substitutions that improved the FVIII cofactor function-substituting activity. For example, amino acid substitutions were introduced into QNK131, a novel L chain for the anti-FIX(a) antibody (variable region: SEQ ID NO: 13), to obtain QAL187 (variable region: SEQ ID NO: 42) and QAL201 (variable region: SEQ ID NO: 43). Similarly, amino acid substitutions were introduced into JNL095, a novel L chain for the anti-FX antibody (variable region: SEQ ID NO: 31), to obtain JYL280 (variable region: SEQ ID NO: 44). For the anti-FIX(a) antibody, QC1 (SEQ ID NO: 95) and CL1 (SEQ ID NO: 99) were used as H chain and L chain constant regions, respectively. For the anti-FX antibody, JC1 (SEQ ID NO: 97) and CL3 (SEQ ID NO: 101) were used as H chain and L chain constant regions, respectively.

The result revealed that some amino acid substitutions shown in Table 8 below can improve the FVIII cofactor function-substituting activity of ACE910 (Emicizumab). In measurement of the FVIII cofactor function-substituting activity, the method described in Reference Example 1 was used for variants with a modified H chain for the anti-FX antibody. For variants with a modified H chain for the anti-FIX(a) antibody, the measurement was performed using the method described in Reference Example 1 except that the concentration of Human factor IXa beta was changed to 450 ng/mL. Table 8 shows the specific activity of each amino acid substitution variant relative to ACE910 (Emicizumab) (each value in the table). In Table 8, (−) indicates that the expression level of the antibody was low.

TABLE 8

FVIII cofactor function-substituting activity of variant bispecific antibodies in which amino acid substitution was introduced into Q499 and J327

| Position | Mutation | A | I | L | M | P | V | G | N | Q | S | T | D | E | H | K | R | F | W | Y |
|---|---|---|---|---|---|---|---|---|---|---|---|---|---|---|---|---|---|---|---|---|
| Modification of H chain of anti-FIX(a) antibody | | | | | | | | | | | | | | | | | | | | |
| 31 | Y | 0.4 | 0.0 | — | — | 0.0 | 0.0 | 0.0 | 0.0 | — | 1.0 | 0.0 | 0.0 | 0.0 | 3.5 | 0.0 | 0.0 | 0.0 | 10.0 | / |
| 32 | Y | 0.6 | 1.3 | 0.0 | 0.0 | 0.0 | 1.5 | — | 1.4 | 2.0 | 0.0 | 6.2 | 2.2 | 0.1 | 0.9 | 1.2 | 0.0 | 6.1 | 0.6 | / |
| 33 | D | — | — | — | 0.0 | — | 0.1 | — | 0.0 | — | — | 0.2 | / | 0.1 | — | — | — | — | — | — |
| 34 | I | 1.2 | / | 10.7 | 8.9 | 0.0 | 0.0 | 2.4 | — | 8.0 | 0.2 | 2.9 | 0.2 | 1.5 | 0.0 | 1.1 | 0.0 | 41.8 | 13.2 | 0.0 |
| 35 | Q | 0.4 | 4.6 | 76.2 | — | 39.0 | 45.7 | 73.9 | 0.0 | / | 22.8 | 56.0 | 0.0 | 0.1 | 0.1 | 1.4 | 0.0 | 0.5 | 0.0 | 0.1 |
| 50 | S | 5.4 | 1.0 | 0.9 | 4.1 | 0.0 | — | 2.8 | 6.0 | 0.0 | / | 0.0 | 3.3 | 0.0 | — | 0.2 | 0.0 | 1.2 | 3.3 | 1.3 |
| 51 | I | 0.0 | / | — | 0.0 | 0.0 | 2.3 | 0.0 | 0.0 | — | 0.3 | 0.0 | 0.0 | — | — | 0.0 | 0.0 | — | 0.0 | 0.0 |
| 52 | S | 1.1 | 4.8 | 0.0 | 0.0 | 0.0 | 3.8 | 1.0 | 9.9 | 8.1 | / | — | 13.1 | 0.0 | 34.0 | 0.1 | — | 26.0 | 8.2 | 2.0 |
| 52a | P | 0.4 | — | 0.7 | — | / | 0.1 | 4.9 | 0.0 | 1.6 | 0.0 | 0.0 | 0.0 | 0.3 | 0.0 | — | 0.0 | 0.0 | 0.1 | 1.3 |
| 53 | S | 0.9 | 0.1 | 0.3 | 0.0 | 0.0 | 0.0 | 1.3 | 0.0 | 0.0 | / | 1.4 | 0.1 | 0.0 | 1.3 | 0.0 | 0.2 | 0.3 | 0.0 | 0.2 |
| 54 | G | 1.3 | 0.0 | 0.0 | — | 0.0 | 0.0 | / | 0.0 | 0.1 | 1.2 | — | 0.0 | 0.0 | — | 0.0 | — | — | 0.0 | 0.1 |
| 55 | Q | 0.0 | 0.0 | — | 0.0 | 0.0 | 0.2 | 3.9 | 0.0 | / | — | 0.0 | — | 0.0 | 4.1 | — | 7.4 | 0.0 | 0.0 | 0.0 |
| 56 | S | — | 0.0 | 1.9 | 13.1 | 0.2 | 0.0 | 3.2 | 0.0 | — | / | 0.2 | 1.1 | 0.6 | 6.2 | 0.8 | 1.9 | 0.0 | — | 25.8 |
| 57 | T | 2.7 | 2.1 | 3.0 | 3.1 | 0.2 | 1.7 | — | 0.9 | 3.8 | 2.6 | / | 0.2 | 1.6 | 1.9 | 4.2 | 0.7 | 2.3 | 1.5 | 2.0 |
| 58 | Y | — | 1.7 | 1.9 | 0.4 | — | 1.1 | 0.2 | 5.0 | 0.6 | 0.6 | 14.7 | 3.8 | — | 3.8 | 3.6 | 0.2 | 4.5 | 1.5 | / |
| 59 | Y | 0.0 | 0.5 | — | 1.0 | 0.0 | 1.0 | 0.0 | 0.1 | — | — | — | 0.0 | 1.5 | — | 0.0 | 0.0 | 1.0 | 0.4 | / |
| 60 | R | 3.7 | 4.1 | 3.4 | 3.9 | 1.2 | 3.4 | 2.8 | — | 4.1 | 3.5 | 2.3 | — | — | 4.1 | 3.7 | / | 4.0 | 0.0 | — |
| 61 | R | 1.8 | 1.5 | 1.5 | 1.6 | 1.7 | 1.6 | 2.0 | 2.1 | 2.2 | 0.0 | 1.9 | 1.1 | 0.7 | 3.7 | — | / | 1.7 | 1.1 | — |
| 62 | E | 3.3 | 1.1 | 1.8 | 1.3 | 3.4 | 1.4 | 4.2 | 4.8 | 4.4 | 5.2 | 4.5 | 6.0 | / | 3.0 | 3.0 | 0.0 | — | 1.6 | 0.0 |
| 63 | V | 2.9 | 2.5 | 3.1 | 1.3 | 1.0 | / | 0.1 | 0.5 | 0.1 | 0.4 | 1.1 | 0.5 | 0.1 | 3.5 | 0.1 | 0.0 | 4.0 | 0.5 | 6.6 |
| 64 | K | 1.2 | 1.5 | 1.3 | 1.2 | 0.0 | 1.1 | 1.1 | 1.0 | 1.2 | 1.3 | 1.1 | 0.4 | 0.4 | 1.2 | / | 4.8 | 0.0 | 0.8 | 1.1 |
| 65 | G | 2.1 | 4.4 | 3.0 | 2.9 | 0.2 | 1.2 | / | 3.5 | 20.4 | 2.3 | 3.1 | 3.8 | 2.5 | 4.1 | 1.4 | 2.7 | 2.5 | 3.5 | 3.3 |
| 95 | R | 0.0 | 0.4 | 0.0 | — | 0.1 | 0.2 | 0.0 | 0.0 | 1.1 | 0.0 | 0.1 | — | — | — | 1.2 | / | 0.0 | 0.0 | 0.0 |
| 96 | T | 5.5 | 0.5 | 0.4 | 1.6 | 0.1 | 1.3 | — | 3.3 | 15.0 | 15.0 | / | 4.2 | 1.5 | 1.6 | 0.5 | 0.3 | 1.3 | 2.1 | 2.6 |
| 97 | G | — | 0.1 | 0.0 | 0.3 | 3.1 | 0.4 | / | 1.4 | 0.7 | 2.1 | 0.4 | 11.6 | 1.8 | 1.2 | 0.2 | 0.1 | 1.0 | 1.9 | 1.1 |
| 98 | R | 4.5 | 9.0 | 9.5 | 5.8 | 2.2 | 4.1 | 5.7 | 7.7 | 7.6 | 5.7 | 8.1 | 3.7 | 4.1 | 5.8 | 4.0 | / | 5.8 | 3.9 | 8.2 |
| 99 | E | 3.4 | 10.4 | 7.0 | 5.5 | 5.8 | 7.0 | 1.7 | 3.0 | 4.3 | 4.0 | 4.8 | 3.4 | / | 4.2 | 2.2 | 2.0 | 3.3 | 1.8 | 3.6 |
| 100 | Y | 1.6 | 5.0 | 1.6 | 3.3 | 2.7 | 3.4 | 1.2 | 3.2 | 1.5 | 1.3 | 1.6 | 3.0 | 1.5 | 3.2 | 1.9 | 2.2 | 2.1 | 3.6 | / |
| 100a | G | 3.4 | 1.1 | 5.1 | 5.8 | 0.4 | 0.6 | / | 2.7 | — | 1.7 | 1.0 | 2.6 | 0.9 | 2.5 | 6.5 | 7.1 | 2.1 | 2.0 | 2.7 |
| 100b | G | 5.3 | 1.0 | 0.4 | 0.4 | 0.8 | 0.9 | / | 1.1 | 1.0 | 2.3 | 1.1 | 1.4 | 1.2 | 0.6 | — | 0.2 | 0.0 | 0.0 | 0.2 |
| 100c | G | 0.2 | 0.0 | 0.0 | 0.0 | 0.1 | 0.0 | / | 1.1 | 0.0 | 0.4 | 0.0 | 0.0 | 0.0 | 0.0 | — | 0.0 | 0.0 | 0.0 | 0.0 |
| 100d | W | 0.0 | 0.5 | 0.3 | 0.3 | 0.3 | 0.6 | 0.0 | 0.0 | 0.0 | 0.1 | 0.1 | 0.0 | 0.0 | 1.4 | 0.0 | 0.0 | 10.3 | / | 3.6 |
| 100e | Y | 3.1 | 4.5 | 3.7 | 3.0 | 0.4 | 4.9 | 0.1 | 5.1 | 3.2 | 3.8 | 5.2 | 1.7 | 1.5 | 9.4 | 1.1 | — | 3.1 | 1.5 | / |
| 100f | F | 11.7 | 24.9 | 7.6 | 8.6 | 7.8 | 23.2 | — | 18.6 | 6.3 | 8.0 | 11.3 | 1.3 | 2.0 | 0.7 | 0.0 | 0.6 | / | 0.1 | 0.7 |
| 101 | D | 3.2 | 4.1 | 2.1 | 1.8 | 8.6 | 3.9 | 2.3 | 3.2 | 2.6 | 3.1 | 2.9 | / | 2.7 | 2.4 | 2.3 | 2.5 | 2.1 | 3.0 | 2.5 |
| 102 | Y | 4.4 | 4.1 | 4.6 | 4.1 | 4.6 | 5.8 | 6.3 | 4.3 | 4.3 | 2.6 | 5.9 | 8.6 | 6.5 | 4.6 | 3.6 | 3.2 | 3.9 | 3.5 | / |
| Modification of H chain of anti-FX antibody | | | | | | | | | | | | | | | | | | | | |
| 31 | D | — | 8.9 | 13.0 | 14.2 | — | 11.0 | 15.5 | 14.7 | 14.6 | 15.3 | 12.5 | / | 14.0 | 17.4 | 12.6 | 11.2 | 13.7 | 13.3 | 13.6 |
| 32 | N | 10.7 | 0.4 | 0.8 | 5.6 | 0.3 | 1.9 | 3.3 | / | 4.1 | 12.5 | 4.2 | 0.2 | 0.8 | 5.2 | 3.1 | 3.5 | 4.4 | 1.5 | 4.3 |
| 33 | N | 0.4 | 1.8 | 2.8 | 1.7 | 0.0 | 1.2 | 1.2 | / | 1.8 | 3.4 | 0.1 | 0.2 | 0.0 | 0.0 | 1.5 | 0.1 | 0.0 | 0.2 | 0.0 |
| 34 | M | 2.6 | 11.0 | 12.1 | / | — | 12.4 | — | — | — | — | 1.6 | — | — | 7.8 | — | — | 7.4 | 1.3 | 3.4 |
| 35 | D | 3.4 | 4.2 | 3.1 | 6.6 | — | 5.0 | 3.5 | 13.1 | 11.4 | 5.0 | 0.3 | / | 11.4 | 6.0 | — | — | 3.5 | 4.8 | 2.3 |
| 50 | D | 3.1 | 0.3 | 0.2 | 0.5 | — | 2.4 | 1.2 | 4.1 | 1.8 | 3.9 | 1.7 | / | 1.3 | 0.1 | 0.1 | 0.0 | 0.6 | 0.0 | 0.1 |

TABLE 8-continued

FVIII cofactor function-substituting activity of variant bispecific antibodies in which amino acid substitution was introduced into Q499 and J327

| Position | Mutation | A | I | L | M | P | V | G | N | Q | S | T | D | E | H | K | R | F | W | Y |
|---|---|---|---|---|---|---|---|---|---|---|---|---|---|---|---|---|---|---|---|---|
| 51 | I | 10.2 | / | 10.3 | 10.2 | — | 12.8 | 1.6 | — | 9.5 | 11.5 | 12.7 | 0.6 | 0.7 | — | 3.1 | 0.1 | 4.8 | 0.7 | 4.7 |
| 52 | N | 1.8 | 0.1 | 0.1 | 0.1 | 0.1 | 0.1 | 0.6 | / | 0.7 | 2.9 | 0.0 | 0.1 | 0.5 | 3.5 | 0.0 | 0.1 | 0.1 | 0.0 | 0.0 |
| 52a | T | 6.0 | 7.7 | 4.2 | 3.9 | 7.2 | 9.0 | 3.2 | — | 0.9 | 11.9 | / | 0.1 | 0.0 | 1.0 | 0.3 | 0.1 | 1.5 | 4.0 | 0.7 |
| 53 | R | 3.7 | 7.4 | 5.0 | 5.3 | 3.0 | 6.9 | 3.9 | 12.4 | 6.0 | 3.8 | 0.3 | 1.4 | 1.9 | 7.2 | 9.8 | / | 7.4 | 8.9 | 5.8 |
| 54 | S | 12.8 | 4.3 | 3.6 | 6.2 | 0.1 | 8.0 | 10.8 | 5.3 | 5.4 | / | 6.3 | 2.7 | 1.1 | 5.8 | 3.1 | 4.7 | 10.1 | 16.0 | 12.2 |
| 55 | G | 11.0 | 6.2 | 8.3 | 8.7 | 3.1 | 8.0 | / | 2.7 | 11.0 | 12.1 | 9.2 | 4.1 | 6.6 | 10.4 | 7.0 | 7.9 | 7.6 | 7.3 | 6.7 |
| 56 | G | 8.3 | 11.2 | 11.4 | 11.6 | — | 8.8 | / | 11.3 | 13.3 | 13.3 | 13.8 | 4.6 | 3.2 | 8.4 | 10.2 | 12.3 | 10.4 | 13.7 | 10.3 |
| 57 | S | 11.9 | 10.9 | 6.5 | 12.2 | 12.1 | 12.9 | 13.7 | 10.6 | 12.9 | / | 10.9 | 6.9 | 0.7 | 2.5 | 0.1 | 0.3 | 0.8 | 3.0 | 0.1 |
| 58 | I | 5.8 | / | 7.7 | 3.9 | — | 3.7 | 1.3 | 6.3 | 7.2 | 2.7 | 11.3 | 0.1 | 2.7 | 3.3 | 7.5 | 4.2 | 4.8 | 2.6 | 5.5 |
| 59 | Y | 3.2 | 11.8 | 5.9 | 3.7 | 0.4 | 1.3 | 1.7 | 5.9 | 7.8 | 7.2 | 9.4 | 6.7 | 6.0 | 12.7 | 4.0 | 3.2 | 4.9 | 6.6 | / |
| 60 | N | 11.0 | 9.0 | 10.4 | 10.2 | 5.0 | 9.6 | 5.2 | / | 6.1 | 2.2 | 1.1 | 10.7 | 4.4 | 2.2 | 4.6 | 10.1 | 9.8 | 10.0 | 11.7 |
| 61 | E | 17.6 | 12.5 | 10.8 | 6.4 | 6.8 | 2.3 | 7.5 | 2.6 | 11.1 | 12.0 | 7.9 | 3.6 | / | 5.3 | 9.6 | 6.9 | 8.1 | 7.7 | 6.9 |
| 62 | E | 9.5 | 9.9 | 10.6 | 11.1 | 9.3 | 11.6 | 13.6 | 13.0 | 15.2 | 4.2 | 2.9 | — | / | 9.3 | 9.8 | 12.6 | 10.0 | 13.7 | 10.9 |
| 63 | F | 12.5 | 11.3 | 6.3 | 12.1 | — | 12.2 | 13.1 | 12.6 | 10.2 | 12.3 | — | 11.3 | 6.3 | 15.9 | 7.8 | 6.2 | / | 16.7 | 16.3 |
| 64 | Q | 16.2 | 14.7 | 11.8 | 16.0 | 9.7 | 14.8 | 15.0 | 15.0 | / | 15.8 | 15.3 | 14.4 | 16.2 | 13.7 | 14.2 | 12.4 | 15.7 | 13.9 | 15.5 |
| 65 | D | 14.3 | — | 12.6 | 15.5 | 16.1 | — | 11.5 | 15.0 | 15.4 | 15.6 | 14.9 | / | 14.2 | 14.8 | 12.9 | 14.5 | 14.9 | 12.4 | 14.8 |
| 95 | R | 0.2 | 0.6 | 1.6 | 1.0 | 0.7 | 1.0 | 0.1 | 0.0 | 0.8 | 0.1 | 0.2 | 0.0 | — | 1.2 | 5.7 | / | 0.0 | 0.4 | 0.3 |
| 96 | K | 3.0 | 2.0 | 1.8 | 4.3 | 0.0 | 3.6 | 1.1 | 1.0 | 2.3 | 1.2 | 1.7 | 0.0 | 1.0 | 1.7 | / | 15.7 | 1.9 | 1.9 | 1.4 |
| 97 | S | 14.8 | 2.2 | 1.6 | 5.2 | 1.4 | 3.7 | 10.2 | 5.4 | 6.5 | / | 7.6 | 2.9 | 3.9 | 7.2 | 3.5 | — | 3.2 | 1.5 | 3.2 |
| 98 | Y | 2.2 | 1.1 | 1.9 | 7.3 | 0.1 | 1.4 | 1.4 | 1.3 | 1.9 | 1.9 | 1.0 | 0.2 | 0.2 | 8.8 | 1.5 | 7.9 | 6.9 | 4.2 | / |
| 99 | G | 4.6 | — | — | 5.2 | 0.0 | 0.5 | / | 7.6 | 7.6 | 6.8 | 1.7 | 8.8 | 3.7 | 6.1 | 5.7 | 7.2 | 6.3 | 3.7 | 4.0 |
| 100 | Y | 12.6 | 8.3 | 14.5 | 10.8 | 6.2 | 10.9 | 9.3 | 12.6 | 12.9 | 12.0 | 11.5 | 10.9 | 7.8 | 12.0 | 12.8 | 12.2 | 13.9 | 6.5 | / |
| 100a | Y | 5.9 | 2.7 | 5.7 | 3.5 | 1.3 | 7.0 | 2.8 | 8.9 | 3.9 | 7.1 | 7.7 | 3.3 | 3.9 | 14.7 | 2.4 | 6.7 | 13.4 | 11.6 | / |
| 100b | L | 4.1 | 10.6 | / | 12.9 | 0.6 | 7.2 | 0.0 | 4.8 | 3.9 | 1.9 | 3.1 | 1.5 | 0.3 | 8.0 | 0.8 | 0.2 | 14.8 | 6.2 | 11.2 |
| 101 | D | 6.5 | 5.2 | 5.4 | 5.3 | 6.7 | 6.8 | 6.7 | 6.7 | 7.0 | 6.8 | 6.2 | / | 7.0 | 3.4 | 4.4 | 4.1 | — | — | — |
| 102 | E | 12.1 | 11.7 | 10.8 | 11.7 | 6.9 | 13.3 | 12.6 | 11.2 | 11.3 | 9.4 | 10.2 | 12.5 | / | 10.3 | 10.9 | 10.5 | 10.5 | 12.7 | 12.9 |

The invention claimed is:

1. A bispecific antibody comprising a first antibody heavy chain and a first antibody light chain that bind to blood coagulation factor IX and/or activated blood coagulation factor IX, and a second antibody heavy chain and a second antibody light chain which bind to blood coagulation factor X, wherein the bispecific antibody is any of (a) to (t) below:

(a) a bispecific antibody which comprises a first antibody heavy chain variable region comprising the amino acid sequence of SEQ ID NO: 56, a first antibody light chain variable region comprising the amino acid sequence of SEQ ID NO: 61, a second antibody heavy chain variable region comprising the amino acid sequence of SEQ ID NO: 73, and a second antibody light chain variable region comprising the amino acid sequence of SEQ ID NO: 84;

(b) a bispecific antibody which comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 73, and a second antibody light chain variable region comprising the amino acid sequence of SEQ ID NO: 84;

(c) a bispecific antibody which comprises a first antibody heavy chain variable region comprising the amino acid sequence of SEQ ID NO: 58, a first antibody light chain variable region comprising the amino acid sequence of SEQ ID NO: 63, a second antibody heavy chain variable region comprising the amino acid sequence of SEQ ID NO: 74, and a second antibody light chain variable region comprising the amino acid sequence of SEQ ID NO: 85;

(d) a bispecific antibody which comprises a first antibody heavy chain variable region comprising the amino acid sequence of SEQ ID NO: 58, a first antibody light chain variable region comprising the amino acid sequence of SEQ ID NO: 64, a second antibody heavy chain variable region comprising the amino acid sequence of SEQ ID NO: 74, and a second antibody light chain variable region comprising the amino acid sequence of SEQ ID NO: 85;

(e) a bispecific antibody which comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 75, and a second antibody light chain variable region comprising the amino acid sequence of SEQ ID NO: 86;

(f) a bispecific antibody which comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 76, and a second antibody light chain variable region comprising the amino acid sequence of SEQ ID NO: 87;

(g) a bispecific antibody which comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 74, and a second antibody light chain variable region comprising the amino acid sequence of SEQ ID NO: 85;

(h) a bispecific antibody which comprises a first antibody heavy chain variable region comprising the amino acid sequence of SEQ ID NO: 59, a first antibody light chain variable region comprising the amino acid sequence of SEQ ID NO: 65, a second antibody heavy chain variable region comprising the amino acid sequence of SEQ ID NO: 74, and a second antibody light chain variable region comprising the amino acid sequence of SEQ ID NO: 85;

(i) a bispecific antibody which comprises a first antibody heavy chain variable region comprising the amino acid sequence of SEQ ID NO: 59, a first antibody light chain variable region comprising the amino acid sequence of SEQ ID NO: 66, a second antibody heavy chain variable region comprising the amino acid sequence of SEQ ID NO: 74, and a second antibody light chain variable region comprising the amino acid sequence of SEQ ID NO: 85;
(j) a bispecific antibody which comprises a first antibody heavy chain variable region comprising the amino acid sequence of SEQ ID NO: 59, a first antibody light chain variable region comprising the amino acid sequence of SEQ ID NO: 66, a second antibody heavy chain variable region comprising the amino acid sequence of SEQ ID NO: 77, and a second antibody light chain variable region comprising the amino acid sequence of SEQ ID NO: 88;
(k) a bispecific antibody which comprises a first antibody heavy chain variable region comprising the amino acid sequence of SEQ ID NO: 59, a first antibody light chain variable region comprising the amino acid sequence of SEQ ID NO: 67, a second antibody heavy chain variable region comprising the amino acid sequence of SEQ ID NO: 77, and a second antibody light chain variable region comprising the amino acid sequence of SEQ ID NO: 88;
(l) a bispecific antibody which comprises a first antibody heavy chain variable region comprising the amino acid sequence of SEQ ID NO: 59, a first antibody light chain variable region comprising the amino acid sequence of SEQ ID NO: 67, a second antibody heavy chain variable region comprising the amino acid sequence of SEQ ID NO: 78, and a second antibody light chain variable region comprising the amino acid sequence of SEQ ID NO: 89;
(m) a bispecific antibody which comprises a first antibody heavy chain variable region comprising the amino acid sequence of SEQ ID NO: 59, a first antibody light chain variable region comprising the amino acid sequence of SEQ ID NO: 68, a second antibody heavy chain variable region comprising the amino acid sequence of SEQ ID NO: 77, and a second antibody light chain variable region comprising the amino acid sequence of SEQ ID NO: 88;
(n) a bispecific antibody which comprises a first antibody heavy chain variable region comprising the amino acid sequence of SEQ ID NO: 59, a first antibody light chain variable region comprising the amino acid sequence of SEQ ID NO: 68, a second antibody heavy chain variable region comprising the amino acid sequence of SEQ ID NO: 78, and a second antibody light chain variable region comprising the amino acid sequence of SEQ ID NO: 89;
(o) a bispecific antibody which comprises a first antibody heavy chain variable region comprising the amino acid sequence of SEQ ID NO: 60, a first antibody light chain variable region comprising the amino acid sequence of SEQ ID NO: 69, a second antibody heavy chain variable region comprising the amino acid sequence of SEQ ID NO: 79, and a second antibody light chain variable region comprising the amino acid sequence of SEQ ID NO: 90;
(p) a bispecific antibody which comprises a first antibody heavy chain variable region comprising the amino acid sequence of SEQ ID NO: 59, a first antibody light chain variable region comprising the amino acid sequence of SEQ ID NO: 70, a second antibody heavy chain variable region comprising the amino acid sequence of SEQ ID NO: 80, and a second antibody light chain variable region comprising the amino acid sequence of SEQ ID NO: 91;
(q) a bispecific antibody which comprises a first antibody heavy chain variable region comprising the amino acid sequence of SEQ ID NO: 60, a first antibody light chain variable region comprising the amino acid sequence of SEQ ID NO: 71, a second antibody heavy chain variable region comprising the amino acid sequence of SEQ ID NO: 79, and a second antibody light chain variable region comprising the amino acid sequence of SEQ ID NO: 90;
(r) a bispecific antibody which comprises a first antibody heavy chain variable region comprising the amino acid sequence of SEQ ID NO: 60, a first antibody light chain variable region comprising the amino acid sequence of SEQ ID NO: 71, a second antibody heavy chain variable region comprising the amino acid sequence of SEQ ID NO: 81, and a second antibody light chain variable region comprising the amino acid sequence of SEQ ID NO: 92;
(s) a bispecific antibody which comprises a first antibody heavy chain variable region comprising the amino acid sequence of SEQ ID NO: 60, a first antibody light chain variable region comprising the amino acid sequence of SEQ ID NO: 69, a second antibody heavy chain variable region comprising the amino acid sequence of SEQ ID NO: 82, and a second antibody light chain variable region comprising the amino acid sequence of SEQ ID NO: 93;
(t) a bispecific antibody which comprises a first antibody heavy chain variable region comprising the amino acid sequence of SEQ ID NO: 105, a first antibody light chain variable region comprising the amino acid sequence of SEQ ID NO: 72, a second antibody heavy chain variable region comprising the amino acid sequence of SEQ ID NO: 83, and a second antibody light chain variable region comprising the amino acid sequence of SEQ ID NO: 94.

2. The bispecific antibody of claim 1, wherein the first antibody heavy chain and antibody light chain comprise constant regions comprising the amino acid sequences set forth in (1) below, and the second antibody heavy chain and antibody light chain comprise constant regions comprising the amino acid sequences set forth in (2) below:
(1) SEQ ID NO: 119 as a heavy chain constant region and SEQ ID NO: 100 as a light chain constant region;
(2) SEQ ID NO: 118 as a heavy chain constant region and SEQ ID NO: 102 as a light chain constant region.

3. A bispecific antibody comprising a first antibody heavy chain and a first antibody light chain which bind to blood coagulation factor IX and/or activated blood coagulation factor IX, and a second antibody heavy chain and a second antibody light chain which bind to blood coagulation factor X, wherein the bispecific antibody is any of (a) to (t) below:
(a) a bispecific antibody which comprises a first antibody heavy chain comprising the amino acid sequence of SEQ ID NO: 120, a first antibody light chain comprising the amino acid sequence of SEQ ID NO: 126, a second antibody heavy chain comprising the amino acid sequence of SEQ ID NO: 138, and a second antibody light chain comprising the amino acid sequence of SEQ ID NO: 149;
(b) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 138, and a second antibody light chain comprising the amino acid sequence of SEQ ID NO: 149;

(c) a bispecific antibody which comprises a first antibody heavy chain comprising the amino acid sequence of SEQ ID NO: 122, a first antibody light chain comprising the amino acid sequence of SEQ ID NO: 128, a second antibody heavy chain comprising the amino acid sequence of SEQ ID NO: 139, and a second antibody light chain comprising the amino acid sequence of SEQ ID NO: 150;

(d) a bispecific antibody which comprises a first antibody heavy chain comprising the amino acid sequence of SEQ ID NO: 122, a first antibody light chain comprising the amino acid sequence of SEQ ID NO: 129, a second antibody heavy chain comprising the amino acid sequence of SEQ ID NO: 139, and a second antibody light chain comprising the amino acid sequence of SEQ ID NO: 150;

(e) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 140, and a second antibody light chain comprising the amino acid sequence of SEQ ID NO: 151;

(f) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 141, and a second antibody light chain comprising the amino acid sequence of SEQ ID NO: 152;

(g) a bispecific antibody which comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 139, and a second antibody light chain comprising the amino acid sequence of SEQ ID NO: 150;

(h) a bispecific antibody which comprises a first antibody heavy chain comprising the amino acid sequence of SEQ ID NO: 123, a first antibody light chain comprising the amino acid sequence of SEQ ID NO: 130, a second antibody heavy chain comprising the amino acid sequence of SEQ ID NO: 139, and a second antibody light chain comprising the amino acid sequence of SEQ ID NO: 150;

(i) a bispecific antibody which comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 139, and a second antibody light chain comprising the amino acid sequence of SEQ ID NO: 150;

(j) a bispecific antibody which comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 142, and a second antibody light chain comprising the amino acid sequence of SEQ ID NO: 153;

(k) a bispecific antibody which comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 142, and a second antibody light chain comprising the amino acid sequence of SEQ ID NO: 153;

(l) a bispecific antibody which comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 143, and a second antibody light chain comprising the amino acid sequence of SEQ ID NO: 154;

(m) a bispecific antibody which comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 142, and a second antibody light chain comprising the amino acid sequence of SEQ ID NO: 153;

(n) a bispecific antibody which comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 143, and a second antibody light chain comprising the amino acid sequence of SEQ ID NO: 154;

(o) a bispecific antibody which comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 144, and a second antibody light chain comprising the amino acid sequence of SEQ ID NO: 155;

(p) a bispecific antibody which comprises a first antibody heavy chain comprising the amino acid sequence of SEQ ID NO: 123, a first antibody light chain comprising the amino acid sequence of SEQ ID NO: 135, a second antibody heavy chain comprising the amino acid sequence of SEQ ID NO: 145, and a second antibody light chain comprising the amino acid sequence of SEQ ID NO: 156;

(q) a bispecific antibody which comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 144, and a second antibody light chain comprising the amino acid sequence of SEQ ID NO: 155;

(r) a bispecific antibody which comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 146, and a second antibody light chain comprising the amino acid sequence of SEQ ID NO: 157;

(s) a bispecific antibody which comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 147, and a second antibody light chain comprising the amino acid sequence of SEQ ID NO: 158;

(t) a bispecific antibody which comprises a first antibody heavy chain comprising the amino acid sequence of SEQ ID NO: 125, a first antibody light chain comprising the amino acid sequence of SEQ ID NO: 137, a second antibody heavy chain comprising the amino acid sequence of SEQ ID NO: 148, and a second antibody light chain comprising the amino acid sequence of SEQ ID NO: 159.

4. A pharmaceutical formulation which comprises the bispecific antibody of claim 1 and a pharmaceutically acceptable carrier.

5. A pharmaceutical formulation which comprises the bispecific antibody of claim 2 and a pharmaceutically acceptable carrier.

6. A pharmaceutical formulation which comprises the bispecific antibody of claim 3 and a pharmaceutically acceptable carrier.

7. The pharmaceutical formulation of claim 4, which is for use in treatment of bleeding, a disease involving bleeding, or a disease caused by bleeding in a subject, wherein the bleeding, the disease involving bleeding, or the disease caused by bleeding is a condition which develops and/or progresses due to a decrease or deficiency in the activity of blood coagulation factor VIII and/or activated blood coagulation factor VIII.

8. The pharmaceutical formulation of claim 5, which is for use in treatment of bleeding, a disease involving bleeding, or a disease caused by bleeding in a subject, wherein the bleeding, the disease involving bleeding, or the disease caused by bleeding is a condition which develops and/or progresses due to a decrease or deficiency in the activity of blood coagulation factor VIII and/or activated blood coagulation factor VIII.

9. The pharmaceutical formulation of claim 6, which is for use in treatment of bleeding, a disease involving bleeding, or a disease caused by bleeding in a subject, wherein the bleeding, the disease involving bleeding, or the disease caused by bleeding is a condition which develops and/or progresses due to a decrease or deficiency in the activity of blood coagulation factor VIII and/or activated blood coagulation factor VIII.

10. The pharmaceutical formulation of claim 7, wherein the condition which develops and/or progresses due to a decrease or deficiency in the activity of blood coagulation factor VIII and/or activated blood coagulation factor VIII is hemophilia A, acquired hemophilia, von Willebrand disease, or a disease with emergence of an inhibitor against blood coagulation factor VIII and/or activated blood coagulation factor VIII.

11. The pharmaceutical formulation of claim 8, wherein the condition which develops and/or progresses due to a decrease or deficiency in the activity of blood coagulation factor VIII and/or activated blood coagulation factor VIII is hemophilia A, acquired hemophilia, von Willebrand disease, or a disease with emergence of an inhibitor against blood coagulation factor VIII and/or activated blood coagulation factor VIII.

12. The pharmaceutical formulation of claim 9, wherein the condition which develops and/or progresses due to a decrease or deficiency in the activity of blood coagulation factor VIII and/or activated blood coagulation factor VIII is hemophilia A, acquired hemophilia, von Willebrand disease, or a disease with emergence of an inhibitor against blood coagulation factor VIII and/or activated blood coagulation factor VIII.

13. A method of treating or reducing the incidence of a condition that develops or progresses due to a deficiency in the activity of blood coagulation factor VIII and/or activated blood coagulation factor VIII, wherein the method comprises administering the pharmaceutical formulation of claim 4 to the subject.

14. A method of treating or reducing the incidence of a condition that develops or progresses due to a deficiency in the activity of blood coagulation factor VIII and/or activated blood coagulation factor VIII, wherein the method comprises administering the pharmaceutical formulation of claim 5 to the subject.

15. A method of treating or reducing the incidence of a condition that develops or progresses due to a deficiency in the activity of blood coagulation factor VIII and/or activated blood coagulation factor VIII, wherein the method comprises administering the pharmaceutical formulation of claim 6 to the subject.

16. The method of claim 13, wherein the condition is hemophilia A, acquired hemophilia, von Willebrand disease, or a disease involving emergence of an inhibitor against blood coagulation factor VIII and/or activated blood coagulation factor VIII.

17. The method of claim 14, wherein the condition is hemophilia A, acquired hemophilia, von Willebrand disease, or a disease involving emergence of an inhibitor against blood coagulation factor VIII and/or activated blood coagulation factor VIII.

18. The method of claim 15, wherein the condition is hemophilia A, acquired hemophilia, von Willebrand disease, or a disease involving emergence of an inhibitor against blood coagulation factor VIII and/or activated blood coagulation factor VIII.

19. The bispecific antibody of claim 1, wherein the bispecific antibody comprises a first antibody heavy chain variable region comprising the amino acid sequence of SEQ ID NO: 56, a first antibody light chain variable region comprising the amino acid sequence of SEQ ID NO: 61, a second antibody heavy chain variable region comprising the amino acid sequence of SEQ ID NO: 73, and a second antibody light chain variable region comprising the amino acid sequence of SEQ ID NO: 84.

20. The bispecific antibody of claim 1, wherein the bispecific antibody comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 73, and a second antibody light chain variable region comprising the amino acid sequence of SEQ ID NO: 84.

21. The bispecific antibody of claim 1, wherein the bispecific antibody comprises a first antibody heavy chain variable region comprising the amino acid sequence of SEQ ID NO: 58, a first antibody light chain variable region comprising the amino acid sequence of SEQ ID NO: 63, a second antibody heavy chain variable region comprising the amino acid sequence of SEQ ID NO: 74, and a second antibody light chain variable region comprising the amino acid sequence of SEQ ID NO: 85.

22. The bispecific antibody of claim 1, wherein the bispecific antibody comprises a first antibody heavy chain variable region comprising the amino acid sequence of SEQ ID NO: 58, a first antibody light chain variable region comprising the amino acid sequence of SEQ ID NO: 64, a second antibody heavy chain variable region comprising the amino acid sequence of SEQ ID NO: 74, and a second antibody light chain variable region comprising the amino acid sequence of SEQ ID NO: 85.

23. The bispecific antibody of claim 1, wherein the bispecific antibody comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 75, and a second antibody light chain variable region comprising the amino acid sequence of SEQ ID NO: 86.

24. The bispecific antibody of claim 1, wherein the bispecific antibody comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 76, and a second antibody light chain variable region comprising the amino acid sequence of SEQ ID NO: 87.

25. The bispecific antibody of claim 1, wherein the bispecific antibody comprises a first antibody heavy chain variable region comprising the amino acid sequence of SEQ ID NO: 57, a first antibody light chain variable region comprising the amino acid sequence of SEQ ID NO: 62, a second antibody heavy chain variable region comprising the amino acid sequence of SEQ ID NO: 74, and a second antibody light chain variable region comprising the amino acid sequence of SEQ ID NO: 85.

26. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 65, a second antibody heavy chain variable region comprising the amino acid sequence of SEQ ID NO: 74, and a second antibody light chain variable region comprising the amino acid sequence of SEQ ID NO: 85.

27. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 66, a second antibody heavy chain variable region comprising the amino acid sequence of SEQ ID NO: 74, and a second antibody light chain variable region comprising the amino acid sequence of SEQ ID NO: 85.

28. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 66, a second antibody heavy chain variable region comprising the amino acid sequence of SEQ ID NO: 77, and a second antibody light chain variable region comprising the amino acid sequence of SEQ ID NO: 88.

29. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 67, a second antibody heavy chain variable region comprising the amino acid sequence of SEQ ID NO: 77, and a second antibody light chain variable region comprising the amino acid sequence of SEQ ID NO: 88.

30. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 67, a second antibody heavy chain variable region comprising the amino acid sequence of SEQ ID NO: 78, and a second antibody light chain variable region comprising the amino acid sequence of SEQ ID NO: 89.

31. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 68, a second antibody heavy chain variable region comprising the amino acid sequence of SEQ ID NO: 77, and a second antibody light chain variable region comprising the amino acid sequence of SEQ ID NO: 88.

32. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 68, a second antibody heavy chain variable region comprising the amino acid sequence of SEQ ID NO: 78, and a second antibody light chain variable region comprising the amino acid sequence of SEQ ID NO: 89.

33. The bispecific antibody of claim 1, wherein the bispecific antibody comprises a first antibody heavy chain variable region comprising the amino acid sequence of SEQ ID NO: 60, a first antibody light chain variable region comprising the amino acid sequence of SEQ ID NO: 69, a second antibody heavy chain variable region comprising the amino acid sequence of SEQ ID NO: 79, and a second antibody light chain variable region comprising the amino acid sequence of SEQ ID NO: 90.

34. The bispecific antibody of claim 1, wherein the bispecific antibody comprises a first antibody heavy chain variable region comprising the amino acid sequence of SEQ ID NO: 59, a first antibody light chain variable region comprising the amino acid sequence of SEQ ID NO: 70, a second antibody heavy chain variable region comprising the amino acid sequence of SEQ ID NO: 80, and a second antibody light chain variable region comprising the amino acid sequence of SEQ ID NO: 91.

35. The bispecific antibody of claim 1, wherein the bispecific antibody comprises a first antibody heavy chain variable region comprising the amino acid sequence of SEQ ID NO: 60, a first antibody light chain variable region comprising the amino acid sequence of SEQ ID NO: 71, a second antibody heavy chain variable region comprising the amino acid sequence of SEQ ID NO: 79, and a second antibody light chain variable region comprising the amino acid sequence of SEQ ID NO: 90.

36. The bispecific antibody of claim 1, wherein the bispecific antibody comprises a first antibody heavy chain variable region comprising the amino acid sequence of SEQ ID NO: 60, a first antibody light chain variable region comprising the amino acid sequence of SEQ ID NO: 71, a second antibody heavy chain variable region comprising the amino acid sequence of SEQ ID NO: 81, and a second antibody light chain variable region comprising the amino acid sequence of SEQ ID NO: 92.

37. The bispecific antibody of claim 1, wherein the bispecific antibody comprises a first antibody heavy chain variable region comprising the amino acid sequence of SEQ ID NO: 60, a first antibody light chain variable region comprising the amino acid sequence of SEQ ID NO: 69, a second antibody heavy chain variable region comprising the amino acid sequence of SEQ ID NO: 82, and a second antibody light chain variable region comprising the amino acid sequence of SEQ ID NO: 93.

38. The bispecific antibody of claim 1, wherein the bispecific antibody comprises a first antibody heavy chain variable region comprising the amino acid sequence of SEQ ID NO: 105, a first antibody light chain variable region comprising the amino acid sequence of SEQ ID NO: 72, a second antibody heavy chain variable region comprising the amino acid sequence of SEQ ID NO: 83, and a second antibody light chain variable region comprising the amino acid sequence of SEQ ID NO: 94.

39. The bispecific antibody of claim 3, wherein the bispecific antibody comprises a first antibody heavy chain comprising the amino acid sequence of SEQ ID NO: 120, a first antibody light chain comprising the amino acid sequence of SEQ ID NO: 126, a second antibody heavy chain comprising the amino acid sequence of SEQ ID NO: 138, and a second antibody light chain comprising the amino acid sequence of SEQ ID NO: 149.

40. The bispecific antibody of claim 3, wherein the bispecific antibody comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 138, and a second antibody light chain comprising the amino acid sequence of SEQ ID NO: 149.

41. The bispecific antibody of claim 3, wherein the bispecific antibody comprises a first antibody heavy chain comprising the amino acid sequence of SEQ ID NO: 122, a first antibody light chain comprising the amino acid sequence of SEQ ID NO: 128, a second antibody heavy chain comprising the amino acid sequence of SEQ ID NO: 139, and a second antibody light chain comprising the amino acid sequence of SEQ ID NO: 150.

42. The bispecific antibody of claim 3, wherein the bispecific antibody comprises a first antibody heavy chain comprising the amino acid sequence of SEQ ID NO: 122, a first antibody light chain comprising the amino acid sequence of SEQ ID NO: 129, a second antibody heavy chain comprising the amino acid sequence of SEQ ID NO: 139, and a second antibody light chain comprising the amino acid sequence of SEQ ID NO: 150.

43. The bispecific antibody of claim 3, wherein the bispecific antibody comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 140, and a second antibody light chain comprising the amino acid sequence of SEQ ID NO: 151.

44. The bispecific antibody of claim 3, wherein the bispecific antibody comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 141, and a second antibody light chain comprising the amino acid sequence of SEQ ID NO: 152.

45. The bispecific antibody of claim 3, wherein the bispecific antibody comprises a first antibody heavy chain comprising the amino acid sequence of SEQ ID NO: 121, a first antibody light chain comprising the amino acid sequence of SEQ ID NO: 127, a second antibody heavy chain comprising the amino acid sequence of SEQ ID NO: 139, and a second antibody light chain comprising the amino acid sequence of SEQ ID NO: 150.

46. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 130, a second antibody heavy chain comprising the amino acid sequence of SEQ ID NO: 139, and a second antibody light chain comprising the amino acid sequence of SEQ ID NO: 150.

47. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 139, and a second antibody light chain comprising the amino acid sequence of SEQ ID NO: 150.

48. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 131, a second antibody heavy chain comprising the amino acid sequence of SEQ ID NO: 142, and a second antibody light chain comprising the amino acid sequence of SEQ ID NO: 153.

49. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 142, and a second antibody light chain comprising the amino acid sequence of SEQ ID NO: 153.

50. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 132, a second antibody heavy chain comprising the amino acid sequence of SEQ ID NO: 143, and a second antibody light chain comprising the amino acid sequence of SEQ ID NO: 154.

51. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 142, and a second antibody light chain comprising the amino acid sequence of SEQ ID NO: 153.

52. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 133, a second antibody heavy chain comprising the amino acid sequence of SEQ ID NO: 143, and a second antibody light chain comprising the amino acid sequence of SEQ ID NO: 154.

53. The bispecific antibody of claim 3, wherein the bispecific antibody comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO:

144, and a second antibody light chain comprising the amino acid sequence of SEQ ID NO: 155.

54. The bispecific antibody of claim 3, wherein the bispecific antibody comprises a first antibody heavy chain comprising the amino acid sequence of SEQ ID NO: 123, a first antibody light chain comprising the amino acid sequence of SEQ ID NO: 135, a second antibody heavy chain comprising the amino acid sequence of SEQ ID NO: 145, and a second antibody light chain comprising the amino acid sequence of SEQ ID NO: 156.

55. The bispecific antibody of claim 3, wherein the bispecific antibody comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 144, and a second antibody light chain comprising the amino acid sequence of SEQ ID NO: 155.

56. The bispecific antibody of claim 3, wherein the bispecific antibody comprises a first antibody heavy chain comprising the amino acid sequence of SEQ ID NO: 124, a first antibody light chain comprising the amino acid sequence of SEQ ID NO: 136, a second antibody heavy chain comprising the amino acid sequence of SEQ ID NO: 146, and a second antibody light chain comprising the amino acid sequence of SEQ ID NO: 157.

57. The bispecific antibody of claim 3, wherein the bispecific antibody comprises a first antibody heavy chain comprising the amino acid sequence of SEQ ID NO: 124, a first antibody light chain comprising the amino acid sequence of SEQ ID NO: 134, a second antibody heavy chain comprising the amino acid sequence of SEQ ID NO: 147, and a second antibody light chain comprising the amino acid sequence of SEQ ID NO: 158.

58. The bispecific antibody of claim 3, wherein the bispecific antibody comprises a first antibody heavy chain comprising the amino acid sequence of SEQ ID NO: 125, a first antibody light chain comprising the amino acid sequence of SEQ ID NO: 137, a second antibody heavy chain comprising the amino acid sequence of SEQ ID NO: 148, and a second antibody light chain comprising the amino acid sequence of SEQ ID NO: 159.

59. The method of claim 16, wherein the condition is hemophilia A.

60. The method of claim 17, wherein the condition is hemophilia A.

61. The method of claim 18, wherein the condition is hemophilia A.

\* \* \* \* \*

SEQUENCE LISTING

<160> NUMBER OF SEQ ID NOS: 287

<210> SEQ ID NO 1
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 1

Tyr Tyr Asp Ile Gln
1               5

<210> SEQ ID NO 2
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 2

Ser Ile Ser Pro Ser Gly Gln Ser Thr Tyr Tyr Arg Arg Glu Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 3

Arg Thr Gly Arg Glu Tyr Gly Gly Gly Trp Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 4

Asp Asn Asn Met Asp
1               5

<210> SEQ ID NO 5
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 5

Asp Ile Asn Thr Arg Ser Gly Gly Ser Ile Tyr Asn Glu Glu Phe Gln
1               5                   10                  15

Asp

<210> SEQ ID NO 6
<211> LENGTH: 10
<212> TYPE: PRT
<213> ORGANISM: Artificial Sequence
<220> FEATURE:
<223> OTHER INFORMATION: An artificially synthesized sequence

```
<400> SEQUENCE: 6

Arg Lys Ser Tyr Gly Tyr Tyr Leu Asp Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 7

Lys Ala Ser Arg Asn Ile Glu Arg Gln Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 8

Gln Ala Ser Arg Lys Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 9

Gln Gln Tyr Ser Asp Pro Pro Leu Thr
1               5

<210> SEQ ID NO 10
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
```

130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Thr Cys Asn Val
                195                 200                 205

Asp His Lys Pro Ser Asn Thr Lys Val Asp Lys Arg Val Glu Ser Lys
                210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Lys Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
                420                 425                 430

Glu Ala Leu His Asn Arg Tyr Thr Gln Lys Ser Leu Ser Leu Ser Pro
                435                 440                 445

<210> SEQ ID NO 11
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
                35                  40                  45

Gly Asp Ile Asn Thr Arg Ser Gly Gly Ser Ile Tyr Asn Glu Glu Phe

```
                50                  55                  60
Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Glu Ser Leu Ser Leu Ser Pro
                435                 440

<210> SEQ ID NO 12
<211> LENGTH: 214
<212> TYPE: PRT
<213> ORGANISM: Artificial Sequence
```

```
<220> FEATURE:
<223> OTHER INFORMATION: An artificially synthesized sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 13

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Arg Pro Leu Thr
                85                  90                  95

Phe Gly Gly Gly Thr Lys Val Glu Ile Lys
            100                 105
```

```
<210> SEQ ID NO 14
<211> LENGTH: 108
<212> TYPE: PRT
<213> ORGANISM: Artificial Sequence
<220> FEATURE:
<223> OTHER INFORMATION: An artificially synthesized sequence

<400> SEQUENCE: 14

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Leu Gly
                85                  90                  95

Ile Thr Phe Gly Pro Gly Thr Lys Val Asp Ile Lys
            100                 105

<210> SEQ ID NO 15
<211> LENGTH: 111
<212> TYPE: PRT
<213> ORGANISM: Artificial Sequence
<220> FEATURE:
<223> OTHER INFORMATION: An artificially synthesized sequence

<400> SEQUENCE: 15

Asp Ile Val Met Thr Gln Thr Pro Leu Ser Leu Ser Val Thr Pro Gly
1               5                   10                  15

Gln Pro Ala Ser Val Ser Cys Lys Ser Ser Gln Ser Leu Leu Arg Thr
            20                  25                  30

Asp Gly Lys Ala Tyr Leu Asp Trp Tyr Leu Gln Lys Pro Gly Gln Ser
        35                  40                  45

Pro Gln Leu Leu Ile Tyr Glu Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Arg
                85                  90                  95

Ile Gln Ala Leu Ser Phe Gly Gly Gly Thr Lys Val Asp Ile Lys
            100                 105                 110

<210> SEQ ID NO 16
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 16

Ser Ser Gly Leu Thr Gln Pro Pro Ser Leu Ser Val Ser Pro Gly Gln
1               5                   10                  15

Thr Ala Ser Ile Thr Cys Ser Gly His Lys Val Gly Asp Lys Tyr Ala
            20                  25                  30

Ser Trp Tyr Gln Gln Lys Pro Gly Gln Ser Pro Val Leu Val Ile Tyr
        35                  40                  45
```

```
Gln Asp Ser Lys Arg Pro Ser Gly Ile Pro Glu Arg Phe Ser Ala Ser
        50                  55                  60

Asn Ser Gly Asn Thr Ala Thr Leu Thr Ile Ser Gly Thr Gln Ala Val
 65                  70                  75                  80

Asp Glu Ala Asp Tyr Tyr Cys Leu Ala Trp Val Pro Asn Ser Gly Tyr
                85                  90                  95

Val Phe Gly Thr Gly Thr Gln Val Thr Val Val
                100                 105
```

<210> SEQ ID NO 17
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 17

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                85                  90                  95

Ser Thr Leu Val Phe Gly Gly Gly Thr Lys Leu Thr Val Leu
                100                 105                 110
```

<210> SEQ ID NO 18
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 18

```
Gln Ser Ala Leu Thr Gln Pro Pro Ser Leu Ser Val Ser Pro Gly Gln
 1               5                  10                  15

Thr Ala Ser Ile Thr Cys Ser Gly His Lys Val Gly Asp Lys Tyr Ala
                20                  25                  30

Ser Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Ala Ser
 50                  55                  60

Asn Ser Gly Asn Thr Ala Thr Leu Thr Ile Ser Gly Thr Gln Ala Val
 65                  70                  75                  80

Asp Glu Ala Asp Tyr Tyr Cys Leu Ala Trp Val Pro Asn Ser Gly Tyr
                85                  90                  95

Val Phe Gly Thr Gly Thr Gln Val Thr Val Val
                100                 105
```

<210> SEQ ID NO 19
<211> LENGTH: 107
<212> TYPE: PRT

<213> ORGANISM: Artificial Sequence
<220> FEATURE:
<223> OTHER INFORMATION: An artificially synthesized sequence

<400> SEQUENCE: 19

Asn Ile Gln Met Thr Gln Ser Pro Ser Ser Val Ser Ala Ser Val Gly
1               5                   10                  15

Asp Thr Val Thr Ile Thr Cys Arg Ala Ser Gln Tyr Ile Ser Asp Arg
            20                  25                  30

Leu Ala Trp Tyr Gln Gln Lys Pro Gly Arg Pro Lys Val Leu Ile
        35                  40                  45

Tyr Arg Ala Ser Asn Leu Gln Ser Gly Val Pro Ser Arg Phe Arg Gly
    50                  55                  60

Ser Gly Ser Gly Thr Asp Phe Thr Leu Thr Ile Asn Ser Leu Gln Pro
65                  70                  75                  80

Glu Asp Phe Ala Ile Tyr Tyr Cys Gln Gln Ala Lys Asn Phe Pro Trp
                85                  90                  95

Ala Phe Gly Gln Gly Thr Lys Val Glu Phe Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 20

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Gly Ala Phe Thr Leu Gln Thr Gly Val Pro Ser Arg Phe Ser Gly
    50                  55                  60

Ser Ala Ser Gly Thr Asp Phe Thr Leu Thr Ile Asn Asn Leu Gln Pro
65                  70                  75                  80

Glu Asp Phe Ala Val Tyr His Cys Gln Gln Ser Tyr Arg Ile Pro Trp
                85                  90                  95

Thr Phe Gly Gln Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 21

Asn Ile Gln Met Thr Gln Ser Pro Ala Ser Leu Ser Ala Ser Val Gly
1               5                   10                  15

Asp Lys Val Thr Ile Thr Cys Gln Ala Ser Gln Asp Ile Gly Thr Ser
            20                  25                  30

Leu Asn Trp Tyr Gln Gln Arg Pro Gly Thr Ala Pro Lys Leu Leu Ile
        35                  40                  45

Phe Asp Thr Ser Asn Leu Glu Lys Gly Val Pro Ser Arg Phe Ser Gly
    50                  55                  60

Ser Lys Ser Glu Thr Tyr Phe Thr Phe Ala Ile Ser Ser Leu Gln Pro
65                  70                  75                  80

Glu Asp Ile Ala Thr Tyr Tyr Cys Gln Gln Ser Tyr Asn Ile Pro Trp
                85                  90                  95

Thr Phe Gly Arg Gly Thr Lys Val Glu Ile Thr
            100                 105

<210> SEQ ID NO 22
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 22

Asp Ile Gln Leu Thr Gln Ser Pro Ser Ser Leu Ser Ala Ser Val Gly
1               5                   10                  15

Asp Ser Val Thr Ile Thr Cys Arg Ala Ser Gln Ser Phe Thr Asn Tyr
                20                  25                  30

Leu Asn Trp Tyr Gln Gln Lys Pro Gly Lys Ala Pro Lys Val Leu Ile
            35                  40                  45

Tyr Gly Ala Ser Thr Leu Gln Thr Gly Val Pro Ser Arg Phe Ser Gly
    50                  55                  60

Gly Gly Ser Gly Ala Glu Tyr Thr Leu Thr Ile Ser Asn Leu Gln Pro
65                  70                  75                  80

Asp Asp Ser Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 23

Asp Ile Val Met Thr Gln Ser Pro Ser Ser Leu Ser Ala Ser Val Gly
1               5                   10                  15

Asp Arg Val Thr Ile Thr Cys Arg Thr Ser Gln Tyr Ile Gly Thr Tyr
                20                  25                  30

Leu Asn Trp Tyr Gln Gln Lys Pro Gly Lys Ala Pro Lys Leu Leu Ile
            35                  40                  45

Asn Ser Val Ser Arg Leu Gln Thr Gly Val Pro Ser Arg Phe Thr Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Pro Trp
                85                  90                  95

Thr Phe Gly Gln Gly Thr Arg Val Glu Ile Lys
            100                 105

<210> SEQ ID NO 24
<211> LENGTH: 112
<212> TYPE: PRT
<213> ORGANISM: Artificial Sequence
<220> FEATURE:
<223> OTHER INFORMATION: An artificially synthesized sequence

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Arg Ser
            20                  25                  30

Asp Gly Lys Thr Tyr Leu Gln Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Glu Arg Phe Ser Gly Ser Gly Ser Gly Thr Asp Phe Thr Leu Glu Ile
65                  70                  75                  80

Ser Arg Val Glu Ala Asp Asp Val Gly Val Tyr Tyr Cys Met Gln Gly
                85                  90                  95

Leu His Leu Pro Trp Thr Phe Gly Gln Gly Thr Lys Val Glu Val Lys
            100                 105                 110

<210> SEQ ID NO 25
<211> LENGTH: 108
<212> TYPE: PRT
<213> ORGANISM: Artificial Sequence
<220> FEATURE:
<223> OTHER INFORMATION: An artificially synthesized sequence

<400> SEQUENCE: 25

Glu Ile Val Leu Thr Gln Ser Pro Gly Thr Leu Ser Leu Ser Pro Gly
1               5                   10                  15

Glu Ser Gly Thr Leu Ser Cys Arg Ala Ser Gln Ser Val Asn Thr Arg
            20                  25                  30

Tyr Leu Ala Trp Tyr Tyr Gln Arg Pro Gly Gln Val Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Gly Asp Ser Gly Val Tyr Tyr Cys Gln Gln Ser Arg Ser Ser Gln
                85                  90                  95

Trp Thr Phe Gly Gln Gly Thr Lys Val Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 26

Val Ile Trp Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Arg
            20                  25                  30

Leu Val Trp Tyr Gln Gln Lys Pro Gly Thr Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Gly Asn Thr Phe Pro Trp
                85                  90                  95

Thr Phe Gly Gln Gly Thr Lys Val Glu Val Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 27

Asn Ile Gln Met Thr Gln Ser Pro Ser Ser Leu Ser Ala Ser Val Gly
1               5                   10                  15

Asp Thr Val Thr Ile Thr Cys Arg Ala Ser Gln Asp Ile Ser Ser Trp
            20                  25                  30

Leu Ala Trp Tyr Gln His Lys Pro Gly Arg Ala Pro Arg Ser Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Ala His Ser Phe Pro Trp
                85                  90                  95

Ser Phe Gly Pro Gly Thr Asn Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 28

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Lys Trp
            20                  25                  30

Leu Ala Trp Tyr Gln Gln Lys Pro Gly Lys Ala Pro Lys Leu Leu Ile
        35                  40                  45

Asp Ser Ala Thr Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Phe Tyr Tyr Cys Gln Gln Gly Lys Ser Phe Pro Trp
                85                  90                  95

Thr Phe Gly Gln Gly Thr Lys Val Glu Ile Lys
            100                 105

<210> SEQ ID NO 29
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 29

```
Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 30
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 30

Ser Tyr Glu Leu Thr Gln Pro Leu Ser Val Ser Val Ala Pro Gly Gln
1               5                   10                  15

Thr Ala Arg Ile Pro Cys Gly Gly Asn Asn Ile Gly Asn Lys Asn Val
            20                  25                  30

His Trp Tyr Gln Gln Lys Pro Gly Gln Ala Pro Val Leu Val Ile Tyr
            35                  40                  45

Arg Asp Thr Asn Arg Pro Ser Gly Ile Pro Glu Arg Phe Ser Gly Ser
50                      55                  60

Asn Ser Gly His Thr Ala Thr Leu Thr Ile Ser Gly Ala Gln Ala Gly
65                  70                  75                  80

Asp Glu Ala Asp Tyr Ser Cys Gln Val Trp Asp Ser Gly Thr Val Val
                85                  90                  95

Phe Gly Gly Gly Thr Lys Leu Thr Val Leu
            100                 105

<210> SEQ ID NO 31
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 31

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
            20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
50                      55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ser Ala Val
                85                  90                  95
```

```
Val Phe Gly Gly Gly Thr Lys Val Thr Val Val
            100                 105

<210> SEQ ID NO 32
<211> LENGTH: 109
<212> TYPE: PRT
<213> ORGANISM: Artificial Sequence
<220> FEATURE:
<223> OTHER INFORMATION: An artificially synthesized sequence

<400> SEQUENCE: 32

Ser Val Leu Thr Gln Pro Pro Ser Leu Ser Ala Ala Pro Gly Gln Arg
1               5                   10                  15

Val Thr Ile Ser Cys Ser Gly Ser Ser Ser Asn Ile Gly Asn His Leu
            20                  25                  30

Val Ser Trp His Gln Gln Phe Pro Gly Thr Ala Pro Lys Ala Leu Ile
        35                  40                  45

Tyr Asp Asn Asp Arg Arg Pro Ser Gly Ile Pro Asp Arg Phe Ser Gly
    50                  55                  60

Ser Lys Ser Gly Thr Ser Ala Thr Leu Asp Ile Thr Gly Leu Gln Thr
65                  70                  75                  80

Gly Asp Glu Ala Asp Tyr Tyr Cys Ala Thr Trp Asp Ala Ser Leu Arg
                85                  90                  95

Ala Val Val Phe Gly Gly Gly Thr Lys Leu Thr Val Leu
            100                 105

<210> SEQ ID NO 33
<211> LENGTH: 111
<212> TYPE: PRT
<213> ORGANISM: Artificial Sequence
<220> FEATURE:
<223> OTHER INFORMATION: An artificially synthesized sequence

<400> SEQUENCE: 33

Gln Ser Val Leu Thr Gln Pro Pro Ser Val Ser Gly Ala Pro Gly Gln
1               5                   10                  15

Arg Val Thr Val Ser Cys Asn Gly Gly Ser Ser Asn Ile Gly Thr Gly
            20                  25                  30

Tyr Asp Val His Trp Tyr Gln Gln Leu Pro Gly Thr Ala Pro Lys Ile
        35                  40                  45

Val Ile Phe Gly Asn Ser Asn Arg Pro Ser Gly Val Pro Gly Arg Phe
    50                  55                  60

Ser Gly Ser Lys Ser Gly Thr Ser Ala Ser Leu Val Ile Ala Gly Leu
65                  70                  75                  80

Gln Ala Glu Asp Glu Ala Asp Tyr Tyr Cys Gln Ser Tyr Asp Arg Ser
                85                  90                  95

Leu Ser Gly Tyr Val Phe Gly Thr Gly Thr Lys Val Thr Val Leu
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 34

Ser Tyr Val Leu Thr Gln Pro Arg Ser Val Ser Gly Pro Gly Gln
1               5                   10                  15
```

Ser Val Thr Ile Ser Cys Thr Gly Thr Ser Ser Asp Val Gly Arg Tyr
            20                  25                  30

Asn Tyr Val Ser Trp Tyr Gln Gln Arg Pro Gly Lys Ala Pro Lys Val
        35                  40                  45

Met Ile Tyr Asp Val Ile Lys Arg Pro Ser Gly Val Pro Ala Arg Phe
    50                  55                  60

Ser Gly Ser Lys Ser Gly Asn Thr Ala Ser Leu Thr Ile Ser Gly Leu
65              70                  75                  80

Gln Pro Glu Asp Glu Ala Asp Tyr Tyr Cys Ser Ser Tyr Ala Gly Ala
                85                  90                  95

Ser Ser Phe Val Phe Gly Thr Gly Thr Lys Val Thr Val Leu
            100                 105                 110

<210> SEQ ID NO 35
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 35

Gln Ser Val Leu Thr Gln Pro Pro Ser Ala Ser Gly Thr Pro Gly Gln
1               5                   10                  15

Arg Val Asn Ile Ser Cys Ser Gly Ser Arg Ser Asn Ile Ala Asn Asn
            20                  25                  30

Tyr Val Ser Trp Tyr Gln His Leu Pro Gly Thr Val Pro Lys Val Leu
        35                  40                  45

Ile Ser Asp Asn Asp Gln Arg Ser Ser Gly Val Pro Asp Arg Phe Ser
    50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Arg Met
                85                  90                  95

Arg Gly Phe Val Phe Gly Ser Gly Thr Lys Val Thr Val Leu
            100                 105                 110

<210> SEQ ID NO 36
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65              70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 37
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 37

Asn Phe Met Leu Thr Gln Pro Pro Ser Val Ser Gly Ala Pro Arg Gln
1               5                   10                  15

Arg Val Thr Ile Ser Cys Ser Gly Ser Ser Asn Ile Gly Asn Arg
            20                  25                  30

Ala Val Ser Trp Tyr Gln His Val Pro Gly Lys Pro Pro Arg Leu Ile
        35                  40                  45

Val Tyr His Asp Asp Val Leu Ser Ser Gly Val Ser Gly Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Ala Arg Leu
                85                  90                  95

Asn Gly Trp Val Phe Gly Gly Gly Thr Lys Leu Thr Val Leu
            100                 105                 110

<210> SEQ ID NO 38
<211> LENGTH: 109
<212> TYPE: PRT
<213> ORGANISM: Artificial Sequence
<220> FEATURE:
<223> OTHER INFORMATION: An artificially synthesized sequence

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Gly Thr Gly Thr Lys Val Thr Val Leu
            100                 105

<210> SEQ ID NO 39
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 39

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Thr Ile Tyr Asp Val Ser Asn Arg Pro Ser Gly Val Ser Asn Arg Phe
 50                  55                  60

Ser Gly Ser Lys Ser Gly Ser Ser Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                85                  90                  95

Gly Thr Tyr Val Phe Gly Thr Gly Thr Thr Val Thr Val Leu
                100                 105                 110

<210> SEQ ID NO 40
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 40

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Arg
                85                  90                  95

Arg Gly Tyr Val Phe Gly Thr Gly Thr Lys Val Thr Val Leu
                100                 105                 110

<210> SEQ ID NO 41
<211> LENGTH: 109
<212> TYPE: PRT
<213> ORGANISM: Artificial Sequence
<220> FEATURE:
<223> OTHER INFORMATION: An artificially synthesized sequence

<400> SEQUENCE: 41

Gln Ser Ala Leu Thr Gln Pro Arg Ser Val Ala Ser Pro Gly Gln
 1               5                  10                  15

Ser Val Thr Ile Ser Cys Thr Gly Thr Ser Ser Asp Val Gly Phe Tyr
                20                  25                  30

Lys Tyr Val Ser Trp Tyr Gln Gln Tyr Pro Gly Lys Ala Pro Lys Leu
            35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                85                  90                  95

Asn Thr Val Phe Gly Thr Gly Thr Lys Val Thr Val Leu
                100                 105

<210> SEQ ID NO 42

<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 42

```
Glu Ile Val Leu Thr Gln Ser Pro Ala Thr Leu Ser Val Ser Pro Gly
1               5                   10                  15
Glu Arg Ala Thr Leu Ser Cys Arg Ala Ser Gln Ser Val Arg Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Lys Ser Pro Leu Thr
                85                  90                  95
Phe Gly Gly Gly Thr Lys Val Glu Ile Lys
            100                 105
```

<210> SEQ ID NO 43
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 43

```
Glu Ile Val Leu Thr Gln Ser Pro Ala Thr Leu Ser Val Ser Pro Gly
1               5                   10                  15
Glu Arg Ala Thr Leu Ser Cys Arg Ala Ser Gln Ser Val Arg Arg Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Lys Ser Pro Leu Thr
                85                  90                  95
Phe Gly Gly Gly Thr Lys Val Glu Ile Lys
            100                 105
```

<210> SEQ ID NO 44
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 44

```
Ser Tyr Val Leu Thr Gln Pro Val Ser Val Ala Arg Gly Gln
1               5                   10                  15
Thr Ala Thr Ile Thr Cys Glu Gly Asn His Ile Gly Asp Lys His Val
            20                  25                  30
His Trp Tyr His Gln Arg Pro Gly Gln Ala Pro Ile Leu Val Met Phe
        35                  40                  45
```

```
Arg Asp Ala Arg Arg Pro Ser Gly Ile Pro Glu Arg Leu Ser Gly Ser
 50                  55                  60

Asn Ser Gly Asn Thr Ala Ser Leu Thr Ile Ser Gly Ala Gln Ala Gly
 65                  70                  75                  80

Asp Glu Gly Asp Tyr Tyr Cys Gln Val Trp Asp Ser Ser Ser Tyr Thr
                 85                  90                  95

Val Phe Gly Gly Gly Thr Lys Val Thr Val Val
                100                 105
```

<210> SEQ ID NO 45
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 45

```
Gln Val Gln Leu Val Glu Ser Gly Gly Gly Leu Val Gln Pro Gly Gly
 1                5                  10                  15

Ser Leu Arg Leu Ser Cys Ala Ala Ser Gly Phe Thr Phe Ser Tyr Tyr
                 20                  25                  30

Asp Ile Gln Trp Val Arg Gln Ala Pro Gly Lys Gly Leu Glu Trp Val
             35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Trp Tyr Phe Asp Tyr
                100                 105                 110

Trp Gly Gln Gly Thr Leu Val Thr Val Ser Ser
        115                 120
```

<210> SEQ ID NO 46
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 46

```
Gln Val Gln Leu Val Gln Ser Gly Ser Glu Leu Lys Lys Pro Gly Ala
 1                5                  10                  15

Ser Val Lys Val Ser Cys Lys Ala Ser Gly Tyr Thr Phe Thr Asp Asn
                 20                  25                  30

Asn Met Asp Trp Val Arg Gln Ala Pro Gly Gln Gly Leu Glu Trp Met
             35                  40                  45

Gly Asp Ile Asn Thr Arg Ser Gly Gly Ser Ile Tyr Asn Glu Glu Phe
 50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
                100                 105                 110

Thr Leu Val Thr Val Ser Ser
        115
```

<210> SEQ ID NO 47
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 48
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 48

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly Arg Glu Tyr Gly Gly Trp Tyr Phe Asp Tyr
            100                 105                 110

Trp Gly Gln Gly Thr Leu Val Thr Val Ser Ser
        115                 120

<210> SEQ ID NO 49
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 49

Gln Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Tyr Tyr
                20                  25                  30

Asp Ile Asn Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly His Asn Tyr Gly Gly Gly Trp Tyr Phe Asp Tyr
            100                 105                 110

Trp Gly Gln Gly Thr Leu Val Thr Val Ser Ser
        115                 120

<210> SEQ ID NO 50
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 50

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr His Cys
            85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 52
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Ile Glu Arg Asn
            20                  25                  30

Leu Ala Trp Tyr Gln Gln Lys Pro Gly Gln Ala Pro Arg Leu Leu Ile
        35                  40                  45

Tyr Arg Ala Asp Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Arg Ala Asp Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 56
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 56

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Arg Thr Gly Arg Glu Tyr Asp Gly Gly Trp Tyr Phe Asp Tyr
            100                 105                 110

Trp Gly Gln Gly Thr Leu Val Thr Val Ser Ser
        115                 120
```

<210> SEQ ID NO 57
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 57

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ala Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Ser Glu Asp Gly Ala Gly Trp Tyr Phe Asp Tyr
            100                 105                 110

Trp Gly Gln Gly Thr Leu Val Thr Val Ser Ser
        115                 120
```

<210> SEQ ID NO 58
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 58

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Asp Gly Gly Trp His Phe Asp Tyr Trp
            100                 105                 110

Gly Gln Gly Thr Leu Val Thr Val Ser Ser
        115                 120
```

-continued

```
<210> SEQ ID NO 59
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Glu Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
        115                 120

<210> SEQ ID NO 60
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
        115                 120

<210> SEQ ID NO 61
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 61

Glu Ile Val Leu Thr Gln Ser Pro Ala Thr Leu Ser Val Ser Pro Gly
1               5                   10                  15
```

Glu Arg Ala Thr Leu Ser Cys Arg Ala Ser Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Pro Leu Thr
                85                  90                  95

Phe Gly Gly Gly Thr Lys Val Glu Ile Lys
            100                 105

<210> SEQ ID NO 62
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 62

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys
            100                 105

<210> SEQ ID NO 63
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 63

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys

<210> SEQ ID NO 64
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 64

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Arg Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Leu Thr
                85                  90                  95

Phe Gly Gly Gly Thr Lys Val Glu Ile Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 65

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 66

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 67

Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Lys Lys Pro Gly Gln Ala Pro Arg Leu Leu Ile
            35                  40                  45

Tyr Gly Ala Ser Arg Arg Glu Thr Gly Ile Pro Asp Arg Phe Ser Gly
        50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 68

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
            35                  40                  45

Tyr Gly Ala Ser Thr Arg Glu Thr Gly Ile Pro Asp Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

```
<210> SEQ ID NO 69
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 69

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 70

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 71

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45
```

Tyr Gly Ala Ser Thr Arg Glu Thr Gly Ile Pro Ala Arg Phe Ser Gly
            50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
               100                 105

<210> SEQ ID NO 72
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 72

Glu Ile Val Leu Thr Gln Ser Pro Ala Thr Leu Ser Val Ser Pro Gly
  1               5                  10                  15

Glu Arg Ala Thr Leu Ser Cys Arg Ala Thr Arg Ser Val Arg Arg Asp
                 20                  25                  30

Leu Ala Trp Tyr Gln Gln Lys Pro Gly Gln Ala Pro Glu Leu Leu Ile
            35                  40                  45

Tyr Gly Ala Ser Arg Arg Glu Thr Gly Ile Pro Ala Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
               100                 105

<210> SEQ ID NO 73
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 73

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Asp Asn
                 20                  25                  30

Asn Met Asp Trp Val Arg Gln Ala Pro Gly Gln Gly Leu Glu Trp Met
            35                  40                  45

Gly Asp Ser Asn Thr Arg Ser Gly Thr Ser Ile Tyr Asn Glu Glu Phe
 50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
               100                 105                 110

Thr Leu Val Thr Val Ser Ser
            115

-continued

```
<210> SEQ ID NO 74
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 74
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asn Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

```
<210> SEQ ID NO 75
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 75
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Val Ile Ser Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

```
<210> SEQ ID NO 76
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 76
```

Gln Val Gln Leu Val Gln Ser Gly Ser Glu Leu Lys Lys Pro Gly Ala
1               5                   10                  15

```
Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Gln Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
            115

<210> SEQ ID NO 77
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
            115

<210> SEQ ID NO 78
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 78

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Arg Ser Ile Tyr Asn Glu Glu Phe
    50                  55                  60

Gln Asp Arg Val Ile Met Thr Val Asp Ile Ser Thr Asp Thr Ala Tyr
```

```
                65                  70                  75                  80
Met Glu Leu Ser Ser Leu Arg Ser Glu Asp Thr Ala Thr Tyr His Cys
                    85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 79
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 79

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 80
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 80

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115
```

<210> SEQ ID NO 81
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 81

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Val Ile Tyr Asn Glu Lys Phe
    50                  55                  60

Gln Asp Arg Val Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115
```

<210> SEQ ID NO 82
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 82

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Ser Ile Tyr Asn Arg Glu Phe
    50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115
```

<210> SEQ ID NO 83
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 83

```
Gln Val Gln Leu Val Gln Ser Gly Ser Glu Leu Lys Lys Pro Gly Ala
```

```
1               5                   10                  15
Ser Val Lys Val Ser Cys Lys Ala Ser Gly Tyr Thr Phe Thr Gln Asn
                20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Glu Trp Gly Gln Gly
                100                 105                 110

Thr Leu Val Thr Val Ser Ser
            115
```

<210> SEQ ID NO 84
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 84

```
Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
                100                 105
```

<210> SEQ ID NO 85
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 85

```
Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
                20                  25                  30

His Trp Tyr His Gln Arg Pro Gly Gln Ala Pro Ile Leu Val Met Phe
            35                  40                  45

Gln Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80
```

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 86
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 86

Ser Tyr Val Leu Thr Gln Pro Val Ser Val Ala Arg Gly Gln
1               5                   10                  15

Thr Ala Thr Ile Thr Cys Thr Gly Asn His Ile Ser Asp Lys His Val
                20                  25                  30

His Trp Tyr His Gln Arg Pro Gly Gln Ala Pro Ile Leu Val Met Phe
            35                  40                  45

Gln Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Asp Tyr Thr
                85                  90                  95

Val Phe Gly Gly Gly Thr Lys Val Thr Val Val
            100                 105

<210> SEQ ID NO 87
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 87

Ser Tyr Val Leu Thr Gln Pro Val Ser Val Ser Val Ala Arg Gly Gln
1               5                   10                  15

Thr Ala Thr Ile Thr Cys Glu Gly Asn Gln Ile Ser Gln Lys Gln Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ala Val Val
                85                  90                  95

Phe Gly Gly Gly Thr Lys Val Thr Val Val
            100                 105

<210> SEQ ID NO 88
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 88

Ser Tyr Val Leu Thr Gln Pro Val Ser Val Ser Val Ala Leu Gly Gln

```
                 1               5                  10                 15
Thr Ala Thr Ile Thr Cys Glu Gly Glu Gln Ile Gly Ser Lys Glu Val
            20                  25                 30

His Trp Tyr His Glu Arg Pro Gly Gln Ala Pro Ile Leu Val Met Phe
            35                  40              45

Arg Asp Ala Arg Arg Pro Ser Gly Ile Pro Glu Arg Leu Ser Gly Ser
         50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                    85                  90                  95

Val Phe Gly Gly Gly Thr Lys Val Thr Val Val
                100                 105

<210> SEQ ID NO 89
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 89

Ser Tyr Val Leu Thr Gln Pro Val Ser Val Ser Val Ala Leu Gly Gln
1               5                   10                  15

Thr Ala Thr Ile Thr Cys Glu Gly Asn Gln Ile Gly Ser Arg Glu Val
            20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
         50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                    85                  90                  95

Phe Gly Gly Gly Thr Lys Val Thr Val Val
                100                 105

<210> SEQ ID NO 90
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 90

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
         50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                    85                  90                  95
```

Val Phe Gly Gly Gly Thr Lys Val Thr Val Val
            100                 105

<210> SEQ ID NO 91
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 91

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 92
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 92

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 93
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 93

Ser Tyr Glu Leu Thr Gln Pro Pro Ser Val Ser Val Ala Leu Gly Gln
1               5                   10                  15

Thr Ala Thr Ile Thr Cys Glu Gly Asn Gln Ile Gly Glu Lys Glu Val

```
            20                  25                  30
His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val
            100                 105

<210> SEQ ID NO 94
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 94

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 95
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110
```

```
Glu Phe Arg Arg Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 96
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 96

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ala His Tyr Thr Arg Lys Glu
305                 310                 315                 320

Leu Ser Leu Ser Pro
                325

<210> SEQ ID NO 97
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 97

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Arg Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175
```

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 98
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 98

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Leu His Glu Ala Leu His Ala His Tyr Thr Arg Glu Glu
305                 310                 315                 320

Leu Ser Leu Ser Pro
                325

<210> SEQ ID NO 99
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 99

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 100
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 100

Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 101
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 101

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 102
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 102

```
Gly Gln Pro Lys Ala Ala Pro Ser Val Thr Leu Phe Pro Pro Ser Ser
1               5                   10                  15

Glu Glu Leu Gln Ala Asn Lys Ala Lys Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Lys Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 103
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 103

```
Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Glu Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 104
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 104

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Arg Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 105
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 105

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Arg Thr Asp Arg Glu Asp His Gly Trp Ile Phe Asp Tyr Trp
            100                 105                 110

Gly Gln Gly Thr Leu Val Thr Val Ser Ser
            115                 120

<210> SEQ ID NO 106
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 106

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Trp Ile Phe Asp Tyr Trp
            100                 105                 110

Gly Gln Gly Thr Leu Val Thr Val Ser Ser
            115                 120

<210> SEQ ID NO 107
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
```

```
            145                 150                 155                 160
Gly Val Glu Val His Asn Ala Lys Thr Lys Pro Arg Glu Gln Tyr
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Cys Thr Leu Pro Pro Ser Gln Glu Glu Met Thr Lys
225                 230                 235                 240
Asn Gln Val Ser Leu Trp Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Leu His Glu Ala Leu His Ala His Tyr Thr Arg Lys Glu
305                 310                 315                 320
Leu Ser Leu Ser Pro
                325

<210> SEQ ID NO 108
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 108

Glu Ile Val Leu Thr Gln Ser Pro Ala Thr Leu Ser Val Ser Pro Gly
1               5                   10                  15
Glu Arg Ala Thr Leu Ser Cys Arg Ala Ser Arg Ser Val Arg Arg Glu
            20                  25                  30
Leu Ala Trp Tyr Gln Gln Lys Pro Gly Gln Ala Pro Glu Leu Leu Ile
        35                  40                  45
Tyr Gly Ala Ser Thr Arg Glu Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Met Ala Val Tyr Tyr Cys Gln Gln Tyr Arg Asp Pro Pro Gly
                85                  90                  95
Thr Phe Gly Gly Gly Thr Lys Val Glu Ile Lys
            100                 105

<210> SEQ ID NO 109
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 109

Gln Val Gln Leu Val Gln Ser Gly Ser Glu Leu Lys Lys Pro Gly Ala
1               5                   10                  15
```

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Val Ile Tyr Asn Glu Glu Phe
50                      55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
            115

<210> SEQ ID NO 110
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 110

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
            275                 280                 285

Arg Leu Thr Val Asp Lys Ser Arg Trp Gln Glu Gly Asn Val Phe Ser
            290                 295                 300

Cys Ser Val Leu His Glu Ala Leu His Ala His Tyr Thr Arg Lys Glu
305                 310                 315                 320

Leu Ser Leu Ser Pro
            325

<210> SEQ ID NO 111
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 111

Ser Tyr Val Leu Thr Gln Pro Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
                100                 105

<210> SEQ ID NO 112
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 112

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Glu Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
                100                 105                 110

Gly Gln Gly Thr Leu Val Thr Val Ser Ser
            115                 120
```

<210> SEQ ID NO 113
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 113

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 114
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 114

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 115
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 115

Ser Tyr Val Leu Thr Gln Pro Val Ser Val Ser Val Ala Leu Gly Gln
1               5                   10                  15

```
Thr Ala Thr Ile Thr Cys Glu Gly Glu Gln Ile Gly Ser Lys Glu Val
                20                  25                  30

His Trp Tyr His Glu Arg Pro Gly Gln Ala Pro Ile Leu Val Met Phe
         35                  40                  45

Arg Asp Ala Arg Arg Pro Ser Gly Ile Pro Glu Arg Leu Ser Gly Ser
 50                  55                  60

Asn Ser Gly Asn Thr Ala Ser Leu Thr Ile Ser Gly Ala Glu Ala Gly
 65                  70                  75                  80

Asp Glu Gly Asp Tyr Tyr Cys Gln Val Trp Asp Ser Ser Ser Tyr Thr
                 85                  90                  95

Val Phe Gly Gly Gly Thr Lys Val Thr Val Val
                100                 105
```

<210> SEQ ID NO 116
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 116

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
        290                 295                 300

Cys Ser Val Leu His Glu Ala Leu His Ala His Tyr Thr Arg Glu Glu
305                 310                 315                 320

Leu Ser Leu Ser Pro
                325

<210> SEQ ID NO 117
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 117

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300
```

Cys Ser Val Leu His Glu Ala Leu His Ala His Tyr Thr Arg Lys Glu
305                 310                 315                 320

Leu Ser Leu Ser Pro
                325

<210> SEQ ID NO 118
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 118

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Glu Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Leu His Glu Ala Leu His Ala His Tyr Thr Arg Glu Glu
305                 310                 315                 320

Leu Ser Leu Ser Pro
                325

<210> SEQ ID NO 119
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 119

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Leu His Glu Ala Leu His Ala His Tyr Thr Arg Lys Glu
305                 310                 315                 320

Leu Ser Leu Ser Pro
                325
```

<210> SEQ ID NO 120
<211> LENGTH: 448
<212> TYPE: PRT
<213> ORGANISM: Artificial Sequence
<220> FEATURE:

<223> OTHER INFORMATION: An artificially synthesized sequence

<400> SEQUENCE: 120

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Asp Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Lys Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Leu His
            420                 425                 430

Glu Ala Leu His Ala His Tyr Thr Arg Lys Glu Leu Ser Leu Ser Pro
        435                 440                 445

<210> SEQ ID NO 121
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ala Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Ser Glu Asp Gly Ala Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Lys Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Leu His
            420                 425                 430

Glu Ala Leu His Ala His Tyr Thr Arg Lys Glu Leu Ser Leu Ser Pro
        435                 440                 445

<210> SEQ ID NO 122
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Asp Gly Gly Trp His Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Lys Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240
```

```
Ser Val Phe Leu Phe Pro Pro Lys Pro Lys Asp Thr Leu Met Ile Ser
                245             250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Lys Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
                420                 425                 430

Ala Leu His Ala His Tyr Thr Arg Lys Glu Leu Ser Leu Ser Pro
            435                 440                 445

<210> SEQ ID NO 123
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Glu Ala Pro Gly Lys Gly Leu Glu Trp Val
            35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160
```

-continued

```
Val Ser Trp Asn Ser Gly Ala Leu Thr Ser Gly Val His Thr Phe Pro
                165                 170                 175
Ala Val Leu Lys Ser Ser Gly Leu Tyr Ser Leu Ser Ser Val Val Thr
            180                 185                 190
Val Pro Ser Ser Ser Leu Gly Thr Gln Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Lys Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Glu Gly Asn Val Phe Ser Cys Ser Val Leu His Glu
            420                 425                 430
Ala Leu His Ala His Tyr Thr Arg Lys Glu Leu Ser Leu Ser Pro
        435                 440                 445

<210> SEQ ID NO 124
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 124

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Tyr Tyr
            20                  25                  30
Asp Ile Gln Trp Val Arg Gln Ala Pro Gly Lys Gly Leu Glu Trp Val
        35                  40                  45
Ser Ser Ile Ser Pro Ser Gly Gln Ser Thr Tyr Tyr Arg Arg Glu Val
    50                  55                  60
Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Arg Thr Gly Arg Glu Glu Gly Trp Ile Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Lys Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Lys Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Leu His Glu
            420                 425                 430

Ala Leu His Ala His Tyr Thr Arg Lys Glu Leu Ser Leu Ser Pro
435                 440                 445

<210> SEQ ID NO 125
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 125

-continued

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser His Tyr
             20                  25                  30

Asp Ile Gln Trp Val Arg Gln Ala Pro Gly Lys Gly Leu Glu Trp Val
             35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Arg Thr Asp Arg Glu Asp His Gly Trp Ile Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Lys Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Lys Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Glu Gly Asn Val Phe Ser Cys Ser Val Leu His Glu
```

```
                    420                 425                 430
Ala Leu His Ala His Tyr Thr Arg Lys Glu Leu Ser Leu Ser Pro
            435                 440                 445
```

<210> SEQ ID NO 126
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 126

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Glu Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 127
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 127

```
Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Glu Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 128
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 128

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Glu Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 129
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 129

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Arg Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Glu Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 130
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 130

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

-continued

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 131
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 131

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 132
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 132
```

Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Lys Lys Pro Gly Gln Ala Pro Arg Leu Leu Ile
        35                  40                  45

Tyr Gly Ala Ser Arg Arg Glu Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Glu Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 133
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 133
```

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Pro Gly

```
                        85                  90                  95
Thr Phe Gly Gly Gly Thr Lys Val Glu Ile Lys Arg Thr Val Ala Ala
                       100                 105                 110

Pro Ser Val Phe Ile Phe Pro Pro Ser Asp Glu Gln Leu Lys Ser Gly
                       115                 120                 125

Thr Ala Glu Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Glu Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 134
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 134

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
                20                  25                  30

Leu Ala Trp Tyr Gln Gln Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
                       100                 105                 110

Pro Ser Val Phe Ile Phe Pro Pro Ser Asp Glu Gln Leu Lys Ser Gly
                       115                 120                 125

Thr Ala Glu Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Glu Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210
```

```
<210> SEQ ID NO 135
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 135

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Glu Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 136
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 136

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95
```

```
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 137
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 137

```
Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Glu Thr Gly Ile Pro Ala Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 138
<211> LENGTH: 444

<212> TYPE: PRT
<213> ORGANISM: Artificial Sequence
<220> FEATURE:
<223> OTHER INFORMATION: An artificially synthesized sequence

<400> SEQUENCE: 138

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Asn
            20                  25                  30
Asn Met Asp Trp Val Arg Gln Ala Pro Gly Gln Gly Leu Glu Trp Met
        35                  40                  45
Gly Asp Ser Asn Thr Arg Ser Gly Thr Ser Ile Tyr Asn Glu Glu Phe
    50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Thr Tyr His Cys
                85                  90                  95
Ala Arg Arg Lys Ser Tyr Gly Tyr Tyr Leu Asp Glu Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Glu Ser Ser Gly Leu Tyr Ser Leu Ser Ser Val Val Thr Val Pro Ser
            180                 185                 190
Ser Ser Leu Gly Thr Gln Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
```

-continued

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Leu His Glu Ala Leu His
        420                 425                 430

Ala His Tyr Thr Arg Glu Glu Leu Ser Leu Ser Pro
    435                 440

<210> SEQ ID NO 139
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 139

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asn Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Leu His Glu Ala Leu His
        420                 425                 430

Ala His Tyr Thr Arg Glu Glu Leu Ser Leu Ser Pro
        435                 440

<210> SEQ ID NO 140
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 140

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Val Ile Ser Asn Glu Glu Phe
    50                  55                  60

Gln Asp Arg Val Ile Met Thr Val Asp Lys Ser Thr Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440

<210> SEQ ID NO 141
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 141

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Gln Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

```
Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440

<210> SEQ ID NO 142
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 142

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
            35                  40                  45

Gly Asp Ile Asn Thr Arg Ser Gly Gly Val Ile Tyr Asn Glu Glu Phe
50                  55                  60
```

```
Gln Asp Arg Leu Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
        435                 440

<210> SEQ ID NO 143
<211> LENGTH: 444
<212> TYPE: PRT
<213> ORGANISM: Artificial Sequence
<220> FEATURE:
<223> OTHER INFORMATION: An artificially synthesized sequence
```

<400> SEQUENCE: 143

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Arg Ser Ile Tyr Asn Glu Glu Phe
    50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
```

```
                405                 410                 415
Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440

<210> SEQ ID NO 144
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 144

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440

<210> SEQ ID NO 145
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 145

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
```

```
                     245                 250                 255
Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
        435                 440

<210> SEQ ID NO 146
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 146

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Lys Phe
    50                  55                  60

Gln Asp Arg Val Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

165                 170                 175
Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
        435                 440

<210> SEQ ID NO 147
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 147

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Ser Ile Tyr Asn Arg Glu Phe
    50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys 85                  90                  95
Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440

<210> SEQ ID NO 148
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 148

Gln Val Gln Leu Val Gln Ser Gly Ser Glu Leu Lys Lys Pro Gly Ala

-continued

```
1               5                   10                  15
Ser Val Lys Val Ser Cys Lys Ala Ser Gly Tyr Thr Phe Thr Gln Asn
                20                  25                  30

Asn Met Asp Trp Val Arg Lys Ala Pro Gly Gln Gly Leu Glu Trp Met
            35                  40                  45

Gly Asp Ile Asn Thr Arg Ser Gly Gly Val Ile Tyr Asn Glu Glu Phe
50                  55                  60

Gln Asp Arg Leu Ile Met Thr Val Asp Lys Ser Thr Asp Thr Ala Tyr
65                  70                  75                  80

Met Glu Leu Ser Glu Leu Arg Ser Gly Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430
```

Ala His Tyr Thr Arg Glu Glu Leu Ser Leu Ser Pro
        435                 440

<210> SEQ ID NO 149
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 149

Ser Tyr Val Leu Thr Gln Pro Val Ser Val Ala Arg Gly Gln
1               5                   10                  15

Thr Ala Thr Ile Thr Cys Glu Gly Asn His Ile Gly Asp Lys His Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 150
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 150

Ser Tyr Val Leu Thr Gln Pro Val Ser Val Ala Arg Gly Gln
1               5                   10                  15

Thr Ala Thr Ile Thr Cys Glu Gly Asn His Ile Gly Asp Lys His Val
            20                  25                  30

His Trp Tyr His Gln Arg Pro Gly Gln Ala Pro Ile Leu Val Met Phe
        35                  40                  45

Gln Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly

```
            65                  70                  75                  80
Asp Glu Gly Asp Tyr Tyr Cys Gln Val Trp Asp Ser Ser Tyr Thr
                85                  90                  95

Val Phe Gly Gly Gly Thr Lys Val Thr Val Gly Gln Pro Lys Ala
               100                 105                 110

Ala Pro Ser Val Thr Leu Phe Pro Ser Ser Glu Glu Leu Gln Ala
               115                 120                 125

Asn Lys Ala Lys Leu Val Cys Leu Ile Ser Asp Phe Tyr Pro Gly Ala
130                135                 140

Val Thr Val Ala Trp Lys Ala Asp Ser Ser Pro Val Lys Ala Gly Val
145                150                 155                 160

Glu Thr Thr Thr Pro Ser Lys Gln Ser Asn Asn Lys Tyr Ala Ala Ser
               165                 170                 175

Ser Tyr Leu Lys Leu Thr Pro Glu Gln Trp Lys Ser His Arg Ser Tyr
               180                 185                 190

Ser Cys Gln Val Thr His Glu Gly Ser Thr Val Glu Lys Thr Val Ala
               195                 200                 205

Pro Thr Glu Cys Ser
210

<210> SEQ ID NO 151
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 151

Ser Tyr Val Leu Thr Gln Pro Val Ser Val Ala Arg Gly Gln
1               5                   10                  15

Thr Ala Thr Ile Thr Cys Thr Gly Asn His Ile Ser Asp Lys His Val
                20                  25                  30

His Trp Tyr His Gln Arg Pro Gly Gln Ala Pro Ile Leu Val Met Phe
                35                  40                  45

Gln Asp Ala Arg Arg Pro Ser Gly Ile Pro Glu Arg Leu Ser Gly Ser
50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Asp Tyr Thr
                85                  90                  95

Val Phe Gly Gly Gly Thr Lys Val Thr Val Gly Gln Pro Lys Ala
               100                 105                 110

Ala Pro Ser Val Thr Leu Phe Pro Ser Ser Glu Glu Leu Gln Ala
               115                 120                 125

Asn Lys Ala Lys Leu Val Cys Leu Ile Ser Asp Phe Tyr Pro Gly Ala
130                135                 140

Val Thr Val Ala Trp Lys Ala Asp Ser Ser Pro Val Lys Ala Gly Val
145                150                 155                 160

Glu Thr Thr Thr Pro Ser Lys Gln Ser Asn Asn Lys Tyr Ala Ala Ser
               165                 170                 175

Ser Tyr Leu Lys Leu Thr Pro Glu Gln Trp Lys Ser His Arg Ser Tyr
               180                 185                 190

Ser Cys Gln Val Thr His Glu Gly Ser Thr Val Glu Lys Thr Val Ala
               195                 200                 205

Pro Thr Glu Cys Ser
```

<210> SEQ ID NO 152
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 152

Ser Tyr Val Leu Thr Gln Pro Val Ser Val Ala Arg Gly Gln
1               5                   10                  15

Thr Ala Thr Ile Thr Cys Glu Gly Asn Gln Ile Ser Gln Lys Gln Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ala Val Val
                85                  90                  95

Phe Gly Gly Gly Thr Lys Val Thr Val Val Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Lys Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 153
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 153

Ser Tyr Val Leu Thr Gln Pro Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

```
Asp Glu Gly Asp Tyr Tyr Cys Gln Val Trp Asp Ser Ser Tyr Thr
                85                  90                  95

Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
                180                 185                 190

Ser Cys Gln Val Thr His Glu Gly Ser Thr Val Glu Lys Thr Val Ala
            195                 200                 205

Pro Thr Glu Cys Ser
        210

<210> SEQ ID NO 154
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 154

Ser Tyr Val Leu Thr Gln Pro Val Ser Val Ala Leu Gly Gln
1               5                   10                  15

Thr Ala Thr Ile Thr Cys Glu Gly Asn Gln Ile Gly Ser Arg Glu Val
                20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Lys Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 155
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 155

```
Ser Tyr Val Leu Thr Gln Pro Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 156
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 156

```
Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Glu Arg Pro Gly Gln Ala Pro Ile Leu Val Ile Tyr
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95
```

Val Phe Gly Gly Gly Thr Lys Val Thr Val Val Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 157
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 157

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 158

<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 158

Ser Tyr Glu Leu Thr Gln Pro Pro Ser Val Ser Val Ala Leu Gly Gln
1               5                   10                  15

Thr Ala Thr Ile Thr Cys Glu Gly Asn Gln Ile Gly Glu Lys Glu Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Lys Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 159
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 159

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala

```
                100             105              110
Ala Pro Ser Val Thr Leu Phe Pro Pro Ser Glu Glu Leu Gln Ala
            115              120             125

Asn Lys Ala Lys Leu Val Cys Leu Ile Ser Asp Phe Tyr Pro Gly Ala
        130              135             140

Val Thr Val Ala Trp Lys Ala Asp Ser Ser Pro Val Lys Ala Gly Val
145             150              155             160

Glu Thr Thr Thr Pro Ser Lys Gln Ser Asn Asn Lys Tyr Ala Ala Ser
                165              170             175

Ser Tyr Leu Lys Leu Thr Pro Glu Gln Trp Lys Ser His Arg Ser Tyr
            180              185             190

Ser Cys Gln Val Thr His Glu Gly Ser Thr Val Glu Lys Thr Val Ala
        195              200             205

Pro Thr Glu Cys Ser
    210

<210> SEQ ID NO 160
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 160

Gln Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser
        115                 120

<210> SEQ ID NO 161
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 161

Gln Val Gln Leu Val Gln Ser Gly Ser Glu Leu Lys Lys Pro Gly Ala
1               5                  10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60
```

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 162
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 162

Arg Ala Ser Gln Ser Val Ser Ser Asn Leu Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 163

Gly Ala Ser Thr Arg Ala Thr
1               5

<210> SEQ ID NO 164
<211> LENGTH: 8
<212> TYPE: PRT
<213> ORGANISM: Artificial Sequence
<220> FEATURE:
<223> OTHER INFORMATION: An artificially synthesized sequence

<400> SEQUENCE: 164

Gln Gln Tyr Lys Arg Pro Leu Thr
1               5

<210> SEQ ID NO 165
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 165

Glu Gly Asn His Ile Gly Asp Lys His Val His
1               5                   10

<210> SEQ ID NO 166
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 166

Arg Asp Ala Arg Arg Pro Ser
1               5

<210> SEQ ID NO 167

```
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 167

Gln Val Trp Asp Ser Ser Ser Ala Val Val
1               5                   10

<210> SEQ ID NO 168
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 168

Tyr Tyr Asp Ile Gln
1               5

<210> SEQ ID NO 169
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 169

Ser Ile Ser Pro Ser Gly Gln Ser Thr Tyr Tyr Arg Arg Glu Val Lys
1               5                   10                  15

Gly

<210> SEQ ID NO 170
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 170

Arg Thr Gly Arg Glu Tyr Asp Gly Gly Trp Tyr Phe Asp Tyr
1               5                   10

<210> SEQ ID NO 171
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 171

Tyr Tyr Asp Ala Gln
1               5

<210> SEQ ID NO 172
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 172

Ser Ile Ser Pro Ser Gly Gln Ser Thr Tyr Tyr Arg Arg Glu Val Lys
1               5                   10                  15

Gly
```

<210> SEQ ID NO 173
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 173

Arg Thr Gly Ser Glu Asp Gly Ala Gly Trp Tyr Phe Asp Tyr
1               5                   10

<210> SEQ ID NO 174
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 174

Tyr Tyr Asp Ile Gln
1               5

<210> SEQ ID NO 175
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 175

Ser Ile Ser Pro Ser Gly Gln Ser Thr Tyr Tyr Arg Arg Glu Val Lys
1               5                   10                  15

Gly

<210> SEQ ID NO 176
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 176

Arg Thr Gly Arg Glu Asp Gly Gly Trp His Phe Asp Tyr
1               5                   10

<210> SEQ ID NO 177
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 177

Tyr Tyr Asp Ile Gln
1               5

<210> SEQ ID NO 178
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 178

Ser Ile Ser Pro Ser Gly Gln Ser Thr Tyr Tyr Arg Arg Glu Val Lys

```
1               5                   10                  15

Gly

<210> SEQ ID NO 179
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 179

Arg Thr Gly Arg Glu Glu Gly Gly Trp Ile Phe Asp Tyr
1               5                   10

<210> SEQ ID NO 180
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 180

Tyr Tyr Asp Ile Gln
1               5

<210> SEQ ID NO 181
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 181

Ser Ile Ser Pro Ser Gly Gln Ser Thr Tyr Tyr Arg Arg Glu Val Lys
1               5                   10                  15

Gly

<210> SEQ ID NO 182
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 182

Arg Thr Gly Arg Glu Glu Gly Gly Trp Ile Phe Asp Tyr
1               5                   10

<210> SEQ ID NO 183
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 183

His Tyr Asp Ile Gln
1               5

<210> SEQ ID NO 184
<211> LENGTH: 17
<212> TYPE: PRT
<213> ORGANISM: Artificial Sequence
<220> FEATURE:
<223> OTHER INFORMATION: An artificially synthesized sequence
```

-continued

```
<400> SEQUENCE: 184

Ser Ile Ser Pro Ser Gly Gln Ser Thr Tyr Tyr Arg Arg Glu Val Lys
1               5                   10                  15

Gly

<210> SEQ ID NO 185
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 185

Arg Thr Asp Arg Glu Asp His Gly Trp Ile Phe Asp Tyr
1               5                   10

<210> SEQ ID NO 186
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 186

Arg Ala Ser Gln Ser Val Arg Arg Asp Leu Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 187

Gly Ala Ser Arg Arg Ala Thr
1               5

<210> SEQ ID NO 188
<211> LENGTH: 8
<212> TYPE: PRT
<213> ORGANISM: Artificial Sequence
<220> FEATURE:
<223> OTHER INFORMATION: An artificially synthesized sequence

<400> SEQUENCE: 188

Gln Gln Tyr Lys Ser Pro Leu Thr
1               5

<210> SEQ ID NO 189
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 189

Arg Ala Thr Gln Ser Val Arg Arg Asp Leu Ala
1               5                   10

<210> SEQ ID NO 190
<211> LENGTH: 7
<212> TYPE: PRT
<213> ORGANISM: Artificial Sequence
<220> FEATURE:
<223> OTHER INFORMATION: An artificially synthesized sequence
```

```
<400> SEQUENCE: 190

Gly Ala Ser Arg Arg Ala Thr
1               5

<210> SEQ ID NO 191
<211> LENGTH: 8
<212> TYPE: PRT
<213> ORGANISM: Artificial Sequence
<220> FEATURE:
<223> OTHER INFORMATION: An artificially synthesized sequence

<400> SEQUENCE: 191

Gln Gln Tyr Arg Ser Pro Leu Thr
1               5

<210> SEQ ID NO 192
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 192

Arg Ala Thr Gln Ser Val Arg Arg Asp Leu Ala
1               5                   10

<210> SEQ ID NO 193
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 193

Gly Ala Ser Arg Arg Ala Thr
1               5

<210> SEQ ID NO 194
<211> LENGTH: 8
<212> TYPE: PRT
<213> ORGANISM: Artificial Sequence
<220> FEATURE:
<223> OTHER INFORMATION: An artificially synthesized sequence

<400> SEQUENCE: 194

Gln Gln Tyr Arg Ser Pro Leu Thr
1               5

<210> SEQ ID NO 195
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 195

Arg Ala Ser Arg Ser Val Arg Arg Glu Leu Ala
1               5                   10

<210> SEQ ID NO 196
<211> LENGTH: 7
<212> TYPE: PRT
<213> ORGANISM: Artificial Sequence
<220> FEATURE:
<223> OTHER INFORMATION: An artificially synthesized sequence
```

```
<400> SEQUENCE: 196

Gly Ala Ser Thr Arg Glu Thr
1               5

<210> SEQ ID NO 197
<211> LENGTH: 8
<212> TYPE: PRT
<213> ORGANISM: Artificial Sequence
<220> FEATURE:
<223> OTHER INFORMATION: An artificially synthesized sequence

<400> SEQUENCE: 197

Gln Gln Tyr Arg Asp Pro Leu Thr
1               5

<210> SEQ ID NO 198
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 198

Arg Ala Ser Arg Ser Val Arg Arg Glu Leu Ala
1               5                   10

<210> SEQ ID NO 199
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 199

Gly Ala Ser Thr Arg Glu Thr
1               5

<210> SEQ ID NO 200
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 200

Gln Gln Tyr Arg Asp Pro Pro Gly Thr
1               5

<210> SEQ ID NO 201
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 201

Arg Ala Ser Arg Ser Val Arg Arg Glu Leu Ala
1               5                   10

<210> SEQ ID NO 202
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 202
```

```
Gly Ala Ser Thr Arg Glu Thr
1               5

<210> SEQ ID NO 203
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 203

Gln Gln Tyr Arg Asp Pro Pro Gly Thr
1               5

<210> SEQ ID NO 204
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 204

Arg Ala Thr Arg Ser Val Arg Arg Asp Leu Ala
1               5                   10

<210> SEQ ID NO 205
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 205

Gly Ala Ser Arg Arg Glu Thr
1               5

<210> SEQ ID NO 206
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 206

Gln Gln Tyr Arg Asp Pro Pro Gly Thr
1               5

<210> SEQ ID NO 207
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 207

Arg Ala Ser Arg Ser Val Arg Arg Glu Leu Ala
1               5                   10

<210> SEQ ID NO 208
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 208
```

Gly Ala Ser Thr Arg Glu Thr
1               5

<210> SEQ ID NO 209
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 209

Gln Gln Tyr Arg Asp Pro Pro Gly Thr
1               5

<210> SEQ ID NO 210
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 210

Arg Ala Ser Arg Ser Val Arg Arg Glu Leu Ala
1               5                   10

<210> SEQ ID NO 211
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 211

Gly Ala Ser Thr Arg Glu Thr
1               5

<210> SEQ ID NO 212
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 212

Gln Gln Tyr Arg Asp Pro Pro Gly Thr
1               5

<210> SEQ ID NO 213
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 213

Arg Ala Ser Arg Ser Val Arg Arg Glu Leu Ala
1               5                   10

<210> SEQ ID NO 214
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 214

Gly Ala Ser Thr Arg Glu Thr

```
1               5
```

<210> SEQ ID NO 215
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 215

```
Gln Gln Tyr Arg Asp Pro Pro Gly Thr
1               5
```

<210> SEQ ID NO 216
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 216

```
Arg Ala Ser Arg Ser Val Arg Arg Glu Leu Ala
1               5                   10
```

<210> SEQ ID NO 217
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 217

```
Gly Ala Ser Thr Arg Glu Thr
1               5
```

<210> SEQ ID NO 218
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 218

```
Gln Gln Tyr Arg Asp Pro Pro Gly Thr
1               5
```

<210> SEQ ID NO 219
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 219

```
Arg Ala Thr Arg Ser Val Arg Arg Asp Leu Ala
1               5                   10
```

<210> SEQ ID NO 220
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 220

```
Gly Ala Ser Arg Arg Glu Thr
1               5
```

```
<210> SEQ ID NO 221
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 221

Gln Gln Tyr Arg Asp Pro Pro Gly Thr
1               5

<210> SEQ ID NO 222
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 222

Asp Asn Asn Met Asp
1               5

<210> SEQ ID NO 223
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 223

Asp Ser Asn Thr Arg Ser Gly Thr Ser Ile Tyr Asn Glu Glu Phe Gln
1               5                   10                  15

Asp

<210> SEQ ID NO 224
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 224

Arg Lys Ser Tyr Gly Tyr Tyr Leu Asp Glu
1               5                   10

<210> SEQ ID NO 225
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 225

Asn Asn Asn Met Asp
1               5

<210> SEQ ID NO 226
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 226

Asp Ile Asn Thr Arg Ser Gly Gly Val Ile Tyr Asn Glu Glu Phe Gln
```

```
1               5                   10                  15

Asn

<210> SEQ ID NO 227
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 227

Arg Lys Ser Tyr Gly Tyr Tyr Leu Asp Val
1               5                   10

<210> SEQ ID NO 228
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 228

Asp Asn Asn Met Asp
1               5

<210> SEQ ID NO 229
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 229

Asp Ile Asn Thr Arg Ser Gly Arg Val Ile Ser Asn Glu Glu Phe Gln
1               5                   10                  15

Asp

<210> SEQ ID NO 230
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 230

Arg Lys Ser Tyr Gly Tyr Tyr Leu Asp Glu
1               5                   10

<210> SEQ ID NO 231
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 231

Gln Asn Asn Met Asp
1               5

<210> SEQ ID NO 232
<211> LENGTH: 17
<212> TYPE: PRT
<213> ORGANISM: Artificial Sequence
<220> FEATURE:
<223> OTHER INFORMATION: An artificially synthesized sequence
```

```
<400> SEQUENCE: 232

Asp Ile Asn Thr Arg Ser Gly Gly Val Ile Tyr Asn Glu Glu Phe Gln
1               5                   10                  15

Gln

<210> SEQ ID NO 233
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 233

Arg Lys Ser Tyr Gly Tyr Tyr Leu Asp Val
1               5                   10

<210> SEQ ID NO 234
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 234

Gln Asn Asn Met Asp
1               5

<210> SEQ ID NO 235
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 235

Asp Ile Asn Thr Arg Ser Gly Gly Val Ile Tyr Asn Glu Glu Phe Gln
1               5                   10                  15

Asp

<210> SEQ ID NO 236
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 236

Arg Lys Ser Tyr Gly Tyr Tyr Leu Asp Val
1               5                   10

<210> SEQ ID NO 237
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 237

His Asn Asn Met Asp
1               5

<210> SEQ ID NO 238
<211> LENGTH: 17
<212> TYPE: PRT
<213> ORGANISM: Artificial Sequence
```

```
<220> FEATURE:
<223> OTHER INFORMATION: An artificially synthesized sequence

<400> SEQUENCE: 238

Asp Ile Asn Thr Arg Ser Gly Arg Ser Ile Tyr Asn Glu Glu Phe Gln
1               5                   10                  15

Asp

<210> SEQ ID NO 239
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 239

Arg Lys Ser Tyr Gly Tyr Tyr Leu Asp Val
1               5                   10

<210> SEQ ID NO 240
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 240

Gln Asn Asn Met Asp
1               5

<210> SEQ ID NO 241
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 241

Asp Ile Asn Thr Arg Ser Gly Gly Val Ile Tyr Asn Glu Glu Phe Gln
1               5                   10                  15

Asp

<210> SEQ ID NO 242
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 242

Arg Lys Ser Tyr Gly Tyr Tyr Leu Asp Val
1               5                   10

<210> SEQ ID NO 243
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 243

Gln Asn Asn Met Asp
1               5

<210> SEQ ID NO 244
```

```
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 244

Asp Ile Asn Thr Arg Ser Gly Gly Val Ile Tyr Asn Glu Glu Phe Gln
1               5                   10                  15
Asp

<210> SEQ ID NO 245
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 245

Arg Lys Ser Tyr Gly Tyr Tyr Leu Asp Glu
1               5                   10

<210> SEQ ID NO 246
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 246

Gln Asn Asn Met Asp
1               5

<210> SEQ ID NO 247
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 247

Asp Ile Asn Thr Arg Ser Gly Gly Val Ile Tyr Asn Glu Lys Phe Gln
1               5                   10                  15
Asp

<210> SEQ ID NO 248
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 248

Arg Lys Ser Tyr Gly Tyr Tyr Leu Asp Val
1               5                   10

<210> SEQ ID NO 249
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 249

His Asn Asn Met Asp
1               5
```

```
<210> SEQ ID NO 250
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 250

Asp Ile Asn Thr Arg Ser Gly Arg Ser Ile Tyr Asn Arg Glu Phe Gln
1               5                   10                  15

Asp

<210> SEQ ID NO 251
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 251

Arg Lys Ser Tyr Gly Tyr Tyr Leu Asp Glu
1               5                   10

<210> SEQ ID NO 252
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 252

Gln Asn Asn Met Asp
1               5

<210> SEQ ID NO 253
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 253

Asp Ile Asn Thr Arg Ser Gly Gly Val Ile Tyr Asn Glu Glu Phe Gln
1               5                   10                  15

Asp

<210> SEQ ID NO 254
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 254

Arg Lys Ser Tyr Gly Tyr Tyr Leu Asp Glu
1               5                   10

<210> SEQ ID NO 255
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 255
```

```
Glu Gly Asn His Ile Gly Asp Lys His Val His
1               5                   10

<210> SEQ ID NO 256
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 256

Arg Asp Ala Arg Arg Pro Ser
1               5

<210> SEQ ID NO 257
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 257

Gln Val Trp Asp Ser Ser Ser Tyr Thr Val
1               5                   10

<210> SEQ ID NO 258
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 258

Glu Gly Asn His Ile Gly Asp Lys His Val His
1               5                   10

<210> SEQ ID NO 259
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 259

Gln Asp Ala Arg Arg Pro Ser
1               5

<210> SEQ ID NO 260
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 260

Gln Val Trp Asp Ser Ser Ser Tyr Thr Val
1               5                   10

<210> SEQ ID NO 261
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 261
```

Thr Gly Asn His Ile Ser Asp Lys His Val His
1               5                   10

<210> SEQ ID NO 262
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 262

Gln Asp Ala Arg Arg Pro Ser
1               5

<210> SEQ ID NO 263
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 263

Gln Val Trp Asp Ser Ser Asp Tyr Thr Val
1               5                   10

<210> SEQ ID NO 264
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 264

Glu Gly Asn Gln Ile Ser Gln Lys Gln Val His
1               5                   10

<210> SEQ ID NO 265
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 265

Arg Asp Ala Arg Arg Pro Ser
1               5

<210> SEQ ID NO 266
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 266

Gln Val Trp Asp Ser Ser Ala Val Val
1               5

<210> SEQ ID NO 267
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 267

Glu Gly Glu Gln Ile Gly Ser Lys Glu Val His

<210> SEQ ID NO 268
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 268

Arg Asp Ala Arg Arg Pro Ser
1               5

<210> SEQ ID NO 269
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 269

Gln Val Trp Asp Ser Ser Ser Tyr Thr Val
1               5                   10

<210> SEQ ID NO 270
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 270

Glu Gly Asn Gln Ile Gly Ser Arg Glu Val His
1               5                   10

<210> SEQ ID NO 271
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 271

Arg Asp Ala Arg Arg Pro Ser
1               5

<210> SEQ ID NO 272
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 272

Gln Val Trp Ala Ser Asp Ala Val Val
1               5

<210> SEQ ID NO 273
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 273

Glu Gly Glu Gln Ile Gly Ser Lys Glu Val His
1               5                   10

<210> SEQ ID NO 274
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 274

Arg Asp Ala Arg Arg Pro Ser
1               5

<210> SEQ ID NO 275
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 275

Gln Val Trp Asp Ser Ser Ser Tyr Thr Val
1               5                   10

<210> SEQ ID NO 276
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 276

Glu Gly Glu Gln Ile Gly Ser Lys Glu Val His
1               5                   10

<210> SEQ ID NO 277
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 277

Arg Asp Ala Arg Arg Pro Ser
1               5

<210> SEQ ID NO 278
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 278

Gln Val Trp Asp Ser Ser Ser Tyr Thr Val
1               5                   10

<210> SEQ ID NO 279
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 279

Glu Gly Glu Gln Ile Gly Ser Lys Glu Val His
1               5                   10

<210> SEQ ID NO 280
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 280

Arg Asp Ala Arg Arg Pro Ser
1               5

<210> SEQ ID NO 281
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 281

Gln Val Trp Asp Ser Ser Ser Tyr Thr Val
1               5                   10

<210> SEQ ID NO 282
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 282

Glu Gly Asn Gln Ile Gly Glu Lys Glu Val His
1               5                   10

<210> SEQ ID NO 283
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 283

Arg Asp Ala Arg Arg Pro Ser
1               5

<210> SEQ ID NO 284
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 284

Gln Val Trp Ala Ser Asp Ala Val Val
1               5

<210> SEQ ID NO 285
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 285

Glu Gly Glu Gln Ile Gly Ser Lys Glu Val His
1               5                   10

```
<210> SEQ ID NO 286
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 286

Arg Asp Ala Arg Arg Pro Ser
1               5

<210> SEQ ID NO 287
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 287

Gln Val Trp Asp Ser Ser Ser Tyr Thr Val
1               5                   10
```